United States Patent
Sahin et al.

(10) Patent No.: US 11,932,693 B2
(45) Date of Patent: Mar. 19, 2024

(54) MONOCLONAL ANTIBODIES DIRECTED AGAINST PROGRAMMED DEATH-1 PROTEIN AND THEIR USE IN MEDICINE

(71) Applicants: BioNTech SE, Mainz (DE); Genmab A/S, Copenhagen V (DK)

(72) Inventors: Ugur Sahin, Mainz (DE); Sina Fellermeier-Kopf, Mainz (DE); Friederike Gieseke, Mainz (DE); Karsten Beckmann, Mainz (DE); Claudia Paulmann, Mainz (DE); Alexander Muik, Mainz (DE); Ivan Kuzmanov, Mainz (DE); Esther Cornelia Wilhelmina Breij, Utrecht (NL); Patricia Garrido Castro, Utrecht (NL); Jordan Blum, Utrecht (NL); Lars Guelen, Utrecht (NL); Joost Neijssen, Utrecht (NL); Bart-Jan De Kreuk, Utrecht (NL); Richard Hibbert, Utrecht (NL); Janine Schuurman, Utrecht (NL); Aran Frank Labrijn, Utrecht (NL)

(73) Assignees: BioNTech SE, Mainz (DE); Genmab A/S, Copenhagen (DK)

( * ) Notice: Subject to any disclaimer, the term of this patent is extended or adjusted under 35 U.S.C. 154(b) by 0 days.

(21) Appl. No.: 18/315,686

(22) Filed: May 11, 2023

(65) Prior Publication Data

US 2023/0365693 A1   Nov. 16, 2023

Related U.S. Application Data

(60) Provisional application No. 63/364,595, filed on May 12, 2022.

(51) Int. Cl.
    *C07K 16/28* (2006.01)
(52) U.S. Cl.
    CPC ...... *C07K 16/2818* (2013.01); *C07K 2317/24* (2013.01); *C07K 2317/92* (2013.01)
(58) Field of Classification Search
    None
    See application file for complete search history.

(56) References Cited

U.S. PATENT DOCUMENTS

2022/0411507 A1*  12/2022  LaFace ............... C07K 16/18

FOREIGN PATENT DOCUMENTS

| EP | 3505535 A1 | | 7/2019 |
| WO | 2021234402 A2 | | 11/2021 |
| WO | WO2022101358 | * | 5/2022 |
| WO | 2022189667 A1 | | 9/2022 |
| WO | 2023057534 A1 | | 4/2023 |

OTHER PUBLICATIONS

Ying et al., J. Biol. Chem. 288(35):25154-64 (Year: 2013).*
Wilkinson et al., PLoS One 15(12):e0260954; doi.org/10.1371/journal.pone.0260954 (Year: 2021).*
Dahan et al., Cancer Cell, 28(3), 285-295, 2015.
Huang, et al., Frontiers in Immunology, 13, 2022.
International Search Report and Written Opinion for Application No. PCT/EP2023/062651, dated Jul. 10, 2023, 69 pages.
Li et al., Annals of Oncology, 32(S5), S361, 2021.
Moreno-Vicente et al., J Immunother Cancer, 10, e003735, 2022.

* cited by examiner

*Primary Examiner* — Jessica H Roark
(74) *Attorney, Agent, or Firm* — Neal, Gerber & Eisenberg LLP

(57) ABSTRACT

The present disclosure relates to antibodies having the ability to bind to the immune checkpoint protein programmed death-1 (PD-1), such as human PD-1, or nucleic acids encoding such antibodies, wherein the antibodies comprise modifications in the Fc region eliminating or reducing a Fc-mediated effector function of the antibodies. The present disclosure also relates to compositions or kits comprising said antibodies or nucleic acids, as well as to the use of these antibodies or nucleic acids or compositions in the field of medicine, preferably in the field of immunotherapy, e.g., for the treatment of cancers. The present invention further relates to methods for inducing an immune response in a subject comprising providing to the subject an antibody of the present disclosure or one or more nucleic acids encoding such an antibody, or a composition comprising said antibody or nucleic acids.

30 Claims, 16 Drawing Sheets

Specification includes a Sequence Listing.

A.

B.

SEQUENCE LISTING

```
Sequence total quantity: 57
SEQ ID NO: 1                 moltype = AA  length = 329
FEATURE                      Location/Qualifiers
REGION                       1..329
                             note = Constant region human HC IgG1m(f)
source                       1..329
                             mol_type = protein
                             organism = synthetic construct
SEQUENCE: 1
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSREE 240
MTKNQVSLTC LVKGFYPSDI AVEWESNGQP ENNYKTTPPV LDSDGSFFLY SKLTVDKSRW 300
QQGNVFSCSV MHEALHNHYT QKSLSLSPG                                  329

SEQ ID NO: 2                 moltype = AA  length = 329
FEATURE                      Location/Qualifiers
REGION                       1..329
                             note = Constant region human HC IgG1m(f)-L234F-L235E-G236R
                              and variants
VARIANT                      117
                             note = X is selected from A, V, L, I, P, F, M or W,
                              preferably I, P, F, M or W, more preferably X is F
VARIANT                      118
                             note = X is selected from L, D or E, preferably D or E,
                              more preferably X is E
VARIANT                      119
                             note = X is any amino acid but not G, preferably X is
                              selected from K, R or H, more preferably X is R
source                       1..329
                             mol_type = protein
                             organism = synthetic construct
SEQUENCE: 2
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPEXXXG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSREE 240
MTKNQVSLTC LVKGFYPSDI AVEWESNGQP ENNYKTTPPV LDSDGSFFLY SKLTVDKSRW 300
QQGNVFSCSV MHEALHNHYT QKSLSLSPG                                  329

SEQ ID NO: 3                 moltype = AA  length = 329
FEATURE                      Location/Qualifiers
REGION                       1..329
                             note = Constant region human HC
                              IgG1m(f)-L234F-L235E-G236R-K409R
source                       1..329
                             mol_type = protein
                             organism = synthetic construct
SEQUENCE: 3
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPEFERG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSREE 240
MTKNQVSLTC LVKGFYPSDI AVEWESNGQP ENNYKTTPPV LDSDGSFFLY SRLTVDKSRW 300
QQGNVFSCSV MHEALHNHYT QKSLSLSPG                                  329

SEQ ID NO: 4                 moltype = AA  length = 329
FEATURE                      Location/Qualifiers
REGION                       1..329
                             note = Constant region human HC IgG1m(f)-E430G
source                       1..329
                             mol_type = protein
                             organism = synthetic construct
SEQUENCE: 4
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG 120
PSVFLFPPKP KDTLMISRTP EVTCVVVDVS HEDPEVKFNW YVDGVEVHNA KTKPREEQYN 180
STYRVVSVLT VLHQDWLNGK EYKCKVSNKA LPAPIEKTIS KAKGQPREPQ VYTLPPSREE 240
MTKNQVSLTC LVKGFYPSDI AVEWESNGQP ENNYKTTPPV LDSDGSFFLY SKLTVDKSRW 300
QQGNVFSCSV MHGALHNHYT QKSLSLSPG                                  329

SEQ ID NO: 5                 moltype = AA  length = 327
FEATURE                      Location/Qualifiers
REGION                       1..327
                             note = Constant region human HC IgG4
source                       1..327
                             mol_type = protein
```

```
                        organism = synthetic construct
SEQUENCE: 5
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPSCP APEFLGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVMHE ALHNHYTQKS LSLSLGK                                      327

SEQ ID NO: 6           moltype = AA  length = 107
FEATURE                Location/Qualifiers
REGION                 1..107
                       note = Constant region human kappa LC
source                 1..107
                       mol_type = protein
                       organism = synthetic construct
SEQUENCE: 6
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 7           moltype = AA  length = 329
FEATURE                Location/Qualifiers
REGION                 1..329
                       note = Heavy chain human IgG1-LALA
source                 1..329
                       mol_type = protein
                       organism = synthetic construct
SEQUENCE: 7
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPEAAGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                    329

SEQ ID NO: 8           moltype = AA  length = 10
FEATURE                Location/Qualifiers
REGION                 1..10
                       note = HCDR3 intersection of Kabat and IMGT (= Kabat)
source                 1..10
                       mol_type = protein
                       organism = synthetic construct
SEQUENCE: 8
AFYDDYDYNV                                                          10

SEQ ID NO: 9           moltype = AA  length = 12
FEATURE                Location/Qualifiers
REGION                 1..12
                       note = HCDR3 IMGT
source                 1..12
                       mol_type = protein
                       organism = synthetic construct
SEQUENCE: 9
ARAFYDDYDY NV                                                       12

SEQ ID NO: 10          moltype = AA  length = 7
FEATURE                Location/Qualifiers
REGION                 1..7
                       note = HCDR2 intersection of Kabat and IMGT (= IMGT)
source                 1..7
                       mol_type = protein
                       organism = synthetic construct
SEQUENCE: 10
ISGGTIG                                                             7

SEQ ID NO: 11          moltype = AA  length = 16
FEATURE                Location/Qualifiers
REGION                 1..16
                       note = HCDR2 Kabat
source                 1..16
                       mol_type = protein
                       organism = synthetic construct
SEQUENCE: 11
IISGGTIGHY ASWAKG                                                   16

SEQ ID NO: 12          moltype = AA  length = 5
FEATURE                Location/Qualifiers
REGION                 1..5
                       note = HCDR1 Kabat
```

```
source                  1..5
                        mol_type = protein
                        organism = synthetic construct
SEQUENCE: 12
SYNMG                                                               5

SEQ ID NO: 13           moltype = AA  length = 8
FEATURE                 Location/Qualifiers
REGION                  1..8
                        note = HCDR1 IMGT
source                  1..8
                        mol_type = protein
                        organism = synthetic construct
SEQUENCE: 13
GFSLYSYN                                                            8

SEQ ID NO: 14           moltype = AA  length = 11
FEATURE                 Location/Qualifiers
REGION                  1..11
                        note = LCDR3 intersection = Kabat = IMGT
source                  1..11
                        mol_type = protein
                        organism = synthetic construct
SEQUENCE: 14
AGGYSSSSDT T                                                        11

SEQ ID NO: 15           moltype = AA  length = 7
FEATURE                 Location/Qualifiers
REGION                  1..7
                        note = LCDR2 Kabat
source                  1..7
                        mol_type = protein
                        organism = synthetic construct
SEQUENCE: 15
QASKLET                                                             7

SEQ ID NO: 16           moltype = AA  length = 8
FEATURE                 Location/Qualifiers
REGION                  1..8
                        note = LCDR1 intersection of Kabat and IMGT (=IMGT)
source                  1..8
                        mol_type = protein
                        organism = synthetic construct
SEQUENCE: 16
QSVYGNNQ                                                            8

SEQ ID NO: 17           moltype = AA  length = 13
FEATURE                 Location/Qualifiers
REGION                  1..13
                        note = LCDR1 Kabat
source                  1..13
                        mol_type = protein
                        organism = synthetic construct
SEQUENCE: 17
QSSQSVYGNN QLS                                                      13

SEQ ID NO: 18           moltype = AA  length = 116
FEATURE                 Location/Qualifiers
REGION                  1..116
                        note = VH MAB-19-0202
source                  1..116
                        mol_type = protein
                        organism = synthetic construct
SEQUENCE: 18
QSVEESGGRL VTPGTPLTLT CTVSGFSLYS YNMGWVRQAP GKGLEYIGII SGGTIGHYAS   60
WAKGRFTISK TSSTTVDLKM TSLTTEDTAT YFCARAFYDD YDYNVWGPGT LVTVSS      116

SEQ ID NO: 19           moltype = AA  length = 111
FEATURE                 Location/Qualifiers
REGION                  1..111
                        note = VL MAB-19-0202
source                  1..111
                        mol_type = protein
                        organism = synthetic construct
SEQUENCE: 19
AAVLTQTPSP VSAAVGGTVT ISCQSSQSVY GNNQLSWYQQ KPGQPPKLLI YQASKLETGV   60
PSRFKGSGSG TQFTLTISDL ESDDAATYYC AGGYSSSSDT TFGGGTEVVV K           111

SEQ ID NO: 20           moltype = AA  length = 118
```

```
FEATURE              Location/Qualifiers
REGION               1..118
                     note = VH IgG1-PD1 (H5 derived from MAB-19-0202)
source               1..118
                     mol_type = protein
                     organism = synthetic construct
SEQUENCE: 20
QVQLVESGGG LVQPGTSLRL SCSVSGFSLY SYNMGWVRQA PGKGLEYIGI ISGGTIGHYA    60
SWAKGRFTIS RDTSKTTLYL QMNSLTTEDT ATYFCARAFY DDYDYNVWGP GTLVTVSS     118

SEQ ID NO: 21        moltype = AA  length = 111
FEATURE              Location/Qualifiers
REGION               1..111
                     note = VL IgG1-PD1 (L4 derived from MAB-19-0202)
source               1..111
                     mol_type = protein
                     organism = synthetic construct
SEQUENCE: 21
AIQLTQSPSS LSASVGGTVT ITCQSSQSVY GNNQLSWYQQ KPGQPPKLLI YQASKLETGV    60
PSRFRGSGSG TQFTLTISSL QSEDFATYYC AGGYSSSSDT TFGGGTEVVV K            111

SEQ ID NO: 22        moltype = AA  length = 288
FEATURE              Location/Qualifiers
source               1..288
                     mol_type = protein
                     organism = Homo sapiens
SEQUENCE: 22
MQIPQAPWPV VWAVLQLGWR PGWFLDSPDR PWNPPTFSPA LLVVTEGDNA TFTCSFSNTS    60
ESFVLNWYRM SPSNQTDKLA AFPEDRSQPG QDCRFRVTQL PNGRDFHMSV VRARRNDSGT   120
YLCGAISLAP KAQIKESLRA ELRVTERRAE VPTAHPSPSP RPAGQFQTLV VGVVGGLLGS   180
LVLLVWVLAV ICSRAARGTI GARRTGQPLK EDPSAVPVFS VDYGELDFQW REKTPEPPVP   240
CVPEQTEYAT IVFPSGMGTS SPARRGSADG PRSAQPLRPE DGHCSWPL                288

SEQ ID NO: 23        moltype = AA  length = 147
FEATURE              Location/Qualifiers
source               1..147
                     mol_type = protein
                     organism = Homo sapiens
SEQUENCE: 23
FLDSPDRPWN PPTFSPALLV VTEGDNATFT CSFSNTSESF VLNWYRMSPS NQTDKLAAFP    60
EDRSQPGQDC RFRVTQLPNG RDFHMSVVRA RRNDSGTYLC GAISLAPKAQ IKESLRAELR   120
VTERRAEVPT AHPSPSPRPA GQFQTLV                                       147

SEQ ID NO: 24        moltype = DNA  length = 2115
FEATURE              Location/Qualifiers
source               1..2115
                     mol_type = other DNA
                     organism = Homo sapiens
SEQUENCE: 24
agtttccctt ccgctcacct ccgctgagc agtggagaag gcggcactct ggtggggctg     60
ctccaggcat gcagatccca caggcgccct ggccagtcgt ctgggcggtg ctacaactgg   120
gctggcggcc aggatggttc ttagactccc cagacaggcc ctggaacccc ccaccttct    180
ccccagccct gctcgtggtg accgaagggg acaacgccac cttcacctgc agcttctcca   240
acacatcgga gagcttcgtg ctaaactggt accgcatgag cccagcaac cagacgagca   300
agctggccgc cttccccgag accgcagcc agcccgcctg ggactgccgc ttccgtgtca   360
cacaactgcc caacgggcgt gacttccaca tgagcgtggt cagggcccgg cgcaatgaca   420
gcggcaccta cctctgtggg gccatctccc tggcccccaa ggcgcagatc aaagagagcc   480
tgcgggcaga gctcagggtg acagagaaa gggcagaagt gcccacagcc caccccagcc   540
cctcacccag gccagccggc cagttccaaa ccctggtggt tggtgtcgtg ggcggcctgc   600
tgggcagcct ggtgctgcta gtctgggtcc tggccgtcat ctgctcccgg gccgcacgag   660
ggacaatagg agccaggcgc accggccagc ccctgaagga ggaccccta gccgtgcctg   720
tgttctctgt ggactatggg gagctggatt ccagtggcg agagaagacc ccggagcccc   780
ccgtgccctg tgtccctgag cagacggagt atgccaccat tgtcttcct agcggaatgg   840
gcacctcatc ccccgcccgc aggggctcag ctgacggcc tcgagtgcc cagccactga   900
ggcctgagga tggacactgc tcttggcccc tctgaccggc ttccttgcc accagtgttc   960
tgcagaccct ccaccatgag cccggggtcag cgcatttcct caggagaagc aggcaggtg  1020
caggccattg caggccgtcc aggggctgag ctgcctgggg cgaccgggg ctccagcctg  1080
cacctgcacc aggcacagcc ccaccacagg actcatgtct caatgcccac agtgagccca  1140
ggcagcaggt gtcacagggg cctacaggga gggcagatg cagtcactgc ttcaggtcct  1200
gccagcacag agctgcctgc gtccagctcc ctgaatctct gctgctgctg ctgctgctgc  1260
tgctgctgcc tgcggcccgg ggctgaaggc gccgtggccc tgcctgacgc ccggagcct   1320
cctgcctgaa cttgggggct ggttggagat ggccttggag cagccaaggt gcccctggca  1380
gtggcatccc gaaacgccct ggacgcaggg cccaagactg gcacaggag tggaggtac    1440
atggggtcgg ggactcccca ggagttatct gctccctggc ctagaga agtttcaggg    1500
aaggtcagaa gagctcctgg ctgtggtggg cagggcagga aaccctcca cctttacaca   1560
tgcccaggca gcacctcagg ccctttgtgg gcagggaag ctgaggcagt aagcgggcag   1620
gcagagctgc aggcctttca ggcccagcca gcactctggc ctcctgccgc cgcattccac  1680
cccagcccct cacaccactc gggagaggga catcctacgg tccccaggtc aggagggcag  1740
ggctggggtt gactcaggcc cctcccagct gtggccacct gggtgttggg agggcagaag  1800
```

```
tgcaggcacc tagggccccc catgtgccca ccctgggagc tctccttgga acccattcct    1860
gaaattattt aaagggttg gccgggctcc caccagggcc tgggtgggaa ggtacaggcg    1920
ttcccccggg gcctagtacc cccgccgtgg cctatccact cctcacatcc acacactgca    1980
cccccactcc tggggcaggg ccaccagcat ccaggcggcc agcaggcacc tgagtggctg    2040
ggacaaggga tccccttcc ctgtggttct attatattat aattataatt aaatatgaga    2100
gcatgctaag gaaaa                                                     2115

SEQ ID NO: 25           moltype = AA  length = 121
FEATURE                 Location/Qualifiers
REGION                  1..121
                        note = VH CD52-CAMPATH-1H
source                  1..121
                        mol_type = protein
                        organism = synthetic construct
SEQUENCE: 25
QVQLQESGPG LVRPSQTLSL TCTVSGFTFT DFYMNWVRQP PGRGLEWIGF IRDKAKGYTT    60
EYNPSVKGRV TMLVDTSKNQ FSLRLSSVTA ADTAVYYCAR EGHTAAPFDY WGQGSLVTVS   120
S                                                                    121

SEQ ID NO: 26           moltype = AA  length = 8
FEATURE                 Location/Qualifiers
REGION                  1..8
                        note = VH CD52-CAMPATH-1H CDR1
source                  1..8
                        mol_type = protein
                        organism = synthetic construct
SEQUENCE: 26
GFTFTDFY                                                             8

SEQ ID NO: 27           moltype = AA  length = 10
FEATURE                 Location/Qualifiers
REGION                  1..10
                        note = VH CD52-CAMPATH-1H CDR2
source                  1..10
                        mol_type = protein
                        organism = synthetic construct
SEQUENCE: 27
IRDKAKGYTT                                                           10

SEQ ID NO: 28           moltype = AA  length = 12
FEATURE                 Location/Qualifiers
REGION                  1..12
                        note = VH CD52-CAMPATH-1H CDR3
source                  1..12
                        mol_type = protein
                        organism = synthetic construct
SEQUENCE: 28
AREGHTAAPF DY                                                        12

SEQ ID NO: 29           moltype = AA  length = 107
FEATURE                 Location/Qualifiers
REGION                  1..107
                        note = VL CD52-CAMPATH-1H
source                  1..107
                        mol_type = protein
                        organism = synthetic construct
SEQUENCE: 29
DIQMTQSPSS LSASVGDRVT ITCKASQNID KYLNWYQQKP GKAPKLLIYN TNNLQTGVPS    60
RFSGSGSGTD FTFTISSLQP EDIATYYCLQ HISRPRTFGQ GTKVEIK                 107

SEQ ID NO: 30           moltype = AA  length = 6
FEATURE                 Location/Qualifiers
REGION                  1..6
                        note = VL CD52-CAMPATH-1H CDR1
source                  1..6
                        mol_type = protein
                        organism = synthetic construct
SEQUENCE: 30
QNIDKY                                                               6

SEQ ID NO: 31           moltype = AA  length = 9
FEATURE                 Location/Qualifiers
REGION                  1..9
                        note = VL CD52-CAMPATH-1H CDR3
source                  1..9
                        mol_type = protein
                        organism = synthetic construct
SEQUENCE: 31
LQHISRPRT                                                            9
```

```
SEQ ID NO: 32             moltype = AA   length = 127
FEATURE                   Location/Qualifiers
REGION                    1..127
                          note = VH gp120-b12
source                    1..127
                          mol_type = protein
                          organism = synthetic construct
SEQUENCE: 32
QVQLVQSGAE VKKPGASVKV SCQASGYRFS NFVIHWVRQA PGQRFEWMGW INPYNGNKEF    60
SAKFQDRVTF TADTSANTAY MELRSLRSAD TAVYYCARVG PYSWDDSPQD NYYMDVWGKG   120
TTVIVSS                                                            127

SEQ ID NO: 33             moltype = AA   length = 8
FEATURE                   Location/Qualifiers
REGION                    1..8
                          note = VH gp120-b12 CDR1
source                    1..8
                          mol_type = protein
                          organism = synthetic construct
SEQUENCE: 33
GYRFSNFV                                                             8

SEQ ID NO: 34             moltype = AA   length = 8
FEATURE                   Location/Qualifiers
REGION                    1..8
                          note = VH gp120-b12 CDR2
source                    1..8
                          mol_type = protein
                          organism = synthetic construct
SEQUENCE: 34
INPYNGNK                                                             8

SEQ ID NO: 35             moltype = AA   length = 20
FEATURE                   Location/Qualifiers
REGION                    1..20
                          note = VH gp120-b12 CDR3
source                    1..20
                          mol_type = protein
                          organism = synthetic construct
SEQUENCE: 35
ARVGPYSWDD SPQDNYYMDV                                               20

SEQ ID NO: 36             moltype = AA   length = 108
FEATURE                   Location/Qualifiers
REGION                    1..108
                          note = VL gp120-b12
source                    1..108
                          mol_type = protein
                          organism = synthetic construct
SEQUENCE: 36
EIVLTQSPGT LSLSPGERAT FSCRSSHSIR SRRVAWYQHK PGQAPRLVIH GVSNRASGIS    60
DRFSGSGSGT DFTLTITRVE PEDFALYYCQ VYGASSYTFG QGTKLERK               108

SEQ ID NO: 37             moltype = AA   length = 7
FEATURE                   Location/Qualifiers
REGION                    1..7
                          note = VL gp120-b12 CDR1
source                    1..7
                          mol_type = protein
                          organism = synthetic construct
SEQUENCE: 37
HSIRSRR                                                              7

SEQ ID NO: 38             moltype = AA   length = 9
FEATURE                   Location/Qualifiers
REGION                    1..9
                          note = VL gp120-b12-CDR3
source                    1..9
                          mol_type = protein
                          organism = synthetic construct
SEQUENCE: 38
QVYGASSYT                                                            9

SEQ ID NO: 39             moltype = AA   length = 29
FEATURE                   Location/Qualifiers
REGION                    1..29
                          note = MAB-19-0202-HC FR1
source                    1..29
```

```
                        mol_type = protein
                        organism = synthetic construct
SEQUENCE: 39
QSVEESGGRL VTPGTPLTLT CTVSGFSLY                                    29

SEQ ID NO: 40           moltype = AA  length = 14
FEATURE                 Location/Qualifiers
REGION                  1..14
                        note = MAB-19-0202-HC FR2
source                  1..14
                        mol_type = protein
                        organism = synthetic construct
SEQUENCE: 40
WVRQAPGKGL EYIG                                                    14

SEQ ID NO: 41           moltype = AA  length = 31
FEATURE                 Location/Qualifiers
REGION                  1..31
                        note = MAB-19-0202-HC FR3
source                  1..31
                        mol_type = protein
                        organism = synthetic construct
SEQUENCE: 41
RFTISKTSST TVDLKMTSLT TEDTATYFCA R                                 31

SEQ ID NO: 42           moltype = AA  length = 11
FEATURE                 Location/Qualifiers
REGION                  1..11
                        note = MAB-19-0202-HC FR4
source                  1..11
                        mol_type = protein
                        organism = synthetic construct
SEQUENCE: 42
WGPGTLVTVS S                                                       11

SEQ ID NO: 43           moltype = AA  length = 23
FEATURE                 Location/Qualifiers
REGION                  1..23
                        note = MAB-19-0202-LC FR1
source                  1..23
                        mol_type = protein
                        organism = synthetic construct
SEQUENCE: 43
AAVLTQTPSP VSAAVGGTVT ISC                                          23

SEQ ID NO: 44           moltype = AA  length = 15
FEATURE                 Location/Qualifiers
REGION                  1..15
                        note = MAB-19-0202-LC FR2
source                  1..15
                        mol_type = protein
                        organism = synthetic construct
SEQUENCE: 44
WYQQKPGQPP KLLIY                                                   15

SEQ ID NO: 45           moltype = AA  length = 32
FEATURE                 Location/Qualifiers
REGION                  1..32
                        note = MAB-19-0202-LC FR3
source                  1..32
                        mol_type = protein
                        organism = synthetic construct
SEQUENCE: 45
GVPSRFKGSG SGTQFTLTIS DLESDDAATY YC                                32

SEQ ID NO: 46           moltype = AA  length = 10
FEATURE                 Location/Qualifiers
REGION                  1..10
                        note = MAB-19-0202-LC FR4
source                  1..10
                        mol_type = protein
                        organism = synthetic construct
SEQUENCE: 46
FGGGTEVVVK                                                         10

SEQ ID NO: 47           moltype = AA  length = 30
FEATURE                 Location/Qualifiers
REGION                  1..30
                        note = MAB-19-0202-H5 FR1
```

```
source                   1..30
                         mol_type = protein
                         organism = synthetic construct
SEQUENCE: 47
QVQLVESGGG LVQPGTSLRL SCSVSGFSLY                                   30

SEQ ID NO: 48            moltype = AA   length = 14
FEATURE                  Location/Qualifiers
REGION                   1..14
                         note = MAB-19-0202-H5 FR2
source                   1..14
                         mol_type = protein
                         organism = synthetic construct
SEQUENCE: 48
WVRQAPGKGL EYIG                                                    14

SEQ ID NO: 49            moltype = AA   length = 32
FEATURE                  Location/Qualifiers
REGION                   1..32
                         note = MAB-19-0202-H5 FR3
source                   1..32
                         mol_type = protein
                         organism = synthetic construct
SEQUENCE: 49
RFTISRDTSK TTLYLQMNSL TTEDTATYFC AR                                32

SEQ ID NO: 50            moltype = AA   length = 11
FEATURE                  Location/Qualifiers
REGION                   1..11
                         note = MAB-19-0202-H5 FR4
source                   1..11
                         mol_type = protein
                         organism = synthetic construct
SEQUENCE: 50
WGPGTLVTVS S                                                       11

SEQ ID NO: 51            moltype = AA   length = 23
FEATURE                  Location/Qualifiers
REGION                   1..23
                         note = MAB-19-0202-L4 FR1
source                   1..23
                         mol_type = protein
                         organism = synthetic construct
SEQUENCE: 51
AIQLTQSPSS LSASVGGTVT ITC                                          23

SEQ ID NO: 52            moltype = AA   length = 15
FEATURE                  Location/Qualifiers
REGION                   1..15
                         note = MAB-19-0202-L4 FR2
source                   1..15
                         mol_type = protein
                         organism = synthetic construct
SEQUENCE: 52
WYQQKPGQPP KLLIY                                                   15

SEQ ID NO: 53            moltype = AA   length = 32
FEATURE                  Location/Qualifiers
REGION                   1..32
                         note = MAB-19-0202-L4 FR3
source                   1..32
                         mol_type = protein
                         organism = synthetic construct
SEQUENCE: 53
GVPSRFRGSG SGTQFTLTIS SLQSEDFATY YC                                32

SEQ ID NO: 54            moltype = AA   length = 10
FEATURE                  Location/Qualifiers
REGION                   1..10
                         note = MAB-19-0202-L4 FR4
source                   1..10
                         mol_type = protein
                         organism = synthetic construct
SEQUENCE: 54
FGGGTEVVVK                                                         10

SEQ ID NO: 55            moltype = AA   length = 329
FEATURE                  Location/Qualifiers
REGION                   1..329
```

-continued

```
source                    note = Constant region human HC IgG1m(f)-L234F-L235E-G236R
                          1..329
                          mol_type = protein
                          organism = synthetic construct
SEQUENCE: 55
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKRVEP KSCDKTHTCP PCPAPEFERG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 56             moltype = AA  length = 447
FEATURE                   Location/Qualifiers
source                    1..447
                          mol_type = protein
                          organism = synthetic construct
SEQUENCE: 56
QVQLVESGGG LVQPGTSLRL SCSVSGFSLY SYNMGWVRQA PGKGLEYIGI ISGGTIGHYA    60
SWAKGRFTIS RDTSKTTLYL QMNSLTTEDT ATYFCARAFY DDYDYNVWGP GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKRVEPKS CDKTHTCPPC PAPEFERGPS   240
VFLFPPKPKD TLMISRTPEV TCVVVDVSHE DPEVKFNWYV DGVEVHNAKT KPREEQYNST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPG                                       447

SEQ ID NO: 57             moltype = AA  length = 218
FEATURE                   Location/Qualifiers
source                    1..218
                          mol_type = protein
                          organism = synthetic construct
SEQUENCE: 57
AIQLTQSPSS LSASVGGTVT ITCQSSQSVY GNNQLSWYQQ KPGQPPKLLI YQASKLETGV    60
PSRFRGSGSG TQFTLTISSL QSEDFATYYC AGGYSSSSDT TFGGGTEVVV KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218
```

MONOCLONAL ANTIBODIES DIRECTED AGAINST PROGRAMMED DEATH-1 PROTEIN AND THEIR USE IN MEDICINE

CROSS-REFERENCE TO RELATED APPLICATIONS

This application claims priority to U.S. Patent Application No. 63/364,595, which was filed on May 12, 2022. The contents of the aforementioned application are incorporated herein by reference in their entireties.

SEQUENCE LISTING

The computer-readable Sequence Listing submitted on May 11, 2023 and identified as follows: 77,977 bytes ST.26 XML document file named "028320-8056 Sequence Listing.xml," created May 11, 2023, is incorporated herein by reference in its entirety.

TECHNICAL FIELD OF THE INVENTION

The present invention relates to antibodies having the ability to bind, preferably specifically bind to the immune checkpoint protein programmed death-1 (PD-1), such as human PD-1, or nucleic acids encoding such antibodies, wherein the antibodies comprise modifications in the Fc region eliminating or reducing a Fc-mediated effector function of the antibodies. The present invention also relates to compositions or kits comprising said antibodies or nucleic acids, as well as to the use of these antibodies or nucleic acids or compositions in the field of medicine, preferably in the field of immunotherapy for the treatment of cancers. The present invention further relates to methods for inducing an immune response in a subject comprising providing to the subject an antibody having the ability to bind to the immune checkpoint protein PD-1, such as human PD-1, or a nucleic acid encoding such an antibody or a composition comprising said antibody or nucleic acid.

BACKGROUND OF THE INVENTION

Immunotherapy aims to enhance or induce specific immune responses in patients to control infectious or malignant diseases. The identification of a growing number of pathogen- and tumor-associated antigens (TAA) led to a broad collection of suitable targets for immunotherapy. Cells presenting immunogenic peptides (epitopes) derived from these antigens can be specifically targeted by either active or passive immunization strategies. Active immunization tends to induce and expand antigen-specific T cells in the patient, which are able to specifically recognize and kill diseased cells. In contrast passive immunization may rely on the adoptive transfer of T cells, which were expanded and optional genetically engineered in vitro (adoptive T cell therapy).

In vertebrates, the evolution of the immune system resulted in a highly effective network based on two types of defense: the innate and the adoptive immunity. In contrast to the evolutionary ancient innate immune system that relies on invariant receptors recognizing common molecular patterns associated with pathogens, the adoptive immunity is based on highly specific antigen receptors on B cells (B lymphocytes) and T cells (T lymphocytes) and clonal selection. The immune system plays a crucial role during cancer development, progression and therapy. $CD8^+$ T cells and NK cells can directly lyse tumor cells and high tumor-infiltration of these cells is generally regarded as favorable for the outcome of various tumor diseases. $CD4^+$ T cells contribute to the anti-tumor immune response by secretion of $IFN\gamma$ or licensing of antigen-presenting dendritic cells (DCs), which in turn prime and activate $CD8^+$ T cells (Kreiter S. et al. Nature 520, 692-6 (2015)). The recognition and elimination of tumor cells by $CD8^+$ T cells depends on antigen presentation via the Major Histocompatibility Complex (MHC) class I. Antigen-specific T cell responses can be elicited by vaccination. Vaccination can be achieved by administering vaccine RNA, i.e., RNA encoding an antigen or epitope against which an immune response is to be induced.

Not only stimulation through antigen receptors (TCR), but also an additional stimulative inducement through conjugated stimulative molecular groups (for example, CD28) could by necessary for activation of T cells. Cancer cells can avoid and suppress immune responses through upregulation of inhibitory immune checkpoint proteins, such as PD-1, and CTLA-4 on T cells or PD-L1 on tumor cells, tumor stroma or other cells within the tumor microenvironment. CTLA4 and PD-1 are known to transmit signals that suppresses T-cell activation. Blocking the activities of these proteins with monoclonal antibodies, and thus restoring T cell function, has delivered breakthrough therapies against cancer.

PD-1 (also known as CD279) is an immunoregulatory receptor expressed on the surface of activated T cells, B cells, and monocytes. The protein PD-1 has two naturally occurring ligands, which are known as PD-L1 (also referred to as CD274) and PD-L2 (also known as CD273). A wide variety of cancers express PD-L1, including melanoma, lung, renal, bladder, esophageal, gastric and other cancers. Thus, in cancer, the PD-1/PD-L1 system can upon the interaction of PD-L1 with PD-1 inhibit the proliferation of T lymphocytes, release of cytokines, and cytotoxicity, thereby providing cancer cells the opportunity to avoid a T cell mediated immune response.

Monoclonal antibodies suitable for regulating the activity of the PD-1/PD-L1 axis are known. The PD-1/PD-L1 interaction can be inhibited by pembrolizumab (also named MK-3475, lambrolizumab or Keytruda). Another monoclonal antibody suitable for this purpose is nivolumab (also named ONO-4538, BMS-936558 or Opdivo).

Antibody-based therapies for cancer have the potential of higher specificity and a lower side effect profile as compared to conventional drugs and may therefore be advantageous to conventional therapies. But by activating the immune system, immune checkpoint inhibitors may also cause autoimmune side effects in some patients. Other patients may fail to respond to the treatment.

Furthermore, anti-PD-1 antibodies have the potential to mitigate autoimmune diseases without the collateral suppression of normal immunity. E.g., an anti-PD-1 binding fragment coupled to an immunotoxin was able to delay disease onset in autoimmune diabetes, and ameliorates symptoms in an autoimmune encephalomyelitis model in mice (Zhao P. et al. Nat Biomed Eng. 3(4): 292-305 (2019)).

Modifications of the Fc-region of antibodies resulting in Fc regions with abrogated interactions with, e.g., Fc-gamma receptors and C1q are known in the art. Examples of amino acid positions that may be modified, e.g., in an IgG1 isotype antibody, include positions L234, L235 and P331. Combinations thereof, such as L234F/L235E/P331S, can cause a profound decrease in binding to human CD64, CD32, CD16 and C1q (Xu et al., 2000, Cell Immunol. 200(1):16-26; Oganesyan et al., 2008, Acta Cryst. (D64):700-4). Also, L234F and L235E amino acid substitutions can result in Fc regions with abrogated interactions with Fc-gamma receptors and C1q (Canfield et al., 1991, J. Exp. Med. (173): 1483-91; Duncan et al., 1988, Nature (332):738-40). A D265A amino acid substitution can decrease binding to all Fcγ receptors and prevent ADCC (Shields et al., 2001, J. Biol. Chem. (276):6591-604). Binding to C1q can be abrogated by mutating positions D270, K322, P329, and P331. Mutating these positions to either D270A or K322A or P329A or P331A can make the antibody deficient in CDC activity (Idusogie E E, et al., 2000, J Immunol. 164: 4178-84).

Thus, despite impressive benefits associated with immune checkpoint inhibitor therapy, there is still an unmet need for the development of improved antibodies targeting these checkpoints and to provide further benefits for immunotherapy, in particular cancer immunotherapy.

SUMMARY OF THE INVENTION

The present disclosure generally provides antibodies useful as therapeutics for treating and/or preventing diseases, such as cancers or infectious diseases. The treatment aims in activating the immune system and/or inducing an immune response.

The antibodies of the present disclosure show binding characteristics to PD-1, preferably to human-PD-1, and the ability to blockade a PD-1/PD-L1 interaction, so that they are capable of inducing an immune response.

The antibodies of the disclosure may have one or more of the following properties: The antibodies of the present disclosure (i) bind, preferably specifically bind, to PD-1; (ii) may have binding properties to PD-1 on immune cells; (iii) may have binding properties to PD-1 epitopes; (iv) may have binding properties to a non-human PD-1 variant, particularly to PD-1 variants from mice, rats, rabbits and primates; (v) may prevent or reduce the induction of inhibitory signals by PD-1; (vi) may inhibit the interaction/binding of ligands of PD-1 with PD-1, preferably of the ligand PD-L1 thereby blocking the inhibitory PD-1/PD-L1 axis, for example, they may inhibit the binding of human PD-L1 to human PD-1; (vii) may inhibit the immunosuppressive signal of PD-L1 or PD-L2; (viii) may enhance or initiate the immune function, preferably by enhancing or initiating a T-cell mediated immune response, preferably by inducing CD8$^+$ cell proliferation; (ix) may inhibit cancer proliferation; (x) may deplete tumor cells and/or suppress cancer metastasis; and/or (xi) may deplete immune cells and/or ameliorates autoimmune disease. Thus, an antibody of the present disclosure having the ability to bind to PD-1 can inhibit the immunosuppressive signal of PD-1 and/or can deplete activate immune cells and, thereby, can ameliorate autoimmune diseases.

The anti-PD-1 antibodies of the present disclosure have a reduced or depleted Fc-mediated effector function. Eliminating or reducing the binding of the Fc region of an antibody to Fc-gamma receptors can be desirable for the avoidance of unwanted inflammatory responses to therapeutic antibodies. For example, a reduced or depleted Fc-mediated effector function can help to avoid potential toxicity to, e.g., T cells which normally express PD-1. Even though the binding of Fc-gamma receptors can be eliminated or reduced by using scFvs od Fab fragments of an antibody, if a pharmacokinetic activity in the form of increased half-life of the antibody is required for therapeutic purposes, full-length antibodies may be preferred. Thus, antibodies comprising a modified Fc region providing a reduced or depleted Fc-mediated effector function may be desirable.

In a first aspect, there is provided an antibody having the ability to bind to PD-1, wherein the antibody comprises a heavy chain having a heavy chain constant region (CH) and a heavy chain variable region (VH), wherein the heavy chain constant region comprises an aromatic or non-polar amino acid at the position corresponding to position 234 in a human IgG1 heavy chain according to EU numbering and an amino acid other than glycine at the position corresponding to position 236 in a human IgG1 heavy chain according to EU numbering.

The antibodies of the first aspect comprise at least two modifications in the Fc region. When an antibody comprises such modifications, it may become an inert, or non-activating, antibody. The term "inertness", "inert" or "non-activating" as used herein, refers to an Fc region which is at least not able to bind any Fc-gamma receptors, induce Fc-mediated cross-linking of FcRs, or induce FcR-mediated cross-linking of target antigens via two Fc regions of individual antibodies, or is not able to bind C1q.

In one embodiment of the first aspect, there is provided an antibody having the ability to bind to PD-1, the antibody comprising a heavy chain having a heavy chain constant region (CH) and a heavy chain variable region (VH), wherein the heavy chain constant region comprises an aromatic or non-polar amino acid at the position corresponding to position 234 in a human IgG1 heavy chain according to EU numbering and an amino acid other than glycine at the position corresponding to position 236 in a human IgG1 heavy chain according to EU numbering, wherein the heavy chain variable region (VH) comprises a HCDR1, HCDR2 and HCDR3 sequence, wherein the HCDR1 sequence is selected from a sequence having or comprising SYN, SEQ ID NO: 12 or SEQ ID NO: 13, the HCDR2 sequence is selected from a sequence having or comprising SEQ ID NO: 10 or SEQ ID NO: 11, and the HCDR3 sequence is selected from a sequence having or comprising SEQ ID NO: 8 or SEQ ID NO: 9.

In one embodiment of the first aspect, there is provided an antibody having the ability to bind to PD-1, the antibody comprising a heavy chain having a heavy chain constant region (CH) and a heavy chain variable region (VH), wherein the heavy chain constant region comprises an aromatic or non-polar amino acid at the position corresponding to position 234 in a human IgG1 heavy chain according to EU numbering and an amino acid other than glycine at the position corresponding to position 236 in a human IgG1 heavy chain according to EU numbering, wherein the antibody comprises a light chain having a light chain variable region (VL) comprising a LCDR1, LCDR2, and LCDR3 sequence, wherein the LCDR1 sequence is selected from a sequence having or comprising SEQ ID NO: 16 or SEQ ID NO: 17, the LCDR2 sequence is selected from a sequence having or comprising QAS or SEQ ID NO: 15, and the LCDR3 sequence is a sequence having or comprising SEQ ID NO: 14.

In one embodiment of the first aspect, there is provided an antibody having the ability to bind to PD-1, the antibody comprising a heavy chain having a heavy chain constant region (CH) and a heavy chain variable region (VH) and a light chain having a light chain variable region (VL), wherein the heavy chain constant region comprises an aromatic or non-polar amino acid at the position corresponding to position 234 in a human IgG1 heavy chain according to EU numbering and an amino acid other than glycine at the position corresponding to position 236 in a human IgG1 heavy chain according to EU numbering, the heavy chain variable region (VH) comprises a HCDR1, HCDR2 and HCDR3 sequence, wherein the HCDR1 sequence is selected from a sequence having or comprising SYN, SEQ ID NO: 12 or SEQ ID NO: 13, the HCDR2 sequence is selected from a sequence having or comprising SEQ ID NO: 10 or SEQ ID NO: 11, and the HCDR3 sequence is selected from a sequence having or comprising SEQ ID NO: 8 or SEQ ID NO: 9, and the light chain variable region (VL) comprises a LCDR1, LCDR2, and LCDR3 sequence, wherein the LCDR1 sequence is selected from a sequence having or comprising SEQ ID NO: 16 or SEQ ID NO: 17, the LCDR2 sequence is selected from a sequence having or comprising QAS or SEQ ID NO: 15, and the LCDR3 sequence is a sequence having or comprising SEQ ID NO: 14.

For example, an antibody having the ability to bind to PD-1 of the first aspect can comprise a heavy chain having a heavy chain constant region (CH) and a heavy chain variable region (VH), and a light chain having a light chain variable region (VH), wherein the heavy chain constant region comprises an aromatic or non-polar amino acid, e.g., phenylalanine (F), at the position corresponding to position 234 in a human IgG1 heavy chain according to EU numbering, optionally an acidic amino acid, e.g., glutamate (E), at position 235 in a human IgG1 heavy chain according to EU numbering and an amino acid other than glycine, e.g., arginine (R), at the position corresponding to position 236 in a human IgG1 heavy chain according to EU numbering, wherein the heavy chain variable region (VH) comprises a HCDR1, HCDR2 and HCDR3 sequence, wherein the HCDR1 sequence is selected from a sequence having or comprising SYN, SEQ ID NO: 12 or SEQ ID NO: 13, the HCDR2 sequence is selected from a sequence having or comprising SEQ ID NO: 10 or SEQ ID NO: 11, and the HCDR3 sequence is selected from a sequence having or comprising SEQ ID NO: 8 or SEQ ID NO: 9, and/or wherein the light chain variable region (VL) comprises a LCDR1, LCDR2, and LCDR3 sequence, wherein the LCDR1 sequence is selected from a sequence having or comprising SEQ ID NO: 16 or SEQ ID NO: 17, the LCDR2 sequence is selected from a sequence having or comprising QAS or SEQ ID NO: 15, and the LCDR3 sequence is a sequence having or comprising SEQ ID NO: 14.

In a second aspect, there is provided a hybridoma capable of producing the antibody of the first aspect.

In a third aspect, there is provided a conjugate comprising an antibody of the first aspect coupled to a moiety or agent.

In a fourth aspect, there is provided a multimer, comprising at least two antibodies of the first aspect or at least two conjugates of the third aspect or a mixture of one or more antibodies of the first aspect and one or more conjugates of the third aspect.

In a fifth aspect, there is provided a nucleic acid comprising genes or nucleic acid sequences encoding:
an antibody of the first aspect or a fragment thereof;
an antibody heavy chain of an antibody of the first aspect or a fragment thereof; or
an antibody light chain of an antibody of the first aspect or a fragment thereof.

The encoded antibody and/or the encoded antibody heavy or light chains may each be a chain as described herein, e.g., as described in line with the embodiments of the first aspect.

In a sixth aspect, there is provided a vector comprising one or more of the nucleic acids of the fifth aspect.

In a seventh aspect, there is provided a host cell comprising a nucleic acid of the fifth aspect or comprising a vector of the sixth aspect.

In an eighth aspect, there is provided a virus comprising a nucleic acid of the fifth aspect or comprising a vector of the sixth aspect.

In a ninth aspect, there is provided a composition, preferably a pharmaceutical composition, comprising an active agent and a pharmaceutically acceptable carrier, wherein the active agent is at least one selected from:
  (i) an antibody of the first aspect;
  (ii) a conjugate of the third aspect;
  (iii) a multimer of the fourth aspect;
  (iv) a nucleic acid of the fifth aspect or a combination of the nucleic acids of the fifth aspect;
  (v) a vector of the sixth aspect or a combination of the vectors of the sixth aspect;
  (vi) a host cell of the seventh aspect or a combination of the host cells of the seventh aspect; and/or
  (vii) a virus of the eighth aspect or a combination of the viruses of the eighth aspect.

In a tenth aspect, there is provided a pharmaceutical composition of the ninth aspect for use in a prophylactic and/or therapeutic treatment of a disease.

In an eleventh aspect, there is provided a method of treating or preventing a disease in a subject comprising administering to a subject at least one active agent, wherein the active agent is at least one selected from:
  (i) an antibody of the first aspect;
  (ii) a conjugate of the third aspect;
  (iii) a multimer of the fourth aspect;
  (iv) a nucleic acid of the fifth aspect or a combination of the nucleic acids of the fifth aspect;
  (v) a vector of the sixth aspect or a combination of the vectors of the sixth aspect;
  (vi) a host cell of the seventh aspect or a combination of the host cells of the seventh aspect; and/or
  (vii) a virus of the eighth aspect or a combination of the viruses of the eighth aspect.

In a twelfth aspect, there is provided a kit for qualitative or quantitative detection of PD-1 in a sample, wherein the kit comprises an antibody of the first aspect or a conjugate of the third aspect or a multimer of the fourth aspect.

In a thirteenth aspect, there is provided the use of an antibody of the first aspect or of a conjugate of the third aspect or of a multimer of the fourth aspect or of a kit of the twelfth aspect in a method of determining the presence or quantity of PD-1 expressed in a sample, the method comprising the steps of:
  (i) contacting a sample with the antibody or the conjugate or the multimer, and
  (ii) detecting the formation of and/or determining the quantity of a complex between the antibody or the conjugate or the multimer and PD-1.

Embodiments of the above aspects, other features and advantages of the instant disclosure will be apparent from the following detailed description and claims. Embodiments pertaining to one aspect can be combined in any manner and in any number with any of the other aspects described herein. Any permutations and combinations of all described elements and features in this application should be considered disclosed by the description of the present application unless the context indicates otherwise.

Figure 1:
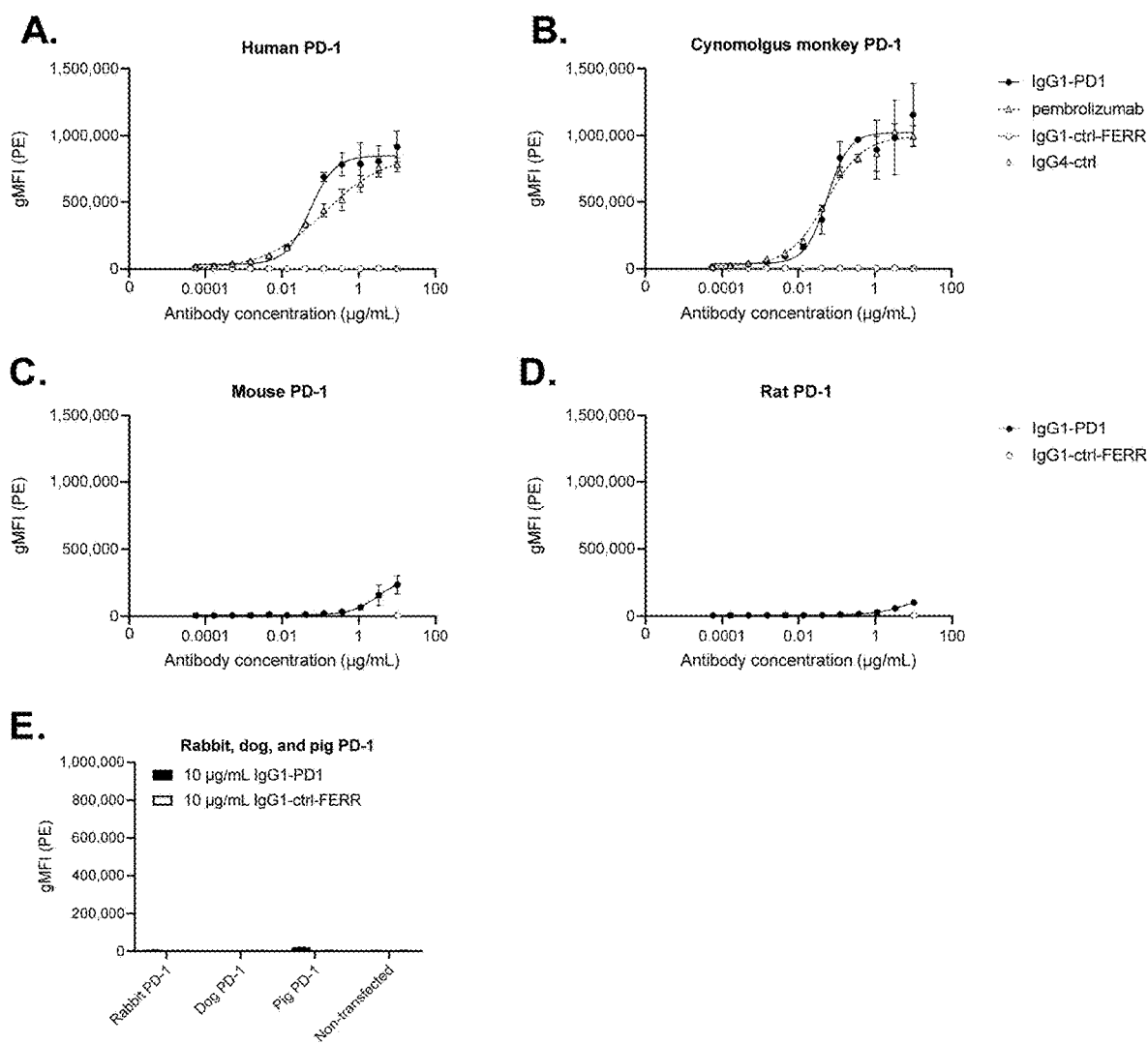
FIG. 1 shows binding of IgG1-PD1 to PD-1 of different species. CHO-S cells transiently transfected with PD-1 of different species were incubated with IgG1-PD1, pembrolizumab, or non-binding control antibodies IgG1-ctrl-FERR and IgG4-ctrl and binding analyzed using flow cytometry. Non-transfected CHO-S cells incubated with IgG1-PD1 were included as a negative control. A-B. Data shown are the geometric mean fluorescence intensities (gMFI)±SD of duplicate wells from one representative experiment out of four experiments. C-D. Data shown are the gMFI ±SD of duplicate wells from one representative experiment out of two experiments. E. Data shown are the geometric mean fluorescence intensities (gMFI)±SD of duplicate wells from one representative experiment out of four experiments. Abbreviations: gMFI=geometric mean fluorescence intensity; PD-1=programmed cell death protein 1; PE=R-Phycoerythrin.

In the following reference is given to sequences and SEQ ID NOs which are shown inter alia in the sequence listing. Also, reference is given to specific examples of antibodies of the first aspect described herein, but without limiting the present disclosure thereto: MAB-19-0202, and MAB-19-0618. These examplatory, but not limiting antibodies of the first aspect are designated herein by referring to the designation of the antibody.

TABLE 1

Sequences

| SEQ ID NO | Name | Sequence |
|---|---|---|
| 1 | constant region human HC IgG1m(f) | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSREEMTKNQVSLTCLVKGFYPSDIAVEWESNGQPENNYKTTPPVLD SDGSFFLYSKLTVDKSRWQQGNVFSCSVMHEALHNHYTQKSLSLSPG |
| 2 | constant region human HC IgG1m(f)- L234F- L235E- G236R and variants | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPEX$_1$X$_2$X$_3$GPSVFLFPPKPKDTLMISRT PEVTCVVVDVSHEDPEVKFNWYVDGVEVHNAKTKPREEQYNSTYRVV SVLTVLHQDWLNGKEYKCKVSNKALPAPIEKTISKAKGQPREPQVYT LPPSREEMTKNQVSLTCLVKGFYPSDIAVEWESNGQPENNYKTTPPV LDSDGSFFLYSKLTVDKSRWQQGNVFSCSVMHEALHNHYTQKSLSLS PG<br>wherein:<br>X$_1$ = A, V, L, I, P, F, M or W, preferably I, P, F, M or W, more preferably F;<br>X$_2$ = L, D or E, preferably D or E, more preferably E;<br>X$_3$ = not G, preferably K, R or H, more preferably R;<br>most preferably X$_1$X$_2$X$_3$ = FER |
| 3 | constant region human HC IgG1m(f)- L234F- L235E- G236R- K409R | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPEFERGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSREEMTKNQVSLTCLVKGFYPSDIAVEWESNGQPENNYKTTPPVLD SDGSFFLYSRLTVDKSRWQQGNVFSCSVMHEALHNHYTQKSLSLSPG |
| 4 | constant region human HC IgG1m(f)- E430G | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPELLGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSREEMTKNQVSLTCLVKGFYPSDIAVEWESNGQPENNYKTTPPVLD SDGSFFLYSKLTVDKSRWQQGNVFSCSVMHGALHNHYTQKSLSLSPG |
| 5 | constant region human HC IgG4 | ASTKGPSVFPLAPCSRSTSESTAALGCLVKDYFPEPVTVSWNSGALT SGVHTFPAVLQSSGLYSLSSVVTVPSSSLGTKTYTCNVDHKPSNTKV DKRVESKYGPPCPSCPAPEFLGGPSVFLFPPKPKDTLMISRTPEVTC VVVDVSQEDPEVQFNWYVDGVEVHNAKTKPREEQFNSTYRVVSVLTV LHQDWLNGKEYKCKVSNKGLPSSIEKTISKAKGQPREPQVYTLPPSQ EEMTKNQVSLTCLVKGFYPSDIAVEWESNGQPENNYKTTPPVLDSDG SFFLYSRLTVDKSRWQEGNVFSCSVMHEALHNHYTQKSLSLSLGK |
| 6 | constant region human kappa LC | RTVAAPSVFIFPPSDEQLKSGTASVVCLLNNFYPREAKVQWKVDNAL QSGNSQESVTEQDSKDSTYSLSSTLTLSKADYEKHKVYACEVTHQGL SSPVTKSFNRGEC |
| 7 | Heavy chain human IgG1-LALA | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKKVEPKSCDKTHTCPPCPAPEAAGGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSREEMTKNQVSLTCLVKGFYPSDIAVEWESNGQPENNYKTTPPVLD SDGSFFLYSKLTVDKSRWQQGNVFSCSVMHEALHNHYTQKSLSLSPG |
| 8 | HCDR 3 intersection of Kabat and IMGT (= Kabat) | AFYDDYDYNV |
| 9 | HCDR 3 IMGT | ARAFYDDYDYNV |
| 10 | HCDR 2 inter- | ISGGTIG |

TABLE 1-continued

Sequences

| SEQ ID NO | Name | Sequence |
|---|---|---|
| | section of Kabat and IMGT (= IMGT) | |
| 11 | HCDR 2 Kabat | IISGGTIGHYASWAKG |
| | HCDR 1 intersection of Kabat and IMGT | SYN |
| 12 | HCDR 1 Kabat | SYNMG |
| 13 | HCDR 1 IMGT | GFSLYSYN |
| 14 | LCDR 3 intersection = Kabat = IMGT | AGGYSSSSDTT |
| | LCDR2 intersection of Kabat and IMGT (= IMGT) | QAS |
| 15 | LCDR2 Kabat | QASKLET |
| 16 | LCDR1 intersection of Kabat and IMGT (= IMGT) | QSVYGNNQ |
| 17 | LCDR1 Kabat | QSSQSVYGNNQLS |
| 18 | VH MAB-19-0202 | QSVEESGGRLVTPGTPLTLTCTVSGFSLYSYNMGWVRQAPGKGLEYI GIISGGTIGHYASWAKGRFTISKTSSTTVDLKMTSLTTEDTATYFCA RAFYDDYDYNVWGPGTLVTVSS |
| 19 | VL MAB-19-0202 | AAVLTQTPSPVSAAVGGTVTISCQSSQSVYGNNQLSWYQQKPGQPPK LLIYQASKLETGVPSRFKGSGSGTQFTLTISDLESDDAATYYCAGGY SSSSDTTFGGGTEVVVK |
| 20 | VH IgG1-PD1 (H5 derived from MAB-19-0202) | QVQLVESGGGLVQPGTSLRLSCSVSGFSLYSYNMGWVRQAPGKGLEY IGIISGGTIGHYASWAKGRFTISRDTSKTTLYLMNSLTTEDTATYF CARAFYDDYDYNVWGPGTLVTVSS |
| 21 | VL IgG1-PD1 (L4 derived from MAB-19-0202) | AIQLTQSPSSLSASVGGTVTITCQSSQSVYGNNQLSWYQQKPGQPPK LLIYQASKLETGVPSRFRGSGSGTQFTLTISSLQSEDFATYYCAGGY SSSSDTTFGGGTEVVVK |
| 22 | Human PD-1 complete | MQIPQAPWPVVWAVLQLGWRPGWFLDSPDRPWNPPTFSPALLVVTEG DNATFTCSFSNTSESFVLNWYRMSPSNQTDKLAAFPEDRSQPGQDCR FRVTQLPNGRDFHMSVVRARRNDSGTYLCGAISLAPKAQIKESLRAE LRVTERRAEVPTAHPSPSPRPAGQFQTLVVGVVGGLLGSLVLLVWVL AVICSRAARGTIGARRTGQPLKEDPSAVPVFSVDYGELDFQWREKTP EPPVPCVPEQTEYATIVFPSGMGTSSPARRGSADGPRSAQPLRPEDG HCSWPL |

TABLE 1-continued

Sequences

| SEQ ID NO | Name | Sequence |
|---|---|---|
| 23 | Human PD-1 complete extracellular domain | FLDSPDRPWNPPTFSPALLVVTEGDNATFTCSFSNTSESFVLNWYRM SPSNQTDKLAAFPEDRSQPGQDCRFRVTQLPNGRDFHMSVVRARRND SGTYLCGAISLAPKAQIKESLRAELRVTERRAEVPTAHPSPSPRPAG QFQTLV |
| 24 | Nucleic acid human PD-1 | agtttcccttccgctcacctccgcctgagcagtggagaaggcggcac tctggtggggctgctccaggcatgcagatcccacaggcgccctggcc agtcgtctgggcggtgctacaactgggctggcggccaggatggttct tagactcccagacaggccctggaaccccccaccttctcccagcc ctgctcgtggtgaccgaaggggacaacgccaccttcacctgcagctt ctccaacacatcggagagcttcgtgctaaactggtaccgcatgagcc ccagcaaccagacggacaagctggccgccttccccgaggaccgcagc cagcccggccaggactgccgcttccgtgtcacacaactgcccaacgg gcgtgacttccacatgagcgtggtcagggcccggcgcaatgacagcg gcacctacctctgtggggccatctcctggccccaaggcgcagatc aaagagagcctgcgggcagagctcagggtgacagagagaagggcaga agtgcccacagcccaccccagcccctcacccaggccagccggccagt tccaaacctggtggttggtgtcgtgggcggcctgctgggcagcctg gtgctgctagtctgggtcctggccgtcatctgctcccgggccgcacg agggacaataggagccaggcgcaccggccagcccctgaaggaggacc cctcagccgtgcctgtgttctctgtggactatggggagctggatttc cagtggcgagagaagacccggagcccccgtgccctgtgtcctga gcagacggagtatgccaccattgtctttcctagcggaatgggcacct catccccgcccgcagggctcagctgacggccctcggagtgccag ccactgaggcctgaggatggacactgctcttggccctctgaccggc ttccttggccaccagtgttctgcagaccctccaccatgagcccggt cagcgcatttcctcaggagaagcaggcagggtgcaggccattgcagg ccgtccaggggctgagctgcctggggggcgaccggggctccagcctgc acctgcaccaggcacagcccaccacaggactcatgtctcaatgccc acagtgagcccaggcagcaggtgtcaccgtcccctacagggagggcc agatgcagtcactgcttcaggtcctgccagcacagagctgcctgcgt ccagctccctgaatctctgctgctgctgctgctgctgctgctgctgc ctgcggccggggctgaaggcgccgtggccctgcctgacgccccgga gcctcctgcctgaacttgggggctggttggagatggccttggagcag ccaaggtgccctggcagtggcatcccgaaacgccctggacgcaggg cccaagactgggcacaggagtggggagtacatggggctggggactcc ccaggagttatctgctccctgcaggcctagagaagtttcagggaagg tcagaagagctcctggctgtggtgggcagggcaggaaacccctccac ctttacacatgcccaggcagcacctcaggcccttgtggggcaggga agctgaggcagtaagcgggcaggcagagctggaggcctttcaggccc agccagcactctggcctcctgccgccgcattccaccccagcccctca caccactcgggagagggacatcctacggtcccaaggtcaggagggca gggctggggttgactcaggcccctcccagctgtggcacctgggtgt tgggagggcagaagtgcaggcacctagggcccccccatgtgcccaccc tgggagctctccttggaacccattcctgaaattatttaaaggggttg gccgggctcccaccagggcctgggtgggaaggtacaggcgttccccc ggggcctagtaccccgccgtggcctatccactcctcacatccacac actgcaccccactcctggggcagggccaccagcatccaggcggcca gcaggcacctgagtggctgggacaagggatccccttccctgtggtt ctattatattataattataattaaatatgagagcatgctaaggaaaa |
| 25 | VH CD52-CAMPATH-1H | QVQLQESGPGLVRPSQTLSLTCTVSGFTFTDFYMNWVRQPPGRGLEW IGFIRDKAKGYTTEYNPSVKGRVTMLVDTSKNQFSLRLSSVTAADTA VYYCAREGHTAAPFDYWGQGSLVTVSS |
| 26 | VH CD52-CAMPATH-1H CDR1 | GFTFTDFY |
| 27 | VH CD52-CAMPATH-1H CDR2 | IRDKAKGYTT |
| 28 | VH CD52-CAMPATH-1H CDR3 | AREGHTAAPFDY |
| 29 | VL CD52-CAMPATH-1H | DIQMTQSPSSLSASVGDRVTITCKASQNIDKYLNWYQQKPGKAPKLL IYNTNNLQTGVPSRFSGSGSGTDFTFTISSLQPEDIATYYCLQHISR PRTFGQGTKVEIK |
| 30 | VL CD52-CAMPATH-1H CDR1 | QNIDKY |

TABLE 1-continued

Sequences

| SEQ ID NO | Name | Sequence |
|---|---|---|
| | VL CD52-CAMPATH-1H CDR2 | NTN |
| 31 | VL CD52-CAMPATH-1H CDR3 | LQHISRPRT |
| 32 | VH gp120-b12 | QVQLVQSGAEVKKPGASVKVSCQASGYRFSNFVIHWVRQAPGQRFEWMGWINPYNGNKEFSAKFQDRVTFTADTSANTAYMELRSLRSADTAVYYCARVGPYSWDDSPQDNYYMDVWGKGTTVIVSS |
| 33 | VH gp120-b12 CDR1 | GYRFSNFV |
| 34 | VH gp120-b12 CDR2 | INPYNGNK |
| 35 | VH gp120-b12 CDR3 | ARVGPYSWDDSPQDNYYMDV |
| 36 | VL gp120-b12 | EIVLTQSPGTLSLSPGERATFSCRSSHSIRSRRVAWYQHKPGQAPRLVIHGVSNRASGISDRFSGSGSGTDFTLTITRVEPEDFALYYCQVYGASSYTFGQGTKLERK |
| 37 | VL gp120-b12 CDR1 | HSIRSRR |
| | VL gp120-b12 CDR2 | GVS |
| 38 | VL gp120-b12-CDR3 | QVYGASSYT |
| 39 | MAB-19-0202-HC FR1 | QSVEESGGRLVTPGTPLTLTCTVSGFSLY |
| 40 | MAB-19-0202-HC FR2 | WVRQAPGKGLEYIG |
| 41 | MAB-19-0202-HC FR3 | RFTISKTSSTTVDLKMTSLTTEDTATYFCAR |
| 42 | MAB-19-0202-HC FR4 | WGPGTLVTVSS |
| 43 | MAB-19-0202-LC FR1 | AAVLTQTPSPVSAAVGGTVTISC |
| 44 | MAB-19-0202-LC FR2 | WYQQKPGQPPKLLIY |
| 45 | MAB-19-0202-LC FR3 | GVPSRFKGSGSGTQFTLTISDLESDDAATYYC |
| 46 | MAB-19-0202-LC FR4 | FGGGTEVVVK |
| 47 | MAB-19-0202-H5 FR1 | QVQLVESGGGLVQPGTSLRLSCSVSGFSLY |
| 48 | MAB-19-0202-H5 FR2 | WVRQAPGKGLEYIG |

TABLE 1-continued

Sequences

| SEQ ID NO | Name | Sequence |
|---|---|---|
| 49 | MAB-19-0202-H5 FR3 | RFTISRDTSKTTLYLQMNSLTTEDTATYFCAR |
| 50 | MAB-19-0202-H5 FR4 | WGPGTLVTVSS |
| 51 | MAB-19-0202-L4 FR1 | AIQLTQSPSSLSASVGGTVTITC |
| 52 | MAB-19-0202-L4 FR2 | WYQQKPGQPPKLLIY |
| 53 | MAB-19-0202-L4 FR3 | GVPSRFRGSGSGTQFTLTISSLQSEDFATYYC |
| 54 | MAB-19-0202-L4 FR4 | FGGGTEVVVK |
| 55 | constant region human HC IgG1m(f)-L234F-L235E-G236R | ASTKGPSVFPLAPSSKSTSGGTAALGCLVKDYFPEPVTVSWNSGALT SGVHTFPAVLQSSGLYSLSSVVTVPSSSLGTQTYICNVNHKPSNTKV DKRVEPKSCDKTHTCPPCPAPEFERGPSVFLFPPKPKDTLMISRTPE VTCVVVDVSHEDPEVKFNWYVDGVEVHNAKTKPREEQYNSTYRVVSV LTVLHQDWLNGKEYKCKVSNKALPAPIEKTISKAKGQPREPQVYTLP PSREEMTKNQVSLTCLVKGFYPSDIAVEWESNGQPENNYKTTPPVLD SDGSFFLYSKLTVDKSRWQQGNVFSCSVMHEALHNHYTQKSLSLSPG |
| 56 | full length heavy chain | QVQLVESGGGLVQPGTSLRLSCSVSGFSLYSYNMGWVRQAPGKGLEY IGIISGGTIGHYASWAKGRFTISRDTSKTTLYLQMNSLTTEDTATYF CARAFYDDYDYNVWGPGTLVTVSSASTKGPSVFPLAPSSKSTSGGTA ALGCLVKDYFPEPVTVSWNSGALTSGVHTFPAVLQSSGLYSLSSVVT VPSSSLGTQTYICNVNHKPSNTKVDKRVEPKSCDKTHTCPPCPAPEF ERGPSVFLFPPKPKDTLMISRTPEVTCVVVDVSHEDPEVKFNWYVDG VEVHNAKTKPREEQYNSTYRVVSVLTVLHQDWLNGKEYKCKVSNKAL PAPIEKTISKAKGQPREPQVYTLPPSREEMTKNQVSLTCLVKGFYPS DIAVEWESNGQPENNYKTTPPVLDSDGSFFLYSKLTVDKSRWQQGNV FSCSVMHEALHNHYTQKSLSLSPG |
| 57 | full length light chain | AIQLTQSPSSLSASVGGTVTITCQSSQSVYGNNQLSWYQQKPGQPPK LLIYQASKLETGVPSRFRGSGSGTQFTLTISSLQSEDFATYYCAGGY SSSSDTTFGGGTEVVVKRTVAAPSVFIFPPSDEQLKSGTASVVCLLN NFYPREAKVQWKVDNALQSGNSQESVTEQDSKDSTYSLSSTLTLSKA DYEKHKVYACEVTHQGLSSPVTKSFNRGEC |

DETAILED DESCRIPTION OF THE INVENTION

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

In the following, the elements of the present disclosure will be described. These elements are listed with specific embodiments, however, it should be understood that they may be combined in any manner and in any number to create additional embodiments. The variously described examples and preferred embodiments should not be construed to limit the present disclosure to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., (1995) *Helvetica Chimica Acta*, CH-4010 Basel, Switzerland.

The practice of the present disclosure will employ, unless otherwise indicated, conventional methods of biochemistry, cell biology, immunology, and recombinant DNA techniques which are explained in the literature in the field (cf., e.g., *Molecular Cloning: A Laboratory Manual, 2<sup>nd</sup>* Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e., the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

Terms such as "reducing" or "inhibiting" relate to the ability to cause an overall decrease, preferably of 5% or greater, 10% or greater, 20% or greater, more preferably of 50% or greater, and most preferably of 75% or greater, in the level. The term "inhibit" or similar phrases includes a complete or essentially complete inhibition, i.e. a reduction to zero or essentially to zero.

Terms such as "increasing", "enhancing", "promoting" or "prolonging" preferably relate to an increase, enhancement, promotion or prolongation by about at least 10%, preferably at least 20%, preferably at least 30%, preferably at least 40%, preferably at least 50%, preferably at least 80%, preferably at least 100%, preferably at least 200% and in particular at least 300%. These terms may also relate to an increase, enhancement, promotion or prolongation from zero or a non-measurable or non-detectable level to a level of more than zero or a level which is measurable or detectable.

The term "PD-1" relates to programmed cell death-1 and includes any variants, conformations, isoforms and species homologs of PD-1 which are naturally expressed by cells or are expressed by cells transfected with the PD-1 gene. Preferably, "PD-1" relates to human PD-1, in particular to a protein having the amino acid sequence (NCBI Reference Sequence: NP_005009.2) as set forth in SEQ ID NO: 22 of the sequence listing, or a protein being preferably encoded by a nucleic acid sequence (NCBI Reference Sequence: NM_005018.2) as set forth in SEQ ID NO: 24 of the sequence listing. Alternative names for "PD-1" include CD279 and SLEB2.

The term "PD-1" includes posttranslationally modified variants, isoforms and species homologs of human PD-1 which are naturally expressed by cells or are expressed in/on cells transfected with the PD-1 gene.

The term "PD-1 variant" shall encompass (i) PD-1 splice variants, (ii) PD-1-posttranslationally modified variants, particularly including variants with different N-glycosylation status, (iii) PD-1 conformation variants. Such variants may include soluble forms of PD-1.

PD-1 is a type I membrane protein that belongs to the immunoglobulin superfamily (The EMBO Journal (1992), vol. 11, issue 11, p. 3887-3895). The human PD-1 protein comprises an extracellular domain composed of the amino acids at positions 24 to 170 of the sequence as set forth in SEQ ID NO: 22 of the sequence listing, a transmembrane domain (amino acids at positions 171 to 191 of the sequence as set forth in SEQ ID NO: 22) and a cytoplasmatic domain (amino acids at positions 192 to 288 of the sequence as set forth in SEQ ID NO: 22). The term "PD-1 fragment" as used herein shall encompass any fragment of a PD-1 protein, preferably an immunogenic fragment. The term also encompasses, for example, the above-mentioned domains of the full length protein or any fragment of these domains, in particular immunogenic fragments. The amino acid sequence of a preferred extracellular domain of the human PD-1 protein is set forth in SEQ ID NO: 23 of the sequence listing.

The term "extracellular portion" or "extracellular domain" in the context as used herein preferably refers to a part of a molecule such as a protein that is facing the extracellular space of a cell and preferably is accessible from the outside of said cell, e.g., by binding molecules such as antibodies located outside the cell. Preferably, the term refers to one or more extracellular loops or domains or a fragment thereof.

In a first aspect, the present disclosure provides an antibody having the ability to bind to PD-1, wherein the antibody comprises a heavy chain constant region, wherein the heavy chain constant region comprises an aromatic or non-polar amino acid at the position corresponding to position 234 in a human IgG1 heavy chain according to EU numbering and an amino acid other than glycine at the position corresponding to position 236 in a human IgG1 heavy chain according to EU numbering.

The term "antibody" (Ab) as used herein refers to an immunoglobulin molecule, a fragment of an immunoglobulin molecule, or a derivative of either thereof, which has the ability to specifically bind to an antigen (in particular an epitope on an antigen) under typical physiological conditions, preferably with a half-life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an effector activity). In particular, the term "antibody" refers to a glycoprotein comprising at least two heavy (H) chains and two light (L) chains inter-connected by disulfide bonds. The term "antibody" includes monoclonal antibodies, recombinant antibodies, human antibodies, humanized antibodies, chimeric antibodies and combinations of any of the foregoing. Each heavy chain is comprised of a heavy chain variable region (VH) and a heavy chain constant region (CH). Each light chain is comprised of a light chain variable region (VL) and a light chain constant region (CL). The variable regions and constant regions are also referred to herein as variable domains and constant domains, respectively. The VH and VL regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, FR4. The CDRs of a VH are termed HCDR1, HCDR2 and HCDR3 (or CDR-H1, CDR-H2 and CDR-H3), the CDRs of a VL are termed LCDR1, LCDR2 and LCDR3 (or CDR-L1, CDR-L2 and CDR-L3). The variable regions of the heavy and light chains contain a binding domain that interacts with an antigen. The constant regions of an antibody comprise the heavy chain constant region (CH) and the light chain constant region (CL), wherein CH can be further subdivided into constant domain CH1, a hinge region, and constant domains CH2 and CH3 (arranged from amino-terminus to carboxy-terminus in the following order: CH1, CH2, CH3). The constant regions of the antibodies may mediate the binding of the immunoglobulin to host tissues or factors, including various cells of the immune system (e.g., effector cells) and components of the complement system such as C1q. Antibodies can be intact immunoglobulins derived from natural sources or from recombinant sources and can be immunoactive portions of intact immunoglobulins. Antibodies are typically tetramers of immunoglobulin molecules. Antibodies may exist in a variety of forms including, for example, polyclonal antibodies, monoclonal antibodies, Fv, Fab and F(ab)$_2$, as well as single chain antibodies and humanized antibodies.

The variable regions of the heavy and light chains of the immunoglobulin molecule contain a binding domain that interacts with an antigen. The terms "binding region", "antigen-binding region" and "antigen-binding portion" are used herein interchangeably and refer to the region which interacts with the antigen and comprises both a VH region and a VL region. An antibody as used herein comprises not only monospecific antibodies, but also multispecific antibodies which comprise multiple, such as two or more, e.g., three or more, different antigen-binding regions.

In an embodiment, the antibodies can be full-length antibodies. The term "full-length" when used in the context of an antibody indicates that the antibody is not a fragment, but contains all of the domains of the particular isotype normally found for that isotype in nature, e.g. the VH, CH1, CH2, CH3, hinge, VL and CL domains for an IgG1 antibody.

The term "humanized antibody" as used herein refers to a molecule having an antigen-binding site that is substantially derived from an immunoglobulin from a non-human species, wherein the remaining immunoglobulin structure of the molecule is based upon the structure and/or sequence of a human immunoglobulin. The antigen-binding site may either comprise complete variable domains fused onto constant domains or only the complementarity determining regions (CDR) grafted onto appropriate framework regions in the variable domains. Antigen binding sites may be wild-type or modified by one or more amino acid substitutions, e.g., modified to resemble human immunoglobulins more closely. Some forms of humanized antibodies preserve all CDR sequences (for example a humanized mouse antibody which contains all six CDRs from the mouse antibody). Other forms have one or more CDRs which are altered with respect to the original antibody.

The term "chimeric antibody" as used herein refers to those antibodies wherein one portion of each of the amino acid sequences of heavy and light chains is homologous to corresponding sequences in antibodies derived from a particular species or belonging to a particular class, while the remaining segment of the chain is homologous to corresponding sequences in another. Typically, the variable region of both light and heavy chains mimics the variable regions of antibodies derived from one species of mammals, while the constant portions are homologous to sequences of antibodies derived from another. One clear advantage to such chimeric forms is that the variable region can conveniently be derived from presently known sources using readily available B-cells or hybridomas from non-human host organisms in combination with constant regions derived from, for example, human cell preparations. While the variable region has the advantage of ease of preparation and the specificity is not affected by the source, the constant region being human, is less likely to elicit an immune response from a human subject when the antibodies are injected than would the constant region from a non human source. However, the definition is not limited to this particular example.

The term "antigen-binding portion" of an antibody (or simply "binding portion"), as used herein, refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include (i) monovalent fragments consisting of the VL, VH, CL and CH domains; and (ii) Fd fragments consisting of the VH and CH domains. A further example is binding-domain immunoglobulin fusion proteins comprising (i) a binding domain polypeptide that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. The binding domain polypeptide can be a heavy chain variable region or a light chain variable region. The binding-domain immunoglobulin fusion proteins are further disclosed in US 2003/0118592 and US 2003/0133939. These antibody fragments are obtained using conventional techniques known to those with skill in the art, and the fragments are screened for utility in the same manner as are intact antibodies.

The term "epitope" means a protein determinant capable of binding to an antibody, wherein the term "binding" herein preferably relates to a specific binding. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. The term "epitope" preferably refers to an antigenic determinant in a molecule, i.e., to a part or fragment of a molecule such as an antigen that is recognized by the immune system. For example, the epitope may be recognized by T cells, B cells or antibodies. An epitope of an antigen may include a continuous or discontinuous portion of the antigen and may be between about 5 and about 100, such as between about 5 and about 50, more preferably between about 8 and about 30, most preferably between about 10 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope is between about 10 and about 25 amino acids in length. The term "epitope" includes B cell epitopes and T cell epitopes.

The term "T cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class II MHC/peptide complexes, the binding peptides are typically about 10 to about 25 amino acids long and are in particular about 13 to about 18 amino acids long, whereas longer and shorter peptides may be effective.

The term "amino acid corresponding to position . . . " and similar expressions as used herein refer to an amino acid position number in a human IgG1 heavy chain. Corresponding amino acid positions in other immunoglobulins may be found by alignment with human IgG1. Thus, an amino acid or segment in one sequence that "corresponds to" an amino acid or segment in another sequence is one that aligns with the other amino acid or segment using a standard sequence alignment program such as ALIGN, ClustalW or similar, typically at default settings and has at least 50%, at least 80%, at least 90%, or at least 95% identity to a human IgG1 heavy chain. It is considered well-known in the art how to align a sequence or segment in a sequence and thereby determine the corresponding position in a sequence to an amino acid position according to the present disclosure.

With reference to, e.g., the amino acid sequence according to SEQ ID NO. 2 of the sequence listing of the present disclosure the amino acid positions corresponding to positions 234 to 236 in a human IgG1 heavy chain according to EU numbering are the amino acid positions 117 to 119 of SEQ ID NO. 2, with F being positioned at position 117 (corresponding to positions 234 in a human IgG1 heavy chain according to EU numbering), E being positioned at position 118 (corresponding to positions 235 in a human IgG1 heavy chain according to EU numbering) and R being positioned at position 119 (corresponding to positions 236 in a human IgG1 heavy chain according to EU numbering). In the sequence as shown below, the FER amino acid sequence is underlined and shown in bold letters.

```
ASTKGPSVFPLAPSSKSTSGGTAALGCLVKDYFPEPVTVSWNSGALTSGVHTFPAVLQSS    60

GLYSLSSVVTVPSSSLGTQTYICNVNHKPSNTKVDKRVEPKSCDKTHTCPPCPAPEFERG   120

PSVFLFPPKPKDTLMISRTPEVTCVVVDVSHEDPEVKFNWYVDGVEVHNAKTKPREEQYN   180

STYRVVSVLTVLHQDWLNGKEYKCKVSNKALPAPIEKTISKAKGQPREPQVYTLPPSREE   240

MTKNQVSLTCLVKGFYPSDIAVEWESNGQPENNYKTTPPVLDSDGSFFLYSKLTVDKSRW   300

QQGNVFSCSVMHEALHNHYTQKSLSLSPG                                  329
```

Unless otherwise indicated herein or otherwise clearly contradicted by the context, all referenced to amino acid positions throughout this disclosure refer to the positions corresponding to the respective positions in a human IgG1 heavy chain according to EU numbering.

In one embodiment of the first aspect, the antibody comprises a heavy chain constant region which has a reduced or depleted Fc-mediated effector function or which induces Fc-mediated effector function to a lesser extent compared to another antibody comprising the same antigen binding regions and heavy chain constant regions (CHs) comprising human IgG1 hinge, CH2 and CH3 regions.

In one particular embodiment of the antibody according to the first aspect, said heavy chain constant region (CHs) are modified so that the antibody induces Fc-mediated effector function to a lesser extent compared to an antibody which is identical except for comprising non-modified heavy chain constant regions (CHs).

The term "Fc-mediated effector function" as used herein refers to such functions in particular being selected from the list of IgG Fc receptor (FcgammaR, FcγR) binding, C1q binding, ADCC, CDC and any combinations thereof.

In the context of the present disclosure, the term "has a reduced or depleted Fc-mediated effector function" used in relation to an antibody, including a multispecific antibody, means that the antibody cause an overall decrease of Fc-mediated effector functions, such function in particular being selected from the list of IgG Fc receptor (FcgammaR, FcγR) binding, C1q binding, ADCC or CDC, preferably of 5% or greater, 10% or greater, 20% or greater, more preferably of 50% or greater, and most preferably of 75% or greater, in the level compared to a human IgG1 antibody comprising (i) the same CDR sequences, in particular comprising the same first and second antigen-binding regions, as said antibody and (ii) two heavy chains comprising human IgG1 hinge, CH2 and CH3 regions. A "depleted Fc-mediated effector function" or similar phrases includes a complete or essentially complete inhibition, i.e., a reduction to zero or essentially to zero.

In the context of the present disclosure, the term "induce Fc-mediated effector function to a lesser extent" used in relation to an antibody, including a multispecific antibody, means that the antibody induces Fc-mediated effector functions, such function in particular being selected from the list of IgG Fc receptor (FcgammaR, FcγR) binding, C1q binding, ADCC or CDC, to a lesser extent compared to a human IgG1 antibody comprising (i) the same CDR sequences, in particular comprising the same first and second antigen-binding regions, as said antibody and (ii) two heavy chains comprising human IgG1 hinge, CH2 and CH3 regions.

The Fc-mediated effector function may be determined by measuring binding of the binding agent to Fcγ receptors, binding to C1q, or induction of Fc-mediated cross-linking of Fcγ receptors. In particular, the Fc-mediated effector function may be determined by measuring binding of the binding agent to C1q and/or IgG FC-gamma RI.

In one embodiment of the antibody of the first aspect, the amino acid at the position corresponding to position 236 in a human IgG1 heavy chain according to EU numbering is a basic amino acid.

The term "amino acid" and "amino acid residue" may herein be used interchangeably, and are not to be understood limiting. Amino acids are organic compounds containing amine ($-NH_2$) and carboxyl ($-COOH$) functional groups, along with a side chain (R group) specific to each amino acid. In the context of the present disclosure, amino acids may be classified based on structure and chemical characteristics.

In the present disclosure, amino acid residues are expressed by using the following abbreviations. Also, unless explicitly otherwise indicated, the amino acid sequences of peptides and proteins are identified from N-terminal to C-terminal (left terminal to right terminal), the N-terminal being identified as a first residue. Amino acids are designated by their 3-letter abbreviation, 1-letter abbreviation, or full name, as follows. Ala: A: alanine; Asp: D: aspartic acid; Glu: E: glutamic acid; Phe: F: phenylalanine; Gly: G: glycine; His: H: histidine; Ile: I: isoleucine; Lys: K: lysine; Leu: L: leucine; Met: M: methionine; Asn: N: asparagine; Pro: P: proline; Gln: Q: glutamine; Arg: R: arginine; Ser: S: serine; Thr: T: threonine; Val: V: valine; Trp: W: tryptophan; Tyr: Y: tyrosine; Cys: C: cysteine.

Naturally occurring amino acids may also be generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids.

In one embodiment of the antibody of the first aspect, the basic amino acid at the position corresponding to position 236 in a human IgG1 heavy chain according to EU numbering is selected from the group consisting of lysine, arginine and histidine. In one embodiment, the basic amino acid at the position corresponding to position 236 in a human IgG1 heavy chain according to EU numbering is arginine (G236R). Such an amino acid substitution is also referred to herein as G236R. The term "G236R" indicates that at position 236 in a human IgG1 heavy chain according to EU numbering the amino acid glycine (G) is substituted by arginine (R). Within the present disclosure similar terms are used for other amino acid positions and amino acids. Unless indicated to the contrary the referenced amino acid position in these terms is the amino acid position in a human IgG1 heavy chain according to EU numbering.

In one embodiment of the antibody of the first aspect, the amino acid at the position corresponding to position 234 in a human IgG1 heavy chain according to EU numbering is an aromatic amino acid. In one embodiment, the aromatic amino acid at this position is selected from the group consisting of phenylalanine, tryptophan and tyrosine.

In one embodiment of the antibody of the first aspect, the amino acid at the position corresponding to position 234 in a human IgG1 heavy chain according to EU numbering is a non-polar amino acid. In one embodiment, the non-polar amino acid at this position is selected from the group consisting of alanine, valine, leucine, isoleucine, proline, phenylalanine, methionine and tryptophan. In one embodiment, the non-polar amino acid at this position is selected from the group consisting of isoleucine, proline, phenylalanine, methionine and tryptophan.

In one embodiment of the antibody of the first aspect, the amino acid at the position corresponding to position 234 in a human IgG1 heavy chain according to EU numbering is phenylalanine (L234F).

Exemplary combinations of possible amino acids at the positions corresponding to positions 234 and 236 in a human IgG1 heavy chain according to EU numbering are set forth in the table below:

TABLE 2

| Amino acid position 234 | Amino acid position 236 |
|---|---|
| Phenylalanine (F) | Arginine (R) |
| Tryptophan (W) | Arginine (R) |
| Tyrosine (Y) | Arginine (R) |
| Alanine (A) | Arginine (R) |
| Valine (V) | Arginine (R) |
| Leucine (L) | Arginine (R) |
| Isoleucine (I) | Arginine (R) |
| Proline (P) | Arginine (R) |
| Methionine (M) | Arginine (R) |
| Phenylalanine (F) | Lysine (K) |
| Tryptophan (W) | Lysine (K) |
| Tyrosine (Y) | Lysine (K) |
| Alanine (A) | Lysine (K) |
| Valine (V) | Lysine (K) |
| Leucine (L) | Lysine (K) |
| Isoleucine (I) | Lysine (K) |
| Proline (P) | Lysine (K) |
| Methionine (M) | Lysine (K) |
| Phenylalanine (F) | Histidine (H) |
| Tryptophan (W) | Histidine (H) |
| Tyrosine (Y) | Histidine (H) |
| Alanine (A) | Histidine (H) |
| Valine (V) | Histidine (H) |
| Leucine (L) | Histidine (H) |
| Isoleucine (I) | Histidine (H) |
| Proline (P) | Histidine (H) |
| Methionine (M) | Histidine (H) |

For example, at the positions corresponding to the positions 234 and 236 in a human IgG1 heavy chain according to EU numbering, in particular the following amino acids may be present in the heavy chain constant region of the antibody of the first aspect: 234F/236R, 234W/236R, 234Y/236R, 234A/236R, 234L/236R, 234F/236K, 234W/236K, 234Y/236K, 234A/236K, 234L/236K, 234F/236H, 234W/236H, 234Y/236H, 234A/236H, or 234L/236H.

The aforementioned amino acids or amino acids substitutions at positions 234 and 236 may be present only in one heavy chain of the antibody or in both heavy chains of the antibody. The respective amino acids present in first and the second heavy chain of the antibody may be selected independently from each other.

For example, at least one heavy chain of the antibody of the first aspect can comprise the following sequence (SEQ ID NO: 2):

```
ASTKGPSVFPLAPSSKSTSGGTAALGCLVKDYFPEPVTVSWNSGALTSGVHTFPAVLQSS   60

GLYSLSSVVTVPSSSLGTQTYICNVNHKPSNTKVDKRVEPKSCDKTHTCPPCPAPEFLRG  120

PSVFLFPPKPKDTLMISRTPEVTCVVVDVSHEDPEVKFNWYVDGVEVHNAKTKPREEQYN  180

STYRVVSVLTVLHQDWLNGKEYKCKVSNKALPAPIEKTISKAKGQPREPQVYTLPPSREE  240

MTKNQVSLTCLVKGFYPSDIAVEWESNGQPENNYKTTPPVLDSDGSFFLYSKLTVDKSRW  300

QQGNVFSCSVMHEALHNHYTQKSLSLSPG                                 329
```

In one embodiment of the antibody of the first aspect, the said heavy chain in which the amino acids at the position corresponding to positions 234 and 236 in a human IgG1 heavy chain according to EU numbering are as specified above, furthermore the amino acid at the position corresponding to position 235 in a human IgG1 heavy chain according to EU numbering is an acidic amino acid. In one embodiment, the acidic amino acid at this position is selected from aspartate or glutamate. In one embodiment, the amino acid at the position corresponding to position 235 in a human IgG1 heavy chain according to EU numbering is glutamate (L235E).

In one embodiment of the antibody of the first aspect, in the heavy chain constant region the amino acids at the position corresponding to positions 234, 235 and 236 in a human IgG1 heavy chain according to EU numbering are a non-polar or aromatic amino acid at position 234, an acidic amino acid at position 235 and a basic amino acid at position 236.

Exemplary combinations of possible amino acids at the positions corresponding to positions 234, 235 and 236 in a human IgG1 heavy chain according to EU numbering are set forth in the table below:

TABLE 3

| Amino acid position 234 | Amino acid position 235 | Amino acid position 236 |
|---|---|---|
| Phenylalanine (F) | Asparatate (D) or Glutamate (E) | Arginine (R) |
| Tryptophan (W) | Asparatate (D) or Glutamate (E) | Arginine (R) |
| Tyrosine (Y) | Asparatate (D) or Glutamate (E) | Arginine (R) |
| Alanine (A) | Asparatate (D) or Glutamate (E) | Arginine (R) |
| Valine (V) | Asparatate (D) or Glutamate (E) | Arginine (R) |
| Leucine (L) | Asparatate (D) or Glutamate (E) | Arginine (R) |
| Isoleucine (I) | Asparatate (D) or Glutamate (E) | Arginine (R) |
| Proline (P) | Asparatate (D) or Glutamate (E) | Arginine (R) |
| Methionine (M) | Asparatate (D) or Glutamate (E) | Arginine (R) |
| Phenylalanine (F) | Asparatate (D) or Glutamate (E) | Lysine (K) |
| Tryptophan (W) | Asparatate (D) or Glutamate (E) | Lysine (K) |
| Tyrosine (Y) | Asparatate (D) or Glutamate (E) | Lysine (K) |
| Alanine (A) | Asparatate (D) or Glutamate (E) | Lysine (K) |
| Valine (V) | Asparatate (D) or Glutamate (E) | Lysine (K) |
| Leucine (L) | Asparatate (D) or Glutamate (E) | Lysine (K) |
| Isoleucine (I) | Asparatate (D) or Glutamate (E) | Lysine (K) |
| Proline (P) | Asparatate (D) or Glutamate (E) | Lysine (K) |
| Methionine (M) | Asparatate (D) or Glutamate (E) | Lysine (K) |
| Phenylalanine (F) | Asparatate (D) or Glutamate (E) | Histidine (H) |
| Tryptophan (W) | Asparatate (D) or Glutamate (E) | Histidine (H) |
| Tyrosine (Y) | Asparatate (D) or Glutamate (E) | Histidine (H) |
| Alanine (A) | Asparatate (D) or Glutamate (E) | Histidine (H) |
| Valine (V) | Asparatate (D) or Glutamate (E) | Histidine (H) |
| Leucine (L) | Asparatate (D) or Glutamate (E) | Histidine (H) |
| Isoleucine (I) | Asparatate (D) or Glutamate (E) | Histidine (H) |
| Proline (P) | Asparatate (D) or Glutamate (E) | Histidine (H) |
| Methionine (M) | Asparatate (D) or Glutamate (E) | Histidine (H) |

For example, at the positions corresponding to the positions 234, 235 and 236 in a human IgG1 heavy chain according to EU numbering, in particular the following amino acids may be present in the heavy chain constant region of the antibody of the first aspect: 234F/235E/236R, 234W/235E/236R, 234Y/235E/236R, 234A/235E/236R, 234L/235E/236R, 234F/235D/236R, 234W/235D/236R, 234Y/235D/236R, 234A/235D/236R, 234L/235D/236R, 234F/235L/236R, 234W/235L/236R, 234Y/235L/236R, 234A/235L/236R, 234L/235L/236R, 234F/235A/236R, 234W/235A/236R, 234Y/235A/236R, 234A/235A/236R, 234L/235A/236R, 234F/235E/236K, 234W/235E/236K, 234Y/235E/236K, 234A/235E/236K, 234L/235E/236K, 234F/235D/236K, 234W/235D/236K, 234Y/235D/236K, 234A/235D/236K, 234L/235D/236K, 234F/235L/236K, 234W/235L/236K, 234Y/235L/236K, 234A/235L/236K, 234L/235L/236K, 234F/235A/236K, 234W/235A/236K, 234Y/235A/236K, 234A/235A/236K, 234L/235A/236K, 234F/235E/236H, 234W/235E/236H, 234Y/235E/236H, 234A/235E/236H, 234L/235E/236H, 234F/235D/236H, 234W/235D/236H, 234Y/235D/236H, 234A/235D/236H, 234L/235D/236H, 234F/235L/236H, 234W/235L/236H, 234Y/235L/236H, 234A/235L/236H, 234L/235L/236H, 234F/235A/236H, 234W/235A/236H, 234Y/235A/236H, 234A/235A/236H, or 234L/235A/236H.

The aforementioned amino acids or amino acids substitutions at positions 234, 235 and 236 may be present only in one heavy chain of the antibody or in both heavy chains of the antibody.

The respective amino acids present in first and the second heavy chain of the antibody may be selected independently from each other.

For example, at least one heavy chain of the antibody of the first aspect can comprise the following sequence (SEQ ID NO: 2 or SEQ ID NO: 55):

```
ASTKGPSVFPLAPSSKSTSGGTAALGCLVKDYFPEPVTVSWNSGALTSGVHTFPAVLQSS    60

GLYSLSSVVTVPSSSLGTQTYICNVNHKPSNTKVDKRVEPKSCDKTHTCPPCPAPEFERG   120

PSVFLFPPKPKDTLMISRTPEVTCVVVDVSHEDPEVKFNWYVDGVEVHNAKTKPREEQYN   180

STYRVVSVLTVLHQDWLNGKEYKCKVSNKALPAPIEKTISKAKGQPREPQVYTLPPSREE   240

MTKNQVSLTCLVKGFYPSDIAVEWESNGQPENNYKTTPPVLDSDGSFFLYSKLTVDKSRW   300

QQGNVFSCSVMHEALHNHYTQKSLSLSPG                                  329
```

Any permutations and combinations of all described amino acid substitutions at positions 234, 236 and 235, if applicable, in this application, e.g., as shown in Tables 2 and 3, should be considered disclosed by the description of the present application unless the context indicates otherwise. For example, in one embodiment of the antibody the first heavy chain comprises the amino acids FER at the position corresponding to positions 234 to 236 in a human IgG1 heavy chain according to EU numbering or the first heavy chain comprises or consists essentially of or consists of an amino acid sequence set forth in SEQ ID NO: 2, and the second heavy chain of said antibody comprises other amino acids, e.g., the amino acids AAG or LLG at the positions corresponding to positions 234 to 236 in a human IgG1 heavy chain according to EU numbering or comprises or the second heavy chain of said antibody comprises or consists essentially of or consists of an amino acid sequence set forth in SEQ ID NO: 1 or 7. In another embodiment of the antibody, the first and the second heavy chains comprise the same amino acids at the position corresponding to positions 234 to 236 in a human IgG1 heavy chain according to EU numbering, i.e., the same aromatic or non-polar amino acid at the position corresponding to position 234 in a human IgG1 heavy chain according to EU numbering, e.g. F, and the same amino acid other than glycine at the position corresponding to position 236 in a human IgG1 heavy chain according to EU numbering, e.g., R, such as the specific combination of FER or FLR.

In one embodiment of the antibody of the first aspect, the antibody comprises at least one or two heavy chain constant regions, the amino acid corresponding to position 234 is phenylalanine, the amino acid corresponding to position 235 is glutamate, and the amino acid corresponding to position 236 is arginine (L234F/L235E/G236R=FER).

In further embodiments of the antibody of the first aspect, the at least one or both heavy chain constant regions can comprise one or more further mutations in the constant region, for example one or more amino acids in the positions corresponding to positions L234, L235, G237, D265, D270, K322, P329, and P331 in a human IgG1 heavy chain according to EU numbering, in addition to the substitution of the amino acid at the position corresponding to position 236 in a human IgG1 heavy chain according to EU numbering.

In one embodiment, the amino acid corresponding to position 234 in a human IgG1 heavy chain according to EU numbering is not L, but is, e.g., selected from F or A, and/or the amino acid corresponding to position 235 in a human IgG1 heavy chain according to EU numbering is not L, but is selected from E or A.

In one embodiment, the amino acid corresponding to position 237 in a human IgG1 heavy chain according to EU numbering is not G, but is, e.g., A, i.e., at least one or both heavy chain constant regions of the antibody can comprise, e.g., the amino acid substitutions G236R/G237A.

In one embodiment, the amino acid corresponding to position 265 in a human IgG1 heavy chain according to EU numbering is not D, but is, e.g., A, i.e., at least one or both heavy chain constant regions of the antibody can comprise, e.g., the amino acid substitutions G236R/D265A.

In one embodiment, the amino acid corresponding to position 270 in a human IgG1 heavy chain according to EU numbering is not D, but is, e.g., A, i.e., at least one or both heavy chain constant regions of the antibody can comprise, e.g., the amino acid substitutions G236R/D270A.

In one embodiment, the amino acid corresponding to position 322 in a human IgG1 heavy chain according to EU numbering is not K, but is, e.g., A, i.e., at least one or both heavy chain constant regions of the antibody can comprise, e.g., the amino acid substitutions G236R/K322A.

In one embodiment, the amino acid corresponding to position 329 in a human IgG1 heavy chain according to EU numbering is not P, but is, e.g., A, i.e., at least one or both heavy chain constant regions of the antibody can comprise, e.g., the amino acid substitutions G236R/P329A.

In one embodiment, the amino acid corresponding to position 331 in a human IgG1 heavy chain according to EU numbering is not P, but is, e.g., A or S, i.e., at least one or both heavy chain constant regions of the antibody can comprise, e.g., the amino acid substitutions G236R/P331A or G236R/P331S.

In one embodiment of the antibody of the first aspect, the positions corresponding to positions 234, 236, and G327 in a human IgG1 heavy chain according to EU numbering have been substituted, at least one or both heavy chain constant regions of the antibody can comprise, e.g., the amino acid substitutions L234F/G236R/G237A.

In one embodiment of the antibody of the first aspect, the positions corresponding to positions 234, 236, and 265 in a human IgG1 heavy chain according to EU numbering have been substituted, at least one or both heavy chain constant regions of the antibody can comprise, e.g., the amino acid substitutions L234F/G236R/D265A.

In one embodiment of the antibody of the first aspect, the positions corresponding to positions 234, 236, and 270 in a human IgG1 heavy chain according to EU numbering have been substituted, at least one or both heavy chain constant regions of the antibody can comprise, e.g., the amino acid substitutions L234F/G236R/D270A.

In one embodiment of the antibody of the first aspect, the positions corresponding to positions 234, 236, and 322 in a human IgG1 heavy chain according to EU numbering have been substituted, at least one or both heavy chain constant regions of the antibody can comprise, e.g., the amino acid substitutions L234F/G236R/K322A.

In one embodiment of the antibody of the first aspect, the positions corresponding to positions 234, 236, and 329 in a human IgG1 heavy chain according to EU numbering have been substituted, at least one or both heavy chain constant regions of the antibody can comprise, e.g., the amino acid substitutions L234F/G236R/P329A.

In one embodiment of the antibody of the first aspect, the positions corresponding to positions 234, 236, and 331 in a human IgG1 heavy chain according to EU numbering have been substituted, at least one or both heavy chain constant regions of the antibody can comprise, e.g., the amino acid substitutions L234F/G236R/P331A or L234F/G236R/P331S.

In one embodiment of the antibody of the first aspect, the antibody comprises one or more a heavy chain constant region (CH) comprising a sequence having at least 70%, at least 75%, at least 80%, at least 85%, at least 90%, at least 95%, at least 97%, at least 99%, or 100% identity to the amino acid sequence of the CH sequence as set forth in SEQ ID NO: 2.

The teaching given herein with respect to specific amino acid sequences, e.g., those shown in the sequence listing, is to be construed so as to also relate to variants of said specific sequences resulting in sequences which are functionally equivalent to said specific sequences, e.g., amino acid sequences exhibiting properties identical or similar to those of the specific amino acid sequences.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all mutants, splice variants, posttranslationally modified variants, conformations, isoforms, allelic variants, species variants, and species homologs, in particular those which are naturally occurring. The term "variant" includes, in particular, fragments of an amino acid sequence.

In one embodiment, the amino acid variants of the heavy chain constant region comprise the respective amino acids at positions 234 and 236, and optionally at position 235, as specified in the specification and in the appended claims.

In one embodiment of the antibody of the first aspect, the antibody comprises one or more, e.g., two heavy chain constant region (CH), wherein the heavy chain constant region comprises the sequence as set forth in SEQ ID NO: 2 or SEQ ID NO: 55.

The antibodies of the first aspect can be of any isotype (e.g., IgG, IgE, IgM, IgD, IgA and IgY), class (e.g. IgG1, IgG2, IgG3, IgG4, IgA1 and IgA2) or subclass of immunoglobulin molecule.

As used herein, the term "isotype" refers to the immunoglobulin class (for instance IgG (such as IgG1, IgG2, IgG3, IgG4), IgD, IgA (such as IgA1, IgA2), IgE, IgM, or IgY) that is encoded by heavy chain constant region genes. When a particular isotype, e.g., IgG1, is mentioned herein, the term is not limited to a specific isotype sequence, e.g., a particular IgG1 sequence, but is used to indicate that the antibody is closer in sequence to that isotype, e.g. IgG1, than to other isotypes. Thus, e.g., an IgG1 antibody disclosed herein may be a sequence variant of a naturally-occurring IgG1 antibody, including variations in the constant regions.

IgG1 antibodies can exist in multiple polymorphic variants termed allotypes (reviewed in Jefferis and Lefranc 2009. *mAbs* Vol 1 Issue 4 1-7) any of which are suitable for use in some of the embodiments herein. Common allotypic variants in human populations are those designated by the letters a, f, n, z or combinations thereof. In any of the embodiments herein, the antibody may comprise a heavy chain Fc region comprising a human IgG Fc region. In further embodiments, the human IgG Fc region comprises a human IgG1.

There are five types of mammalian immunoglobulin heavy chains, i.e., α, δ, ε, γ, and μ which account for the different isotypes of antibodies, i.e., IgA, IgD, IgE, IgG, and IgM. As opposed to the heavy chains of soluble immunoglobulins, the heavy chains of membrane or surface immunoglobulins comprise a transmembrane domain and a short cytoplasmic domain at their carboxy-terminus.

In mammals there are two types of light chains, i.e., lambda and kappa. The immunoglobulin chains comprise a variable region and a constant region. The constant region is essentially conserved within the different isotypes of the immunoglobulins, wherein the variable part is highly divers and accounts for antigen recognition.

For example or in an embodiment, an antibody, preferably a monoclonal antibody, of the present invention is a IgG1, κ isotype or λ isotype, preferably comprising human IgG1/κ or human IgG1/λ constant parts, or the antibody, preferably the monoclonal antibody, is derived from a IgG1, λ (lambda) or IgG1, κ (kappa) antibody, preferably from a human IgG1, λ (lambda) or a human IgG1, κ (kappa) antibody.

In one embodiment of the first aspect, the antibody comprises a light chain having a light chain constant region comprising a sequence having at least 70%, at least 75%, at least 80%, at least 85%, at least 90%, at least 95%, at least 97%, at least 99%, or 100% identity to the amino acid sequence of the LC sequence as set forth in SEQ ID NO: 6. In one embodiment, the antibody comprises a light chain having a light chain constant region comprising the sequence as set forth in SEQ ID NO: 6.

In one embodiment of the invention, the binding agent is a full-length IgG1 antibody, e.g., e.g., IgG1, κ. In one embodiment of the invention, the binding agent is a full-length human IgG1 antibody, e.g., IgG1, κ.

Other isotypes can be obtained by isotype switching. As used herein, "isotype switching" refers to the phenomenon by which the class, or isotype, of an antibody changes from one Ig class to one of the other Ig classes.

In one embodiment of the antibody of the first aspect, the antibodies of the first aspect can be derivatized, linked to or co-expressed to other binding specificities. In another embodiment, the antibodies of the first aspect can be derivatized, linked to or co-expressed with another functional molecule, e.g., another peptide or protein (e.g., a Fab' fragment). For example, an antibody of the first aspect can be functionally linked (e.g., by chemical coupling, genetic fusion, noncovalent association or otherwise) to one or more other molecular entities, such as another antibody (e.g., to produce a bispecific or a multispecific antibody).

The term "antibody derivatives" refers to any modified form of an antibody, e.g., a conjugate of the antibody and another agent or antibody. As used herein, an antibody is "derived from" a particular germline sequence if the antibody is obtained from a system by immunizing an animal or by screening an immunoglobulin gene library, and wherein the selected antibody is at least 90%, more preferably at least 95%, even more preferably at least 96%, 97%, 98%, or 99% identical in amino acid sequence to the amino acid sequence encoded by the germline immunoglobulin gene. Typically, an antibody derived from a particular germline sequence will display no more than 10 amino acid differences, more preferably, no more than 5, or even more preferably, no more than 4, 3, 2, or 1 amino acid difference from the amino acid sequence encoded by the germline immunoglobulin gene.

The antibodies of the first aspect may be human antibodies. The term "human antibody", as used herein, is intended to include antibodies having variable and constant regions derived from human germline immunoglobulin sequences. The human antibodies of the first aspect may include amino acid residues not encoded by human germline immunoglobulin sequences (e.g., mutations introduced by random or site-specific mutagenesis in vitro or by somatic mutation in vivo).

The term "monoclonal antibody" as used herein refers to a preparation of antibody molecules of single molecular composition. A monoclonal antibody displays a single binding specificity and affinity for a particular epitope. In one embodiment, the monoclonal antibodies are produced by a hybridoma which includes a B cell obtained from a non-human animal, e.g., mouse, fused to an immortalized cell.

The antibodies of the first aspect may be recombinant antibodies. The term "recombinant antibody", as used herein, includes all antibodies that are prepared, expressed, created or isolated by recombinant means and/or genetic engineering, such as (a) antibodies isolated from an animal (e.g., a mouse) that is transgenic or transchromosomal with respect to the immunoglobulin genes or a hybridoma prepared therefrom, (b) antibodies isolated from a host cell transformed to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences. Preferably, a "recombinant object" such as a recombinant cell in the context of the present disclosure is not occurring naturally. The amino acid variants described herein may be readily prepared by the skilled person, e.g., by recombinant DNA manipulation. The manipulation of nucleotide sequences for preparing proteins and peptides having substitutions, additions, insertions or deletions, is described in detail in Sambrook et al. (1989), for example.

As used herein, a "heterologous antibody" is defined in relation to a transgenic organism producing such an antibody. This term refers to an antibody having an amino acid sequence or an encoding nucleic acid sequence corresponding to that found in an organism not consisting of the transgenic organism, and being generally derived from a species other than the transgenic organism.

As used herein, a "heterohybrid antibody" refers to an antibody having light and heavy chains of different organismal origins. For example, an antibody having a human heavy chain associated with a murine light chain is a heterohybrid antibody.

The antibodies of the first aspect are preferably isolated. An "isolated antibody" as used herein, is intended to refer to an antibody which is substantially free of other antibodies having different antigenic specificities (e.g., an isolated antibody that specifically binds to PD-1 is substantially free of antibodies that specifically bind antigens other than PD-1). An isolated antibody that specifically binds to an epitope, isoform or variant of human PD-1 may, however, have cross-reactivity to other related antigens, e.g., from other species (e.g., PD-1 species homologs). Moreover, an isolated antibody may be substantially free of other cellular material and/or chemicals. In one embodiment of the first aspect, a combination of "isolated" monoclonal antibodies relates to antibodies having different specificities and being combined in a well defined composition.

As used herein the term "naturally occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin (antibody) gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

I. Mechanisms of Antibody Action

Although the following provides considerations regarding the mechanism underlying the therapeutic efficacy of antibodies of the first aspect it is not to be considered as limiting to the invention in any way.

The antibodies described herein preferably interact with the immune checkpoint PD-1. By binding to PD-1, the interaction of PD-1 with its ligands (PD-L1 and PD-L2) is inhibited. PD-L1 is expressed for example on tumor cells and antigen-presenting cells of the tumor microenvironment. The interaction of PD-1 and PD-L1 would result in abrogation of an immune response, preferably a T-cell mediated immune response, so that by blocking PD-1 with an antibody of the first aspect such an abrogation of the immune response is prevented or at least reduced, or said in other words an immune response is induced.

Even though PD-1 and its ligands interact with each other in preventing or reducing an immune response, for achieving this effect a PD-1 blockade might be advantageous over a ligand blockade. This is because a blockade of e.g., PD-L1 might still result in a reduced immune response, since an inhibitory signaling between diseased cells expressing PD-L2 and lymphocytes expressing PD-1 could help in inhibiting the immune response by the immune system.

The immune system has the ability to recognize and destroy diseased cells via two separate modalities: innate and adaptive immunity. The innate component consists of macrophages, natural killer (NK) cells, monocytes, and granulocytes. These cells identify molecular patterns involved in cellular transformation and release various cytokines and inflammatory mediators. The innate response lacks the memory capability for foreign antigens, a feature present in adaptive immune response. This latter component of immune system also features specificity for foreign antigens, imparted by presence of receptors on lymphocytes.

Antigen presenting cells (APCs) also play a role in the adaptive response—they engulf foreign antigens and present them to the lymphocytes in the context of major histocompatibility complex. $CD4^+$ T cells bear receptors that recognize antigens in the context of MHC class II molecules, which then enables them to release cytokines and further activate $CD8^+$ lymphocytes (CTLs) or B cells. CTLs are part of cell-mediated immunity and are capable of eliminating cells after recognition of antigens presented in the context of MHC class I molecules, via apoptosis or perforin-mediated cell lysis. It is widely accepted that T-cell mediated immunity plays a vital role in the anti-tumor response. B cells are involved in release of immunoglobulins and as such are part of the humoral immune system.

The term "immune response" refers to an integrated bodily response to a target such as an antigen or a cell expressing an antigen and preferably refers to a cellular immune response or a cellular as well as a humoral immune response. The immune response may be protective/preventive/prophylactic and/or therapeutic.

"Inducing an immune response" may mean that there was no immune response before induction, but it may also mean that there was a certain level of immune response before induction and after induction said immune response is enhanced. Thus, "inducing an immune response" also includes "enhancing an immune response". Preferably, after inducing an immune response in a subject, said subject is protected from developing a disease such as a cancer disease or the disease condition is ameliorated by inducing an immune response. Inducing an immune response in this case may mean that the disease condition of the subject is ameliorated, that the subject does not develop metastases, or that the subject being at risk of developing a cancer disease does not develop a cancer disease.

The terms "cellular immune response" and "cellular response" or similar terms refer to an immune response directed to cells. The innate cellular immune response is driven by macrophages, natural killer (NK) cells, monocytes, and granulocytes. The adaptive cellular immune response is characterized by presentation of an antigen in the context of MHC class I or class II involving T cells or T-lymphocytes which act as either "helpers" or "killers". The helper T cells (also termed $CD4^+$ T cells) play a central role by regulating the immune response and the killer cells (also termed cytotoxic T cells, cytolytic T cells, $CD8^+$ T cells or CTLs) kill diseased cells such as cancer cells, preventing the production of more diseased cells. In embodiments, the present disclosure involves the stimulation of an anti-tumor CTL response against tumor cells expressing one or more tumor antigens and preferably presenting such tumor antigens on MHC class I.

A "tumor antigen" as used herein covers any substance, preferably a peptide or protein, that is a target of and/or induces an immune response such as a specific reaction with antibodies or T-lymphocytes (T cells). Preferably, an antigen comprises at least one epitope such as a T cell epitope. The tumor antigen or a T cell epitope thereof is preferably presented by a cell, preferably by an antigen presenting cell which includes a diseased cell, in particular a cancer cell, in the context of MHC molecules, which results in an immune response against the antigen (including cells expressing the antigen).

The antibodies of the first aspect are characterized by their binding properties to PD-1 and preferably their ability to inhibit the immunosuppressive signal of PD-1.

According to the disclosure, the term "binding" preferably relates to "specific binding". As used herein, the terms "binding" or "capable of binding" or "having the ability to bind" in the context of the binding of an antibody to a predetermined antigen or epitope typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less, when determined using Bio-Layer Interferometry (BLI) or, for instance, when determined using surface plasmon resonance (SPR) technology in a BIAcore 3000 instrument using the antigen as the ligand and the antibody as the analyte. The antibody binds to the predetermined antigen with an affinity corresponding to a $K_D$ that is at least ten-fold lower, such as at least 100-fold lower, for instance at least 1,000-fold lower, such as at least 10,000-fold lower, for instance at least 100,000-fold lower than its $K_D$ for binding to a non-specific antigen (e.g., BSA, casein) other than the predetermined antigen or a closely-related antigen. The amount with which the affinity is higher is dependent on the $K_D$ of the antibody, so that when the $K_D$ of the antibody is very low (that is, the antibody is highly specific), then the degree to which the affinity for the antigen is lower than the affinity for a non-specific antigen may be at least 10,000-fold.

The term "$k_d$" ($sec^{-1}$), as used herein, refers to the dissociation rate constant of a particular antibody-antigen interaction. Said value is also referred to as the $k_{off}$ value.

The term "$K_D$" (M), as used herein, refers to the dissociation equilibrium constant of a particular antibody-antigen interaction.

Two antibodies have the "same specificity" if they bind to the same antigen and to the same epitope. Whether an antibody to be tested recognizes the same epitope as a certain antigen-binding antibody, i.e., the antibodies bind to the same epitope, may be tested by different methods well known to a person skilled in the art.

The competition between the antibodies can be detected by a cross-blocking assay. For example, a competitive ELISA assay may be used as a cross-blocking assay. E.g., target antigen may be coated on the wells of a microtiter plate and antigen-binding antibody and candidate competing test antibody may be added. The amount of the antigen-binding antibody bound to the antigen in the well indirectly correlates with the binding ability of the candidate competing test antibody that competes therewith for binding to the same epitope. Specifically, the larger the affinity of the candidate competing test antibody is for the same epitope, the smaller the amount of the antigen-binding antibody bound to the antigen-coated well. The amount of the antigen-binding antibody bound to the well can be measured by labeling the antibody with detectable or measurable labeling substances.

An antibody competing for binding to an antigen with another antibody, e.g., an antibody comprising heavy and light chain variable regions as described herein, or an antibody having the specificity for an antigen of another antibody, e.g., an antibody comprising heavy and light chain variable regions as described herein, may be an antibody comprising variants of said heavy and/or light chain variable regions as described herein, e.g. modifications in the CDRs and/or a certain degree of identity as described herein.

In one embodiment of the antibody of the first aspect, there is provided an antibody having the ability to bind to PD-1, wherein the antibody comprises a heavy chain variable region (VH) comprising a complementarity-determining region 3 (HCDR3) having or comprising a sequence as set forth in any one of SEQ ID NO: 8. In one embodiment of the antibody of the first aspect, there is provided an antibody having the ability to bind to PD-1, wherein the antibody comprises a heavy chain variable region (VH) comprising a complementarity-determining region 3 (HCDR3) having or comprising a sequence as set forth in any one of SEQ ID NO: 9.

In one embodiment of the antibody of the first aspect, the heavy chain variable region (VH) of the said antibody comprises a complementarity-determining region 2 (HCDR2) having or comprising a sequence as set forth in any one of SEQ ID NO: 10. In one embodiment, the HCDR2 of the heavy chain variable region (VH) has or comprises a sequence as set forth in any one of SEQ ID NO: 11.

In one embodiment of the antibody of the first aspect, the heavy chain variable region (VH) of the said antibody comprises a complementarity-determining region 1 (HCDR1) having or comprising a sequence selected from SYN. In one embodiment, the HCDR1 of the heavy chain variable region (VH) has or comprises a sequence as set forth in any one of SEQ ID NO: 12. In one embodiment, the HCDR1 of the heavy chain variable region (VH) has or comprises a sequence as set forth in any one of SEQ ID NO: 13.

In one embodiment of the antibody of the first aspect, the antibody comprises a heavy chain variable region (VH) comprising a HCDR3 sequence having or comprising a sequence as set forth in SEQ ID NO: 8 or SEQ ID NO: 9 and preferably further comprising a HCDR1 sequence having or comprising SYN, a sequence as set forth in SEQ ID NO: 12 or SEQ ID NO: 13 and/or a HCDR2 sequence having or comprising a sequence as set forth in SEQ ID NO: 10 or SEQ ID NO: 11.

In one embodiment of the antibody of the first aspect, the antibody comprises a heavy chain variable region (VH) comprising a HCDR1, HCDR2 and HCDR3 sequence, wherein the HCDR1 sequence is selected from a sequence having or comprising SYN, SEQ ID NO: 12 or SEQ ID NO: 13, the HCDR2 sequence is selected from a sequence having or comprising SEQ ID NO: 10 or SEQ ID NO: 11, and the HCDR3 sequence is selected from a sequence having or comprising SEQ ID NO: 8 or SEQ ID NO: 9.

In one embodiment of the antibody of the first aspect, the antibody comprises a heavy chain variable region (VH) comprising a HCDR1, HCDR2, and HCDR3 sequence, wherein the HCDR1, HCDR2 and HCDR3 sequence is or comprises SYN, SEQ ID NO: 10 and SEQ ID NO: 8, respectively.

In one embodiment of the antibody of the first aspect, the antibody comprises a heavy chain variable region (VH) comprising a HCDR1, HCDR2, and HCDR3 sequence, wherein the HCDR1, HCDR2 and HCDR3 sequence is or comprises SEQ ID NO: 12, SEQ ID NO: 11 and SEQ ID NO: 8, respectively.

In one embodiment of the antibody of the first aspect, the antibody comprises a heavy chain variable region (VH) comprising a HCDR1, HCDR2, and HCDR3 sequence, wherein the HCDR1, HCDR2 and HCDR3 sequence is or comprises SEQ ID NO: 13, SEQ ID NO: 10 and SEQ ID NO: 9, respectively.

In one embodiment of the first aspect, the antibody comprises a light chain having a light chain variable region (VL).

The antibodies of the first aspect is characterized by comprising a heavy chain variable region (VH) preferably comprising a complementarity-determining region 3 (HCDR3) having or comprising a sequence as set forth herein. In preferred embodiments the complementarity-determining region 1 and 2 of VH is further specified. In one embodiment, these antibodies of the first aspect further comprise a light chain variable region (VL) comprising at least one of:

a complementarity-determining region 3 (LCDR3) having or comprising a sequence as set forth in any one of SEQ ID NO: 14;

a complementarity-determining region 2 (LCDR2) having or comprising a sequence QAS. In one embodiment, the light chain variable region (VL) comprises a complementarity-determining region 2 (LCDR2) having or comprising a sequence as set forth in any one of SEQ ID NO: 15, and/or a complementarity-determining region 1 (LCDR1) having or comprising a sequence as set forth in any one of SEQ ID NO: 16. In one embodiment, the light chain variable region (VL) comprises a complementarity-determining region 1 (LCDR1) having or comprising a sequence as set forth in any one of SEQ ID NO: 17.

In one embodiment of the said antibodies of the first aspect, the antibody comprises a light chain variable region (VL) comprising a LCDR3 sequence having or comprising SEQ ID NO: 14 and preferably further comprising a LCDR1 sequence having or comprising SEQ ID NO: 16 or SEQ ID NO: 17 and/or a LCDR2 sequence having or comprising SEQ ID NO: 15.

In one embodiment, the antibody of the first aspect comprises a light chain variable region (VL) comprising a LCDR1, LCDR2, and LCDR3 sequence, wherein the LCDR1 sequence is selected from a sequence having or comprising SEQ ID NO: 16 or SEQ ID NO: 17, the LCDR2 sequence is selected from a sequence having or comprising QAS or SEQ ID NO: 15, and the LCDR3 sequence is a sequence having or comprising SEQ ID NO: 14.

In one embodiment, the antibody of the first aspect comprises a light chain variable region (VL) comprising a LCDR1, LCDR2, and LCDR3 sequence, wherein the LCDR1, LCDR2 and LCDR3 sequence is or comprises SEQ ID NO: 16, QAS, and SEQ ID NO: 14, respectively.

In one embodiment, the antibody of the first aspect comprises a light chain variable region (VL) comprising a LCDR1, LCDR2, and LCDR3 sequence, wherein the LCDR1, LCDR2 and LCDR3 sequence is or comprises SEQ ID NO: 17, SEQ ID NO: 15, and SEQ ID NO: 14, respectively.

In one embodiment of the antibody of the first aspect, the antibody comprises a heavy chain variable region (VH) comprising a HCDR1, HCDR2, and HCDR3 sequence and a light chain variable region (VL) comprising a LCDR1, LCDR2, and LCDR3 sequence, wherein the HCDR1, HCDR2 and HCDR3 sequence comprises or has the sequence SYN, as set forth in SEQ ID NO: 10 and SEQ ID NO: 8, respectively, and the LCDR1, LCDR2 and LCDR3 sequence comprises or has the sequence as set forth in SEQ ID NO: 16, QAS, and SEQ ID NO: 14, respectively. A specific, but not limiting example of such an antibody is MAB-19-0202.

In one embodiment of the antibody of the first aspect, the antibody comprises a heavy chain variable region (VH) comprising a HCDR1, HCDR2, and HCDR3 sequence and a light chain variable region (VL) comprising a LCDR1, LCDR2, and LCDR3 sequence, wherein the HCDR1, HCDR2 and HCDR3 sequence comprises or has the sequence as set forth in SEQ ID NO: 12, SEQ ID NO: 11, and SEQ ID NO: 8, respectively, and the LCDR1, LCDR2 and LCDR3 sequence comprises or has the sequence as set forth in SEQ ID NO: 17, SEQ ID NO: 15, and SEQ ID NO:

14, respectively. A specific, but not limiting example of such an antibody is MAB-19-0202.

In one embodiment of the antibody of the first aspect, the antibody comprises a heavy chain variable region (VH) comprising a HCDR1, HCDR2, and HCDR3 sequence and a light chain variable region (VL) comprising a LCDR1, LCDR2, and LCDR3 sequence, wherein the HCDR1, HCDR2 and HCDR3 sequence comprises or has the sequence as set forth in SEQ ID NO: 13, SEQ ID NO: 10, and SEQ ID NO: 9, respectively, and the LCDR1, LCDR2 and LCDR3 sequence comprises or has the sequence as set forth in SEQ ID NO: 16, QAS, and SEQ ID NO: 14, respectively. A specific, but not limiting example of such an antibody is MAB-19-0202.

The terms "a heavy chain variable region" (also referred to as "VH") and "a light chain variable region" (also referred to as "VL") are used here in their most general meaning and comprise any sequences that are able to comprise complementarity determining regions (CDR), interspersed with other regions, which also termed framework regions (FR). The framework regions inter alia space the CDRs so that they are able to form the antigen-binding site, in particular after folding and pairing of VH and VL. Preferably each VH and VL is composed of three CDRs and four FRs, arranged from amino-terminus to carboxy-terminus in the following order: FR1, CDR1, FR2, CDR2, FR3, CDR3, FR4. That is, the terms "a heavy chain variable region" and "a light chain variable region" are not to be construed to be limited to such sequences as they can be found in a native antibody or in the VH and VL sequences as exemplified herein (SEQ ID NOs: 18 to 21 of the sequence listing). These terms include any sequences capable of comprising and adequately positioning CDRs, for example such sequences as derived from VL and VH regions of native antibodies or as derived from the sequences as set forth in SEQ ID NOs: 18 to 21 of the sequence listing. It will be appreciated by those skilled in the art that in particular the sequences of the framework regions can be modified (includings both variants with regard to amino acid substitutions and variants with regard to the sequence length, i.e., insertion or deletion variants) without losing the characteristics of the VH and VL, respectively. In a preferred embodiment any modification is limited to the framework regions. But, a person skilled in the art is also well aware of the fact that also CDR, hypervariable and variable regions can be modified without losing the ability to bind PD-1. For example, CDR regions will be either identical or highly homologous to the regions specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions specifically disclosed herein.

The CDRs as specified herein have been identified by using two different CDR identification methods. The first numbering scheme used herein is according to Kabat (Wu and Kabat, 1970; Kabat et al., 1991), the second scheme is the IMGT numbering (Lefranc, 1997; Lefranc et al., 2005). In a third approach, the intersection of both identification schemes has been used.

In one embodiment of the antibody of the first aspect, the antibody comprises one or more CDRs, a set of CDRs or a combination of sets of CDRs as described herein comprises said CDRs together with their intervening framework regions (also referred to as framing region or FR herein) or with portions of said framework regions. Preferably, the portion will include at least about 50% of either or both of the first and fourth framework regions, the 50% being the C-terminal 50% of the first framework region and the N-terminal 50% of the fourth framework region. Construction of antibodies of the first aspect made by recombinant DNA techniques may result in the introduction of residues N- or C-terminal to the variable regions encoded by linkers introduced to facilitate cloning or other manipulation steps, including the introduction of linkers to join variable regions of the disclosure to further protein sequences including immunoglobulin heavy chains, other variable domains (for example in the production of diabodies) or protein labels.

In one embodiment of the antibody of the first aspect, the antibody comprises a heavy chain variable region (VH) comprising a sequence having at least 70%, at least 75%, at least 80%, at least 85%, at least 90%, at least 95%, at least 97%, at least 99%, or 100% identity to the amino acid sequence of the VH sequence as set forth in any one of SEQ ID NO: 18.

The heavy chain variable region (VH) preferably comprises at least one, more preferably two, still more preferably all three of the CDR sequences of an antibody heavy chain variable region having or comprising the sequences as set forth in any one of SEQ ID NO: 8 to 13, or having the sequence SYN, respectively.

In one embodiment of the antibody of the first aspect, the antibody comprises a heavy chain variable region (VH), wherein the VH comprises the sequence as set forth in any one of SEQ ID NO: 18.

In one embodiment of the antibody of the first aspect, the antibody comprises a light chain variable region (VL) comprising a sequence having at least 70%, at least 75%, at least 80%, at least 85%, at least 90%, at least 95%, at least 97%, at least 99%, or 100% identity to the amino acid sequence of the VL sequence as set forth in any one of SEQ ID NO: 19.

The light chain variable region (VL) preferably comprises at least one, more preferably two, still more preferably all three of the CDR sequences of an antibody light chain variable region having or comprising the sequences as set forth in any one of SEQ ID NO: 14 to 17, or having the sequence QAS, respectively.

In one embodiment of the antibody of the first aspect, the antibody comprises a light chain variable region (VL), wherein the VL comprises the sequence as set forth in any one of SEQ ID NO: 19.

In one embodiment of the antibody of the first aspect, the antibody comprises a heavy chain variable region (VH) and a light chain variable region (VL), wherein the VH comprises or has the sequence as set forth in SEQ ID NO: 18 and the VL comprises or has the sequence as set forth in SEQ ID NO: 19. A specific, but not limiting example of such an antibody is MAB-19-0202. Also encompassed by the present disclosure are variants of the said heavy chain variable regions (VH) and the said light chain variable regions (VL) and the respective combinations of these variant VHs and VLs.

Antibodies of the first aspect may be derived from different species, including but not limited to rabbit, mouse, rat, guinea pig and human. The antibodies can be polyclonal or monoclonal. In one embodiment or a preferred embodiment, the antibodies of the first aspect are monoclonal. Antibodies of the first aspect may, in one embodiment, include chimeric molecules in which an antibody constant region derived from one species, preferably human, is combined with the antigen binding site derived from another species. In one embodiment, the antibodies are monoclonal chimeric antibodies, wherein the constant region is preferably a human immunoglobin constant part, for example a human IgG1/κ constant part. Moreover, in one embodiment, antibodies of the first aspect include humanized molecules, preferably monoclonal humanized molecules, in which the antigen binding sites of an antibody derived from a non-human species are combined with constant and framework regions of human origin. In one embodiment, an antibody of the first aspect comprises one or more CDRs, a set of CDRs or a combination of sets of CDRs as described herein comprises said CDRs in a human antibody framework. In one or a preferred embodiment, the antibody of the first aspect is a monoclonal humanized antibody, wherein the constant region is preferably a human immunoglobin constant part, for example a human IgG1/κ constant part.

In one embodiment of the antibody of the first aspect, the antibody comprises a heavy chain variable region (VH) comprising a sequence having at least 70%, at least 75%, at least 80%, at least 85%, at least 90%, at least 95%, at least 97%, at least 99%, or 100% identity to the amino acid sequence of the VH sequence as set forth in any one of SEQ ID NO: 20. In one embodiment, the antibody comprises a heavy chain variable region (VH), wherein the VH comprises the sequence as set forth in any one of SEQ ID NO: 20. In one embodiment, the antibody comprises a light chain variable region (VL) comprising a sequence having at least 70%, at least 75%, at least 80%, at least 85%, at least 90%, at least 95%, at least 97%, at least 99%, or 100% identity to the amino acid sequence of the VL sequence as set forth in any one of SEQ ID NO: 21. In one embodiment, the antibody comprises a light chain variable region (VL), wherein the VL comprises the sequence as set forth in any one of SEQ ID NO: 21.

In one embodiment of the antibody of the first aspect, the antibody comprises a heavy chain variable region (VH) and a light chain variable region (VL), wherein the VH comprises or has the sequence as set forth in SEQ ID NO: 20 and the VL comprises or has the sequence as set forth in SEQ ID NO: 21, or respective variants of these sequences. Another example of an antibody of the first aspect may comprise a VH comprising or having the sequence as set forth in SEQ ID NO: 20, or a variant thereof, and a VL comprising or having the sequence as set forth in SEQ ID NO: 21, or a variant thereof. A specific, but not limiting example of such an antibody is MAB-19-0618. The antibody MAB-19-0618 has been derived from MAB-19-0202. Also encompassed by the present disclosure are variants of the said heavy chain variable regions (VH) and the said light chain variable regions (VL) and the respective combinations of these variant VHs and VLs.

In one embodiment of the antibody of the first aspect, the antibody comprises a heavy chain and a light chain, which heavy chain comprises a heavy chain constant region comprising or having the sequence as set forth in SEQ ID NO: 2 or 55 and a heavy chain variable region (VH) comprising or having the sequence as set forth in SEQ ID NO: 20, and which light chain comprises a light chain constant region comprising or having the sequence as set forth in SEQ ID NO: 6 and a light chain variable region (VL) comprising or having the sequence as set forth in SEQ ID NO: 21.

In one embodiment of the antibody of the first aspect, the antibody comprises a heavy chain and a light chain, which heavy chain comprises a heavy chain constant region comprising or having the sequence as set forth in SEQ ID NO: 2 or 55 and a heavy chain variable region (VH) comprising the CDR1, CDR2 and CDR3 sequences of the sequence as set forth in SEQ ID NO: 20, and which light chain comprises a light chain constant region comprising or having the sequence as set forth in SEQ ID NO: 6 and a light chain variable region comprising the CDR1, CDR2 and CDR3 sequences of the sequence as set forth in SEQ ID NO: 21. For example, the CDR1, CDR2 and CDR3 sequences are as specified herein.

With reference to the specific examples of a monoclonal chimeric antibody (MAB-19-0202) and a monoclonal humanized antibody of the first aspect, the respective sequences are shown in Tables 3, 4, 6 and 7 of the Examples. The exemplary humanized antibody MAB-19-0618 is a humanized variant of MAB-19-0202.

In one embodiment of the antibody of the first aspect, the antibody is a monoclonal, chimeric or a monoclonal, humanized antibody or a fragment of such an antibody. The antibodies can be whole antibodies or antigen-binding fragments thereof including, for example, bispecific antibodies. Furthermore, the antigen-binding fragments can include binding-domain immunoglobulin fusion proteins comprising (i) a binding domain polypeptide (such as a heavy chain variable region or a light chain variable region) that is fused to an immunoglobulin hinge region polypeptide, (ii) an immunoglobulin heavy chain CH2 constant region fused to the hinge region, and (iii) an immunoglobulin heavy chain CH3 constant region fused to the CH2 constant region. Such binding-domain immunoglobulin fusion proteins are further disclosed in US 2003/0118592 and US 2003/0133939.

In one embodiment of the antibody of the first aspect, the antibody or an antigen binding portion thereof comprises at least two heavy chains and at least two light chains, wherein the antibody comprises the same heavy chains and/or the same light chains, e.g., the heavy chains and/or light chains as specified herein above or below. For example, an antibody of the first aspect can comprise two heavy chains having the sequences as set forth in SEQ ID NO: 20 and SEQ ID NO: 2 or 55, or respective variants of these sequences, and two light chains having the sequences as set forth in SEQ ID NO: 21 and SEQ ID NO: 6, or respective variants of these sequences.

In one embodiment of the antibody of the first aspect, one or more, preferably both heavy chain constant regions have been modified so that binding of C1q to said antibody is reduced compared to a wild-type antibody, preferably reduced by at least 70%, at least 80%, at least 90%, at least 95%, at least 97%, or 100%. In one embodiment, the C1q binding can be determined by ELISA.

By "wild-type" or "WT" or "native" herein is meant an amino acid sequence that is found in nature, including allelic variations. A wild-type amino acid sequence, peptide or protein has an amino acid sequence that has not been intentionally modified.

In one embodiment of the antibody of the first aspect, one or more, preferably both heavy chain constant regions have been modified so that binding to one or more of the IgG Fc-gamma receptors to the antibody is reduced compared to a wild-type antibody, preferably by at least 70%, at least 80%, at least 90%, at least 95%, at least 97% or 100%. In one embodiment, the one or more IgG Fc-gamma receptors are selected from at least one of Fc-gamma RI, Fc-gamma RII, and Fc-gamma RIII. In one embodiment, the IgG Fc-gamma receptor is Fc-gamma RI.

In one embodiment of the antibody of the first aspect, the antibody is not capable of inducing Fc-gamma RI-mediated effector functions or wherein the induced Fc-gamma RI-mediated effector functions are reduced compared to a wild-type antibody, preferably by at least 70%, at least 80%, at least 90%, at least 95%, at least 97% or 100%.

In one embodiment of the antibody of the first aspect, the antibody is not capable of inducing at least one of complement dependent cytotoxicity (CDC) mediated lysis, antibody dependent cellular cytotoxicity (ADCC) mediated lysis, apoptosis, homotypic adhesion and/or phagocytosis or wherein at least one of complement dependent cytotoxicity (CDC) mediated lysis, antibody dependent cellular cytotoxicity (ADCC) mediated lysis, apoptosis, homotypic adhesion and/or phagocytosis is induced in a reduced extent, preferably reduced by at least 70%, at least 80%, at least 90%, at least 95%, at least 97% or 100%.

Antibody-dependent cell-mediated cytotoxicity is also referred to as "ADCC" herein. ADCC describes the cell-killing ability of effector cells as described herein, in particular lymphocytes, which preferably requires the target cell being marked by an antibody.

ADCC preferably occurs when antibodies bind to antigens on tumor cells and the antibody Fc domains engage Fc receptors (FcR) on the surface of immune effector cells. Several families of Fc receptors have been identified, and specific cell populations characteristically express defined Fc receptors. ADCC can be viewed as a mechanism to directly induce a variable degree of immediate tumor destruction that leads to antigen presentation and the induction of tumor-directed T-cell responses. Preferably, in vivo induction of ADCC will lead to tumor-directed T-cell responses and host-derived antibody responses.

Complement-dependent cytotoxicity is also referred to as "CDC" herein. CDC is another cell-killing method that can be directed by antibodies. IgM is the most effective isotype for complement activation. IgG1 and IgG3 are also both very effective at directing CDC via the classical complement-activation pathway. Preferably, in this cascade, the formation of antigen-antibody complexes results in the uncloaking of multiple C1q binding sites in close proximity on the $C_H2$ domains of participating antibody molecules such as IgG molecules (C1q is one of three subcomponents of complement C1). Preferably these uncloaked C1q binding sites convert the previously low-affinity C1q-IgG interaction to one of high avidity, which triggers a cascade of events involving a series of other complement proteins and leads to the proteolytic release of the effector-cell chemotactic/activating agents C3a and C5a. Preferably, the complement cascade ends in the formation of a membrane attack complex, which creates pores in the cell membrane that facilitate free passage of water and solutes into and out of the cell and may lead to apoptosis.

In one embodiment of the antibody of the first aspect, the antibody has reduced or depleted effector functions. In one embodiment, the antibody does not mediate ADCC or CDC or both.

In one embodiment of the antibody of the first aspect, one or more, preferably both heavy chain constant regions of the antibody have been modified so that binding of neonatal Fc receptor (FcRn) to the antibody is unaffected, as compared to a wild-type antibody.

In one embodiment of the antibody of the first aspect, the PD-1 to which the antibody is able to bind is human PD-1. In one embodiment, the PD-1 has or comprises the amino acid sequence as set forth in SEQ ID NO: 22 or SEQ ID NO: 23, or the amino acid sequence of PD-1 has at least 70%, at least 75%, at least 80%, at least 85%, at least 90%, at least 95%, at least 97%, at least 99%, or 100% identity to the amino acid sequence as set forth in SEQ ID NO: 22 or SEQ ID NO: 23, or is an immunogenic fragment thereof. In one embodiment, the antibody has the ability to bind to a native epitope of PD-1 present on the surface of living cells.

The antibodies of the first aspect can be used synergistically with traditional chemotherapeutic agents or other immune therapies attacking tumors, for example by employing other antibodies targeting tumor antigens thereby inducing an immune response against these tumors cells or by employing other checkpoint inhibitors or activators or angiogenesis inhibitors.

II. Production of Antibodies

Antibodies of the first aspect can be produced by a variety of techniques, including conventional monoclonal antibody methodology, e.g., the standard somatic cell hybridization technique of Kohler and Milstein, Nature 256: 495 (1975). Although somatic cell hybridization procedures are preferred, in principle, other techniques for producing monoclonal antibodies can be employed, e.g., viral or oncogenic transformation of B-lymphocytes or phage display techniques using libraries of antibody genes.

The preferred animal system for preparing hybridomas that secrete monoclonal antibodies is the murine system. Hybridoma production in the mouse is a very well established procedure. Immunization protocols and techniques for isolation of immunized splenocytes for fusion are known in the art. Fusion partners (e.g., murine myeloma cells) and fusion procedures are also known.

Other preferred animal systems for preparing hybridomas that secrete monoclonal antibodies are the rat and the rabbit system (e.g., described in Spieker-Polet et al., Proc. Natl. Acad. Sci. U.S.A. 92:9348 (1995), see also Rossi et al., Am. J. Clin. Pathol. 124: 295 (2005)).

In yet another preferred embodiment, human monoclonal antibodies directed against PD-1 can be generated using transgenic or transchromosomal mice carrying parts of the human immune system rather than the mouse system. These transgenic and transchromosomic mice include mice known as HuMAb mice and KM mice, respectively, and are collectively referred to herein as "transgenic mice". The production of human antibodies in such transgenic mice can be performed as described in detail for CD20 in WO 2004/035607.

Yet another strategy for generating monoclonal antibodies is to directly isolate genes encoding antibodies from lymphocytes producing antibodies of defined strategy e.g. see Babcock et al., 1996; *A novel strategy for generating monoclonal antibodies from single, isolated lymphocytes producing antibodies of defined strategy*. For details of recombinant antibody engineering see also Welschof and Kraus, Recombinant antibodies for cancer therapy ISBN-0-89603-918-8 and Benny K. C. Lo Antibody Engineering ISBN 1-58829-092-1.

Immunizations

To generate antibodies to PD-1, animals, for example rabbits or mice, can be immunized with carrier-conjugated peptides derived from the PD-1 sequence, an enriched preparation of recombinantly expressed PD-1 antigen or fragments thereof and/or cells expressing PD-1, as described. Alternatively, rabbits or mice can be immunized with DNA encoding full length human PD-1 or fragments thereof. In the event that immunizations using a purified or enriched preparation of the PD-1 antigen do not result in antibodies, rabbits or mice can also be immunized with cells expressing PD-1, e.g., a cell line, to promote immune responses.

The immune response can be monitored over the course of the immunization protocol with plasma and serum samples being obtained by tail vein or retroorbital bleeds. Rabbits or mice with sufficient titers of anti-PD-1 immunoglobulin can be used for fusions. Rabbits or mice can be boosted intraperitonealy or intravenously with PD-1 expressing cells 3 days before sacrifice and removal of the spleen to increase the rate of specific antibody secreting hybridomas.

Generation of Hybridomas Producing Monoclonal Antibodies

To generate hybridomas producing monoclonal antibodies to PD-1, splenocytes and lymph node cells from immunized animals, e.g., rabbits or mice, can be isolated and fused to an appropriate immortalized cell line, such as a mouse or rabbit myeloma cell line. The resulting hybridomas can then be screened for the production of antigen-specific antibodies. Individual wells can then be screened by ELISA for antibody secreting hybridomas. By immunofluorescence and FACS analysis using PD-1 expressing cells, antibodies with specificity for PD-1 can be identified. The antibody secreting hybridomas can be replated, screened again, and if still positive for anti-PD-1 monoclonal antibodies can be subcloned by limiting dilution. The stable subclones can then be cultured in vitro to generate antibody in tissue culture medium for characterization.

Generation of Transfectomas Producing Monoclonal Antibodies

Antibodies of the first aspect also can be produced in a host cell transfectoma using, for example, a combination of recombinant DNA techniques and gene transfection methods as are well known in the art (Morrison, S. (1985) Science 229: 1202).

The term "transfectoma", as used herein, includes recombinant eukaryotic host cells expressing an antibody, such as CHO cells, NS/0 cells, HEK293 cells, HEK293T cells, HEK293T/17 plant cells, or fungi, including yeast cells.

For example, in one embodiment, the gene(s) of interest, e.g., antibody genes, can be ligated into an expression vector such as a eukaryotic expression plasmid such as used by the GS gene expression system disclosed in WO 87/04462, WO 89/01036 and EP 338 841 or other expression systems well known in the art. The purified plasmid with the cloned antibody genes can be introduced in eukaryotic host cells such as CHO cells, NS/0 cells, Sp2/0 cells, COS cells, Vero cells, HeLa cells, HEK293T cells, HEK293T/17 or HEK293 cells or alternatively other eukaryotic cells like plant derived cells, fungal or yeast cells. The method used to introduce these genes can be methods described in the art such as electroporation, lipofectine, lipofectamine or others. After introduction of these antibody genes in the host cells, cells expressing the antibody can be identified and selected. These cells represent the transfectomas which can then be amplified for their expression level and upscaled to produce antibodies. Recombinant antibodies can be isolated and purified from these culture supernatants and/or cells.

Alternatively, the cloned antibody genes can be expressed in other expression systems, including prokaryotic cells, such as microorganisms, e.g., *E. coli*. Furthermore, the antibodies can be produced in transgenic non-human animals, such as in milk from sheep and rabbits or in eggs from hens, or in transgenic plants; see e.g. Verma, R., et al. (1998) J. Immunol. Meth. 216: 165-181; Pollock, et al. (1999) J. Immunol. Meth. 231: 147-157; and Fischer, R., et al. (1999) Biol. Chem. 380: 825-839.

The amino acid sequence variants described herein may readily be prepared by the skilled person, for example, by recombinant DNA manipulation. The manipulation of DNA sequences for preparing proteins and peptides having substitutions, additions, insertions or deletions, is described in detail in Sambrook et al. (1989), for example.

Antibodies of the first aspect also can be produced in genetically modified viruses, such as RNA viruses, using recombinant DNA techniques well known to persons skilled in the art. Recombinant viral genomes, which can be used to rescue virus particles expressing an antibody or a fragment thereof, can for example be obtained by a method called 'reverse genetics'.

Use of Partial Antibody Sequences to Express Intact Antibodies (i.e., Humanization and Chimerisation).

a) Chimerization

Murine or rabbit monoclonal antibodies can be used as therapeutic antibodies in humans, but as these antibodies can be highly immunogenic in man when repetitively applied, this may lead to a reduction of the therapeutic effect. The main immunogenicity is mediated by the heavy chain constant regions. The immunogenicity of murine or rabbit antibodies in man can be reduced or completely avoided if respective antibodies are chimerized or humanized. Chimeric antibodies are antibodies, the different portions of which are derived from different animal species, such as those having a variable region derived from a murine or rabbit antibody and a human immunoglobulin constant region. Chimerisation of antibodies is achieved by joining of the variable regions of the murine or rabbit antibody heavy and light chain with the constant region of human heavy and light chain (e.g., as described by Kraus et al., in Methods in Molecular Biology series, *Recombinant antibodies for cancer therapy*, ISBN-0-89603-918-8). In a preferred embodiment, chimeric antibodies are generated by joining human kappa-light chain constant region to murine or rabbit light chain variable region. In an also preferred embodiment chimeric antibodies can be generated by joining human lambda-light chain constant region to murine or rabbit light chain variable region. The preferred heavy chain constant regions for generation of chimeric antibodies are IgG1, IgG3 and IgG4. Other preferred heavy chain constant regions for generation of chimeric antibodies are IgG2, IgA, IgD and IgM.

b) Humanization

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332: 323-327; Jones, P. et al. (1986) Nature 321: 522-525; and Queen, C. et al. (1989) Proc. Natl. Acad. Sci. U.S.A. 86: 10029-10033). Such framework sequences can be obtained from public DNA databases that include germline antibody gene sequences. These germline sequences will differ from mature antibody gene sequences because they will not include completely assembled variable genes, which are formed by V (D) J joining during B cell maturation. Germline gene sequences will also differ from the sequences of a high affinity secondary repertoire antibody at individual evenly across the variable region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see WO 99/45962). Partial heavy and light chain sequences spanning the CDR regions are typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266: 19867-19870); and HindIII sites are engineered upstream of the translation initiation sites.

For both the heavy and light chain variable regions, the optimized coding and corresponding non-coding, strand sequences are broken down into 30-50 nucleotides approximately at the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed chimerized or humanized heavy and light chain variable regions are then combined with cloned promoter, leader, translation initiation, constant region, 3' untranslated, polyadenylation, and transcription termination sequences to form expression vector constructs. The heavy and light chain expression constructs can be combined into a single vector, co-transfected, serially transfected, or separately transfected into host cells which are then fused to form a host cell expressing both chains. Plasmids for use in construction of expression vectors for human IgGκ are available for the skilled person. The plasmids can be constructed so that PCR amplified V heavy and V kappa light chain cDNA sequences could be used to reconstruct complete heavy and light chain minigenes. These plasmids can be used to express completely human, or chimeric IgG1, Kappa or IgG4, Kappa antibodies. Similar plasmids can be constructed for expression of other heavy chain isotypes, or for expression of antibodies comprising lambda light chains.

Thus, according to the present disclosure, the structural features of the anti-PD-1 antibodies of the first aspect, can be used to create structurally related humanized anti-PD-1 antibodies that retain at least one functional property of the antibodies of the first aspect, such as binding to PD-1. More specifically, one or more CDR regions as disclosed herein can be combined recombinantly with known human framework regions and CDRs to create additional, recombinantly engineered, humanized anti-PD-1 antibodies of the first aspect.

The antibody of the first aspect is obtainable by a method comprising the step of immunizing an animal, e.g., transgenic mice, with a protein or peptide having an amino acid sequence as set forth in SEQ ID NO: 22 or SEQ ID NO: 23, or an immunogenic fragment thereof, or a nucleic acid or host cell or virus expressing said protein or peptide, or an immunogenic fragment thereof. Preferably, the thus obtained antibody is specific for the afore mentioned protein, peptides or immunogenic fragments thereof. The nucleic acid or host cell or virus may be a nucleic acid or a host cell or a virus as disclosed herein.

The present disclosure also provides isolated B cells from a non-human animal as described above. The isolated B cells can then be immortalized by fusion to an immortalized cell to provide a source (e.g., a hybridoma) of antibodies of the first aspect. Such hybridomas (i.e., which produce antibodies of the first aspect) are also included within the scope of the disclosure.

Thus, in a second aspect, there is provided a hybridoma capable of producing the antibody of the first aspect. As exemplified herein, antibodies of the first aspect can be obtained directly from hybridomas which express the antibody, or can be cloned and recombinantly expressed in a host cell (e.g., a CHO cell, or a lymphocytic cell). Alternatively, they can be produced recombinantly in a transgenic non-human animal or plant.

III. Characterization of Antibodies

Binding to Antigen Expressing Cells

The ability of the antibodies to bind PD-1 and/or to block the PD-1/ligand interaction can be determined using standard binding assays, reporter gene blockade assays, T cell proliferation assays, etc., such as those set forth in the examples.

Characterization of Binding of Antibodies

To purify anti-PD-1 antibodies, selected hybridomas can be grown in two-liter spinner-flasks for monoclonal antibody purification. Alternatively, anti-PD-1 antibodies can be produced in dialysis based bioreactors. Supernatants can be filtered and, if necessary, concentrated before affinity chromatography with protein G-sepharose or protein A-sepharose. Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C. To determine if the selected anti-PD-1 monoclonal antibodies bind to unique epitopes, site-directed or multi-site directed mutagenesis can be used.

Determining the PD-1 Binding Specificity

The binding potency of anti-PD-1 antibodies to PD-1 can be determined by ELISA techniques. For example, PD-1/Fc chimera can be coated on microtiter plates. After blocking, the anti-PD-1-antibodies to be tested can be added and incubated. Then, after performing a washing procedure, anti-human-IgG coupled to e.g., horseradish peroxidase can be added for detection.

The binding ability of anti-PD-1 antibodies to cell surface expressed PD-1 can be analyzed using HEK-293 cells ectopically expressing PD-1. Anti-PD-1 antibodies can be added to these cells at various concentrations and incubated. Anti-Ig antibodies conjugated with a fluorescence tag can be added then and cell-associated immunofluorescent signals can be recorded.

Determining the Blocking Ability

The potency of anti-PD-1 antibodies to block the PD-1/PD-L1 interaction can be analyzed using a PD-1/PD-L1 blockade bioassay. PD-L1 expressing cells can be incubated with the antibodies to be tested at various concentrations. After adding PD-1 expressing effector cells and incubating the thus obtained mixture, for example, a luciferase assay reagent can be added and the luminescence can be determined. A PD-1/PD-L1 blockade bioassay (Promega, Cat No. J12150), or comparable kits, may be used as described by the manufacturer.

For characterizing the ability of the anti-PD1 antibodies to induce T-cell proliferation in an antigen-specific assay with active PD-1/PD-L1 axis, dendritic cells (DCs), expressing a tumor antigen, can be performed. Such an assay is detailed, in a non-limiting manner, in Example 5 below.

Flow Cytometric Analysis and Immunofluorescence Microscopy

In order to demonstrate presence of anti-PD-1 antibodies in sera of immunized animals or binding of monoclonal antibodies to living cells expressing PD-1, flow cytometry or immunofluorescence microscopy analysis can be used in a manner well known to the skilled person.

Epitope Mapping

Mapping of epitopes recognized by antibodies of the first aspect can be performed as described in detail in "*Epitope Mapping Protocols*", Methods in Molecular Biology by Glenn E. Morris ISBN-089603-375-9 and in "*Epitope Mapping: A Practical Approach*", Practical Approach Series, 248 by Olwyn M. R. Westwood, Frank C. Hay.

IV. Bispecific/Multispecific Antibodies which Bind to PD-1

In one embodiment of the antibody of the first aspect, the antibodies to PD-1 can be derivatized or linked to another functional molecule, e.g., another peptide or protein (e.g., a Fab' fragment) to generate a bispecific or multispecific molecule which binds to multiple binding sites or target epitopes. For example, an antibody of the first aspect can be functionally linked (e.g., by chemical coupling, genetic fusion, noncovalent association or otherwise) to one or more other binding molecules, such as another antibody, peptide or binding mimetic.

Accordingly, the present disclosure includes bispecific and multispecific molecules comprising at least one first binding specificity for PD-1 and a second binding specificity (or further binding specificities) for a second target epitope (or for further target epitopes).

In one embodiment of the antibody of the first aspect, the antibody is a multispecific antibody comprising a first antigen-binding region binding to PD-1 and at least one further antigen-binding region binding to another antigen. In one embodiment, the antibody is a bispecific antibody comprising a first antigen-binding region binding to PD-1 and a second antigen-binding region binding to another antigen.

The term "bispecific molecule" is intended to include any agent, e.g., a protein, peptide, or protein or peptide complex, which has two different binding specificities. For example, the molecule may bind to, or interact with (a) a cell surface antigen, and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with (a) a cell surface antigen, (b) an Fc receptor on the surface of an effector cell, and (c) at least one other component. Accordingly, the disclosure includes, but is not limited to, bispecific, trispecific, tetraspecific, and other multispecific molecules which are directed to PD-1, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90: 6444-6448; Poljak, R. J., et al. (1994) Structure 2: 1121-1123).

As used herein, the term "heteroantibodies" refers to two or more antibodies, derivatives thereof, or antigen-binding regions linked together, at least two of which have different specificities. These different specificities include a binding specificity for an Fc receptor on an effector cell, and a binding specificity for an antigen or epitope on a target cell, e.g., a tumor cell.

In one embodiment of the antibody of the first aspect, the first antigen-binding region of the multispecific antibody binding to PD-1 comprises the heavy chain variable region (VH) and/or the light chain variable region (VL) as set forth herein.

In one embodiment of the antibody of the first aspect, the first and second binding arms of the multispecific antibody are derived from full-length antibodies, such as from full-length IgG1, λ (lambda) or IgG1, κ (kappa) antibodies as mentioned above. In one embodiment, the first and second binding arms are derived from monoclonal antibodies. For example or in a preferred embodiment, the first and/or second binding arm is derived from a IgG1, κ isotype or λ isotype, preferably comprising human IgG1/κ or human IgG1/λ constant parts.

The said first antigen-binding region binding to PD-1 of the multispecific or bispecific antibody of the present invention may comprise heavy and light chain variable regions of an antibody which competes for PD-1 binding with PD-L1 and/or PD-L2. In one embodiment of the multispecific or bispecific antibody, the first antigen-binding region binding to PD-1 comprises the heavy chain variable region (VH) and/or the light chain variable region (VL) as set forth herein.

In one embodiment of the multi- or bispecific antibody, the second binding specificity can be directed to another immune checkpoint, thereby either inhibiting or activating/stimulating the respective checkpoint. Other checkpoint inhibitors which may be targeted include, but are not limited to CTLA4, PD-L1, TIM-3, KIR or LAG-3. Checkpoint activators, which may be targeted by the second binding specifity include, but are not limited to CD27, CD28, CD40, CD122, CD137, OX40, GITR, or ICOS. Therefore, included are bispecific and multispecific molecules capable of binding both to at least one other checkpoint and to inhibit PD-1 by a respective binding. The second binding specifity may be antagonistic, such as anti-CTLA4, anti-PD-L1, anti-TIM-3, anti-KIR or anti-LAG-3, or may be agonistic, such as anti-CD27, anti-CD28, anti-CD40, anti-CD122, anti-CD137, anti-OX40, anti-GITR, or anti-ICOS. Also encompassed are multispecific molecules capable of binding to PD-1 and in addition to at least one other immune checkpoint. Preferred combinations of binding specifities include anti-PD1 and anti-PD-L1 or anti-PD-1 and anti-CTLA4.

For example, CD28 provides a stimulative inducement that could be necessary for the activation of T cells. The same applies e.g., for CD137. CD137 (4-1BB, TNFRSF9) is a member of the tumor necrosis factor (TNF) receptor (TNFR) superfamily. CD137 is a co-stimulatory molecule on CD8+ and CD4+ T cells, regulatory T cells (Tregs), natural killer (NK) and NKT cells, B cells and neutrophils. On T cells, CD137 is not constitutively expressed, but induced upon T-cell receptor (TCR) activation. Stimulation via its natural ligand 4-1BBL or agonist antibodies leads to signaling using TNFR-associated factor (TRAF)-2 and TRAF-1 as adaptors. Early signaling by CD137 involves K-63 poly-ubiquitination reactions that ultimately result in activation of the nuclear factor (NF)-κB and mitogen-activated protein (MAP)-kinase pathways. Signaling leads to increased T cell co-stimulation, proliferation, cytokine production, maturation and prolonged CD8+ T-cell survival. Agonistic antibodies against CD137 have been shown to promote anti-tumor control by T cells in various pre-clinical models (Murillo et al. 2008 Clin. Cancer Res. 14(21): 6895-6906). Antibodies stimulating CD137 can induce survival and proliferation of T cells, thereby enhancing the anti-tumor immune response. Antibodies stimulating CD137 have been disclosed in the prior art, and include urelumab, a human IgG4 antibody (WO 2005/035584) and utomilumab, a human IgG2 antibody (Fisher et al. 2012 Cancer Immunol. Immunother. 61: 1721-1733).

In one embodiment of the multi- or bispecific antibody, the second binding specificity can provide an antiangiogenesis activity. Thus, the second binding specificity can be capable of targeting vascular endothelial growth factor (VEGF) or its receptor VEGFR (for example VEGFR1, 2, 3). Alternatively or in addition, the second binding specificity may be capable of targeting PDGFR, c-Kit, Raf and/or RET.

In one embodiment of the multi- or bispecific antibody, the second or the further binding specificities of the bispecific or multispecific molecules of the first aspect can be directed to and are capable of binding to a tumor antigen, which enables a specificity of the antibody for cancer cells. In one embodiment, the cancer cells can be selected from the group consisting of melanoma, lung cancer, renal cell carcinoma, bladder cancer, breast cancer, gastric and gastroesophageal junction cancers, pancreatic adenocarcinoma, ovarian cancer and lymphomas. The tumor antigen can be a surface antigen or an antigen presented in the context of MHC. The binding specificity could for example be based on a B-cell receptor (antibody) or a T cell receptor.

The term "tumor antigen" as used herein refers to a constituent of cancer cells which may be derived from the cytoplasm, the cell surface and the cell nucleus. In particular, it refers to those antigens which are produced intracellularly or as surface antigens on tumor cells. A tumor antigen is typically expressed preferentially by cancer cells (e.g., it is expressed at higher levels in cancer cells than in non-cancer cells) and in some instances it is expressed solely by cancer cells. Examples of tumor antigens include, without limitation, p53, ART-4, BAGE, beta-catenin/m, Bcr-abL CAMEL, CAP-1, CASP-8, CDC27/m, CDK4/m, CEA, the cell surface proteins of the claudin family, such as CLAUDIN-6, CLAUDIN-18.2 and CLAUDIN-12, c-MYC, CT, Cyp-B, DAM, ELF2M, ETV6-AML1, G250, GAGE, GnT-V, Gap 100, HAGE, HER-2/neu, HPV-E7, HPV-E6, HAST-2, hTERT (or hTRT), LAGE, LDLR/FUT, MAGE-A, preferably MAGE-A1, MAGE-A2, MAGE-A3, MAGE-A4, MAGE-A5, MAGE-A6, MAGE-A7, MAGE-A8, MAGE-A9, MAGE-A10, MAGE-A11, or MAGE-A12, MAGE-B, MAGE-C, MART-1/Melan-A, MC1R, Myosin/m, MUC1, MUM-1, MUM-2, MUM-3, NA88-A, NF1, NY-ESO-1, NY-BR-1, p190 minor BCR-abL, Pml/RARa, PRAME, proteinase 3, PSA, PSM, RAGE, RU1 or RU2, SAGE, SART-1 or SART-3, SCGB3A2, SCP1, SCP2, SCP3, SSX, SURVIVIN, TEL/AML1, TPI/m, TRP-1, TRP-2, TRP-2/INT2, TPTE, WT, and WT-1.

In one embodiment, the second antigen to be targeted is selected from the group consisting of NY-ESO-1 (UniProt P78358), Tyrosinase (UniProt P14679), MAGE-A3 (UniProt P43357), TPTE (UniProt P56180), KLK2 (UniProt P20151), PSA (KLK3) (UniProt P07288), PAP (ACPP, UniProt P15309), HOXB13 (UniProt Q92826), NKX3-1 (UniProt Q99801), HPV16 E6/E7 (UniProt P03126/P03129); HPV18 E6/E7 (UniProt P06463/P06788); HPV31 E6/E7 (UniProt P17386/P17387); HPV33 E6/E7 (UniProt P06427/P06429); HPV45 E6/E7 (UniProt P21735/P21736); HPV58 E6/E7 (UniProt P26555/P26557), PRAME (UniProt P78395), ACTL8 (UniProt Q9H568), CXorf61 (KKLC1, UniProt Q5H943), MAGE-A9B (UniProt P43362), CLDN6 (UniProt P56747), PLAC1 (UniProt Q9HBJ0), and p53 (UniProt P04637).

Methods of treatment involving these antigens may aim at the treatment of cancer, wherein the cancer cells are characterized by expression of the respective antigen. It is also possible to use antigens described herein, in particular NY-ESO-1, Tyrosinase, MAGE-A3, TPTE, KLK2, PSA (KLK3), PAP (ACPP), HOXB13, NKX3-1, HPV16 E6/E7; HPV18 E6/E7; HPV31 E6/E7; HPV33 E6/E7; HPV45 E6/E7; HPV58 E6/E7, PRAME, ACTL8, CXorf61 (KKLC1), MAGE-A9B, CLDN6, PLAC1, and p53, in combination. Methods of treatment involving such combination of antigens may aim at the treatment of cancer, wherein the cancer cells are characterized by expression of two or more antigens of the respective combination of antigens or wherein the cancer cells of a large fraction (e.g., at least 80%, at least 90% or even more) of patients having a certain cancer to be treated express one or more of the respective antigens of a combination. Such combination may comprise a combination of at least 2, at least 3, at least 4, at least 5, or at least 6 antigens. Thus, the combination may comprise 3, 4, 5, 6, 7, or 8 antigens.

For the treatment of cutaneous melanoma the further binding specificity/specifities may at least target one of the following antigens: NY-ESO-1, Tyrosinase, MAGE-A3, and/or TPTE.

For the treatment of prostate cancer the further binding specificity/specifities may at least target one of the following antigens: KLK2, PSA (KLK3), PAP (ACPP), HOXB13, and/or NKX3-1.

For the treatment of breast cancer the further binding specificity/specifities may at least target one of the following antigens: PRAME, ACTL8, CXorf61 (KKLC1), MAGEA3, MAGE-A9B, CLDN6, NY-ESO-1, and/or PLAC1.

For the treatment of ovarian cancer the further binding specificity/specifities may at least target one of the following antigens: CLDN6, p53, and/or PRAME.

As used herein, the term "effector cell" refers to an immune cell which is involved in the effector phase of an immune response, as opposed to the cognitive and activation phases of an immune response. Exemplary immune cells include cells of myeloid or lymphoid origin, e.g, lymphocytes (e.g., B cells and T cells including cytolytic T cells (CTLs), killer cells, natural killer cells, macrophages, monocytes, eosinophils, neutrophils, polymorphonuclear cells, granulocytes, mast cells, and basophils.

"Target cell" shall mean any undesirable cell in a subject (e.g., a human or animal) that can be targeted by an antibody of the first aspect. In preferred embodiments, the target cell is a tumor cell.

Bispecific and multispecific molecules of the first aspect can be made using chemical techniques (see e.g., D. M. Kranz et al. (1981) Proc. Natl. Acad. Sci. USA 78:5807), "polydoma" techniques (see U.S. Pat. No. 4,474,893, to Reading), or recombinant DNA techniques.

In particular, bispecific and multispecific molecules of the first aspect can be prepared by conjugating the constituent binding specificities, e.g., the anti-CTLA4 and anti-PD-1 binding specificities, using methods known in the art. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl-4-(N-maleimidomethyl)cyclo-hexane-1-carboxylate (sulfo-SMCC) (see e.g., Karpovsky et al. (1984) J. Exp. Med. 160: 1686; Liu, M A et al. (1985) Proc. Natl. Acad. Sci. USA 82: 8648). Other methods include those described by Paulus (Behring Ins. Mitt. (1985) No. 78, 118-132); Brennan et al. (Science (1985) 229: 81-83), and Glennie et al. (J. Immunol. (1987) 139: 2367-2375). Preferred conjugating agents are SATA and sulfo-SMCC, both available from Pierce Chemical Co. (Rockford, IL).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a mAb×mAb, mAb× Fab, Fab×F(ab')$_2$ or ligand×Fab fusion protein. A bispecific and multispecific molecule of the first aspect, e.g., a bispecific molecule, can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. Nos. 5,260,203; 5,455,030; 4,881,175; 5,132,405; 5,091,513; 5,476,786; 5,013,653; 5,258,498; and 5,482,858. Accordingly, the present disclosure encompasses all these antibody formats.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a γ-counter or a scintillation counter or by autoradiography.

V. Immunoconjugates

An anti-PD-1 antibody of the first aspect can be conjugated to a moiety or agent. Such conjugates are referred to herein also as "immunoconjugates".

In a third aspect, there is provided a conjugate comprising an antibody of the first aspect coupled to a moiety or agent. In one embodiment of the third aspect, the moiety or agent is selected from the group consisting of a radioisotope, an enzyme, a dye, a drug, a toxin and a cytotoxic agent. The dye can, for example, be a fluorescence dye or fluorescent tag. In one embodiment, the moiety or agent is capable of achieving immune cell activation. For example, the moiety or agent can be CD80 which interacts with CD28 on T cells.

The antibodies of the first aspect can be coupled to or functionally linked (e.g., by chemical coupling, genetic fusion, noncovalent association or otherwise) to one or more other molecular entities, such as another antibody having a binding specificity to PD-1. The one or more other antibodies are preferably antibodies of the first aspect.

The moiety or agent can be an enzyme bound to the antibody. Such antibodies can be used for enzyme immunoassays, such as enzyme-linked immunosorbent assays (ELISA) or enzyme multiplied immunoassay technique (EMIT), or Westernblots for example.

Alternatively or in addition, a radionuclide (radioisotope) can be bound to the antibody as a moiety or agent. Such conjugates may be used in therapy but also for diagnostic purposes (radioimmunoassays, positron emission tomography ("immuno-PET")). The radionuclides may be conjugated to the antibodies via complexing agents. Antibodies of the first aspect also can be conjugated to a radioisotope, e.g., iodine-131, yttrium-90 or indium-111, to generate cytotoxic radiopharmaceuticals for treating a disorder, such as a cancer. The antibodies according to the first aspect may be attached to a linker-chelator, e.g., tiuxetan, which allows for the antibody to be conjugated to a radioisotope.

Alternatively or in addition, the moiety or agent may be a tag, for example a fluorescent tag, also known as fluorescent label or fluorescent probe. Ethidium bromide, fluorescein and green fluorescent protein are common tags.

Also encompassed by the third aspect are conjugates comprising a therapeutic moiety or a therapeutic agent. The therapeutic moiety or a therapeutic agent may be a cytokine or CD80, which binds to CD28 resulting in a costimulatory signal in the T cell response. The therapeutic moiety or a therapeutic agent may also be a cytotoxin or a drug (e.g., an immunosuppressant). Immunoconjugates which include one or more cytotoxins are referred to as "immunotoxins". A cytotoxin or cytotoxic agent includes any agent that is detrimental to and, in particular, kills cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Suitable therapeutic agents for forming immunoconjugates of the third aspect include, but are not limited to, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin, bleomycin, sulfate, carmustine, chlorambucil, cyclophosphamide or ricin A.

The antibody conjugates of the third aspect can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *Pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "*Monoclonal Antibodies For Immunotargeting Of Drugs In Cancer Therapy*", in Monoclonal Antibodies And Cancer Therapy, Reisfeld et al. (eds.), pp. 243-56 (Alan R. Liss, Inc. 1985); Hellstrom et al., "*Antibodies For Drug Delivery*", in Controlled Drug Delivery (2nd Ed.), Robinson et al. (eds.), pp. 623-53 (Marcel Dekker, Inc. 1987); Thorpe, "*Antibody Carriers Of Cytotoxic Agents In Cancer Therapy: A Review*", in Monoclonal Antibodies '84: Biological And Clinical Applications, Pinchera et al. (eds.), pp. 475-506 (1985); "*Analysis, Results, And Future Prospective Of The Therapeutic Use Of Radiolabeled Antibody In Cancer Therapy*", in Monoclonal Antibodies For Cancer Detection And Therapy, Baldwin et al. (eds.), pp. 303-16 (Academic Press 1985), and Thorpe et al., "*The Preparation And Cytotoxic Properties Of Antibody-Toxin Conjugates*", Immunol. Rev., 62: 119-58 (1982). The moiety, e.g., the therapeutic moiety, or the agent of the conjugate may be conjugated to the antibody by a linker sequence. Suitable linker sequences are known to the skilled person.

In a fourth aspect, there is provided a multimer, comprising at least two antibodies of the first aspect or at least two conjugates of the third aspect or a mixture of one or more antibodies of the first aspect and one or more conjugates of the third aspect. In one embodiment, the multimer comprising 4 to 8 antibodies of the first aspect or 4 to 8 conjugates of the third aspect. The antibodies or conjugates of the multimer of these aspects may be linked to each other by peptides. Multimers of the fourth aspect are characterized by an increased number of antigen binding sites to PD-1.

Accordingly, encompassed are a large variety of antibody conjugates, bispecific and multispecific molecules, and fusion proteins, all of which bind to PD-1 expressing cells and which can be used to target other molecules to such cells.

VI. Nucleic Acids Encoding an Antibody

In a fifth aspect the present disclosure also relates to nucleic acids or nucleic acid molecules comprising genes or nucleic acid sequences encoding antibodies or parts thereof, e.g., an antibody chain, as described herein, e.g., an antibody heavy chain of an antibody having the ability to bind to PD-1 as described herein with regard to the first aspect and/or an antibody light chain of an antibody having the ability to bind to PD-1 as described herein with regard to the first aspect.

The term "nucleic acid molecule" or "nucleic acid", as used herein, is intended to include deoxyribonucleic acid (DNA) or ribonucleic acid (RNA) molecules, e.g., in vitro transcribed RNA (IVT RNA). Nucleic acids, as used herein, include genomic DNA, cDNA, mRNA, recombinantly produced and chemically synthesized molecules. According to the fourth aspect, a nucleic acid may be present as a single-stranded or double-stranded and linear or covalently circularly closed molecule. For example, the nucleic acid is double-stranded DNA. A nucleic can be employed for introduction into, i.e. transfection of, cells, for example, in the form of RNA which can be prepared by in vitro transcription from a DNA template. The RNA can moreover be modified before application by stabilizing sequences, capping, and polyadenylation.

As used herein, the term "nucleic acid encoding" means that nucleic acid, if present in the appropriate environment, preferably within a cell, can be expressed to produce a protein or peptide it encodes.

The nucleic acids according to the fifth aspect can be isolated. The term "isolated nucleic acid" as used herein means that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid which is available for manipulation by recombinant DNA techniques.

In one embodiment of the fifth aspect, the nucleic acid, e.g., the RNA, is associated with at least one agent having a stabilizing effect on the nucleic acid. The stabilizing effect can comprise protection from RNA degradation. In one embodiment of this aspect, the at least one agent forms a complex with and/or encloses said RNA. In one embodiment the at least one agent comprises at least one agent selected from the group consisting of an RNA-complexing lipid, an RNA complexing polymer and an RNA-complexing peptide or protein. For example, the at least one agent selected from at least one out of the group consisting of polyethyleneimine, protamine, a poly-L-lysine, a poly-L-arginine and a histone.

Nucleic acids may, according to the fifth aspect, be present alone or in combination with other nucleic acids, which may be homologous or heterologous. In preferred embodiments, a nucleic acid is functionally linked to expression control sequences which may be homologous or heterologous with respect to said nucleic acid. The term "homologous" means that a nucleic acid is also functionally linked to the expression control sequence naturally and the term "heterologous" means that a nucleic acid is not functionally linked to the expression control sequence naturally.

A nucleic acid, such as a nucleic acid expressing RNA and/or protein or peptide, and an expression control sequence are "functionally" linked to one another, if they are covalently linked to one another in such a way that expression or transcription of said nucleic acid is under the control or under the influence of said expression control sequence. If the nucleic acid is to be translated into a functional protein, then, with an expression control sequence functionally linked to a coding sequence, induction of said expression control sequence results in transcription of said nucleic acid, without causing a frame shift in the coding sequence or said coding sequence not being capable of being translated into the desired protein or peptide.

The term "expression control sequence" as used herein comprises promoters, ribosome binding sites, enhancers and other control elements which regulate transcription of a gene or translation of a mRNA. In particular embodiments, the expression control sequences can be regulated. The exact structure of expression control sequences may vary as a function of the species or cell type, but generally comprises 5'-untranscribed and 5'- and 3'-untranslated sequences (5'-UTR; 3'-UTR) which are involved in initiation of transcription and translation, respectively, such as TATA box, capping sequence, CAAT sequence, and the like. More specifically, 5'-untranscribed expression control sequences comprise a promoter region which includes a promoter sequence for transcriptional control of the functionally linked nucleic acid. Expression control sequences may also comprise enhancer sequences or upstream activator sequences. Expression control sequences or regulatory sequences can be homologous or heterologous with respect to the nucleic acid.

The term "promoter" or "promoter region" as used herein relates to a nucleic acid sequence which is located upstream (5') to the nucleic acid sequence being expressed and controls expression of the sequence by providing a recognition and binding site for RNA-polymerase. The "promoter region" may include further recognition and binding sites for further factors which are involved in the regulation of transcription of a gene. A promoter may control the transcription of a prokaryotic or eukaryotic gene. Furthermore, a promoter may be "inducible" and may initiate transcription in response to an inducing agent or may be "constitutive" if transcription is not controlled by an inducing agent. A gene which is under the control of an inducible promoter is not expressed or only expressed to a small extent if an inducing agent is absent. In the presence of the inducing agent the gene is switched on or the level of transcription is increased. This is mediated, in general, by binding of a specific transcription factor.

Promoters which are preferred according to the fifth aspect include promoters for SP6, T3 and T7 polymerase, human U6 RNA promoter, CMV promoter, and artificial hybrid promoters thereof (e.g., CMV) where a part or parts are fused to a part or parts of promoters of genes of other cellular proteins such as e.g., human GAPDH (glyceraldehyde-3-phosphate dehydrogenase), and including or not including (an) additional intron(s).

The term "expression" is used herein in its most general meaning and comprises the production of RNA or of RNA and protein/peptide. It also comprises partial expression of nucleic acids. Furthermore, expression may be carried out transiently or stably.

In one embodiment of the fifth aspect, the nucleic acid is RNA, more preferably in vitro transcribed RNA (IVT RNA) or synthetic RNA.

A nucleic, such as the RNA, can be employed for introduction into, i.e., transfection of, cells, in particular, in the form of RNA which can be prepared by in vitro transcription from a DNA template. The RNA can moreover be modified before application by stabilizing sequences, capping, and polyadenylation.

As used herein, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a β-D-ribofuranosyl group. The term "RNA" comprises double-stranded RNA, single-stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

The term "RNA" as used herein includes and preferably relates to "mRNA". The term "mRNA" means "messenger-RNA" and relates to a "transcript" which is generated by using a DNA template and encodes a peptide or polypeptide. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA. Typically, an mRNA comprises a 5'-UTR, a protein coding region, and a 3'-UTR. mRNA only possesses limited half-life in cells and in vitro. The mRNA may be generated by in vitro transcription from a DNA template. The in vitro transcription methodology is known to the skilled person. For example, there is a variety of in vitro transcription kits commercially available. As used herein, the term "transcription" relates to a process, wherein the genetic code in a DNA sequence is transcribed into RNA.

The stability and translation efficiency of RNA may be modified as required. RNA molecules with increased stability and improved translation efficiency may for example be advantageous for the RNA encoded antibodies of the present disclosure. For example, RNA may be stabilized and its translation increased by one or more modifications having stabilizing effects and/or increasing translation efficiency of RNA. Such modifications are described, for example, in PCT/EP2006/009448 incorporated herein by reference. In order to increase expression of the RNA used according to the present disclosure, it may be modified within the coding region, i.e., the sequence encoding the expressed peptide or protein, preferably without altering the sequence of the expressed peptide or protein, so as to increase the GC-content to increase mRNA stability and to perform a codon optimization and, thus, enhance translation in cells.

The term "modification" in the context of the RNA as used herein includes any modification of an RNA which is not naturally present in said RNA.

The RNA according to the fifth aspect may have modified ribonucleotides in order to increase its stability and/or decrease cytotoxicity. For example, in one embodiment, the RNA comprises 5-methylcytidine which is substituted partially or completely, preferably completely, for cytidine.

In some embodiments, one or more uridine in the RNA described herein is replaced by a modified nucleoside. In some embodiments, the modified nucleoside is a modified uridine. In some embodiments, the modified uridine replacing uridine is independently selected from pseudouridine (ψ), N1-methyl-pseudouridine (m1ψ), or 5-methyl-uridine (m5U). The uridines of the RNA can be substituted partially or completely, preferably completely.

In some embodiments, at least one RNA comprises a modified nucleoside in place of at least one uridine. In some embodiments, at least one RNA comprises a modified nucleoside in place of each uridine. In some embodiments, each RNA comprises a modified nucleoside in place of at least one uridine. In some embodiments, each RNA comprises a modified nucleoside in place of each uridine.

In one embodiment, the RNA comprises other modified nucleosides or comprises further modified nucleosides, e.g., modified cytidine. For example, in one embodiment, in the RNA 5-methylcytidine is substituted partially or completely, preferably completely, for cytidine. In one embodiment, the RNA comprises 5-methylcytidine and one or more selected from pseudouridine (ψ), N1-methyl-pseudouridine ($m^1\psi$), and 5-methyl-uridine ($m^5U$). In one embodiment, the RNA comprises 5-methylcytidine and N1-methyl-pseudouridine ($m^1\psi$). In some embodiments, the RNA comprises 5-methylcytidine in place of each cytidine and N1-methyl-pseudouridine ($m^1\psi$) in place of each uridine.

In one embodiment, the term "modification" relates to providing an RNA with a 5'-cap or 5'-cap analog. The term "5'-cap" refers to a cap structure found on the 5'-end of an mRNA molecule and generally consists of a guanosine nucleotide connected to the mRNA via an unusual 5' to 5' triphosphate linkage.

Providing an RNA with a 5'-cap or 5'-cap analog may be achieved by in vitro transcription of a DNA template in presence of said 5'-cap or 5'-cap analog, wherein said 5'-cap is co-transcriptionally incorporated into the generated RNA strand, or the RNA may be generated, for example, by in vitro transcription, and the 5'-cap may be attached to the RNA post-transcriptionally using capping enzymes, for example, capping enzymes of vaccinia virus.

In some embodiments, RNA according to the fifth aspect comprises a 5'-UTR and/or a 3'-UTR.

The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5'-end, upstream of the start codon of a protein-encoding region. A 5'-UTR is downstream of the 5'-cap (if present), e.g., directly adjacent to the 5'-cap. A 3'-UTR, if present, is located at the 3'-end, downstream of the termination codon of a protein-encoding region, but the term "3'-UTR" does preferably not include the poly-A sequence. Thus, the 3'-UTR is upstream of the poly-A sequence (if present), e.g., directly adjacent to the poly-A sequence.

In corporation of a 3'-UTR into the 3'-non translated region of an RNA molecule can result in an enhancement in translation efficiency. A synergistic effect may be achieved by incorporating two or more of such 3'-non translated regions. The 3'-non translated regions may be autologous or heterologous to the RNA into which they are introduced. In one particular embodiment the 3'-non translated region is derived from the human β-globin gene.

In order to increase stability and/or expression of the RNA according to the fifth aspect, it may be modified so as to be present in conjunction with a poly-A sequence, preferably having a length of 10 to 500, more preferably 30 to 300, even more preferably 65 to 200 and especially 100 to 150 adenosine residues. The poly-A sequence may be unmasked.

The term "poly(A) tail" or "poly-A sequence" as used herein relates to an uninterrupted or interrupted sequence of adenyl (A) residues which typically is located on the 3'-end of a RNA molecule and "unmasked poly-A sequence" means that the poly-A sequence at the 3'-end of an RNA molecule ends with an A of the poly-A sequence and is not followed by nucleotides other than A located at the 3'-end, i.e., downstream, of the poly-A sequence.

In some embodiments, a poly-A tail is attached during RNA transcription, e.g., during preparation of in vitro transcribed RNA, based on a DNA template comprising repeated dT nucleotides (deoxythymidylate) in the strand complementary to the coding strand. The DNA sequence encoding a poly-A tail (coding strand) is referred to as poly(A) cassette.

In some embodiments, the poly(A) cassette present in the coding strand of DNA essentially consists of dA nucleotides, but is interrupted by a random sequence of the four nucleotides (dA, dC, dG, and dT). Such random sequence may be 5 to 50, 10 to 30, or 10 to 20 nucleotides in length. Such a cassette is disclosed in WO 2016/005324 A1, hereby incorporated by reference. Any poly(A) cassette disclosed in WO 2016/005324 A1 may be used in the present disclosure. A poly(A) cassette that essentially consists of dA nucleotides, but is interrupted by a random sequence having an equal distribution of the four nucleotides (dA, dC, dG, dT) and having a length of e.g., 5 to 50 nucleotides shows, on DNA level, constant propagation of plasmid DNA in E. coli and is still associated, on RNA level, with the beneficial properties with respect to supporting RNA stability and translational efficiency is encompassed. Consequently, in some embodiments, the poly-A tail contained in an RNA molecule described herein essentially consists of A nucleotides, but is interrupted by a random sequence of the four nucleotides (A, C, G, U). Such random sequence may be 5 to 50, 10 to 30, or 10 to 20 nucleotides in length.

In this context, "essentially consists of" means that most nucleotides in the poly-A tail, typically at least 75%, at least 80%, at least 85%, at least 90%, at least 95%, at least 96%, at least 97%, at least 98%, or at least 99% by number of nucleotides in the poly-A tail are A nucleotides, but permits that remaining nucleotides are nucleotides other than A nucleotides, such as U nucleotides (uridylate), G nucleotides (guanylate), or C nucleotides (cytidylate). In this context, "consists of" means that all nucleotides in the poly-A tail, i.e., 100% by number of nucleotides in the poly-A tail, are A nucleotides. The term "A nucleotide" or "A" refers to adenylate.

In some embodiments, no nucleotides other than A nucleotides flank a poly-A tail at its 3'-end, i.e., the poly-A tail is not masked or followed at its 3'-end by a nucleotide other than A.

A combination of the above described modifications, i.e., incorporation of a poly-A sequence, unmasking of a poly-A sequence and incorporation of one or more 3'-non translated regions, has a synergistic influence on the stability of RNA and increase in translation efficiency.

The term "stability" of RNA relates to the "half-life" of RNA. "Half-life" relates to the period of time which is needed to eliminate half of the activity, amount, or number of molecules. In the context as used herein, the half-life of an RNA is indicative for the stability of said RNA. The half-life of RNA may influence the "duration of expression" of the RNA. It can be expected that RNA having a long half-life will be expressed for an extended time period.

Of course, if according to the present disclosure it is desired to decrease stability and/or translation efficiency of RNA, it is possible to modify RNA so as to interfere with the function of elements as described above increasing the stability and/or translation efficiency of RNA.

The term "expression" is used herein its most general meaning and comprises the production of RNA and/or peptides, polypeptides or proteins, e.g., by transcription and/or translation. With respect to RNA, the term "expression" or "translation" relates in particular to the production of peptides, polypeptides or proteins. It also comprises partial expression of nucleic acids.

Moreover, expression can be transient or stable. According to the present disclosure, an antibody is expressed in a cell if the antibody can be detected in the cell or a lysate thereof by conventional techniques for protein detection such as techniques using antibodies specifically binding to the PD-1 antibody.

In the context as used herein, the term "transcription" relates to a process, wherein the genetic code in a DNA sequence is transcribed into RNA. Subsequently, the RNA may be translated into protein. As used herein, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are encompassed by the term "vector". According to the present disclosure, the RNA used preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

The term "translation" as used herein relates to the process in the ribosomes of a cell by which a strand of messenger RNA directs the assembly of a sequence of amino acids to make a peptide, polypeptide or protein.

Terms such as "RNA capable of expressing" and "RNA encoding" are used interchangeably herein and with respect to a particular peptide or polypeptide mean that the RNA, if present in the appropriate environment, preferably within a cell, can be expressed to produce said peptide or polypeptide. Preferably, RNA according to the fifth aspect is able to interact with the cellular translation machinery to provide the peptide or polypeptide it is capable of expressing.

Terms such as "transferring", "introducing" or "transfecting" are used interchangeably herein and relate to the introduction of nucleic acids, in particular exogenous or heterologous nucleic acids, in particular RNA into a cell. According to the present disclosure, the cell can form part of an organ, a tissue and/or an organism. According to the present disclosure, the administration of a nucleic acid is either achieved as naked nucleic acid or in combination with an administration reagent. Preferably, administration of nucleic acids is in the form of naked nucleic acids. Preferably, the RNA is administered in combination with stabilizing substances such as RNase inhibitors. The present disclosure also envisions the repeated introduction of nucleic acids into cells to allow sustained expression for extended time periods.

In a sixth aspect, the present disclosure provides a vector comprising one or more of the nucleic acids of the fifth aspect.

Where appropriate, the vector of the sixth aspect can further comprise a promoter, which controls expression of the nucleic acid. The term "vector" is used herein in its most general meaning and comprises any intermediary vehicle for a nucleic acid which enables said nucleic acid, for example, to be introduced into prokaryotic and/or eukaryotic cells and, where appropriate, to be integrated into a genome. Vectors of this kind are preferably replicated and/or expressed in the cells. Vectors comprise plasmids, phagemids, bacteriophages or viral genomes such as adenoviral or baculoviral vectors, cosmids or other vectors e.g., conventionally in genetic engineering, but also liposomes. Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments. The term "plasmid" as used herein generally relates to a construct of extrachromosomal genetic material, usually a circular DNA duplex, which can replicate independently of chromosomal DNA.

The vector of the sixth aspect may comprise further genes such as marker genes which allow for the selection of the vector in a suitable host cell and under suitable conditions. Furthermore, the vector may comprise expression control elements allowing proper expression of the coding regions in suitable hosts. Such control elements are known to the skilled artisan and may include a promoter, a splice cassette, and a translation initiation codon. For example, the nucleic acid of the fifth aspect is functionally linked to the above expression control sequences allowing expression in eukaryotic or prokaryotic cells. Control elements ensuring expression in eukaryotic or prokaryotic cells are well known to those skilled in the art. Methods for construction of nucleic acid molecules according to the fifth aspect, for construction of vectors comprising the above nucleic acid molecules, for introduction of the vectors into appropriately chosen host cells, for causing or achieving the expression are well-known in the art.

Vectors for cloning or for expression, using recombinant techniques, are known in the art, and comprise, e.g., plasmid-based expression vectors, adenovirus vectors, retroviral vectors or baculovirus vectors. Examples of vectors comprise pGEX, pET, pLexA, pBI, pVITRO, pVIVO, and pST, such as pST4.

The type of vector for expression of an antibody of the first aspect either can be a vector type in which the antibody heavy chain and light chain are present in different vectors or a vector type in which the heavy chain and light chain are present in the same vector.

In one embodiment of the sixth aspect, the vector is a multilamellar vesicle, an unilamellar vesicle, or a mixture thereof.

In one embodiment of the sixth aspect, the vector is a liposome. In one embodiment, the vector is a cationic liposome. The liposome or cationic liposome can comprise a phospholipid such as phosphatidylcholine and/or a sterol such as cholesterol. In one embodiment, the liposome or cationic liposome has a particle diameter in the range of from about 50 nm to about 200 nm.

In one embodiment of the sixth aspect, the vesicle, liposome or cationic liposome further comprises a ligand for site specific targeting. The said ligand is for example an antibody. In one embodiment, the ligand, e.g., the antibody is capable of binding to a cancer cell, in particular a cancer cell as described herein. In one embodiment, the vector releases the RNA at a tumor cell and/or enters a tumor cell. In one embodiment, the ligand, e.g., the antibody binds to a protein associated with the surface of a diseased cell such as a tumor cell. For example, the ligand or antibody may bind to an extracellular portion of the disease-associated antigen.

In one embodiment of the sixth aspect, the RNA of the fifth aspect may be present in RNA lipoplex particles. The RNA lipoplex particles and compositions comprising RNA lipoplex particles described herein are useful for delivery of RNA to a target tissue after parenteral administration, in particular after intravenous administration. The RNA lipoplex particles may be prepared using liposomes and mixing the liposomes with RNA. RNA lipoplex particles can, for example, be obtained by mixing the RNA with liposomes or with at least one cationic lipid for example by using an ethanol injection technique.

The term "ethanol injection technique" refers to a process, in which an ethanol solution comprising lipids is rapidly injected into an aqueous solution through a needle. This action disperses the lipids throughout the solution and promotes lipid structure formation, for example lipid vesicle formation such as liposome formation. Generally, the RNA lipoplex particles described herein are obtainable by adding RNA to a colloidal liposome dispersion. Using the ethanol injection technique, such colloidal liposome dispersion is, in one embodiment, formed as follows: an ethanol solution comprising lipids, such as cationic lipids like DOTMA and additional lipids, is injected into an aqueous solution under stirring. In one embodiment, the RNA lipoplex particles described herein are obtainable without a step of extrusion.

The term "extruding" or "extrusion" refers to the creation of particles having a fixed, cross-sectional profile. In particular, it refers to the downsizing of a particle, whereby the particle is forced through filters with defined pores.

RNA lipoplex particles may have an average diameter that in one embodiment ranges from about 200 nm to about 1000 nm, from about 200 nm to about 800 nm, from about 250 to about 700 nm, from about 400 to about 600 nm, from about 300 nm to about 500 nm, or from about 350 nm to about 400 nm. In an embodiment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm.

The RNA lipoplex particles can exhibit a polydispersity index less than about 0.5, less than about 0.4, or less than about 0.3. By way of example, the RNA lipoplex particles can exhibit a polydispersity index in a range of about 0.1 to about 0.3.

The term "polydispersity index" is used herein as a measure of the size distribution of an ensemble of particles, e.g., nanoparticles. The polydispersity index is calculated based on dynamic light scattering measurements by the so-called cumulant analysis.

A composition comprising the RNA lipoplex particles may comprise at least one buffer and/or a stabilizer and/or a chelating agent. For example, a stabilizer may avoid substantial loss of the product quality and, in particular, substantial loss of RNA activity during freezing, lyophilization, spray-drying or storage such as storage of the frozen, lyophilized or spray-dried composition. Chelating agents refer to chemical compounds that are capable of forming at least two coordinate covalent bonds with a metal ion, thereby generating a stable, water-soluble complex. Without wishing to be bound by theory, chelating agents reduce the concentration of free divalent ions, which may otherwise induce accelerated RNA degradation. Examples of suitable chelating agents include, without limitation, ethylenediaminetetraacetic acid (EDTA), a salt of EDTA, desferrioxamine B, deferoxamine, dithiocarb sodium, penicillamine, pentetate calcium, a sodium salt of pentetic acid, succimer, trientine, nitrilotriacetic acid, trans-diaminocyclohexanetetraacetic acid (DCTA), diethylenetriaminepentaacetic acid (DTPA), bis(aminoethyl)glycolether-N,N,N',N'-tetraacetic acid, iminodiacetic acid, citric acid, tartaric acid, fumaric acid, or a salt thereof.

Lyophilized or spray-dried compositions can be reconstituted before use. In an embodiment the stabilizer is a carbohydrate. The term "carbohydrate", as used herein refers to and encompasses monosaccharides, disaccharides, trisaccharides, oligosaccharides, and polysaccharides. In embodiments of the disclosure, the stabilizer is mannose, glucose, sucrose or trehalose. According to the present disclosure, the RNA lipoplex particle compositions may have a stabilizer concentration suitable for the stability of the composition, in particular for the stability of the RNA lipoplex particles and for the stability of the RNA.

The term "freezing" relates to the solidification of a liquid, usually with the removal of heat.

The term "lyophilizing" or "lyophilization" refers to the freeze-drying of a substance by freezing it and then reducing the surrounding pressure to allow the frozen medium in the substance to sublimate directly from the solid phase to the gas phase.

The term "spray-drying" refers to spray-drying a substance by mixing (heated) gas with a fluid that is atomized (sprayed) within a vessel (spray dryer), where the solvent from the formed droplets evaporates, leading to a dry powder.

The term "reconstitute" relates to adding a solvent such as water to a dried product to return it to a liquid state such as its original liquid state.

The composition comprising the RNA lipoplex particles can be in a liquid or a solid. Non-limiting examples of a solid include a frozen form or a lyophilized form.

In the context of the present disclosure, the term "particle" relates to a structured entity formed by molecules or molecule complexes. In one embodiment, the term "particle" relates to a micro- or nano-sized structure, such as a micro- or nano-sized compact structure.

The term "RNA lipoplex particle" as used herein relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In one embodiment, a RNA lipoplex particle is a nanoparticle.

As used in the present disclosure, "nanoparticle" refers to a particle comprising RNA and at least one cationic lipid and having an average diameter suitable for intravenous administration.

The term "average diameter" refers to the mean hydrodynamic diameter of particles as measured by dynamic light scattering (DLS) with data analysis using the so-called cumulant algorithm, which provides as results the so-called $Z_{average}$ with the dimension of a length, and the polydispersity index (PI), which is dimensionless (Koppel, D., J. Chem. Phys. 57, 1972, pp 4814-4820, ISO 13321). Here "average diameter", "diameter" or "size" for particles is used synonymously with this value of the $Z_{average}$.

In one embodiment, the nucleic acid of the fifth aspect or the vector of the sixth aspect comprises a nucleic acid sequence encoding an antibody chain as described in the first and aspect. For example, the nucleic acid sequence encoding an antibody or an antibody chain may comprise a nucleic acid sequence encoding an antibody as described herein, e.g., MAB-19-0202, MAB-19-0618), or a heavy chain or a light chain, of one of these antibodies.

The antibody chain can be a heavy chain (H chain=HC) or a light chain (L chain=LC), each preferably as described herein. In one embodiment, the H chain comprises a heavy chain variable region (VH) and a heavy chain constant region, wherein the heavy chain constant region can comprise a heavy chain $CH_1$ constant region or a combination of a heavy chain $CH_1$ constant region, a heavy chain $CH_2$ constant region and a heavy chain $CH_3$ constant region. In one embodiment, the $CH_1$ constant domain and the $CH_2$ constant domain can be connected by a hinge region positioned between the $CH_1$ constant domain and the $CH_2$ constant domain.

In one embodiment, the L chain comprises a light chain variable region (VL) and a light chain constant region, wherein the light chain constant region can be a CL kappa constant domain or a CL lambda constant domain. For example, the light chain constant region can have or comprise a sequence as set out in SEQ ID NO: 6 or is a variant thereof.

In one embodiment, the nucleic acid encoding an antibody or an antibody chain of the first aspect comprises a nucleic acid sequence encoding a heavy chain variable region (VH) comprising at least one of a HCDR1, HCDR2, and HCDR3 sequence as exemplified herein (SEQ ID NOs: 8-13 of the sequence listing, SYN). That is the nucleic acid of the fifth aspect can comprise a nucleic acid sequence encoding HCDR1, HCDR2 or HCDR3 sequence as exemplified herein or the nucleic aid can comprise a nucleic acid sequence encoding for a heavy chain variable region (VH) comprising any of the combination of the HCDR1, HCDR2 and HCDR3 sequence as defined herein. Preferred combinations of the individual HCDR1 to HCDR3 sequences are as specified above with regard to the respective amino acid sequences of the first aspect. This teaching applies accordingly to the nucleic acid sequences of the fifth aspect.

In one embodiment, the nucleic acid of the fifth aspect comprises a nucleic acid sequence encoding a light chain variable region (VL) comprising at least one of a LCDR1, LCDR2, and LCDR3 sequence as exemplified herein (SEQ ID NOs: 14-17 of the sequence listing, QAS). That is the nucleic acid can comprise a nucleic acid sequence encoding LCDR1, LCDR2 or LCDR3 sequence as exemplified herein or the nucleic aid can comprise a nucleic acid sequence encoding for a light chain variable region (VL) comprising any of the combination of the LCDR1, LCDR2 and LCDR3 sequence as defined herein. Preferred combinations of the individual LCDR1 to LCDR3 sequences are as specified above with regard to the respective amino acid sequences of the first aspect. This teaching applies accordingly to the nucleic acid sequences of the fifth aspect.

In one embodiment, the nucleic acid of the fifth aspect comprises a nucleic acid sequence encoding VH and VL sequences as exemplified herein (SEQ ID NOs: 18-21 of the sequence listing).

In one embodiment, there is provided a nucleic acid or a vector comprising a nucleic acid, such as RNA or an RNA-based vector, or a vector suitable for in vitro transcription, comprising a nucleic acid sequence encoding a heavy chain variable region (VH) and/or a light chain variable region (VL) of an antibody that binds to PD-1 according to the first aspect.

In one embodiment, a variant nucleic acid sequence comprises/encodes for one or more of the respective CDR1, CDR2 and CDR3 amino acid sequences as specified herein. That is, the variant nucleic acid sequence encoding a heavy chain variable region (VH) may comprise/encodes for one or more of a HCDR1, HCDR2 and HCDR3 amino acid sequence as specified herein, wherein for the specific combinations of the CDR sequences reference is made to the respective disclosure herein. For example, the variant nucleic acid sequence can comprise/encode for a HCDR1, HCDR2, and HCDR3 amino acid sequence as specified herein.

The variant nucleic acid sequence encoding a light chain variable region (VL) may comprise/encodes for one or more of a LCDR1, LCDR2 and LCDR3 amino acid sequence as specified herein, wherein for the specific combinations of the CDR sequences reference is made to the respective disclosure herein. For example, the variant nucleic acid sequence can comprise/encode for a LCDR1, LCDR2, and LCDR3 amino acid sequence as specified herein.

The variant nucleic acid sequence may encode for a heavy chain variable region (VH) or a light chain variable region (VL) capable of providing the same binding specificity and/or functionality provided by the heavy chain variable region (VH) or the light chain variable region (VL) of the parent sequence, respectively.

The nucleic acids of the fifth aspect or the vectors (such as RNA or RNA-based vectors) of the sixth aspect for generating anti-PD-1 antibody may be produced by an in vitro transcription method.

Such a method comprises a step of inserting a DNA sequence of a heavy chain variable region (VH) or a light chain variable region (VL), as defined hereinabove, into the IVT-vector (e.g., a pST4 vector) using standard cloning techniques. The vector may comprise a 5'-UTR as defined herein, a 3'-UTR as defined herein, a poly(A) tail as defined hereinabove, e.g., a poly (A) tail comprising of 30 adenine nucleotides, a linker (L) and further (A30LA70). In addition, the IVT vector may optionally comprise a nucleic acid sequence encoding for a secretory signal peptide, e.g., a secretory signal peptide as defined herein.

To generate templates for in vitro transcription, the plasmid DNAs can be linearized downstream of the poly(A) tail-encoding region using, e.g., a restriction endonuclease, thereby generating a template to transcribe mRNA, e.g., by using a T7 RNA polymerase.

During in vitro transcription, the RNA may be modified to minimize immunogenicity, and the RNA may be capped at its 5'-end.

The thus obtained, optionally capped, RNA is used to transfect host cells, e.g., NS0 cells, Sp2/0 cells, HEK293 cells or derivates thereof, such as HEK293T, HEK293T/17 and/or HEK293F, COS cells, Vero cells and/or HeLa cells. In one embodiment, the mammalian host cell is selected from HEK293, HEK293T and/or HEK293T/17 cells. For transfection, liposomes, e.g., as described hereinabove, may be used.

The transfected cells are used to express the antibodies or antibody chains or fragments thereof. In order to express both the H chain and the L chain of the anti-PD-1 antibody, the host cells are preferably transfected with both types of RNA, i.e., individual RNAs, each encoding the H chain and the L chain of the anti-PD-1 antibody.

The anti-PD-1 antibody can be produced intracellularly, in the periplasmic space, or can be directly secreted into the medium. If the antibody is produced intracellularly, the cells may be lysed afterwards and the cell debris is to be removed, e.g., by centrifugation or ultrafiltration. The skilled person is familiar with suitable methods for isolating intracellularly produced antibodies. The same applies for methods for isolating antibodies which are secreted to the periplasmic space. Where the antibody is secreted into the medium, e.g., by using a secretory signal peptide, supernatants from such expression systems may be first concentrated, e.g., by using a commercially available protein concentration filter. A protease inhibitor, e.g, PMSF may be included in any of the foregoing steps to inhibit proteolysis and antibiotics may be included to prevent the growth of contaminants. The anti-PD-1 antibodies prepared from the transfected host cells can be purified, e.g., by using chromatography, such as affinity chromatography, gel electrophoresis, flow cytometry and/or dialysis.

The teaching given herein with respect to specific nucleic acid and amino acid sequences, e.g., those shown in the sequence listing, is to be construed so as to also relate to modifications of said specific sequences resulting in sequences which are functionally equivalent to said specific sequences, e.g., amino acid sequences exhibiting properties identical or similar to those of the specific amino acid sequences and nucleic acid sequences encoding amino acid sequences exhibiting properties identical or similar to those of the amino acid sequences encoded by the specific nucleic acid sequences. One important property is to retain binding of an antibody to its target or to sustain the desired effector functions of an antibody. Preferably, a sequence modified with respect to a specific sequence, when it replaces the specific sequence in an antibody retains binding of said antibody to PD-1 and preferably functions of said antibody as described herein, e.g., inhibiting the immunosuppressive of PD-1 on cells expressing PD-1, CDC mediated lysis or ADCC mediated lysis.

For example, variants of nucleic acid and amino acid sequences, as described herein, encode or provide antibody or antigen-binding fragments, which provide at least one of the following properties:
  (i) being capable of binding, preferably specifically binding to PD-1, e.g., human PD-1;
  (ii) being capable of blocking binding of PD-1 to its ligand;
  (iii) being capable of binding to the same antigen, to which the parent antibody binds, preferably with an affinity that is sufficient to provide for diagnostic and/or therapeutic use; and/or
  (iv) being capable of providing reduced or depleted effector functions.

It will be appreciated by those skilled in the art that in particular the sequences of the CDR, hypervariable and variable regions can be modified without losing the ability to bind PD-1. For example, CDR regions will be either identical or highly homologous to the regions specified herein. By "highly homologous" it is contemplated that from 1 to 5, preferably from 1 to 4, such as 1 to 3 or 1 or 2 substitutions may be made in the CDRs. In addition, the hypervariable and variable regions may be modified so that they show substantial homology with the regions specifically disclosed herein.

The term "variant" as used herein also refers to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all mutants, splice variants, posttranslationally modified variants, conformations, isoforms, allelic variants, species variants, and species homologs, in particular those which are naturally occurring. The term "variant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible.

Amino acid addition variants comprise amino- and/or carboxy-terminal fusions of one or more amino acids, such as 1, 2, 3, 5, 10, 20, 30, 50, or more amino acids.

Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants.

Amino acid substitution variants are characterized by at least one residue in the sequence being removed and another residue being inserted in its place. Substitution of one amino acid for another may be classified as a conservative or non-conservative substitution. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. In the context of the present disclosure, a "conservative substitution" is a substitution of one amino acid with another amino acid having similar structural and/or chemical characteristics, such substitution of one amino acid residue for another amino acid residue of the same class as defined in any of the two tables above: for example, leucine may be substituted with isoleucine as they are both aliphatic, branched hydrophobes. Similarly, aspartic acid may be substituted with glutamic acid since they are both small, negatively charged residues. In one embodiment, conservative amino acid substitutions include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS:needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Needleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

With respect to nucleic acid molecules, the term "variant" includes degenerate nucleic acid sequences, wherein a degenerate nucleic acid as used herein is a nucleic acid that differs from a reference nucleic acid in codon sequence due to the degeneracy of the genetic code.

Furthermore, a "variant" of a given nucleic acid sequence as used herein includes nucleic acid sequences comprising single or multiple such as at least 2, at least 4, or at least 6 and preferably up to 3, up to 4, up to 5, up to 6, up to 10, up to 15, or up to 20 nucleotide substitutions, deletions and/or additions.

Preferably the degree of identity between a given nucleic acid sequence and a nucleic acid sequence which is a variant of said given nucleic acid sequence will be at least 70%, preferably at least 75%, preferably at least 80%, more preferably at least 85%, even more preferably at least 90% or most preferably at least 95%, 96%, 97%, 98% or 99%. The degree of identity is preferably given for a region of at least about 30, at least about 50, at least about 70, at least about 90, at least about 100, at least about 150, at least about 200, at least about 250, at least about 300, or at least about 400 nucleotides. In preferred embodiments, the degree of identity is given for the entire length of the reference nucleic acid sequence.

"Sequence identity" between two nucleic acid sequences indicates the percentage of nucleotides that are identical between the sequences.

The term "percentage identity" is intended to denote a percentage of nucleotides which are identical between the two sequences to be compared, obtained after the best alignment, this percentage being purely statistical and the differences between the two sequences being distributed randomly and over their entire length. Sequence comparisons between two nucleotide sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Needleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

The percentage identity is calculated by determining the number of identical positions between the two sequences being compared, dividing this number by the number of positions compared and multiplying the result obtained by 100 so as to obtain the percentage identity between these two sequences.

The terms "part", "fragment" and "portion" are used interchangeably herein and refer to a continuous or discontinuous fraction of a structure. With respect to a particular structure such as an amino acid sequence or protein or a nucleic acid sequence the terms "part", "fragment" and "portion" thereof may designate a continuous or a discontinuous fraction of said structure. Preferably, a "part", "fragment" and "portion" of a structure such as an amino acid sequence or a nucleic acid sequence preferably comprises, preferably consists of at least 10%, at least 20%, at least 30%, at least 40%, at least 50%, at least 60%, at least 70%, at least 80%, at least 85%, at least 90%, at least 92%, at least 94%, at least 96%, at least 98%, at least 99% of the entire structure or amino acid sequence or nucleic acid sequence. A portion, a part or a fragment of a structure preferably comprises one or more functional properties of said structure. For example, a portion, a part or a fragment of an epitope, peptide or protein is preferably immunologically equivalent to the epitope, peptide or protein it is derived from. If the portion, part or fragment is a discontinuous fraction said discontinuous fraction is preferably composed of 2, 3, 4, 5, 6, 7, 8, or more parts of a structure, each part being a continuous element of the structure. For example, a discontinuous fraction of an amino acid sequence may be composed of 2, 3, 4, 5, 6, 7, 8, or more, preferably not more than 4 parts of said amino acid sequence, wherein each part preferably comprises at least 5 continuous amino acids, at least 10 continuous amino acids, preferably at least 20 continuous amino acids, preferably at least 30 continuous amino acids of the amino acid sequence.

It is to be understood that the nucleic acids described herein also include nucleic acids modified for the sake of optimizing the codon usage in a particular host cell or organism. Differences in codon usage among organisms can lead to a variety of problems concerning heterologous gene expression. Codon optimization by changing one or more nucleotides of the original sequence can result in an optimization of the expression of a nucleic acid, in particular in optimization of translation efficacy, in a homologous or heterologous host in which said nucleic acid is to be expressed. For example, if nucleic acids derived from human and encoding constant regions and/or framework regions of antibodies are to be used, e.g., for preparing chimeric or humanised antibodies, it may be preferred to modify said nucleic acids for the sake of optimization of codon usage, in particular if said nucleic acids, optionally fused to heterologous nucleic acids such as nucleic acids derived from other organisms as described herein, are to be expressed in cells from an organism different from human such as mouse or hamster. For example, the nucleic acid sequences encoding human light and heavy chain constant regions, can be modified to include one or more, preferably, at least 1, 2, 3, 4, 5, 10, 15, 20 and preferably up to 10, 15, 20, 25, 30, 50, 70 or 100 or more nucleotide replacements resulting in an optimized codon usage but not resulting in a change of the amino acid sequence.

The term "genetic material" includes isolated nucleic acid, either DNA or RNA, a section of a double helix, a section of a chromosome, or an organism's or cell's entire genome, in particular its exome or transcriptome.

The term "mutation" refers to a change of or difference in the nucleic acid sequence (nucleotide substitution, addition or deletion) compared to a reference. A "somatic mutation" can occur in any of the cells of the body except the germ cells (sperm and egg) and therefore are not passed on to children. These alterations can (but do not always) cause cancer or other diseases. Preferably a mutation is a non-synonymous mutation. The term "non-synonymous mutation" refers to a mutation, preferably a nucleotide substitution, which does result in an amino acid change such as an amino acid substitution in the translation product.

The term "mutation" as used herein includes point mutations, Indels, fusions, chromothripsis and RNA edits. The term "Indel" as used herein describes a special mutation class, defined as a mutation resulting in a colocalized insertion and deletion and a net gain or loss in nucleotides. In coding regions of the genome, unless the length of an indel is a multiple of 3, they produce a frameshift mutation. Indels can be contrasted with a point mutation; where an Indel inserts and deletes nucleotides from a sequence, a point mutation is a form of substitution that replaces one of the nucleotides. The term "chromothripsis" as used herein refers to a genetic phenomenon by which specific regions of the genome are shattered and then stitched together via a single devastating event. The term "RNA edit" or "RNA editing" as used herein refers to molecular processes in which the information content in an RNA molecule is altered through a chemical change in the base makeup. RNA editing includes nucleoside modifications such as cytidine (C) to uridine (U) and adenosine (A) to inosine (I) deaminations, as well as non-templated nucleotide additions and insertions. RNA editing in mRNAs effectively alters the amino acid sequence of the encoded protein so that it differs from that predicted by the genomic DNA sequence.

According to the present disclosure, a "reference" may be used to correlate and compare the results obtained from a tumor specimen. Typically the "reference" may be obtained on the basis of one or more normal specimens, in particular specimens which are not affected by a cancer disease, either obtained from a patient or one or more different individuals, preferably healthy individuals, in particular individuals of the same species. A "reference" can be determined empirically by testing a sufficiently large number of normal specimens.

In a seventh aspect, there are provided cells or host cells comprising a nucleic acid of the fifth aspect or a vector of the sixth aspect.

Cells can be transfected with any carriers with which the nucleic acid of the fifth aspect, for example the RNA can be associated, e.g., by forming complexes with the RNA or forming vesicles in which the RNA is enclosed or encapsulated, resulting in increased stability of the RNA compared to naked RNA. Carriers useful according to the disclosure include, for example, lipid-containing carriers such as cationic lipids, liposomes, in particular cationic liposomes, and micelles, and nanoparticles, such as lipoplex particles. Cationic lipids may form complexes with negatively charged nucleic acids. Any cationic lipid may be used according to the disclosure.

Cells which can be transfected also comprise host cells, which will become recombinant. The term "recombinant host cell", as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "recombinant host cell" as used herein. The host cell can be prokaryotic and/or eukaryotic host cells. Into these host cells, an exogenous nucleic acid and/or a vector can be introduced. In one embodiment, the host cell is an eukaryotic host cell, preferably a mammalian host cell. In one embodiment, the mammalian host cell is a CHO (Chinese hamster ovary) cell, a derivate of the CHO cell line, such as CHO-K1 and CHO pro-3, or a lymphocytic cell. In one embodiment, the mammalian host cell is selected from mouse myeloma cells, such as NS0 and Sp2/0, HEK293 (human embryonic kidney) cells or derivates thereof, such as HEK293T, HEK293T/17 and/or HEK293F, COS and Vero cells (both green African monkey kidney), and/or HeLa (human cervical cancer) cells. In one embodiment, the mammalian host cell is selected from HEK293, HEK293T and/or HEK293T/17 cells. Further examples of host cells are microorganisms, such as *E. coli*, and fungi, such as yeast, e.g., *Saccharomyces cerevisiae* or filamentous fungi, such as *Neurospora* and *Aspergillus* hosts. Host cells and recombinant host cells include, for example, transfectomas, such as CHO cells, NS/0 cells, Sp2/0 cells, COS cells, Vero cells, HeLa cells, HEK293 cells, HEK293T cells, HEK293T/17 cells, and lymphocytic cells.

The host cells used to produce the antibodies as defined herein may be cultured in a variety of media, which are commercially available and well known to the skilled person. Any of these media may be supplemented as necessary with hormones and/or other growth factors.

In an eighth aspect, there is provided a virus comprising a nucleic acid of the fifth aspect or a vector of the sixth aspect.

Instead of providing/administering the nucleic acids by using carriers as include, for example, lipid-containing carriers such as cationic lipids, liposomes, in particular cationic liposomes, and micelles, and nanoparticles, such as lipoplex particles, according to the present disclosure the nucleic acids of interest can be provided/administered also by using recombinant host cells, preferably those as specified above, or recombinant viruses encoding the antibody or an antibody fragment derived from the antibody.

These viruses may be DNA or RNA viruses. Several viral vectors have shown promising results with regard to their potential to enhance immunotherapy of malignant diseases. Replication competent and replication incompetent viruses can be used, with the latter group being preferred. Herpes virus, adenovirus, vaccinia, reovirus, and New Castle Disease viruses are examples of preferred viruses useful according to the present disclosure. In one embodiment the virus or viral vector is selected from the group consisting of adenoviruses, adeno-associated viruses, pox viruses, including vaccinia virus and attenuated pox viruses, Semliki Forest virus, reoviruses, retroviruses, New Castle Disease viruses, Sindbis virus and Ty virus-like particles. Particular preference is given to adenoviruses and retroviruses. The retroviruses are typically replication-deficient (i.e., they are incapable of generating infectious particles).

Methods of introducing nucleic acids into cells in vitro or in vivo comprise transfection of nucleic acid calcium phosphate precipitates, transfection of nucleic acids associated with DEAE, transfection or infection with the above viruses carrying the nucleic acids of interest, liposome-mediated transfection, and the like. In particular embodiments, preference is given to directing the nucleic acid to particular cells. In such embodiments, a carrier used for administering a nucleic acid to a cell (e.g., a retrovirus or a liposome) may have a bound target control molecule. For example, a molecule such as an antibody specific for a surface membrane protein on the target cell or a ligand for a receptor on the target cell may be incorporated into or attached to the nucleic acid carrier. Preferred antibodies comprise antibodies which bind selectively a tumor antigen. If administration of a nucleic acid via liposomes is desired, proteins binding to a surface membrane protein associated with endocytosis may be incorporated into the liposome formulation in order to make target control and/or uptake possible. Such proteins comprise capsid proteins or fragments thereof which are specific for a particular cell type, antibodies to proteins which are internalized, proteins addressing an intracellular site, and the like.

Preferably, the introduction of RNA which encodes a peptide or polypeptide into a cell, in particular into a cell present in vivo, results in expression of said peptide or polypeptide in the cell. In particular embodiments, the targeting of the nucleic acids to particular cells is preferred. In such embodiments, a carrier which is applied for the administration of the nucleic acid to a cell (for example, a retrovirus or a liposome), exhibits a targeting molecule. For example, a molecule such as an antibody which is specific for a surface membrane protein on the target cell or a ligand for a receptor on the target cell may be incorporated into the nucleic acid carrier or may be bound thereto. In case the nucleic acid is administered by liposomes, proteins which bind to a surface membrane protein which is associated with endocytosis may be incorporated into the liposome formulation in order to enable targeting and/or uptake. Such proteins encompass capsid proteins of fragments thereof which are specific for a particular cell type, antibodies against proteins which are internalized, proteins which target an intracellular location etc.

It is to be understood that, unless indicated otherwise herein or clearly contradicted by context, that the teaching provided with regard to nucleic acids encoding an antibody under point VI herein is applicable accordingly to nucleic acids/polynucleotides encoding a peptide or protein comprising an epitope of an antigen. Spleen targeting RNA lipoplex particles, which may be beneficially used for expressing RNA in antigen presenting cells, are described in WO 2013/143683, herein incorporated by reference.

VII. Pharmaceutical Compositions

In a ninth aspect, the present disclosure provides a composition, e.g., a pharmaceutical composition, comprising one or a combination of antibodies, including the conjugates and/or multimers of the first, third and/or fourth aspect and/or comprising one or a combination of nucleic acids comprising a nucleic acid sequence encoding an antibody, including host cells or vectors comprising the said nucleic acid of the fifth, sixth and/or seventh aspect. The pharmaceutical compositions may be formulated with pharmaceutically acceptable carriers or diluents as well as any other known adjuvants and excipients in accordance with conventional techniques such as those disclosed in Remington: The Science and Practice of Pharmacy, 19th Edition, Gennaro, Ed., Mack Publishing Co., Easton, P A, 1995. In one embodiment, the compositions include a combination of multiple (e.g., two or more) isolated antibodies. In another embodiment, the compositions include a combination of multiple (e.g., two or more) nucleic acids, vectors or host cells.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for cardiovascular (e.g., intravenous or intraarterial), intramuscular, subcutaneous, parenteral, spinal or epidermal administration (e.g., by injection or infusion). Depending on the route of administration, the active compound, i.e., antibody, bispecific and multispecific molecule, nucleic acids, vectors, may be coated in a material to protect the compound from the action of acids and other natural conditions that may inactivate the compound.

A "pharmaceutically acceptable substance" refers to a substance that retains the desired biological activity of the parent compound and does not impart any undesired toxicological effects (see e.g., Berge, S. M., et al. (1977) J. Pharm. Sci. 66: 1-19).

The carrier can be a solvent or dispersion medium comprising, for example, water, ethanol, polyol (for example, glycerol, propylene glycol, and liquid polyethylene glycol, and the like), saline and aqueous buffer solutions, vegetable oils, such as olive oil, and injectable organic esters, such as ethyl oleate and suitable mixtures thereof. The proper fluidity can be maintained, for example, by the use of a coating such as lecithin, by the maintenance of the required particle size in the case of dispersion and by the use of surfactants.

The carrier or the composition of the ninth aspect can also comprise pharmaceutically acceptable salts. Examples of pharmaceutically acceptable salts that may be comprised include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The composition of the ninth aspect may also comprise antioxidants. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The compositions of the ninth aspect may also contain adjuvants such as preservatives, wetting agents, emulsifying agents and dispersing agents. Prevention of the presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, for example, sugars, polyalcohols such as mannitol, sorbitol, or sodium chloride in the composition. In addition, prolonged absorption of the injectable pharmaceutical form may be brought about by the inclusion of agents which delay absorption, for example, monostearate salts and gelatin.

Pharmaceutically acceptable carriers include sterile aqueous solutions or dispersions and sterile powders for the extemporaneous preparation of sterile injectable solutions or dispersions. The use of such media and agents for pharmaceutically active substances is known in the art. Except insofar as any conventional media or agent is incompatible with the active compound, use thereof in the pharmaceutical compositions of the ninth aspect is contemplated. Supplementary active compounds can also be incorporated into the compositions.

Pharmaceutically compositions typically must be sterile and stable under the conditions of manufacture and storage. The composition can be formulated as a solution, microemulsion, liposome, or other ordered structure suitable to high drug concentration.

In one embodiment of the ninth aspect, the pharmaceutical composition is formulated for parenteral administration, preferably for cardiovascular, in particular intravenous or intraarterial administration.

A composition of the ninth aspect can be administered by a variety of methods known in the art. As will be appreciated by the skilled artisan, the route and/or mode of administration will vary depending upon the desired results. The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Methods for the preparation of such formulations are generally known to those skilled in the art. See, e.g., Sustained and Controlled Release Drug Delivery Systems, J. R. Robinson, ed., Marcel Dekker, Inc., New York, 1978.

To administer a compound (e.g., an antibody or a nucleic acid or a vector or a combination of nucleic acids or vectors of the aforementioned aspects) by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) J. Neuroimmunol. 7: 27).

Sterile injectable solutions can be prepared by incorporating the active compound in the required amount in an appropriate solvent with one or a combination of ingredients enumerated above, as required, followed by sterilization microfiltration.

Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic effect to be achieved, and (b) the limitations inherent in the art of compounding such an active compound for the treatment of sensitivity in individuals.

Pharmaceutical formulations or compositions of the ninth aspect include those suitable for oral, nasal, topical (including buccal and sublingual), rectal, vaginal and/or parenteral administration. The formulations may conveniently be presented in unit dosage form and may be prepared by any methods known in the art of pharmacy. The amount of active ingredient to produce a single dosage form will vary depending upon the subject being treated, and the particular mode of administration. The amount of active ingredient to produce a single dosage form will generally be that amount of the composition which produces a therapeutic effect.

Dosage forms for the topical or transdermal administration of compositions of the ninth aspect include powders, sprays, ointments, pastes, creams, lotions, gels, solutions, patches and inhalants. The active compound may be mixed under sterile conditions with a pharmaceutically acceptable carrier, and with any preservatives or other adjuvants or excipients which may be required.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In one embodiment, the anti-PD-1 antibody is to be administered as protein, wherein the antibody can have been obtained from hybridomas, transfectomas or by in vitro transcription, as described herein. In one embodiment, the anti-PD-1 antibody is to be administered as one or more nucleic acids or as one or more vectors as defined herein, e.g., as RNA or liposomes comprising the RNA or one or more RNAs which encode for the antibody or a chain of the antibody or a fragment of such antibody or chain.

In one embodiment the antibodies of the first aspect are administered in crystalline form by subcutaneous injection, see, Yang et al. (2003) PNAS, 100 (12): 6934-6939.

When the compounds of the present disclosure are administered as pharmaceuticals, to humans and animals, they can be given alone or as a pharmaceutical composition comprising, for example, from about 0.01 percent to about ninety-nine percent of active ingredient, preferably from about 0.1 percent to about 90 percent, most preferably from about 1 percent to about 50 percent, in combination with a pharmaceutically acceptable carrier, preferably a pharmaceutically acceptable carrier as specified above. In addition, adjuvants and/or excipients, such as antioxidants or preservatives, may be comprised in addition.

Regardless of the route of administration selected, the compounds of the present disclosure, which may be used in a suitable hydrated form, and/or the pharmaceutical compositions of the ninth aspect, are formulated into pharmaceutically acceptable dosage forms by conventional methods known to those of skill in the art.

Pharmaceutical compositions can be administered with medical devices known in the art. For example, in a preferred embodiment, a pharmaceutical composition of the ninth aspect can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present disclosure include those described in: U.S. Pat. No. 4,487,603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system.

Many other such implants, delivery systems, and modules are known to those skilled in the art. In certain embodiments, the antibodies of the above aspects can be formulated to ensure proper distribution in vivo. For example, the blood-brain barrier (BBB) excludes many highly hydrophilic compounds. To ensure that the therapeutic compounds of the disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, and thus enhance targeted drug delivery (see, e.g., V. V. Ranade (1989) J. Clin. Pharmacol. 29: 685). Exemplary targeting moieties include folate or biotin (see, e.g., U.S. Pat. No. 5,416,016 to Low et al.); mannosides (Umezawa et al., (1988) Biochem. Biophys. Res. Commun. 153: 1038); antibodies (P. G. Bloeman et al. (1995) FEBS Lett. 357: 140; M. Owais et al. (1995) Antimicrob. Agents Chemother. 39: 180); and surfactant protein A receptor (Briscoe et al. (1995) Am. J. Physiol. 1233: 134).

In one embodiment, the therapeutic compounds of the disclosure are formulated in liposomes. In a more preferred embodiment, the liposomes include a targeting moiety. In a most preferred embodiment, the therapeutic compounds in the liposomes are delivered by bolus injection to a site proximal to the desired area, e.g., the site of a tumor. The composition must be fluid to the extent that easy syringability exists. It must be stable under the conditions of manufacture and storage and must be preserved against the contaminating action of microorganisms such as bacteria and fungi.

In a further embodiment, antibodies of the above aspects can be formulated to prevent or reduce their transport across the placenta. This can be done by methods known in the art, e.g., by PEGylation of the antibodies or by use of F(ab)2' fragments. Further references can be made to Cunningham-Rundles C, Zhuo Z, Griffith B, Keenan J. (1992), "*Biological activities of polyethylene-glycol immunoglobulin conjugates. Resistance to enzymatic degradation.*" J. Immunol. Methods, 152: 177-190; and to Landor M. (1995), "*Maternal-fetal transfer of immunoglobulins*", Ann. Allergy Asthma Immunol. 74: 279-283.

The composition must be sterile and fluid to the extent that the composition is deliverable by syringe. In addition to water, the carrier can be an isotonic buffered saline solution, ethanol, polyol (for example, glycerol, propylene glycol, and liquid polyethyelene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

VIII. Uses and Methods of the Invention

The antibodies, conjugates, multimers, nucleic acids, vectors, host cells and viruses of the above aspects have numerous therapeutic utilities involving the treatment of diseases involving cells expressing PD-1 or its ligands (PD-L1 and/or PD-L2).

Therefore, in a further aspect the present disclosure is concerned with the medical use of the antibodies, conjugates, multimers, nucleic acids, vectors, host cells, viruses or compositions of the above aspects. In this regard the disclosure provides antibodies, conjugates, multimers, nucleic acids, vectors, host cells, viruses or compositions, preferably pharmaceutical compositions, for use in the treatment of a disease, e.g., for use in tumor/cancer treatment. The expression "for use in the treatment of a disease, e.g., for use in tumor/cancer treatment" is used herein also replaceable with "for use as a medicament, especially in a method of treatment of cancer"; or the use of said products in the preparation of a pharmaceutical formulation for use in said method of treatment in humans (or more generically a subject in need thereof).

In following, when describing preferred uses and methods of the present disclosure, reference is made to the antibodies of the first aspect. But, it is to be understood that, unless indicated otherwise herein or clearly contradicted by context, that this teaching is also applicable to the other active agents comprising the antibodies or encoding the same, i.e., the conjugates of the third aspect, the multimers of the fourth aspect, nucleic acids of the fifth aspect, vectors of the sixth aspect, host cells of the seventh aspect, viruses of the eighth aspect or compositions of the ninth aspect.

For example, the antibodies or nucleic acids can be administered to cells in culture, e.g., in vitro or ex vivo, or to subjects, preferably human subjects, e.g., in vivo, to treat or prevent a variety of diseases such as those described herein.

In a tenth aspect, there is provided a pharmaceutical composition of the ninth aspect for use in a prophylactic and/or therapeutic treatment of a disease.

The term "disease" as used herein refers to any pathological state, including cancer or tumor, in particular those forms of tumors or cancer described herein, or autoimmune diseases.

By "tumor" or "cancer" is meant an abnormal group of cells or tissue that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be either benign or malignant. These terms as used herein also comprise metastases. As used herein, the terms "cancer" and "cancer disease" are used interchangeably with the terms "tumor" and "tumor disease".

By "metastasis" is meant the spread of cancer cells from its original site to another part of the body. The formation of metastasis is a very complex process and depends on detachment of malignant cells from the primary tumor, invasion of the extracellular matrix, penetration of the endothelial basement membranes to enter the body cavity and vessels, and then, after being transported by the blood, infiltration of target organs. Finally, the growth of a new tumor at the target site depends on angiogenesis. Tumor metastasis often occurs even after the removal of the primary tumor because tumor cells or components may remain and develop metastatic potential. In one embodiment, the term "metastasis" relates to "distant metastasis" which relates to a metastasis which is remote from the primary tumor and the regional lymph node system.

By "treat" is meant to administer a compound or composition to a subject in order to prevent or eliminate a disease, including reducing the size of a tumor or the number of tumors in a subject; arrest or slow a disease in a subject; inhibit or slow the development of a new disease in a subject; decrease the frequency or severity of symptoms and/or recurrences in a subject who currently has or who previously has had a disease; and/or prolong, i.e., increase the lifespan of the subject.

In particular, the term "treatment of a disease" includes curing, shortening the duration, ameliorating, preventing, slowing down or inhibiting progression or worsening, or preventing or delaying the onset of a disease or the symptoms thereof.

By "being at risk" is meant a subject, i.e., a patient, that is identified as having a higher than normal chance of developing a disease, in particular cancer, compared to the general population. In addition, a subject who has had, or who currently has, a disease, in particular cancer is a subject who has an increased risk for developing a disease, as such a subject may continue to develop a disease. Subjects who currently have, or who have had, a cancer also have an increased risk for cancer metastases.

In one embodiment of the tenth aspect, the disease is cancer growth and/or cancer metastasis. In one embodiment, the disease is characterized by comprising diseased cells or cancer cells which are characterized by expressing PD-L1 and/or being characterized by association of PD-L1 with their surface.

In one embodiment of the tenth aspect, the pharmaceutical composition of the ninth aspect is for use in a method of preventing or treating cancer or a tumor disease.

These tumors include solid tumors and/or hematological malignancies. Examples of tumor diseases which can be treated and/or prevented encompass all cancers and tumor entities which include, but are not limited to, carcinoma, lymphoma, blastoma, sarcoma, and leukemia. More particularly, examples of such cancers include bone cancer, blood cancer, lung cancer, liver cancer, pancreatic cancer, skin cancer, cancer of the head or neck, cutaneous or intraocular melanoma, uterine cancer, ovarian cancer, rectal cancer, cancer of the anal region, stomach cancer, colon cancer, breast cancer, prostate cancer, uterine cancer, carcinoma of the sexual and reproductive organs, Hodgkin's Disease (Hodgkin's lymphoma), cancer of the esophagus, cancer of the small intestine, cancer of the endocrine system, cancer of the thyroid gland, cancer of the parathyroid gland, cancer of the adrenal gland, sarcoma of soft tissue, cancer of the bladder, cancer of the kidney, renal cell carcinoma, carcinoma of the renal pelvis, neoplasms of the central nervous system (CNS), neuroectodermal cancer, spinal axis tumors, glioma, meningioma, and pituitary adenoma. These cancers may be in early, intermediate or advanced stages, e.g. metastasis. In one embodiment, the cancer to be treated is in an advanced stage.

Examples of cancers which are particularly susceptible for a PD-1 pathway blockade therapy include, but are not limited to, melanoma, including metastatic melanomas, lymphomas, including Hodgkin's lymphomas, lung cancer, including non-small cell lung cancer (NSCLC), for example advanced NSCLC, and small cell lung cancer, renal cell carcinoma, bladder cancer, breast cancer, including advanced triple negative breast cancer, gastric and gastroesophageal junction cancers, pancreatic adenocarcinoma, and ovarian cancer. In one embodiment of the tenth aspect, the cancer is selected from the group consisting of melanoma, lung cancer, renal cell carcinoma, bladder cancer, breast cancer, gastric and gastroesophageal junction cancers, pancreatic adenocarcinoma, ovarian cancer, kidney tumor, glioblastoma and lymphomas, preferably Hodgkin's lymphomas.

In one embodiment of the tenth aspect, the pharmaceutical composition of the ninth aspect is to be specifically delivered to, accumulated in and/or are retained in a target organ or tissue. In one embodiment, the vector or the virus releases the nucleic acid at the target organ or tissue and/or enters cells at the target organ or tissue. In one embodiment, the antibody is to be expressed in cells of the target organ or tissue.

In one embodiment of the tenth aspect, the treatment is a monotherapy or a combination therapy. Preferably, the combinatorial treatment is at least one treatment selected from the group consisting chemotherapy, molecular-targeted therapy, radiation therapy, and other forms of immune therapy. The term "immunotherapy" relates to a treatment involving a specific immune reaction.

The antibodies of the first aspect, conjugates of the third aspect, multimers of the fourth aspect, nucleic acids of the fifth aspect, vectors of the sixth aspect, host cells of the seventh aspect, viruses of the eighth aspect or compositions, preferably pharmaceutical compositions, of the ninth aspect are intended for use in the treatment of a disease in a subject in need thereof.

As used herein, the term "subject" is intended to include human and non-human animals which respond to the antibodies against PD-1. The term "non-human animal" includes all vertebrates, e.g., mammals and non-mammals, such as non-human primates, domesticated animals, such as sheep, dog, cat, cattle, horses, goats, chickens, amphibians, reptiles, etc., laboratory animals, such as mice, rats, rabbits, guinea pigs, etc. Preferred subjects include human patients having disorders that can be corrected or ameliorated by killing diseased cells and/or having a disease, preferably a disease as described herein. The terms "subject", "individual", "organism" or "patient" are used interchangeably.

The term "in vivo" relates to the situation in a subject.

In one embodiment of the tenth aspect, the subject is a human subject.

In an eleventh aspect, there is provided a method of treating or preventing a disease in a subject comprising administering to a subject at least one active agent, wherein the active agent is at least one selected from:
(i) an antibody of the first aspect;
(ii) a conjugate of the third aspect;
(iii) a multimer of the fourth aspect;
(iv) a nucleic acid of the fifth aspect or a combination of nucleic acids of the fifth aspect;
(v) a vector of the sixth aspect or a combination of vectors of the sixth aspect;
(vi) a host cell of the seventh aspect or a combination of host cells of the seventh aspect; and/or
(vii) a virus of the eighth aspect or a combination of viruses of the eighth aspect.

In one embodiment of the method of the eleventh aspect, a nucleic acid, vector, host cell or virus encoding a heavy chain of an antibody of the first aspect is administered in combination with another nucleic acid, vector host cell or virus encoding a light chain of an antibody of the first aspect.

In one embodiment of the method of the eleventh aspect, the nucleic acid, vector, host cell or virus to be administered can encode both a heavy chain and a light chain of an antibody of the first aspect.

In one embodiment of the method of the eleventh aspect, a pharmaceutical composition of the tenth aspect is administered to the subject.

In one embodiment of the method of the eleventh aspect, the subject has a diseased organ or tissue characterized by cells expressing PD-L1 and/or being characterized by association of PD-L1 with their surface.

In one embodiment of the method of the eleventh aspect, the disease is cancer growth and/or cancer metastasis.

In one embodiment of the method of the eleventh aspect, the method is for treating or preventing cancer growth and/or cancer metastasis in a subject that has or is at risk of developing cancers and/or cancer metastases.

In one embodiment of the method of the eleventh aspect, an effective amount of the active agent is provided. Preferably, the antibody is provided at a dose in the range of 0.1 to 20 mg/kg, more preferably in a range of 0.3 to 10 mg/kg, in one or multiple doses. The said dose may be provided for example every 1 to 4 weeks, still more preferably every 2 to 3 weeks, for example very 2 or 3 weeks.

In one embodiment of the method of the eleventh aspect, the cancer is selected from the group consisting of melanoma, lung cancer, renal cell carcinoma, bladder cancer, breast cancer, gastric and gastroesophageal junction cancers, pancreatic adenocarcinoma, ovarian cancer, kidney tumor, glioblastoma and lymphomas, preferably Hodgkin's lymphomas.

In one embodiment of the method of the eleventh aspect, the active agent or the pharmaceutical composition is administered into the cardiovascular system, preferably the active agent or the pharmaceutical composition is administered by intravenous or intraarterial administration such as administration into a peripheral vein. In one embodiment of the method, the active agent or the pharmaceutical composition are specifically delivered to, accumulate in and/or are retained in a target organ or tissue. In one embodiment of the method, the target organ or tissue is a cancer tissue, in particular a cancer tissue as specified herein. For example, the diseased organ or tissue can be characterized by cells expressing a disease-associated antigen and/or being characterized by association of a disease-associated antigen with their surface. The disease-associated antigen can be a tumor-associated antigen. The disease-associated antigen can be associated with the surface of a diseased cell such as a tumor cell. In one embodiment of the method, the vector, the host cell or the virus releases the nucleic acid at the target organ or tissue and/or enters cells at the target organ or tissue, preferably, wherein the antibody is expressed in cells of the target organ or tissue.

In one embodiment of the method of the eleventh aspect, the treatment is a monotherapy or a combination therapy. Preferably, the combinatorial treatment is at least one treatment selected from the group consisting of chemotherapy, molecular-targeted therapy, radiation therapy, and other forms of immune therapy. Other forms of immune therapy include vaccination e.g., RNA vaccination and/or may target other checkpoint inhibitors, thereby either inhibiting (antagonists) or activating/stimulating (agonists) the respective other checkpoint. Other checkpoint inhibitors which may be targeted include, but are not limited to CTLA4, PD-L1, TIM-3, KIR or LAG-3. Checkpoint activators which may be targeted by the second binding specificity include, but are not limited to CD27, CD28, CD40, CD122, CD137, OX40, GITR, or ICOS. For example: Preferred combinations of binding specificities include anti-PD1 and anti-PD-L1 or anti-PD-1 and anti-CTLA4. Alternatively or in addition, the immune therapy can provide an antiangiogenesis activity. For example, by targeting the vascular endothelial growth factor (VEGF) or its receptor VEGFR (for example VEGFR1, 2, 3). Alternatively or in addition, it may be capable of targeting PDGFR, c-Kit, Raf and/or RET.

In one embodiment of the method of the eleventh aspect, the treatment is a combination therapy, wherein the treatment comprises administering to the subject:
 (i) peptide or protein comprising an epitope for inducing an immune response against an antigen in the subject, or a polynucleotide encoding the peptide or protein; and
 (ii) at least one selected from an antibody of the first aspect, a conjugate of the third aspect, a multimer of the fourth aspect, a nucleic acid of the fifth aspect, a vector of the sixth aspect, a host cell of the seventh aspect, and/or a virus of the seventh aspect.

In one embodiment, the peptide or protein comprising an epitope for inducing an immune response against an antigen in the subject or the polynucleotide encoding the peptide or protein and the at least one active compound as specified in (ii) are administered sequentially. In one embodiment, the at least one active compound as specified in (ii) is administered following administration of the peptide or protein comprising an epitope for inducing an immune response against an antigen in the subject or the polynucleotide encoding the peptide or protein. In one embodiment, the at least one active compound as specified in (ii) is administered 6 hours or later, 12 hours or later or 24 hours or later following administration of the peptide or protein comprising an epitope for inducing an immune response against an antigen in the subject or the polynucleotide encoding the peptide or protein. In one embodiment, the at least one active compound as specified in (ii) is administered between 12 hours and 48 hours following administration of the peptide or protein comprising an epitope for inducing an immune response against an antigen in the subject or the polynucleotide encoding the peptide or protein.

In one embodiment of the method of the eleventh aspect, the method comprises administering to the subject an RNA encoding the peptide or protein comprising an epitope for inducing an immune response against an antigen in the subject.

As used herein, a sample may be any sample useful according to the present disclosure, in particular a biological sample such a tissue sample, including bodily fluids, and/or a cellular sample and may be obtained in the conventional manner such as by tissue biopsy, including punch biopsy, and by taking blood, bronchial aspirate, sputum, urine, feces or other body fluids. The term "biological sample" as used herein also includes fractions of biological samples.

A therapeutic effect in the treatments and uses discussed herein is preferably achieved through the functional properties of the antibodies of the first aspect to mediate killing of cells, e.g., by inhibiting the immunosuppressive signal of PD-1 on cells expressing PD-1, preferably by forming a complex of the antibody and PD-1 and/or by inducing an immune response, more preferably a T cell mediated immune response.

In one embodiment, the anti-PD-1 antibody is administered as protein, wherein the antibody can have been obtained from hybridomas, transfectomas or by in vitro transcription, as described herein. In one embodiment, the anti-PD-1 antibody is administered as one or more nucleic acids or as one or more vectors as defined herein, e.g., as RNA or liposomes comprising the RNA or one or more RNAs which encode for the antibody or a chain of the antibody or a fragment of such antibody or chain.

Antibodies of the first aspect can be initially tested for their binding activity associated with therapeutic or diagnostic uses in vitro. For example, the antibodies can be tested using bindings assays, reporter gene blockade assays, and/or T cell proliferation assays as described herein.

The antibodies of the first aspect can be used to elicit in vivo or in vitro one or more of the following biological activities: to bind to, preferably specifically bind to PD-1; to have binding properties to PD-1 on either cancer cells or normal cells; to have binding properties to PD-1 epitopes; to have binding properties to a non-human PD-1 variant, particularly PD-1 variants from mice, rats, rabbits and primates; to prevent or reduce the induction of inhibitory signals by PD-1; to inhibit the interaction/binding of ligands of PD-1 with PD-1, preferably of the ligand PD-L1, for example, inhibiting the binding of human PD-L1 to human PD-1; to inhibit the immunosuppressive signal of PD-L1 or PD-L2; to enhancing or initiating the immune function (through this mechanism), preferably by enhancing or initiating a T-cell mediated immune response; to inhibit cancer proliferation; and/or to deplete tumor cells and/or suppress cancer metastasis.

Combination strategies in cancer treatment may be desirable due to a resulting synergistic effect, which may be considerably stronger than the impact of a monotherapeutic approach. Therefore, it is also encompassed by the present disclosure that the antibodies of the first aspect, the conjugate of the third aspect, the a multimer of the fourth aspect the nucleic acid of the fifth aspect, the vector of the sixth aspect, the host cell host cell of the seventh aspect, the virus of the eighth aspect and/or the pharmaceutical compositions of the ninth aspect also can be administered in combination therapy, i.e., combined with other agents.

For example, the anti-PD-1 antibodies of the first aspect can be co-administered with one or other more therapeutic agents, e.g., a cytotoxic agent, a radiotoxic agent, antiangiogenic agent or and immunosuppressive agent to reduce the induction of immune responses against the antibodies of the first aspect. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as listed above. Co-administration of the anti-PD-1 antibodies of the first aspect with chemotherapeutic agents provides two anti-cancer agents which operate via different mechanisms yielding a cytotoxic effect to tumor cells. Such co-administration can solve problems due to development of resistance to drugs or a change in the antigenicity of the tumor cells which would render them unreactive with the antibody.

The antibodies or compositions of the above aspects can be used in conjunction with chemotherapy. Therapeutic agents for chemotherapy include, but are not limited to one or more chemotherapeutics, such as Taxol derivatives, taxotere, gemcitabin, antimetabolites (e.g., methotrexate, 6-mercaptopurine, 6-thioguanine, cytarabine, fludarabin, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin (Adriamycin)), antibiotics (e.g., dactinomycin (formerly actinomycin), bleomycin, mithramycin, and anthramycin (AMC), and anti-mitotic agents (e.g., vincristine and vinblastine). In a preferred embodiment, the therapeutic agent is a cytotoxic agent or a radiotoxic agent. In another embodiment, the therapeutic agent is an immunosuppressant. In yet another embodiment, the therapeutic agent is GM-CSF. In a preferred embodiment, the therapeutic agent is doxorubicin, cisplatin (Platinol), bleomycin, sulfate, carmustine, chlorambucil, cyclophosphamide (Cytoxan, Procytox, Neosar) or ricin A.

In another embodiment, antibodies of the first aspect may be administered in combination with chemotherapeutic agents, which preferably show therapeutic efficacy in patients suffering from cancers which are particularly susceptible for a PD-1 pathway blockade, such as melanoma, including metastatic melanomas, Hodgkin's lymphomas, lung cancer, including non-small cell lung cancer (NSCLC), for example advanced NSCLC, and small cell lung cancer, renal cell carcinoma, bladder cancer, advanced triple negative breast cancer, including advanced triple negative breast cancer, gastric and gastroesophageal junction cancers, pancreatic adenocarcinoma, or ovarian cancer.

In one embodiment, the antibodies or the pharmaceutical composition of the above aspects is administered with an immunotherapeutic agent. As used herein "immunotherapeutic agent" relates to any agent that may be involved in activating a specific immune response and/or immune effector function(s). The present disclosure contemplates the use of an antibody as an immunotherapeutic agent. Without wishing to be bound by theory, antibodies are capable of achieving a therapeutic effect against cancer cells through various mechanisms, including inducing apoptosis, block components of signal transduction pathways or inhibiting proliferation of tumor cells. In certain embodiments, the antibody is a monoclonal antibody. Non-limiting examples of anti-cancer antibodies and potential antibody targets (in brackets) which may be used in combination with the present disclosure include: Abagovomab (CA-125), Abciximab (CD41), Adecatumumab (EpCAM), Afutuzumab (CD20), Alacizumab pegol (VEGFR2), Altumomab pentetate (CEA), Amatuximab (MORAb-009), Anatumomab mafenatox (TAG-72), Apolizumab (HLA-DR), Arcitumomab (CEA), Atezolizumab (PD-L1), Bavituximab (phosphatidylserine), Bectumomab (CD22), Belimumab (BAFF), Bevacizumab (VEGF-A), Bivatuzumab mertansine (CD44 v6), Blinatumomab (CD 19), Brentuximab vedotin (CD30 TNFRSF8), Cantuzumab mertansin (mucin CanAg), Cantuzumab ravtansine (MUC1), Capromab pendetide (prostatic carcinoma cells), Carlumab (CNT0888), Catumaxomab (EpCAM, CD3), Cetuximab (EGFR), Citatuzumab bogatox (EpCAM), Cixutumumab (IGF-1 receptor), Claudiximab (Claudin), Clivatuzumab tetraxetan (MUC1), Conatumumab (TRAIL-R2), Dacetuzumab (CD40), Dalotuzumab (insulin-like growth factor I receptor), Denosumab (RANKL), Detumomab (B-lymphoma cell), Drozitumab (DR5), Ecromeximab (GD3 ganglioside), Edrecolomab (EpCAM), Elotuzumab (SLAMF7), Enavatuzumab (PDL192), Ensituximab (NPC-1C), Epratuzumab (CD22), Ertumaxomab (HER2/neu, CD3), Etaracizumab (integrin αvβ), Farletuzumab (folate receptor 1), FBTA05 (CD20), Ficlatuzumab (SCH 900105), Figitumumab (IGF-1 receptor), Flanvotumab (glycoprotein 75), Fresolimumab (TGF-β), Galiximab (CD80), Ganitumab (IGF-I), Gemtuzumab ozogamicin (CD33), Gevokizumab (ILIβ), Girentuximab (carbonic anhydrase 9 (CA-IX)), Glembatumumab vedotin (GPNMB), Ibritumomab tiuxetan (CD20), Icrucumab (VEGFR-1), Igovoma (CA-125), Indatuximab ravtansine (SDC1), Intetumumab (CD51), Inotuzumab ozogamicin (CD22), Ipilimumab (CD 152), Iratumumab (CD30), Labetuzumab (CEA), Lexatumumab (TRAIL-R2), Libivirumab (hepatitis B surface antigen), Lintuzumab (CD33), Lorvotuzumab mertansine (CD56), Lucatumumab (CD40), Lumiliximab (CD23), Mapatumumab (TRAIL-R1), Matuzumab (EGFR), Mepolizumab (IL5), Milatuzumab (CD74), Mitumomab (GD3 ganglioside), Mogamulizumab (CCR4), Moxetumomab pasudotox (CD22), Nacolomab tafenatox (C242 antigen), Naptumomab estafenatox (5T4), Namatumab (RON), Necitumumab (EGFR), Nimotuzumab (EGFR), Nivolumab (IgG4), Ofatumumab (CD20), Olaratumab (PDGF-R a), Onartuzumab (human scatter factor receptor kinase), Oportuzumab monatox (EpCAM), Oregovomab (CA-125), Oxelumab (OX-40), Panitumumab (EGFR), Patritumab (HER3), Pemtumoma (MUC1), Pertuzuma (HER2/neu), Pintumomab (adenocarcinoma antigen), Pritumumab (vimentin), Racotumomab (N-glycolylneuraminic acid), Radretumab (fibronectin extra domain-B), Rafivirumab (rabies virus glycoprotein), Ramucirumab (VEGFR2), Rilotumumab (HGF), Rituximab (CD20), Robatumumab (IGF-1 receptor), Samalizumab (CD200), Sibrotuzumab (FAP), Siltuximab (IL6), Tabalumab (BAFF), Tacatuzumab tetraxetan (alpha-fetoprotein), Taplitumomab paptox (CD 19), Tenatumomab (tenascin C), Teprotumumab (CD221), Ticilimumab (CTLA4), Tigatuzumab (TRAIL-R2), TNX-650 (IL13), Tositumomab (CD20), Trastuzumab (HER2/neu), TRBS07 (GD2), Tremelimumab (CTLA4), Tucotuzumab celmoleukin (EpCAM), Ublituximab (MS4A1), Urelumab (4-1 BB), Volociximab (integrin α5β1), Votumumab (tumor antigen CTAA 16.88), Zalutumumab (EGFR), and Zanolimumab (CD4).

For example, according to the tenth or eleventh aspect, the subject being administered the antibodies of the first aspect is additionally treated with one or more antibodies targeting another immune checkpoint. Immune checkpoint inhibitors activating the tumor defense by interrupting inhibitory interactions between antigen-presenting cells and T lymphocytes include, but are not limited to anti-PD-L1, anti-CTLA4, anti-TIM-3, anti-KIR and/or anti-LAG-3. Also encompassed are immunotherapeutic agents which stimulate activating checkpoints, such as CD27, CD28, CD40, CD122, CD137, OX40, GITR, or ICOS, i.e., for example anti-CD27, anti-CD28, anti-CD40, anti-CD122, anti-CD137, anti-OX40, anti-GITR, and/or anti-ICOS. Particularly preferred combinations therapies include, but are not limited to the combination of anti-PD1 and anti-PD-L1, thereby increasing the efficiency and the blockade of the PD1 pathway by targeting both components, or the combination of anti-PD-1 and anti-CTLA4 in order to prevent the blockade of both the PD1 pathway and the CTLA4 pathway. For example, combinations of binding specificities include anti-PD1 and anti-PD-L1 or anti-PD-1 and anti-CTLA4. Alternatively or in addition, the immune therapy can provide an antiangiogenesis activity. For example, by targeting the vascular endothelial growth factor (VEGF) or its receptor VEGFR (for example VEGFR1, 2, 3). Alternatively or in addition, it may be capable of targeting PDGFR, c-Kit, Raf and/or RET.

In another embodiment of the tenth or eleventh aspect, the subject being administered the antibody is additionally treated with an antiangiogenesis agent, including antibodies targeting vascular endothelial growth factor (VEGF) or its receptor VEGFR, and one or more chemical compounds inhibiting angiogenesis. Pretreatment with or parallel application of these drugs may improve the penetration of antibodies in bulk tumors.

For example, the antiangiogenesis agents may target VEGF. A suitbale VEGF inhibitor is Bevacizumab. Other examples include, but are not limited to, multikinase inhibitors that inhibits VEGFR1, 2, 3, PDGFR, c-Kit, Raf and/or RET (e.g., Sunitinib, Sorafenib, Pazopanib).

In another embodiment of the tenth or eleventh aspect, the subject being administered the antibody is additionally treated with a compound inhibiting growth factor receptor signaling including monoclonal antibodies binding to the EGFR receptor as well as chemical compounds inhibiting signaling initiated by the EGFR receptor.

In another embodiment of the tenth or eleventh aspect, such therapeutic agents include agents leading to the depletion or functional inactivation of regulatory T cells like low dose cyclophosphamide, and/or anti-IL2 or anti-IL2-receptor antibodies.

In still another embodiment tenth or eleventh aspect, the antibodies of the first or second aspect may be administered in combination with one or more antibodies selected from anti-CD25 antibodies, anti-EPCAM antibodies, and anti-CD40 antibodies.

In yet a further embodiment tenth or eleventh aspect, the antibodies of the first aspect may be administered in combination with an anti-C3b(i) antibody in order to enhance complement activation.

The antibodies of the first aspect can also be used in combination with one or more vaccines, wherein the vaccines are for stimulating the immune system against an antigen expressed by diseased cells such as tumor cells. For example, the antigen can be one or more of the tumor antigens as specified herein. The vaccination can be achieved by administering vaccine RNA, i.e., RNA encoding an antigen or epitope against which an immune response is to be induced. Alternatively, a peptide or protein comprising an epitope for inducing an immune response against an antigen can be administered.

Thus, in another embodiment of the tenth or eleventh aspect, the antibodies of the first aspect may be administered in combination with a vaccination therapy, i.e., in combination with at least one peptide or protein comprising an epitope for inducing an immune response against an antigen in the subject, or at least one polynucleotide/nucleic acid encoding the peptide or protein.

Accordingly, the present disclosure also provides a composition, preferably a pharmaceutical composition, comprising (i) peptide or protein comprising an epitope for inducing an immune response against an antigen in a subject, or a polynucleotide encoding the peptide or protein; and (ii) at least one selected from an antibody of the first aspect, a conjugate of the third aspect, a multimer of the fourth aspect, a nucleic acid of the fifth aspect, a vector of the sixth aspect, a host cell of the seventh, and/or a virus of the eighth aspect. In one embodiment, the composition comprises RNA encoding the peptide or protein comprising an epitope for inducing an immune response against an antigen in a subject.

The term "antigen" relates to an agent comprising an epitope against which an immune response or an immune effector molecule such as antibody is directed and/or is to be directed. The term "antigen" includes, in particular, proteins and peptides. In one embodiment, an antigen is a disease-associated antigen, such as a tumor antigen.

The term "disease-associated antigen" is used in its broadest sense to refer to any antigen associated with a disease which preferably contains an epitope that will stimulate a host's immune system to make a cellular antigen-specific immune response and/or a humoral antibody response against the disease. The disease-associated antigen, an epitope thereof, or an agent, such as peptide or protein inducing an immune response, targeting the disease-associated antigen or epitope may therefore be used for therapeutic purposes, in particular for vaccination. Disease-associated antigens may be associated with infection by microbes, typically microbial antigens, or associated with cancer, typically tumors.

In one embodiment, the antigen against which an immune response is to be directed (i.e., disease associated antigen) is a tumor antigen, preferably as specified herein. More preferably, the at least one tumor antigen is selected from the group consisting of NY-ESO-1 (UniProt P78358), Tyrosinase (UniProt P14679), MAGE-A3 (UniProt P43357), TPTE (UniProt P56180), KLK2 (UniProt P20151), PSA (KLK3) (UniProt P07288), PAP (ACPP, UniProt P15309), HOXB13 (UniProt Q92826), NKX3-1 (UniProt Q99801), HPV16 E6/E7 (UniProt P03126/P03129); HPV18 E6/E7 (UniProt P06463/P06788); HPV31 E6/E7 (UniProt P17386/P17387); HPV33 E6/E7 (UniProt P06427/P06429); HPV45 E6/E7 (UniProt P21735/P21736); HPV58 E6/E7 (UniProt P26555/P26557), PRAME (UniProt P78395), ACTL8 (UniProt Q9H568), CXorf61 (KKLC1, UniProt Q5H943), MAGE-A9B (UniProt P43362), CLDN6 (UniProt P56747), PLAC1 (UniProt Q9HBJ0), and p53 (UniProt P04637). The peptide or protein that is used for vaccination (i.e., vaccine antigen) may comprise said antigen or an epitope thereof. The vaccine antigen in one embodiment is administered in the form of RNA encoding the vaccine antigen. Methods of treatment involving these antigens may aim at the treatment of cancer, wherein the cancer cells are characterized by expression of the respective antigen. It is also possible to use antigens described herein, in particular NY-ESO-1, Tyrosinase, MAGE-A3, TPTE, KLK2, PSA (KLK3), PAP (ACPP), HOXB13, NKX3-1, HPV16 E6/E7; HPV18 E6/E7; HPV31 E6/E7; HPV33 E6/E7; HPV45 E6/E7; HPV58 E6/E7, PRAME, ACTL8, CXorf61 (KKLC1), MAGE-A9B, CLDN6, PLAC1, and p53, in combination. Methods of treatment involving such combination of antigens may aim at the treatment of cancer, wherein the cancer cells are characterized by expression of two or more antigens of the respective combination of antigens or wherein the cancer cells of a large fraction (e.g., at least 80%, at least 90% or even more) of patients having a certain cancer to be treated express one or more of the respective antigens of a combination. Such combination may comprise a combination of at least 2, at least 3, at least 4, at least 5, or at least 6 antigens. Thus, the combination may comprise 3, 4, 5, 6, 7, or 8 antigens. In this case, each antigen of the combination may be addressed by administering peptide or protein (i.e., vaccine antigen) comprising said antigen or an epitope thereof, or RNA encoding the peptide or protein. In one particularly preferred embodiment, each antigen of the combination is addressed by administering RNA encoding a peptide or protein comprising the antigen. Thus, vaccination may encompass the administration of different RNA molecules, wherein each of said different RNA molecules encodes a peptide or protein comprising an antigen of a combination of antigens. The different vaccine antigens or RNAs encoding different vaccine antigens of a combination may be administered in a mixture, sequentially, or a combination thereof.

In one embodiment, the antigen combination comprises, preferably consists of NY-ESO-1, Tyrosinase, MAGE-A3, and TPTE. This combination may be used for the treatment of cutaneous melanoma.

In one embodiment, the antigen combination comprises, preferably consists of KLK2, PSA (KLK3), PAP (ACPP), HOXB13, and NKX3-1. This combination may be used for the treatment of prostate cancer.

In one embodiment, the antigen combination comprises, preferably consists of PRAME, ACTL8, CXorf61 (KKLC1), MAGEA3, MAGE-A9B, CLDN6, NY-ESO-1, and PLAC1. This combination may be used for the treatment of breast cancer such as triple negative breast cancer, in particular estrogen receptor negative & progesteron receptor negative & HER2 negative breast cancer.

In one embodiment, the antigen combination comprises, preferably consists of CLDN6, p53, and PRAME. This combination may be used for the treatment of ovarian cancer, such as epithelial ovarian cancer.

The vaccine described herein may consist of one or more RNAs targeting one or more antigens expressed in a disease such as cancer. The active principle may be single-stranded mRNA that is translated into the respective protein upon entering antigen-presenting cells (APCs). In addition to wildtype or codon-optimized sequences encoding the antigen sequence, the RNA may contain one or more structural elements optimized for maximal efficacy of the RNA with respect to stability and translational efficiency (5'-cap, 5'-UTR, 3'-UTR, poly(A)-tail). In one embodiment, the RNA contains all of these elements. In one embodiment, beta-S-ARCA(D1) may be utilized as specific capping structure at the 5'-end of the RNA drug substances. As 5'-UTR sequence, the 5'-UTR sequence of the human alpha-globin mRNA, optionally with an optimized 'Kozak sequence' to increase translational efficiency may be used. As 3'-UTR sequence, two re-iterated 3'-UTRs of the human beta-globin mRNA placed between the coding sequence and the poly(A)-tail to assure higher maximum protein levels and prolonged persistence of the mRNA may be used. Alternatively, the 3'-UTR may be a combination of two sequence elements (FI element) derived from the "amino terminal enhancer of split" (AES) mRNA (called F) and the mitochondrial encoded 12S ribosomal RNA (called I). These were identified by an ex vivo selection process for sequences that confer RNA stability and augment total protein expression (see, WO 2017/060314, herein incorporated by reference). Furthermore, a poly(A)-tail measuring 110 nucleotides in length, consisting of a stretch of 30 adenosine residues, followed by a 10 nucleotide linker sequence (of random nucleotides) and another 70 adenosine residues may be used. This poly(A)-tail sequence was designed to enhance RNA stability and translational efficiency in dendritic cells.

Furthermore, sec (secretory signal peptide) and/or MITD (MHC class I trafficking domain) may be fused to the antigen-encoding regions in a way that the respective elements are translated as N- or C-terminal tag, respectively. Fusion-protein tags derived from the sequence encoding the human MHC class I complex (HLA-B51, haplotype A2, B27/B51, Cw2/Cw3), have been shown to improve antigen processing and presentation. Sec may correspond to the 78 bp fragment coding for the secretory signal peptide, which guides translocation of the nascent polypeptide chain into the endoplasmatic reticulum. MITD may correspond to the transmembrane and cytoplasmic domain of the MHC class I molecule, also called MHC class I trafficking domain. Antigens such as CLDN6 having their own secretory signal peptide and transmembrane domain may not require addition of fusion tags. Sequences coding for short linker peptides predominantly consisting of the amino acids glycine (G) and serine (S), as commonly used for fusion proteins may be used as GS/Linkers.

The antigen may be administered in combination with helper epitopes to break immunological tolerance. The helper epitopes may be tetanus toxoid-derived, e.g., P2P16 amino acid sequences derived from the tetanus toxoid (TT) of *Clostridium tetani*. These sequences may support to overcome self-tolerance mechanisms for efficient induction of immune responses to self-antigens by providing tumor-unspecific T-cell help during priming. The tetanus toxoid heavy chain includes epitopes that can bind promiscuously to MHC class II alleles and induce CD4$^+$ memory T cells in almost all tetanus vaccinated individuals. In addition, the combination of TT helper epitopes with tumor-associated antigens is known to improve the immune stimulation compared to the application of tumor-associated antigen alone by providing CD4$^+$ mediated T-cell help during priming. To reduce the risk of stimulating CD8$^+$ T cells, two peptide sequences known to contain promiscuously binding helper epitopes may be used to ensure binding to as many MHC class II alleles as possible, e.g., P2 and P16.

In one embodiment, a vaccine antigen comprises an amino acid sequence which breaks immunological tolerance. In one embodiment, the amino acid sequence which breaks immunological tolerance comprises helper epitopes, preferably tetanus toxoid-derived helper epitopes. The amino acid sequence which breaks immunological tolerance may be fused to the C-terminus of the vaccine sequence, e.g., antigen sequence, either directly or separated by a linker. Optionally, the amino acid sequence which breaks immunological tolerance may link the vaccine sequence and the MITD. In case the vaccine antigen is administered in the form of RNA encoding the vaccine antigen, the amino acid sequence which breaks immunological tolerance may be RNA encoded. In one embodiment, the antigen-targeting RNAs are applied together with RNA coding for a helper-epitope to boost the resulting immune response. This RNA coding for a helper-epitope may contain structural elements optimized for maximal efficacy of the RNA with respect to stability and translational efficiency (5'-cap, 5'-UTR, 3'-UTR, poly(A)-tail) described above for the antigen-encoding RNA. Furthermore, sec (secretory signal peptide) and/or MITD (MHC class I trafficking domain) may be fused to the helper-epitope-encoding regions in a way that the respective elements are translated as N- or C-terminal tag, respectively, as described above for the antigen-encoding RNA. In one embodiment, RNAs are co-administered with an additional RNA coding for the tetanus toxoid (TT) derived helper epitopes P2 and P16 (P2P16) in order to boost the resulting immune response.

The vaccine RNA may be complexed with liposomes to generate serum-stable RNA-lipoplexes (RNA$_{(LIP)}$) for intravenous (i.v.) administration. If a combination of different RNAs is used, the RNAs may be separately complexed with liposomes to generate serum-stable RNA-lipoplexes (RNA$_{(LIP)}$) for intravenous (i.v.) administration. RNA$_{(LIP)}$ targets antigen-presenting cells (APCs) in lymphoid organs which results in an efficient stimulation of the immune system.

In one embodiment, vaccine RNA is co-formulated as lipoplex particles with an RNA encoding an amino acid sequence which breaks immunological tolerance.

As used herein, "tumor antigen" or "cancer antigen" includes (i) tumor-specific antigens, (ii) tumor-associated antigens, (iii) embryonic antigens on tumors, (iv) tumor-specific membrane antigens, (v) tumor-associated membrane antigens, (vi) growth factor receptors, and (xi) any other type of antigen or material that is associated with a cancer.

Any tumor antigen (preferably expressed by a tumor cell) can be targeted by the vaccination disclosed herein. In one embodiment, the tumor antigen is presented by a tumor cell and thus can be targeted by T cells. Vaccination as disclosed herein preferably activates T cells specific for MHC presented tumor antigens. The tumor antigen may be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

The peptide and protein antigen can be 2-100 amino acids, including for example, at least 5 amino acids, at least 10 amino acids, at least 15 amino acids, at least 20 amino acids, at least 25 amino acids, at least 30 amino acids, at least 35 amino acids, at least 40 amino acids, at least 45 amino acids, or at least 50 amino acids in length. In some embodiments, a peptide can be greater than 50 amino acids. In some embodiments, the peptide can be greater than 100 amino acids.

The peptide or protein antigen can be any peptide or protein that can induce or increase the ability of the immune system to develop antibodies and T cell responses to a target antigen, e.g., disease-associated antigen.

In yet another embodiment, the antibodies of the first aspect may be administered in conjunction with radio-therapy and/or autologous peripheral stem cell or bone marrow transplantation.

Also encompassed by the present disclosure is a combination therapy including a composition of the ninth aspect with at least one anti-inflammatory agent or at least one immunosuppressive agent. In one embodiment such therapeutic agents include one or more anti-inflammatory agents, such as a steroidal drug or a NSAID (nonsteroidal anti-inflammatory drug). Preferred agents include, for example, aspirin and other salicylates, Cox-2 inhibitors, such as rofecoxib (Vioxx) and celecoxib (Celebrex), NSAIDs such as ibuprofen (Motrin, Advil), fenoprofen (Nalfon), naproxen (Naprosyn), sulindac (Clinoril), diclofenac (Voltaren), piroxicam (Feldene), ketoprofen (Orudis), diflunisal (Dolobid), nabumetone (Relafen), etodolac (Lodine), oxaprozin (Daypro), and indomethacin (Indocin). A combination therapy according to the present disclosure may also comprise a combination of (i) the antibodies of the first aspect with (ii) a vaccination treatment/therapy as specified above, and (iii) at least one anti-inflammatory agent or at least one immunosuppressive agent.

Bispecific and multispecific molecules of the above aspects can be used to interact with another immune checkpoint. Thereby either inhibiting or activating/stimulating the respective other checkpoint. Other checkpoint inhibitors which may be targeted include, but are not limited to CTLA4, PD-L1, TIM-3, KIR or LAG-3, checkpoint activators which may be targeted by the second binding specificity include, but are not limited to CD27, CD28, CD40, CD122, CD137, OX40, GITR, or ICOS. Preferred combinations of binding specificities include anti-PD1 and anti-PD-L1 or anti-PD-1 and anti-CTLA4.

Alternatively or in addition, bispecific or multispecific molecules of the above aspects can be used to provide an antiangiogenesis activity by targeting for example the vascular endothelial growth factor (VEGF) or its receptor VEGFR (for example VEGFR1, 2, 3). The second binding specifity may also be capable of targeting PDGFR, c-Kit, Raf and/or RET.

Alternatively or in addition, bispecific or multispecific molecules of the above aspects can be used to target a tumor antigen, preferably a tumor antigen as specified supra, which enables a specificity of the antibody of the first aspect for cancer cells.

For the uses and methods of the tenth and eleventh aspect actual dosage levels of the active ingredients, which may be comprised in a pharmaceutical composition, preferably a pharmaceutical composition as described above, may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved. In general, a suitable daily dose of a composition of the disclosure will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic composition may be administered as two, three, four, five, six or more sub-doses administered separately at appropriate intervals throughout the day, optionally, in unit dosage forms. While it is possible for a compound of the present disclosure to be administered alone, it is preferable to administer the compound as a pharmaceutical composition (formulation).

In one embodiment, the antibodies of the first aspect may be administered by infusion, preferably slow continuous infusion over a long period, such as more than 24 hours, in order to reduce toxic side effects. The administration may also be performed by continuous infusion over a period of from 2 to 24 hours, such as of from 2 to 12 hours. Such regimen may be repeated one or more times as necessary, for example, after 6 months or 12 months. The dosage can be determined or adjusted by measuring the amount of circulating anti-PD-1 antibodies upon administration in a biological sample by using anti-idiotypic antibodies which target the anti-PD-1 antibodies.

In yet another embodiment, the antibodies are administered by maintenance therapy, such as, e.g., once a week for a period of 6 months or more.

A "therapeutically effective dosage" for tumor therapy can be measured by objective tumor responses which can either be complete or partial. A complete response (CR) is defined as no clinical, radiological or other evidence of disease. A partial response (PR) results from a reduction in aggregate tumor size of greater than 50%. Median time to progression is a measure that characterizes the durability of the objective tumor response.

A "therapeutically effective dosage" for tumor therapy can also be measured by its ability to stabilize the progression of disease. The ability of a compound to inhibit cancer can be evaluated in an animal model system predictive of efficacy in human tumors. Alternatively, this property of a composition can be evaluated by examining the ability of the compound to inhibit cell growth or apoptosis by in vitro assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

The expression "for use in the treatment of a disease, e.g., for use in tumor/cancer treatment" is used herein also replaceable with "for use as a medicament, especially in a method of treatment of cancer"; or the use of said products in the preparation of a pharmaceutical formulation for use in said method of treatment in humans (or more generically a subject in need thereof).

Alternative to the use of the antibodies, conjugates, multimers, nucleic acids, vectors, host cells, viruses or compositions of the above aspects in tumor/cancer treatment, the antibodies, conjugates, multimers, nucleic acids, vectors, host cells, viruses or compositions of the above aspects can be used in the treatment of other diseases for which treatment an induction of an immune response is required. Accordingly, the antibodies, conjugates, multimers, nucleic acids, vectors, host cells, viruses or compositions of the above aspects may be effective on infection treatment. Infection treatment may include, for example, infections with human hepatitis virus (hepatitis B, Hepatitis C, hepatitis A, or hepatitis E), human retrovirus, human immunodeficiency virus (HIV1, HIV2), human T leukemia virus (HTLV1, HTLV2), or human lymphocytic cell type virus, simple herpes virus type 1 or 2, epstein-barr virus, cytomegalovirus, varicella-zoster virus, human herpesvirus including human herpesvirus 6, poliovirus, measles virus, rubella virus, Japanese encephalitis virus, mumps virus, influenza virus, adenovirus, enterovirus, rhinovirus, virus developing severely acute respiratory syndrome (SARS), ebola virus, west nile virus, or of these virus modified artificially.

Still further alternative to the use of the antibodies, conjugates, multimers, nucleic acids, vectors, host cells, viruses or compositions of the above aspects in tumor/cancer treatment, the antibodies, conjugates, multimers, nucleic acids, vectors, host cells, viruses or compositions of the above aspects can be used in the treatment of other diseases for which treatment a depletion of activated immune cells is required. Accordingly, the antibodies, conjugates, multimers, nucleic acids, vectors, host cells, viruses or compositions of the above aspects may be effective for the treatment of an autoimmune disease. Autoimmune diseases may include, for example, coeliac disease, inflammatory bowel disease, multiple sclerosis, rheumatoid arthritis and systemic lupus erythematosus.

Unless the context indicates otherwise, the disclosure with regard to preferred embodiments of the uses and methods of the disclosure disclosed above relative to the treatment of cancer, applies also for the treatment of infection diseases or autoimmune diseases.

Also within the scope of the present disclosure are kits comprising the antibodies, conjugates or multimers of the above aspects and instructions for use. The kit can further contain one or more additional reagents, such as antibodies targeting the anti-PD-1 antibody of the first aspect, enzyme substrates or other substrates, enzymes for obtaining a color development, etc.

Thus, in a twelfth aspect, there is provided kit for qualitative or quantitative detection of PD-1 in a sample, wherein the kit comprises an antibody of the first or second aspect or a conjugate of the forth aspect or a multimer of the fifth aspect.

The kit of the oh the twelfth aspect may be used for qualitative or quantitative detection of PD-1 in a sample.

In one embodiment, there are provided methods for detecting the presence of PD-1 antigen in a sample, or measuring the amount of PD-1 antigen, comprising contacting the sample, and a control sample, with an antibody which specifically binds to PD-1, the antibody being preferably an antibody as disclosed herein, under conditions that allow for formation of a complex between the antibody or portion thereof and PD-1. The formation of a complex is then detected, wherein a difference complex formation between the sample compared to the control sample is indicative for the presence of PD-1 antigen in the sample.

In still another embodiment, there is provided a method for detecting the presence or quantifying the amount of PD-1-expressing cells in vivo or in vitro. The method comprises (i) administering to a subject an antibody of the first aspect conjugated to a detectable marker; (ii) exposing the subject to a means for detecting said detectable marker to identify areas containing PD-1-expressing cells.

Methods as described above are useful, in particular, for diagnosing PD-1-related diseases and/or the localization of PD-1-related diseases. Preferably an amount of PD-1 in a sample which is higher than the amount of PD-1 in a control sample is indicative for the presence of a PD-1-related disease in a subject, in particular a human, from which the sample is derived.

In yet another embodiment conjugates of the third aspect can be used to target compounds (e.g., therapeutic agents, labels, etc.) to cells which have PD-1 expressed on their surface by linking such compounds to the antibody. Thus, the disclosure also provides methods for localizing ex vivo or in vitro cells expressing PD-1.

The above aspects described in detail by the figures and examples below, which are used only for illustration purposes and which are not be construed as limiting the scope of the invention. Owing to the description and the examples, further embodiments which are likewise included in the invention are accessible to the skilled worker.

The disclosure in particular relates to the following items:
1. An antibody having the ability to bind to PD-1, wherein the antibody comprises a heavy chain having a heavy chain constant region (CH) and a heavy chain variable region (VH), wherein the heavy chain constant region comprises an aromatic or non-polar amino acid at the position corresponding to position 234 in a human IgG1 heavy chain according to EU numbering and an amino acid other than glycine at the position corresponding to position 236 in a human IgG1 heavy chain according to EU numbering.

2. The antibody of item 1, wherein the antibody has a reduced or depleted Fc-mediated effector function.
3. The antibody of item 1 or 2, wherein the amino acid at the position corresponding to position 236 is a basic amino acid.
4. The antibody of item 2 or 3, wherein the basic amino acid is selected from the group consisting of lysine, arginine and histidine.
5. The antibody of any one of items 1 to 4, wherein the basic amino acid is arginine (G236R).
6. The antibody of any one of items 1 to 5, wherein the amino acid at the position corresponding to position 234 is an aromatic amino acid.
7. The antibody of item 6, wherein the aromatic amino acid is selected from the group consisting of phenylalanine, tryptophan and tyrosine.
8. The antibody of any one of items 1 to 5, wherein the amino acid at the position corresponding to position 234 is a non-polar amino acid.
9. The antibody of item 8, wherein the non-polar amino acid is selected from the group consisting of alanine, valine, leucine, isoleucine, proline, phenylalanine, methionine and tryptophan.
10. The antibody of item 8 or 9, wherein the non-polar amino acid is selected from the group consisting of isoleucine, proline, phenylalanine, methionine and tryptophan.
11. The antibody of any one of items 1 to 10, wherein the amino acid at the corresponding to position 234 is phenylalanine (L234F).
12. The antibody of any one of items 1 to 11, wherein the amino acid at the position corresponding to position 235 in a human IgG1 heavy chain according to EU numbering in said heavy chain constant region is an acidic amino acid.
13. The antibody of item 12, wherein the acidic amino acid is aspartate or glutamate.
14. The antibody of any one of items 1 to 13, wherein the amino acid at the position corresponding to position 235 is glutamate (L235E).
15. The antibody of any one of items 1 to 14, wherein the amino acids at the position corresponding to positions 234, 235 and 236 in the heavy chain constant region are a non-polar or an aromatic amino acid at position 234, an acidic amino acid at position 235 and a basic amino acid at position 236.
16. The antibody of any one of items 1 to 15, wherein the amino acid corresponding to position 234 is phenylalanine, the amino acid corresponding to position 235 is glutamate, and the amino acid corresponding to position 236 is arginine (L234F/L235E/G236R).
17. The antibody of any one of items 1 to 16, wherein the heavy chain constant region comprises a sequence having at least 70%, at least 75%, at least 80%, at least 85%, at least 90%, at least 95%, at least 97%, at least 99%, or 100% identity to the amino acid sequence of the heavy chain constant region sequence as set forth in SEQ ID NO: 2.
18. The antibody of any one of items 1 to 17, wherein the heavy chain constant region comprises the sequence as set forth in SEQ ID NO: 2 or 55.
19. The antibody of any one of items 1 to 18, wherein the isotype of the heavy chain constant region is IgG1.
20. The antibody of any one of items 1 to 19, wherein the heavy chain variable region (VH) comprises a complementarity-determining region 3 (HCDR3) having or comprising a sequence as set forth in SEQ ID NO: 8.
21. The antibody of any one of items 1 to 20, wherein the HCDR3 of the heavy chain variable region (VH) has or comprises a sequence as set forth in SEQ ID NO: 9.
22. The antibody of any one of items 1 to 21, wherein the heavy chain variable region (VH) comprises a complementarity-determining region 2 (HCDR2) having or comprising a sequence as set forth in SEQ ID NO: 10.
23. The antibody of item 22, wherein the HCDR2 of the heavy chain variable region (VH) has or comprises a sequence as set forth in SEQ ID NO: 11.
24. The antibody of any one of items 1 to 23, wherein the heavy chain variable region (VH) comprises a complementarity-determining region 1 (HCDR1) having or comprising a sequence selected from SYN.
25. The antibody of item 24, wherein the HCDR1 of the heavy chain variable region (VH) has or comprises a sequence as set forth in SEQ ID NO: 12.
26. The antibody of item 24, wherein the HCDR1 of the heavy chain variable region (VH) has or comprises a sequence as set forth in SEQ ID NO: 13.
27. The antibody of any one of items 1 to 26, wherein the antibody comprises a heavy chain variable region (VH) comprising a HCDR1, HCDR2 and HCDR3 sequence, wherein the HCDR1 sequence is selected from a sequence having or comprising SYN, SEQ ID NO: 12 or SEQ ID NO: 13, the HCDR2 sequence is selected from a sequence having or comprising SEQ ID NO: 10 or SEQ ID NO: 11, and the HCDR3 sequence is selected from a sequence having or comprising SEQ ID NO: 8 or SEQ ID NO: 9.
28. The antibody of any one of items 1 to 27, wherein the antibody comprises a heavy chain variable region (VH) comprising a HCDR1, HCDR2, and HCDR3 sequence, wherein the HCDR1, HCDR2 and HCDR3 sequence is or comprises SYN, SEQ ID NO: 10 and SEQ ID NO: 8, respectively.
29. The antibody of any one of items 1 to 28, wherein the antibody comprises a heavy chain variable region (VH) comprising a HCDR1, HCDR2, and HCDR3 sequence, wherein the HCDR1, HCDR2 and HCDR3 sequence is or comprises SEQ ID NO: 12, SEQ ID NO: 11 and SEQ ID NO: 8, respectively.
30. The antibody of any one of items 1 to 28, wherein the antibody comprises a heavy chain variable region (VH) comprising a HCDR1, HCDR2, and HCDR3 sequence, wherein the HCDR1, HCDR2 and HCDR3 sequence is or comprises SEQ ID NO: 13, SEQ ID NO: 10 and SEQ ID NO: 9, respectively.
31. The antibody of any one of items 1 to 30, wherein the antibody comprises a light chain having a light chain variable region (VL).
32. The antibody of any one of items 1 to 31, wherein the antibody comprises a light chain variable region (VL) comprising at least one of:
  a complementarity-determining region 3 (LCDR3) having or comprising a sequence as set forth in SEQ ID NO: 14;
  a complementarity-determining region 2 (LCDR2) having or comprising a sequence selected from QAS or a sequence as set forth in SEQ ID NO: 15; and/or
  a complementarity-determining region 1 (LCDR1) having or comprising a sequence as set forth in SEQ ID NO: 16 or in SEQ ID NO: 17.
33. The antibody of item 32, wherein the antibody comprises a light chain variable region (VL) comprising a LCDR1, LCDR2, and LCDR3 sequence, wherein the LCDR1 sequence is selected from a sequence having or comprising SEQ ID NO: 16 or SEQ ID NO: 17, the LCDR2 sequence is selected from a sequence having or comprising QAS or SEQ ID NO: 15, and the LCDR3 sequence is a sequence having or comprising SEQ ID NO: 14.
34. The antibody of any one of items 31 to 33, wherein the antibody comprises a light chain variable region (VL) comprising a LCDR1, LCDR2, and LCDR3 sequence, wherein the LCDR1, LCDR2 and LCDR3 sequence is or comprises SEQ ID NO: 16, QAS, and SEQ ID NO: 14, respectively.
35. The antibody of any one of items 31 to 34, wherein the antibody comprises a light chain variable region (VL) comprising a LCDR1, LCDR2, and LCDR3 sequence, wherein the LCDR1, LCDR2 and LCDR3 sequence is or comprises SEQ ID NO: 17, SEQ ID NO: 15, and SEQ ID NO: 14, respectively.
36. The antibody of any one of items 1 to 19, comprising the heavy chain variable region (VH) as specified in any one of items 20 to 30 and the light chain variable region (VL) as specified in any one items 31 to 35.
37. The antibody of any one of items 1 to 36, wherein the antibody comprises a heavy chain variable region (VH) comprising a HCDR1, HCDR2, and HCDR3 sequence and a light chain variable region (VL) comprising a LCDR1, LCDR2, and LCDR3 sequence, wherein the HCDR1, HCDR2 and HCDR3 sequence comprises or has the sequence SYN, as set forth in SEQ ID NO: 10 and SEQ ID NO: 8, respectively, and the LCDR1, LCDR2 and LCDR3 sequence comprises or has the sequence as set forth in SEQ ID NO: 16, QAS, and SEQ ID NO: 14, respectively.
38. The antibody of any one of items 1 to 36, wherein the antibody comprises a heavy chain variable region (VH) comprising a HCDR1, HCDR2, and HCDR3 sequence and a light chain variable region (VL) comprising a LCDR1, LCDR2, and LCDR3 sequence, wherein the HCDR1, HCDR2 and HCDR3 sequence comprises or has the sequence as set forth in SEQ ID NO: 12, SEQ ID NO: 11, and SEQ ID NO: 8, respectively, and the LCDR1, LCDR2 and LCDR3 sequence comprises or has the sequence as set forth in SEQ ID NO: 17, SEQ ID NO: 15, and SEQ ID NO: 14, respectively.
39. The antibody of any one of items 1 to 36, wherein the antibody comprises a heavy chain variable region (VH) comprising a HCDR1, HCDR2, and HCDR3 sequence and a light chain variable region (VL) comprising a LCDR1, LCDR2, and LCDR3 sequence, wherein the HCDR1, HCDR2 and HCDR3 sequence comprises or has the sequence as set forth in SEQ ID NO: 13, SEQ ID NO: 10, and SEQ ID NO: 9, respectively, and the LCDR1, LCDR2 and LCDR3 sequence comprises or has the sequence as set forth in SEQ ID NO: 16, QAS, and SEQ ID NO: 14, respectively.
40. The antibody of any one of items 1 to 39, wherein the antibody comprises a heavy chain variable region (VH) comprising a sequence having at least 70%, at least 75%, at least 80%, at least 85%, at least 90%, at least 95%, at least 97%, at least 99%, or 100% identity to the amino acid sequence of the VH sequence as set forth in SEQ ID NO: 18.
41. The antibody of any one of items 1 to 39, wherein the antibody comprises a heavy chain variable region (VH), wherein the VH comprises the sequence as set forth in SEQ ID NO: 18.
42. The antibody of any one of items 1 to 41, wherein the antibody comprises a light chain variable region (VL) comprising a sequence having at least 70%, at least 75%, at least 80%, at least 85%, at least 90%, at least 95%, at least 97%, at least 99%, or 100% identity to the amino acid sequence of the VL sequence as set forth in SEQ ID NO: 19.
43. The antibody of any one of items 1 to 42, wherein the antibody comprises a light chain variable region (VL), wherein the VL comprises the sequence as set forth in SEQ ID NO: 19.
44. The antibody of any one of items 1 to 43, wherein the antibody comprises a heavy chain variable region (VH) and a light chain variable region (VL), wherein the VH comprises or has the sequence as set forth in SEQ ID NO: 18 and the VL comprises or has the sequence as set forth in SEQ ID NO: 19.
45. The antibody of any one of items 1 to 39, wherein the antibody comprises a heavy chain variable region (VH) comprising a sequence having at least 70%, at least 75%, at least 80%, at least 85%, at least 90%, at least 95%, at least 97%, at least 99%, or 100% identity to the amino acid sequence of the VH sequence as set forth in SEQ ID NO: 20.
46. The antibody of item 45, wherein the antibody comprises a heavy chain variable region (VH), wherein the VH comprises the sequence as set forth in SEQ ID NO: 20.
47. The antibody of item 45, wherein the antibody comprises a heavy chain comprising the VH comprising the sequence as set forth in SEQ ID NO: 20, and the heavy chain constant region comprising the sequence as set forth in SEQ ID NO: 2 or SEQ ID NO: 55.
48. The antibody of item 45, wherein the antibody comprises a heavy chain comprising the sequence as set forth in SEQ ID NO: 56.
49. The antibody of any one of items 1 to 48, wherein the antibody comprises a light chain variable region (VL) comprising a sequence having at least 70%, at least 75%, at least 80%, at least 85%, at least 90%, at least 95%, at least 97%, at least 99%, or 100% identity to the amino acid sequence of the VL sequence as set forth in SEQ ID NO: 21.
50. The antibody of item 49, wherein the antibody comprises a light chain variable region (VL), wherein the VL comprises the sequence as set forth in SEQ ID NO: 21.
51. The antibody of item 49, wherein the antibody comprises a light chain comprising the VL comprising the sequence as set forth in SEQ ID NO: 21, and a light chain constant region comprising the sequence as set forth in SEQ ID NO: 6.
52. The antibody of item 49, wherein the antibody comprises a light chain comprising the sequence as set forth in SEQ ID NO: 57.
53. The antibody of any one of items 1 to 48, wherein the antibody comprises a heavy chain variable region (VH) and a light chain variable region (VL), wherein the VH comprises or has the sequence as set forth in SEQ ID NO: 20 and the VL comprises or has the sequence as set forth in SEQ ID NO: 21.
54. The antibody of any one of items 1 to 53, wherein the antibody comprises
    (i) a heavy chain having a heavy chain constant region (CH) comprising the sequence as set forth in SEQ ID NO: 2 or 55 and a heavy chain variable region (VH) comprising the sequence as set forth in SEQ ID NO: 20, and (ii) a light chain having a light chain constant region (CL) comprising the sequence as set forth in SEQ ID NO: 6 and a light chain variable region (VL) comprising the sequence as set forth in SEQ ID NO: 21.

55. The antibody of any one of items 1 to 53, wherein the antibody comprises a heavy chain having the sequence as set forth in SEQ ID NO: 56, and a light chain having the sequence as set forth in SEQ ID NO: 57.

56. The antibody of any one of items 1 to 55, which is a monoclonal, chimeric or humanized antibody or a fragment of such an antibody.

57. The antibody of any one of items 1 to 56, wherein binding of complement protein C1q to the constant region of the antibody is reduced compared to a corresponding wild-type antibody, preferably by at least 70%, at least 80%, at least 90%, at least 95%, at least 97% or 100%.

58. The antibody of any one of items 1 to 57, wherein binding to one or more of the IgG Fc-gamma receptors to the antibody is reduced compared to a corresponding wild-type antibody, preferably by at least 70%, at least 80%, at least 90%, at least 95%, at least 97% or 100%.

59. The antibody of item 58, wherein the one or more IgG Fc-gamma receptors are selected from at least one of Fc-gamma RI, Fc-gamma RII, and Fc-gamma RIII.

60. The antibody of item 58, wherein the IgG Fc-gamma receptor is Fc-gamma RI.

61. The antibody of any one of items 1 to 60, wherein the antibody is not capable of inducing Fc-gamma RI-mediated effector functions or wherein the induced Fc-gamma RI-mediated effector functions are reduced compared to a corresponding wild-type antibody, preferably by at least 70%, at least 80%, at least 90%, at least 95%, at least 97% or 100%.

62. The antibody of any one of items 1 to 61, wherein the antibody is not capable of inducing at least one of complement dependent cytotoxicity (CDC) mediated lysis, antibody dependent cellular cytotoxicity (ADCC) mediated lysis, apoptosis, homotypic adhesion and/or phagocytosis or wherein at least one of complement dependent cytotoxicity (CDC) mediated lysis, antibody dependent cellular cytotoxicity (ADCC) mediated lysis, apoptosis, homotypic adhesion and/or phagocytosis is induced in a reduced extent, preferably reduced by at least 70%, at least 80%, at least 90%, at least 95%, at least 97% or 100%.

63. The antibody of any one of items 1 to 62, wherein binding of neonatal Fc receptor (FcRn) to the antibody is unaffected, as compared to a corresponding wild-type antibody.

64. The antibody of any one of items 1 to 63, wherein PD-1 is human PD-1.

65. The antibody of item 64, wherein the PD-1 has or comprises the amino acid sequence as set forth in SEQ ID NO: 22 or SEQ ID NO: 23, or the amino acid sequence of PD-1 has at least 70%, at least 75%, at least 80%, at least 85%, at least 90%, at least 95%, at least 97%, at least 99%, or 100% identity to the amino acid sequence as set forth in SEQ ID NO: 22 or SEQ ID NO: 23, or is an immunogenic fragment thereof.

66. The antibody of any one of items 1 to 65, which binds to a native epitope of PD-1 present on the surface of living cells.

67. The antibody of any one of items 1 to 66, wherein the antibody is a multispecific antibody comprising a first antigen-binding region binding to PD-1 and at least one further antigen-binding region binding to another antigen.

68. The antibody of item 67, wherein the antibody is a bispecific antibody comprising a first antigen-binding region binding to PD-1 and a second antigen-binding region binding to another antigen.

69. The antibody of item 67 or 68, wherein the first antigen-binding region binding to PD-1 comprises the heavy chain variable region (VH) and/or the light chain variable region (VL) as set forth in any one of items 1 to 60.

70. A hybridoma capable of producing the antibody of any one of items 1 to 69.

71. A conjugate comprising an antibody of any one of items 1 to 69 coupled to a moiety or agent.

72. The conjugate of item 71, wherein the moiety or agent is selected from the group consisting of a radioisotope, an enzyme, a dye, a drug, a toxin and a cytotoxic agent.

73. A multimer, comprising at least two antibodies of any one of items 1 to 69 or at least two conjugates of item 71 or 72 or a mixture of one or more antibodies of any one of items 1 to 69 and one or more conjugates of item 71 or 72.

74. The multimer of item 73, comprising 4 to 8 antibodies of any one of items 1 to 69 or conjugates of item 71 or 72.

75. A nucleic acid comprising a nucleic acid sequence encoding an antibody of any one of items 1 to 69 or encoding an antibody heavy chain as specified in any one items 1 to 30 or 37 to 66 and/or encoding an antibody light chain as specified in any one of items 31 to 39, 42, 43, or 49 to 66, or a fragment thereof.

76. The nucleic acid of item 75, wherein the nucleic acid is RNA.

77. A vector comprising one ore more of the nucleic acids of item 75 or 76.

78. The vector of item 77, wherein the vector is a multilamellar vesicle, an unilamellar vesicle, or a mixture thereof.

79. The vector of item 77 or 78, wherein the vector is a liposome.

80. The vector of item 79, wherein the liposome is a cationic liposome.

81. The vector of item 79 or 80, wherein the liposome has a particle diameter in the range of from about 50 nm to about 200 nm.

82. A host cell comprising a nucleic acid of item 75 or 76 or comprising a vector of any one of items 77 to 81.

83. A virus comprising a nucleic acid of item 75 or 76 or comprising a vector of any one of items 77 to 81.

84. A pharmaceutical composition comprising an active agent and a pharmaceutically acceptable carrier, wherein the active agent is at least one selected from:
(i) an antibody of any one of items 1 to 69;
(ii) a conjugate of item 71 or 72;
(iii) a multimer of item 73 or 74;
(iv) a nucleic acid of item 75 or 76 or a combination thereof;
(v) a vector of any one of items 77 to 81 or a combination thereof;
(vi) a host cell of item 82 or a combination thereof; and/or
(vii) a virus of item 83 or a combination thereof.

85. The pharmaceutical composition of item 84, which is formulated for parenteral administration.

86. The pharmaceutical composition of item 85, which is formulated for cardiovascular, in particular intravenous or intraarterial administration.
87. The pharmaceutical composition of any one of items 84 to 86 for use in a prophylactic and/or therapeutic treatment of a disease.
88. The pharmaceutical composition of item 87, wherein the disease is cancer growth and/or cancer metastasis.
89. The pharmaceutical composition of item 87 or 88, wherein the disease is characterized by comprising diseased cells or cancer cells which are characterized by expressing PD-L1 and/or being characterized by association of PD-L1 with their surface.
90. The pharmaceutical composition of any one of items 84 to 89 for use in a method of preventing or treating cancer.
91. The pharmaceutical composition of any one of items 88 to 90, wherein the cancer is selected from the group consisting of melanoma, lung cancer, renal cell carcinoma, bladder cancer, breast cancer, gastric and gastroesophageal junction cancers, pancreatic adenocarcinoma, ovarian cancer and lymphomas.
92. The pharmaceutical composition of any one of items 84 to 91, wherein the pharmaceutical composition is to be specifically delivered to, accumulated in and/or are retained in a target organ or tissue.
93. The pharmaceutical composition of any one of items 84 to 92, wherein the vector or the virus releases the nucleic acid at the target organ or tissue and/or enters cells at the target organ or tissue.
94. The pharmaceutical composition of any one of items 84 to 93, wherein the antibody is to be expressed in cells of the target organ or tissue.
95. The pharmaceutical composition of any one of items 84 to 94, wherein the treatment is a monotherapy or a combination therapy.
96. The pharmaceutical composition of item 95, wherein the combinatorial treatment is at least one treatment selected from the group consisting chemotherapy, molecular-targeted therapy, radiation therapy, and other forms of immune therapy.
97. The pharmaceutical composition of any one of items 84 to 96, wherein the subject is a human.
98. A method of treating or preventing a disease in a subject comprising administering to a subject at least one active agent, wherein the active agent is at least one selected from:
(i) an antibody of any one of items 1 to 69;
(ii) a conjugate of item 71 or 72;
(iii) a multimer of item 73 or 74;
(iv) a nucleic acid of item 75 or 76 or a combination thereof;
(v) a vector of any one of items 77 to 81 or a combination thereof;
(vi) a host cell of item 82 or a combination thereof; and/or
(vii) a virus of item 83 or a combination thereof.
99. The method of item 98, wherein a pharmaceutical composition of any one of items 84 to 86 is administered to the subject.
100. The method of item 98 or 99, wherein the subject has a diseased organ or tissue characterized by cells expressing PD-L1 and/or being characterized by association of PD-L1 with their surface.
101. The method of any one of items 98 to 100, wherein the disease is cancer growth and/or cancer metastasis.
102. The method of item 101, wherein the cancer is selected from the group consisting of melanoma, lung cancer, renal cell carcinoma, bladder cancer, breast cancer, gastric and gastroesophageal junction cancers, pancreatic adenocarcinoma, ovarian cancer and lymphomas.
103. The method of any one of items 98 to 102, wherein the active agent or the pharmaceutical composition is administered into the cardiovascular system.
104. The method of item 103, wherein the active agent or the pharmaceutical composition is administered by intravenous or intraarterial administration such as administration into a peripheral vein.
105. The method of any one of items 98 to 104, wherein the active agent or the pharmaceutical composition are specifically delivered to, accumulate in and/or are retained in a target organ or tissue.
106. The method of any one of items 98 to 105, wherein the vector, the host cell or the virus releases the nucleic acid at the target organ or tissue and/or enters cells at the target organ or tissue.
107. The method of item 106, wherein the antibody is expressed in cells of the target organ or tissue.
108. The method of any one of items 98 to 107, wherein the treatment is a monotherapy or a combination therapy.
109. The method of item 108, wherein the combinatorial treatment is at least one treatment selected from the group consisting chemotherapy, molecular-targeted therapy, radiation therapy, and other forms of immune therapy.
110. The method of any one of items 98 to 109, wherein the subject is a human.
111. A kit for qualitative or quantitative detection of PD-1 in a sample, wherein the kit comprises an antibody of any one of items 1 to 69 or a conjugate of item 71 or 72 or a multimer of item 73 or 74.
112. Use of an antibody of any one of items 1 to 69 or of a conjugate of item 71 or 72 or of a multimer of item 73 or 74 or of a kit of item 111 in a method of determining the presence or quantity of PD-1 expressed in a sample, the method comprising the steps of:
(ii) contacting a sample with the antibody or the conjugate or the multimer, and
(ii) detecting the formation of and/or determining the quantity of a complex between the antibody or the conjugate or the multimer and PD-1.

EXAMPLES

The techniques and methods used herein are described herein or carried out in a manner known per se and as described, for example, in Sambrook et al., Molecular Cloning: A Laboratory Manual, $2^{nd}$ Edition (1989) Cold Spring Harbor Laboratory Press, Cold Spring Harbor, N.Y. All methods including the use of kits and reagents are carried out according to the manufacturers' information unless specifically indicated.

Example 1: Generation of IgG1-PD1 and Screening Materials

PD-1 and FcγR Constructs
Plasmids encoding various full-length PD-1 variants were generated: human (*Homo sapiens*; UniProtKB ID: Q15116), cynomolgus monkey (*Macaca fascicularis*; UniProtKB ID: B0LAJ3), dog (*Canis familiaris*; UniProtKB ID: E2RPS2), rabbit (*Oryctolagus cuniculus*; UniProtKB ID: G1SUF0), pig (*Sus scrofa*; UniProtKB ID: A0A287A1C3), rat (*Rattus norvegicus*; UniProtKB ID: D3ZIN8), and mouse (*Mus musculus*; UniProtKB ID: Q02242), as well as a plasmid encoding human FcγRIa (UniProt KB ID: P12314).

Generation of CHO-S Cell Lines Transiently Expressing Full-Length PD-1 or FcγR Variants CHO-S cells (a subclone of CHO cells adapted to suspension growth; ThermoFisher Scientific, cat. no. R800-07) were transfected with PD-1 or FcγR plasmids using FreeStyle™ MAX Reagent (ThermoFisher Scientific, cat. no. 16447100) and OptiPRO™ serum-free medium (ThermoFisher Scientific, cat. no. 12309019), according to the manufacturer's instructions.

Production of Antibody Variants

IgG1-PD1

Three New Zealand White rabbits were immunized with recombinant human His-tagged PD-1 protein (R&D Systems, cat. no. 8986-PD). Single B cells from blood were sorted and supernatants screened for production of PD-1 specific antibodies by human PD-1 enzyme-linked immunosorbent assay (ELISA), cellular human PD-1 binding assay and by human PD-1/PD-L1 blockade bioassay. From screening-positive B cells, RNA was extracted, and sequencing was performed. The variable regions of heavy and light chain were gene synthesized and cloned N-terminal of human immunoglobulin constant parts (IgG1/κ) containing mutations L234A and L235A (LALA) wherein the amino acid position number is according to Eu numbering (SEQ ID NO: 7) to minimize interactions with Fcγ receptors.

Transient transfections of HEK293-FreeStyle cells using 293-free transfection reagent (Novagen/Merck) were executed by Tecan Freedom Evo device. Produced chimeric antibodies were purified from cell supernatant using protein-A affinity chromatography on a Dionex Ultimate 3000 HPLC with plate autosampler. Purified antibodies were used for further analysis in particular retesting by human PD-1 ELISA, cellular human PD-1 binding assay, human PD-1/PD-L1 blockade bioassay, and T-cell proliferation assay. The chimeric rabbit antibody MAB-19-0202 (SEQ ID NO: 18 and 19) was identified as best performing clone and subsequently humanized.

The variable region sequences of the chimeric PD-1 antibody MAB-19-0202 are shown in the following tables. Table 4 shows the variable regions of the heavy chain, while table 5 shows the variable regions of the light chain. In both cases the framing regions (FRs) as well as the complementarity determining regions (CDRs) according to Kabat numbering are defined. The underlined amino acids indicate the CDRs according to the IMGT numbering. The bold letters indicate the intersection of Kabat and IMGT numbering.

TABLE 4

HEAVY CHAIN

| Sequence ID | FR1 | CDR1 | SEQ ID# | FR2 | CDR2 | SEQ ID# | FR3 | CDR3 | SEQ ID# | FR4 |
|---|---|---|---|---|---|---|---|---|---|---|
| MAB-19-0202-HC SEQ ID NO: 18 | QSVEE SGGRL VTPGT PLTLT CTVSG FSLY | SYN MG | 12 | WVRQ APGK GLEY IG | IIS GGT IGH YAS WAK G | 11 | RFTIS KTSST TVDLK MTSLT TEDTA TYFCA R | AFY DDY DYN V | 8 | WGPG TLVT VSS |

TABLE 5

LIGHT CHAIN

| Sequence ID | FR1 | CDR1 | SEQ ID# | FR2 | CDR2 | SEQ ID# | FR3 | CDR3 | SEQ ID# | FR4 |
|---|---|---|---|---|---|---|---|---|---|---|
| MAB-19-0202-LC SEQ ID NO: 19 | AAVLT QTPSP VSAAV GGTVT ISC | QSS QSV YGN NQL S | 17 | WYQQ KPGQ PPKL LIY | QAS KLE T | 15 | GVPSR FKGSG SGTQF TLTIS DLESD DAATY YC | AGG YSS SSD TT | 14 | FGGG TEVV VK |

Transient transfections of HEK293-FreeStyle cells using 293-free transfection reagent (Novagen/Merck) were executed by Tecan Freedom Evo device. Produced chimeric antibodies were purified from cell supernatant using protein-A affinity chromatography on a Dionex Ultimate 3000 HPLC with plate autosampler. Purified antibodies were used for further analysis in particular retesting by human PD-1 ELISA, cellular human PD-1 binding assay, human PD-1/PD-L1 blockade bioassay, and T-cell proliferation assay. The chimeric rabbit antibody MAB-19-0202 (SEQ ID NO: 18 and 19) was identified as best performing clone and subsequently humanized.

Humanized heavy and light chain variable region antibody sequences were generated by structural modelling-assisted CDR grafting, gene synthesized and cloned N-terminal of human immunoglobulin constant parts (IgG1/κ with LALA mutations). Humanized antibodies were used for further analysis in particular retesting by human PD-1 ELISA, cellular human PD-1 binding assay, human PD-1/PD-L1 blockade bioassay, and the T-cell proliferation assay. The humanized antibody MAB-19-0618 (SEQ ID NO: 20 and 21) was identified as best performing clone.

The allocation of the humanized light and heavy chains to antibody ID of the recombinant humanized sequences are listed in Table 6. The variable region sequences of the humanized light and heavy chains are shown in Table 7 and 8. Table 7 shows the variable regions of the heavy chain, while table 8 shows the variable regions of the light chain. In both cases the framing regions (FRs) as well as the complementarity determining regions (CDRs) according to Kabat numbering are defined. The underlined amino acids indicate the CDRs according to the IMGT numbering.

TABLE 6

| antibody ID | light chain humanized variant | Light chain SEQ ID NO: | heavy chain humanized variant | Heavy chain SEQ ID NO: |
|---|---|---|---|---|
| MAB-19-0618 | MAB-19-0202-L4 | 21 | MAB-19-0202-H5 | 20 |

TABLE 7

HEAVY CHAIN

| Sequence ID | FR1 | CDR1 | FR2 | CDR2 | FR3 | CDR3 | FR4 |
|---|---|---|---|---|---|---|---|
| MAB-19-0202-H5 SEQ ID NO: 20 | QVQLV ESGGG LVQPG TSLRL SCSVS GFSLY | SYN MG | WVRQ APGK GLEY IG | IIS GGT IGH YAS WAK G | RFTIS RDTSK TTLYL QMNSL TTEDT ATYFC AR | AFY DDY DYN V | WG PG TL VT VS S |

TABLE 8

LIGHT CHAIN

| Sequence ID | FR1 | CDR1 | FR2 | CDR2 | FR3 | CDR3 | FR4 |
|---|---|---|---|---|---|---|---|
| MAB-19-0202-L4 SEQ ID NO: 21 | AIQLT QSPSS LSASV GGTVT ITC | QSS QSV YGN NQL S | WYQQ KPGQ PPKL LIY | QAS KLE T | GVPSR FRGSG SGTQF TLTIS SLQSE DFATY YC | AGG YSS SSD TT | FGGG TEVV VK |

The sequences of the variable regions of the heavy and light chains of MAB-19-0618 were gene synthesized and cloned by ligation-independent cloning (LIC) into expression vectors with codon-optimized sequences encoding the human IgG1m(f) heavy chain constant domain containing the Fc-silencing mutations L234F, L235E and G236R (FER) wherein the amino acid position number is according to Eu numbering (SEQ ID NO: 2 or SEQ ID NO: 55) and the human kappa light chain constant domain (SEQ ID NO: 6). The resulting antibody was designated IgG1-PD1.

The GS Xceed® Expression System (Lonza) was used to generate a stable cell line expressing IgG1-PD1. The sequences encoding the heavy and light chain of IgG1-PD1 were cloned into the expression vectors pXC-18.4 and pXC-Kappa (containing the glutamine synthetase [GS] gene), respectively, by Lonza Biologics plc. Next, a double gene vector (DGV) encoding both the heavy and light chain of IgG1-PD1 was constructed by ligating the complete expression cassette from the heavy chain vector into the light chain vector. The DNA of this DGV was linearized with the restriction enzyme PvuI-HF (New England Biolabs, R3150L) and used for stable transfection of CHOK1SV® GS-KO® cells. IgG1-PD1 was purified for functional characterization.

IgG1-CD52-E430G

A human IgG1 antibody with an E430G hexamerization-enhancing mutation (WO2013/004842 A2) in the Fc domain (SEQ ID NO: 4) and antigen-binding domains identical to CAMPATH-1H, a CD52-specific antibody, was used as a positive control in C1q binding and FcγR signaling experiments (Crowe et al., 1992 Clin Exp Immunol. 87(1):105-110) (SEQ ID NO. 25 and 29).

Control Antibodies

Human IgG1 antibodies with antigen-binding domains identical to b12, an HIV1 gp120-specific antibody, were used as negative controls in several experiments (Barbas et al., J Mol Biol. 1993 Apr. 5; 230(3):812-2). $V_H$ and $V_L$ domains of b12 (SEQ ID NO. 32 and 36) were prepared by de novo gene synthesis (GeneArt Gene Synthesis; ThermoFisher Scientific, Germany) and cloned into expression vectors containing a human IgG1 heavy chain constant region (i.e. CH1, hinge, CH2 and CH3 region) of the human IgG1m(f) allotype (SEQ ID NO: 1) or a variant thereof (containing the L234F/L235E/G236R mutations and an additional, in the context of this study functionally irrelevant, K409R mutation in the Fc domain, abbreviated as the FERR mutations) (SEQ ID NO: 3) or containing a human IgG4 heavy chain constant region (SEQ ID NO: 5); or the constant region of the human kappa light chain (LC) (SEQ ID NO: 6), as appropriate for the selected binding domains. Antibodies were obtained by transfection of heavy and light chain expression vectors in production cell lines and purified for functional characterization.

Example 2: Binding of IgG1-PD1 to PD-1 from Various Species

Binding of IgG1-PD1 to PD-1 of species commonly used for nonclinical toxicology studies was assessed by flow cytometry using CHO-S cells transiently expressing PD-1 from different animal species.

CHO-S cells ($5 \times 10^4$ cells/well) were seeded in round-bottom 96-well plates. Antibody dilutions ($1.7 \times 10^{-4}$-30 μg/mL or $5.6 \times 10^{-5}$-10 μg/mL, 3fold dilutions) of IgG1-PD1, IgG1-ctrl-FERR, and pembrolizumab were prepared in Genmab (GMB) fluorescence-activated cell sorting (FACS) buffer (phosphate-buffered saline [PBS; Lonza, cat. no. BE17-517Q, diluted to 1×PBS in distilled water] supplemented with 0.1% [w/v] bovine serum albumin [BSA; Roche, cat. no. 10735086001] and 0.02% [w/v] sodium azide [NaN₃; bioWORLD, cat. no. 41920044-3]). An IgG4 isotype control (BioLegend, cat. no. 403702) for pembrolizumab was included only at the highest concentration tested (30 μg/mL or 10 μg/mL). Cells were centrifuged, supernatant was removed, and cells were incubated in 50 μL of the antibody dilutions for 30 min at 4° C. Cells were washed twice with GMB FACS buffer and incubated with 50 μL secondary antibody R-phycoerythrin (PE)-conjugated goat-anti-human IgG F(ab')₂ (Jackson ImmunoResearch, cat. no. 109-116-098; diluted 1:500 in GMB FACS buffer) for 30 min at 4° C., protected from light. Cells were washed twice with GMB FACS buffer, resuspended in GMB FACS buffer supplemented with 2 mM ethylenediaminetetraacetic acid (EDTA; Sigma-Aldrich, cat. no. 03690) and 4',6-diamidino-2-phenylindole (DAPI) viability marker (1:5,000; BD Pharmingen, cat. no. 564907). Antibody binding to viable cells (as identified by DAPI exclusion) was analyzed by flow cytometry on an Intellicyt® iQue PLUS Screener (Intellicyt Corporation) using FlowJo software. Binding curves were analyzed using non-linear regression analysis (four-parameter dose-response curve fits) in GraphPad Prism.

Binding of IgG1-PD1 to PD-1 of different species was evaluated by flow cytometry using CHO-S cells transiently transfected to express human, cynomolgus monkey, dog, rabbit, pig, rat, or mouse PD-1 protein on the cell surface. Dose-dependent binding of IgG1-PD1 was observed for human and cynomolgus monkey PD-1 (FIG. 1A-B). Pembrolizumab demonstrated comparable binding. Substantially reduced cross-reactivity of IgG1-PD1, and only at the highest concentrations, was observed to rodent PD-1 (mouse, rat; FIGS. 1C-D) and no binding was observed to PD-1 of other species frequently used in toxicology studies (rabbit, dog, pig; FIG. 1E). No IgG1-PD1 binding was observed to non-transfected control cells (FIG. 1E), nor was binding of IgG1-ctrl-FERR, included as a negative control, observed to PD-1 of any of the tested species (FIG. 1).

In conclusion, IgG1-PD1 showed comparable binding to membrane-expressed human and cynomolgus monkey PD-1 and significantly lower or no binding to mouse, rat, rabbit, dog, and pig PD-1.

Example 3: Binding to Human and Cynomolgus Monkey PD-1 Determined by Surface Plasmon Resonance Binding of immobilized IgG1-PD1, pembrolizumab, and nivolumab to human and cynomolgus monkey PD-1 was analyzed by surface plasmon resonance (SPR) using a Biacore 8K SPR system. Recombinant human and cynomolgus monkey PD-1 extracellular domain (ECD) with a C-terminal His-tag were obtained from Sino Biological (cat. no. HPLC-10377-H08H and 90311-C08H, respectively).

Biacore Series S Sensor Chips CM5 (Cytiva, cat. no. 29149603) were covalently coated with anti-Fc antibody using amine coupling and the Human Antibody Capture Kit, Type 2 (Cytiva, cat. no. BR100050 and BR100839) according to the manufacturer's instructions.

Subsequently, IgG1-PD1 (2 nM), nivolumab (Bristol-Myers Squibb, lot no. ABP6534; 1.25 nM), and pembrolizumab (Merck Sharp & Dohme, lot. no. T019263; 1.25 nM), diluted in HBS-EP+ buffer (Cytiva, cat. no. BR100669; diluted to 1× in distilled water [B Braun, cat. no. 00182479E]), were captured onto the surface at 25° C., with a flow rate of 10 μL/min and a contact time of 60 seconds. This resulted in captured levels of approximately 50 resonance units (RU).

After three start-up cycles of HBS-EP+ buffer, human or cynomolgus monkey PD-1 ECD samples (0.19-200 nM; 2-fold dilution in HBS-EP+ buffer; 12 cycles) were injected to generate binding curves. Each sample that was analyzed on an antibody coated surface (active surface) was also analyzed on a parallel flow cell without antibody (reference surface), which was used for background correction.

At the end of each cycle, the surface was regenerated using 10 mM Glycine-HCl pH 1.5 (Cytiva, cat. no. BR100354). The data were analyzed using the predefined "Multi-cycle kinetics using capture" evaluation method in the Biacore Insight Evaluation software (Cytiva). The sample with the highest concentration of human or cynomolgus monkey PD-1 (200 nM) was omitted from analysis to allow better curve fits of the data.

Immobilized IgG1-PD1 bound to human PD-1 ECD with a binding affinity ($K_D$) of 1.45±0.05 nM (Table 9). Nivolumab and pembrolizumab bound human PD-1 ECD with a binding affinity comparable to the $K_D$ of IgG1-PD1, ie, with $K_D$ values in the low nanomolar range (4.43±0.08 nM and 3.59±0.10 nM, respectively) (Table 9).

Immobilized IgG1-PD1 bound to cynomolgus monkey PD-1 ECD with a $K_D$ of 2.74±0.58 nM (Table 10), comparable to the affinity of IgG1-PD1 for human PD-1. Nivolumab and pembrolizumab bound cynomolgus monkey PD-1 ECD with a binding affinity comparable to the $K_D$ of IgG1-PD1 for cynomolgus monkey PD-1 ECD and comparable to the $K_D$ of nivolumab and pembrolizumab for human PD-1 ECD, ie, with $K_D$ values in the low nanomolar range (2.93±0.58 nM and 0.90±0.06 nM, respectively) (Table 10).

TABLE 9

Binding affinities of PD-1 antibodies to the extracellular domain of human PD-1 as determined by surface plasmon resonance. The association rate constant $k_a$ (1/Ms), dissociation rate constant $k_d$ (1/s) and equilibrium dissociation constant $K_D$ (M) of IgG1-PD1, nivolumab, and pembrolizumab for the ECD of human PD-1 were determined by SPR.

| Antibody | $K_D$ (M) | | $k_a$ (1/M × s) | | $k_d$ (1/s) | |
| --- | --- | --- | --- | --- | --- | --- |
| | Average | SD | Average | SD | Average | SD |
| IgG1-PD1[a] | 1.45 × $10^{-9}$ | 4.51 × $10^{-11}$ | 5.17 × $10^5$ | 2.03 × $10^4$ | 7.51 × $10^{-4}$ | 9.61 × $10^{-6}$ |
| Nivolumab[b] | 4.43 × $10^{-9}$ | 8.49 × $10^{-11}$ | 4.06 × $10^5$ | 3.54 × $10^3$ | 1.80 × $10^{-3}$ | 2.12 × $10^{-5}$ |
| Pembrolizumab[b] | 3.59 × $10^{-9}$ | 9.90 × $10^{-11}$ | 2.12 × $10^6$ | 1.36 × $10^6$ | 7.57 × $10^{-3}$ | 4.71 × $10^{-3}$ |

[a]Average and SD from three independent experiments.
[b]Average and SD from two independent experiments.
Abbreviations:
$K_D$ = equilibrium dissociation constant;
$k_a$ = association rate constant;
$k_d$ = dissociation rate constant or off-rate;
SD = standard deviation.

TABLE 10

Binding affinities of PD-1 antibodies to the extracellular domain of cynomolgus monkey PD-1 as determined by surface plasmon resonance. The association rate constant $k_a$ (1/Ms), dissociation rate constant $k_d$ (1/s) and equilibrium dissociation constant $K_D$ (M) of IgG1-PD1, nivolumab, and pembrolizumab for the ECD of cynomolgus monkey PD-1 were determined by SPR.

| Antibody | $K_D$ (M) | | $k_a$ (1/M × s) | | $k_d$ (1/s) | |
| --- | --- | --- | --- | --- | --- | --- |
| | Average | SD | Average | SD | Average | SD |
| IgG1-PD1[a] | 2.74 × $10^{-9}$ | 5.79 × $10^{-10}$ | 5.34 × $10^5$ | 9.39 × $10^4$ | 1.43 × $10^{-3}$ | 7.23 × $10^{-5}$ |
| Nivolumab[b] | 2.93 × $10^{-9}$ | 5.81 × $10^{-10}$ | 3.28 × $10^5$ | 5.07 × $10^4$ | 9.43 × $10^{-4}$ | 9.07 × $10^{-5}$ |
| Pembrolizumab[b] | 8.99 × $10^{-10}$ | 5.73 × $10^{-11}$ | 7.14 × $10^5$ | 3.04 × $10^4$ | 6.42 × $10^{-4}$ | 6.86 × $10^{-5}$ |

[a]Average and SD from three independent experiments.
[b]Average and SD from two independent experiments.
Abbreviations:
$K_D$ = equilibrium dissociation constant;
$k_a$ = association rate constant;
$k_d$ = dissociation rate constant or off-rate;
SD = standard deviation.

Example 4: Effect of IgG1-PD1 on PD-1 Ligand Binding and PD-1/PD-L1 Signaling

To confirm that IgG1-PD1 functions as a classical immune checkpoint inhibitor, the capacity of IgG1-PD1 to disrupt PD-1 ligand binding and PD-1 checkpoint function was assessed in vitro.

Competitive binding of IgG1-PD1 with recombinant human PD-L1 and PD-L2 to membrane-expressed human PD-1 was assessed by flow cytometry. CHO-S cells transiently transfected with human PD-1 (see Example 1; 5×10⁴ cells/well) were added to the wells of a round-bottom 96-well plate (Greiner, cat. no. 650180), pelleted, and placed on ice. Biotinylated recombinant human PD-L1 (R&D Systems, cat. no. AVI156) or PD-L2 (R&D Systems, cat. no. AVI1224), diluted in PBS (Cytiva, cat. no. SH3A3830.03), was added to the cells (final concentration: 1 μg/mL), immediately after which a concentration range of IgG1-PD1, pembrolizumab (MSD, lot no. T019263 and T036998), or IgG1-ctrl-FERR, diluted in PBS, was added (final concentrations: 30 μg/mL-0.5 ng/mL in three-fold dilution steps). Cells were then incubated for 45 min at RT. Cells were washed twice with PBS and incubated with 50 μL streptavidin-allophycocyanin (R&D Systems, cat. no. F0050; diluted 1:20 in PBS) for 30 min at 4° C., protected from light. Cells were washed twice with PBS and resuspended in 20 μL GMB FACS buffer. Streptavidin-allophycocyanin binding was analyzed by flow cytometry on an Intellicyt® iQue Screener PLUS (Sartorius) using FlowJo software.

The effect of IgG1-PD1 on the functional interaction of PD-1 and PD-L1 was determined using a bioluminescent cell-based PD-1/PD-L1 blockade reporter assay (Promega, cat. no. J1255), essentially as described by the manufacturer. Briefly, cocultures of PD-L1 aAPC/CHO-K1 Cells and PD-1 Effector Cells were incubated with serially diluted IgG1-PD1, pembrolizumab (MSD, lot no. 10749880 or T019263), nivolumab (Bristol-Myers Squibb, lot no. 11024601), or IgG1-ctrl-FERR (final assay concentrations: 15—0.0008 μg/mL in 3-fold dilutions or 10—0.0032 μg/mL in 5-fold dilutions) for 6 h at 37° C., 5% CO₂. Cells were then incubated at RT with reconstituted Bio-Glo™ for 5-30 min, after which luminescence (in relative light units [RLU]) was measured using an Infinite® F200 PRO Reader (Tecan) or an EnVision Multilabel Plate Reader (PerkinElmer).

Figure 2:
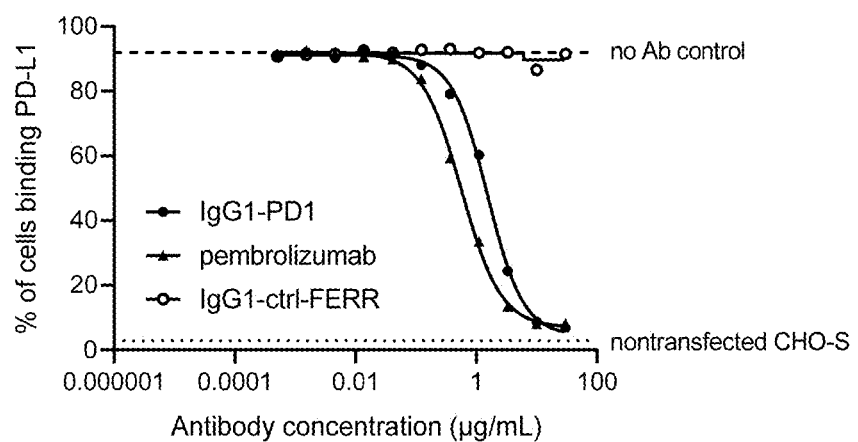
FIG. 2 shows competitive binding of IgG1-PD1 with PD-L1 and PD-L2 to human PD-1. CHO-S cells transiently transfected with human PD-1 were incubated with 1 µg/mL biotinylated recombinant human PD-L1 (A) or PD-L2 (B) in the presence of IgG1-PD1 or pembrolizumab. IgG1-ctrl-FERR was included as a negative control. Cells were stained with streptavidin-allophycocyanin, and the percentage of cells binding biotinylated PD-L1 or PD-L2 was determined by measuring the percentage of streptavidin-allophycocyanin$^+$ cells using flow cytometry. The percentage of streptavidin-allophycocyanin$^+$ cells in the no antibody control and in a non-transfected sample are indicated with dashed lines. Data shown are from single replicates from one representative experiment out of three separate experiments. Abbreviations: Ab=antibody; CHO-S=Chinese hamster ovary, suspension; ctrl=control; FERR=L234F/L235E/G236R-K409R; PD-1=programmed cell death protein 1; PD-L1=programmed cell death 1 ligand 1; PD-L2=programmed cell death 1 ligand 2.
Figure 2:
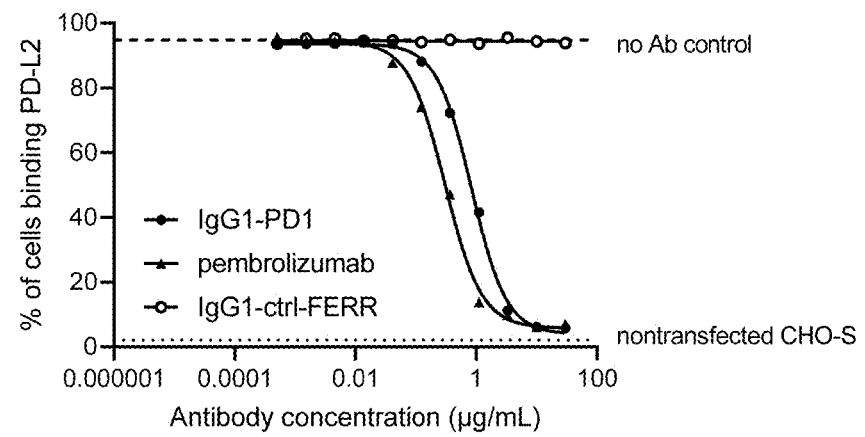

Dose-response curves were analyzed by non-linear regression analysis (four-parameter dose-response curve fits) using GraphPad Prism software, and the concentrations at which 50% of the maximal (inhibitory) effect was observed ($EC_{50}/IC_{50}$) were derived from the fitted curves. IgG1-PD1 disrupted binding of human PD-L1 and PD-L2 to membrane-expressed human PD-1 in a dose-dependent manner (FIG. 2), with $IC_{50}$ values of 2.059±0.653 µg/mL (13.9±4.4 nM) for PD-L1 binding inhibition and 1.659±0.721 µg/mL (11.2±4.9 nM) for PD-L2 binding inhibition, ie, in the nanomolar range (Table 11). Pembrolizumab showed PD-L1 and PD-L2 binding inhibition with comparable potency, i.e., with $IC_{50}$ values in the nanomolar range.

Figure 3:
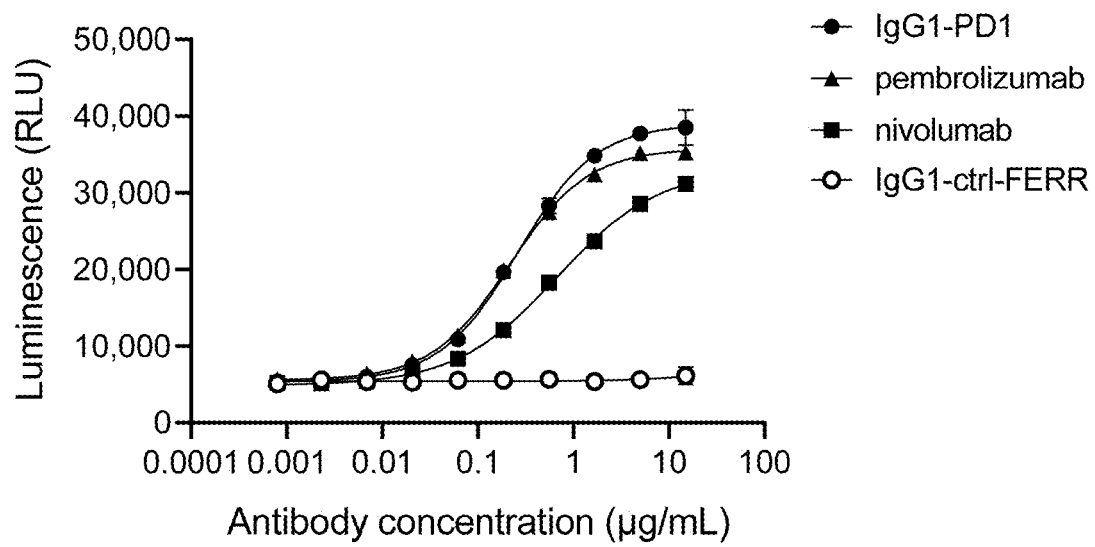
FIG. 3 shows functional inhibition of the PD-1/PD-L1 checkpoint by IgG1-PD1. Blockade of the PD-1/PD-L1 axis was tested using a cell-based bioluminescent PD-1/PD-L1 blockade reporter assay. Data shown are mean luminescence ±SD of duplicate wells in one representative experiment out of five (pembrolizumab and IgG1-PD1), three (IgG1-ctrl-FERR) or two (nivolumab) experiments. Abbreviations: FERR=L234F/L235E/G236R-K409R; PD1=programmed cell death protein 1; PD-L1=programmed cell death 1 ligand 1; RLU=relative light units; SD=standard deviation.

Functional blockade of the PD-1/PD-L1 axis was tested using a cell-based bioluminescent PD-1/PD-L1 blockade reporter assay. Cocultures of reporter Jurkat T cells expressing human PD-1 and harboring an NFAT-RE-driven luciferase, and PD-L1 aAPC/CHOK1 cells expressing human PD-L1 and an antigen-independent TCR activator, were incubated in absence and presence of concentration dilution series of IgG1-PD1, pembrolizumab, or nivolumab. IgG1-ctrl-FERR was included as a negative control. Blockade of the PD-1/PD-L1 interaction results in the release of the PD1/PDL1 mediated inhibitory signal, leading to TCR activation and NFAT-RE-mediated luciferase expression (luminescence measured). IgG1-PD1 induced a dose-dependent increase of TCR signaling in PD-1+ reporter T cells (FIG. 3). The $EC_{50}$ was 0.165±0.056 µg/mL (1.12±0.38 nM; Table 12). Pembrolizumab similarly alleviated PD-1 mediated inhibition of TCR signaling, with an $EC_{50}$ of 0.129±0.051 µg/mL (0.86±0.34 nM), ie, with comparable potency. Nivolumab alleviated the inhibition of TCR signaling with an $EC_{50}$ of 0.479±0.198 µg/mL (3.28±1.36 nM), i.e., with slightly lower potency.

In summary, IgG1-PD1 acts as a classical immune checkpoint inhibitor in vitro, by blocking PD-1 ligand binding and disrupting PD-1 immune checkpoint function.

TABLE 11

$IC_{50}$ values of IgG1-PD1-mediated inhibition of PD-1 ligand binding
$IC_{50}$ values were calculated from the competition binding curves.

| Competitive binding with human PD-L1 (average $IC_{50}$ [±SD]) | | | | Competitive binding with human PD-L2 (average $IC_{50}$ [±SD]) | | | |
|---|---|---|---|---|---|---|---|
| IgG1-PD1 | | pembrolizumab | | IgG1-PD1 | | pembrolizumab | |
| µg/mL | nM | µg/mL | nM | µg/mL | nM | µg/mL | nM |
| 2.059 [±0.653] | 13.9 [±4.4] | 1.134 [±0.493] | 7.6 [±3.3] | 1.659 [±0.721] | 11.2 [±4.9] | 1.186 [±0.770] | 8.0 [±5.2] |

Abbreviations:
$IC_{50}$ = concentration at which 50% of the inhibitory effect was observed;
PD-1 = programmed cell death protein 1;
PD-L1 = programmed cell death 1 ligand 1;
PD-L2 = programmed cell death 1 ligand 2;
SD = standard deviation.

TABLE 12

$EC_{50}$ of PD-1/PD-L1 checkpoint blockade
Cocultures of PD-1+ reporter T cells and PD-L1 aAPC/CHO-K cells were incubated with concentration series of IgG1-PD1, pembrolizumab, or nivolumab in PD-1/PD-L1 blockade reporter assays. Inhibition of PD-1/PD-L1 checkpoint function, resulting in downstream TCR signaling and luciferase expression in the reporter T cells, was determined by measuring luminescence. From the resulting dose-response curves, $EC_{50}$ values were calculated.
Average $EC_{50}$ [±SD]

| IgG1-PD1 | | Pembrolizumab | | Nivolumab | |
|---|---|---|---|---|---|
| µg/mL | nM | µg/mL | nM | µg/mL | nM |
| 0.165 [±0.056] | 1.12 [±0.38] | 0.129 [±0.051] | 0.86 [±0.34] | 0.479 [±0.198] | 3.28 [±1.36] |

Abbreviations:
aAPC = artificial antigen-presenting cell;
CHO = Chinese hamster ovary;
$EC_{50}$ = concentration at which 50% of the maximal effect is observed;
PD-1 = programmed cell death protein 1;
PD-L1 = programmed cell death 1 ligand 1;
SD = standard deviation;
TCR = T-cell receptor.

Example 5: Antigen-Specific Proliferation Assay to Determine the Capacity of IgG1-PD1 to Enhance Proliferation of Activated T Cells To determine the capacity of IgG1-PD1 to enhance T-cell proliferation, an antigen-specific proliferation assay was conducted using PD-1-overexpressing human CD8+ T cells.

HLA-A*02+ peripheral blood mononuclear cells (PBMCs) were obtained from healthy donors (Transfusionszentrale, University Hospital, Mainz, Germany). Monocytes were isolated from PBMCs by magnetic-activated cell sorting (MACS) technology using anti-CD14 MicroBeads (Miltenyi; cat. no. 130-050-201), according to the manufacturer's instructions. The peripheral blood lymphocytes (PBLs, CD14-negative fraction) were cryopreserved for T-cell isolation. For differentiation into immature DCs (iDCs), 1×10⁶ monocytes/mL were cultured for five days in RPMI 1640 (Life Technologies GmbH, cat. no. 61870-010) containing 5% pooled human serum (One Lambda Inc., cat. no. A25761), 1 mM sodium pyruvate (Life technologies GmbH, cat. no. 11360-039), 1× non-essential amino acids (Life Technologies GmbH, cat. no. 11140-035), 100 IU/mL penicillin-streptomycin (Life Technologies GmbH, cat. no. 15140-122), 100 ng/mL granulocyte-macrophage colony-stimulating factor (GM-CSF; Miltenyi, cat. no. 130-093-868) and 50 ng/mL interleukin-4 (IL-4; Miltenyi, cat. no. 130-093-924). Once during these five days, half of the medium was replaced with fresh medium. iDCs were harvested by collecting non-adherent cells and adherent cells were detached by incubation with Dulbecco's phosphate-buffered saline (DPBS) containing 2 mM EDTA for 10 min at 37°. After washing with DPBS iDCs were cryopreserved in RPMI 1640 containing 10% DMSO (AppliChem GmbH, cat. no A3672,0050) and 10% human albumin (CSL Behring, PZN 00504775) for future use in antigen-specific T cell assays.

One day prior to the start of an antigen-specific CD8+ T cell proliferation assay, frozen PBLs and iDCs from the same donor were thawed. CD8+ T cells were isolated from PBLs by MACS technology using anti-CD8 MicroBeads (Miltenyi, cat. no. 130-045-201), according to the manufacturer's instructions. About 10×10⁶ to 15×10⁶ CD8+ T cells were electroporated with each 10 µg of in vitro translated (IVT)-RNA encoding the alpha and beta chains of a murine TCR specific for human claudin-6 (CLDN6; HLA-A*02-restricted; described in WO 2015150327 A1) plus 10 µg IVT-RNA encoding PD-1 (UniProt Q15116) in 250 µL X-Vivo15 medium (Lonza, cat. no. BE02-060Q). The cells were transferred to a 4-mm electroporation cuvette (VWR International GmbH, cat. no. 732-0023) and electroporated using the BTX ECM® 830 Electroporation System (BTX; 500 V, 1×3 ms pulse). Immediately after electroporation, cells were transferred into fresh IMDM GlutaMAX medium (Life Technologies GmbH, cat. no. 319800-030) containing 5% pooled human serum and rested at 37° C., 5% $CO_2$ for at least 1 hour. T cells were labeled using 1.6 µM carboxyfluorescein succinimidyl ester (CFSE; Life Technologies GmbH, cat. No V12883) in PBS according to the manufacturer's instructions and incubated in IMDM medium supplemented with 5% human AB serum overnight.

Up to $5\times10^6$ thawed iDCs were electroporated with 2 µg IVT-RNA encoding full-length human CLDN6 (WO 2015150327 A1), in 250 µL X-Vivo15 medium, using the electroporation system as described above (300 V, 1×12 ms pulse) and incubated in IMDM medium supplemented with 5% pooled human serum overnight.

The next day, cells were harvested. Cell-surface expression of CLDN6 on iDCs, as well as cell-surface expression of the CLDN6-specific TCR and PD-1 on T cells was confirmed by flow cytometry. To this end, iDCs were stained with a DyLight650-conjugated CLDN6-specific antibody (non-commercially available; in-house production). T cells were stained with a brilliant violet (BV)421-conjugated anti-mouse TCR-β chain antibody (Becton Dickinson GmbH, cat. no. 562839) and an allophycocyanin (APC)-conjugated anti-human PD-1 antibody (Thermo Fisher Scientific, cat. no. 17-2799-42).

Electroporated iDCs were incubated with electroporated, CFSE-labeled T cells at a ratio of 1:10 in the presence of IgG1-PD1, pembrolizumab (Keytruda®, MSD Sharp & Dohme GmbH, PZN 10749897), or nivolumab (Opdivo®, Bristol-Myers Squibb, PZN 11024601) at 4-fold serial dilutions (range 0.00005 to 0.8 µg/mL) in IMDM medium containing 5% pooled human serum in a 96-well round-bottom plate. The negative control antibody IgG1-ctrl-FERR was used at a single concentration of 0.8 µg/mL. After 4 d of culture, the cells were stained with an APC-conjugated anti-human CD8 antibody. T-cell proliferation was evaluated by flow cytometry analysis of CFSE dilution in $CD8^+$ T cells using a BD FACSCelesta™ flow cytometer (Becton Dickinson GmbH).

Flow cytometry data was analyzed using FlowJo software version 10.7.1. CFSE label dilution of $CD8^+$ T cells was assessed using the proliferation modeling tool in FlowJo, and expansion indices calculated using the integrated formula. Dose-response curves were generated in GraphPad Prism version 9 (GraphPad Software, Inc.) using a 4-parameter logarithmic fit. Statistical significance was determined by Friedman's test and Dunn's multiple comparisons test using GraphPad Prism version 9.

Figure 4:
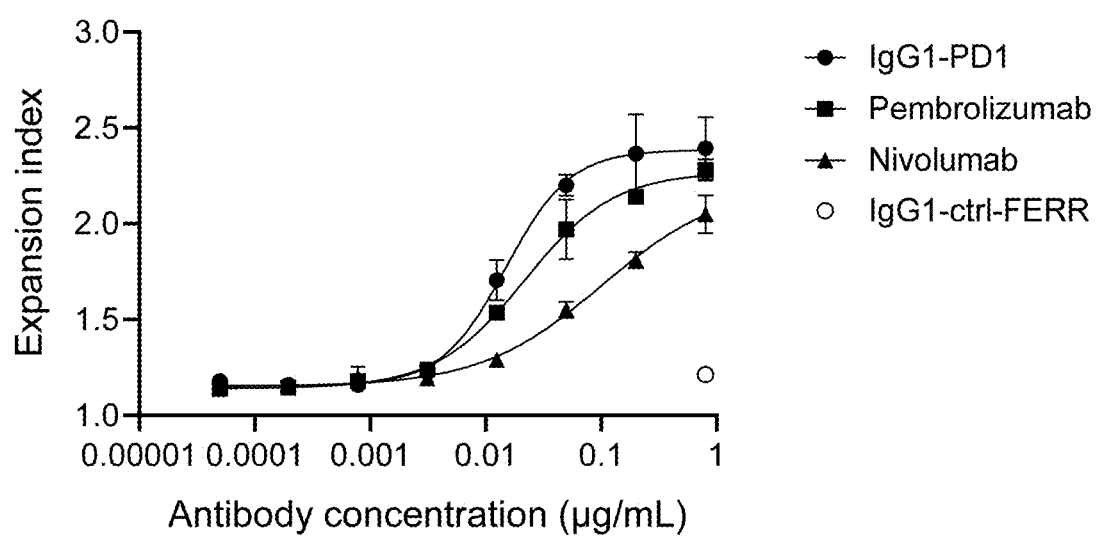
FIG. 4 shows the enhancement of CD8$^+$ T-cell proliferation by IgG1-PD1 in an antigen-specific T-cell proliferation assay. Human CD8$^+$ T cells were electroporated with RNA encoding a CLDN6-specific TCR and RNA encoding PD-1 and labeled with CFSE. The T cells were then co-cultured with iDCs electroporated with CLDN6-encoding RNA, in the presence of IgG1-PD1, pembrolizumab, nivolumab, or IgG1-ctrl-FERR. CFSE dilution in T cells was analyzed by flow cytometry after 4 d and used to calculate the expansion index. Data from one representative donor (26268_B) out of four donors evaluated in three independent experiments are shown. Error bars represent SD of duplicate wells. Curves were fitted by 4-parameter logarithmic fit using GraphPad Prism. Abbreviations: CFSE=carboxyfluorescein succinimidyl ester; FERR=L234F/L235E/G236R-K409R; PD1=programmed cell death protein 1; SD=standard deviation.

Antigen-specific proliferation of $CD8^+$ T cells was enhanced by IgG1-PD1 in a dose-dependent manner (FIG. 4), with $EC_{50}$ values in the picomolar range (Table 13). Treatment with pembrolizumab or nivolumab also enhanced T-cell proliferation in a dose-dependent manner. The average $EC_{50}$ of pembrolizumab was comparable to IgG1-PD1, whereas the $EC_{50}$ of nivolumab was significantly (P=0.0267) higher than that of IgG1-PD1.

TABLE 13

$EC_{50}$ values in the antigen-specific proliferation assay
$EC_{50}$ values of IgG1-PD1, pembrolizumab, and nivolumab were determined using the $CD8^+$ T-cell expansion indices as measured by an antigen-specific T-cell proliferation assay. Data shown are the values calculated based on the 4-parameter logarithmic fit.
Average $EC_{50}$ [±SD]

| IgG1-PD1 | | Pembrolizumab | | Nivolumab | |
| --- | --- | --- | --- | --- | --- |
| µg/mL | nM | µg/mL | nM | µg/mL | nM |
| 0.0124 [±0.0018] | 0.0837 [±0.0123] | 0.0152 [±0.0049] | 0.1018 [±0.0333] | 0.0701 [±0.0238] | 0.4802 [±0.1632] |

Abbreviations:
$EC_{50}$ = half-maximal effective concentration;
FERR = L234F/L235E/G236R-K409R;
PD1 = programmed cell death protein 1;
SD = standard deviation.

Example 6: Effect of IgG1-PD1 on Cytokine Secretion in an Allogeneic MLR Assay

To investigate the capacity of IgG1-PD1 to enhance cytokine secretion in a mixed lymphocyte reaction (MLR) assay, three unique, allogeneic pairs of human mature dendritic cells (mDCs) and $CD8^+$ T cells were cocultured in the presence of IgG1-PD1. The levels of IFNγ were measured using an IFNγ-specific immunoassay, while the levels of monocyte chemoattractant protein-1 (MCP-1), GM-CSF, interleukin (IL)-1β, IL-2, IL-4, IL-5, IL-6, IL-8, IL-10, IL12-p40, IL-15, IL-17α, and tumor necrosis factor (TNFα) were determined using a customized Luminex multiplex immunoassay.

Human $CD14^+$ monocytes were obtained from healthy donors (BioIVT). For differentiation into immature dendritic cells (iDCs), monocytes were cultured for 6 d in RPMI-1640 complete medium (ATCC modification formula; Thermo Fisher, cat. no. A1049101) supplemented with 10% heat-inactivated fetal bovine serum (FBS; Gibco, cat. no. 16140071), 100 ng/mL GM-CSF and 300 ng/mL IL-4 (BioLegend, cat. no. 766206) at 37° C. On day 4, the medium was replaced with fresh medium with supplements. To mature the iDCs, the cells were incubated in RPMI-1640 complete medium supplemented with 10% FBS, 100 ng/mL GM-CSF, 300 ng/mL IL-4, and 5 µg/mL lipopolysaccharide (LPS; Thermo Fisher Scientific, cat. no. 00 4976 93) at 37° C. for 24 h prior to start of the MLR assay. In parallel, purified $CD8^+$ T cells obtained from allogeneic healthy donors (BioIVT) were thawed and incubated in RPMI-1640 complete medium supplemented with 10% FBS and 10 ng/mL IL-2 (BioLegend, cat. no. 589106) at 37° C. O/N.

The next day, the LPS-matured dendritic cells (mDCs) and allogeneic $CD8^+$ T cells were harvested and resuspended in prewarmed AIM-V medium (Thermo Fisher Scientific, cat. no. 12055091) at $4\times10^5$ cells/mL and $4\times10^6$ cells/mL, respectively. The mDCs (20,000 cells/well) were incubated with allogeneic naïve $CD8^+$ T cells (200,000 cells/well) in the presence of an antibody concentration range (0.001-30 µg/mL) of IgG1-PD1, IgG1-ctrl-FERR, or pembrolizumab (MSD, cat. no. T019263) or in the presence of 30 µg/mL IgG4 isotype control (BioLegend, cat. no. 403702) in AIM-V medium in a 96-well round-bottom plate at 37° C.

After 5 d, cell-free supernatant was transferred from each well to a new 96-well plate and stored at −80° C. until further analysis of cytokine concentrations.

The IFNγ levels were determined using an IFNγ-specific immunoassay (Alpha Lisa IFNγ kit; Perkin Elmer, cat. no. AL217) on an Envision instrument, according to the manufacturer's instructions.

The levels of MCP-1, GM-CSF, IL-1β, IL-2, IL-4, IL-5, IL-6, IL-8, IL-10, IL12-p40, IL-15, IL-17α and TNFα were determined using a customized Luminex® multiplex immunoassay (Millipore, order no. SPR1526) based on the Human TH17 Magnetic Bead Panel (MILLIPLEX®). Briefly, cell-free supernatants were thawed and 10 µL of each sample was added to 10 µL Assay Buffer in wells of a 384-well plate (Greiner Bio-One, cat. no. 781096) prewashed with 1× Wash Buffer. In parallel, 10 µL of Standard or Control in Assay Buffer was added to the wells, after which 10 µL of assay medium was added. Magnetic beads against the different cytokines were mixed and diluted to 1× concentrations in Bead Diluent, after which 10 µL of the mixed beads was added to each well. The plate was sealed and incubated at 4° C., shaking, O/N. Wells were washed three times with 60 µL 1× Wash Buffer. Subsequently, 10 µL of Custom Detection Antibodies was added to each well, and the plate was sealed and incubated at RT, shaking, for 1 h. Next, 10 µL of streptavidin-PE was added to each well, and the plate was sealed and incubated at RT, shaking, for 30 min. Wells were washed three times with 60 µL 1× Wash Buffer as described above, after which beads were resuspended in 75 µL Luminex Sheath Fluid by shaking at RT for 5 min. Samples were run on a Luminex FlexMap 3D system.

At the start and at the end of the MLR assay, expression of PD-1 on the CD8$^+$ T cells and expression of PD-L1 on the mDCs was confirmed by flow cytometry using PE-Cy7-conjugated anti-PD-1 (BioLegend, cat. no. 329918; 1:20), allophycocyanin-conjugated anti-PD-L1 (BioLegend, cat. no. 329708; 1:80), BUV496-conjugated anti-CD3 (BD Biosciences, cat. no. 612940; 1:20), and BUV395-conjugated anti-CD8 (BD Biosciences, cat. no. 563795; 1:20).

Figure 5:
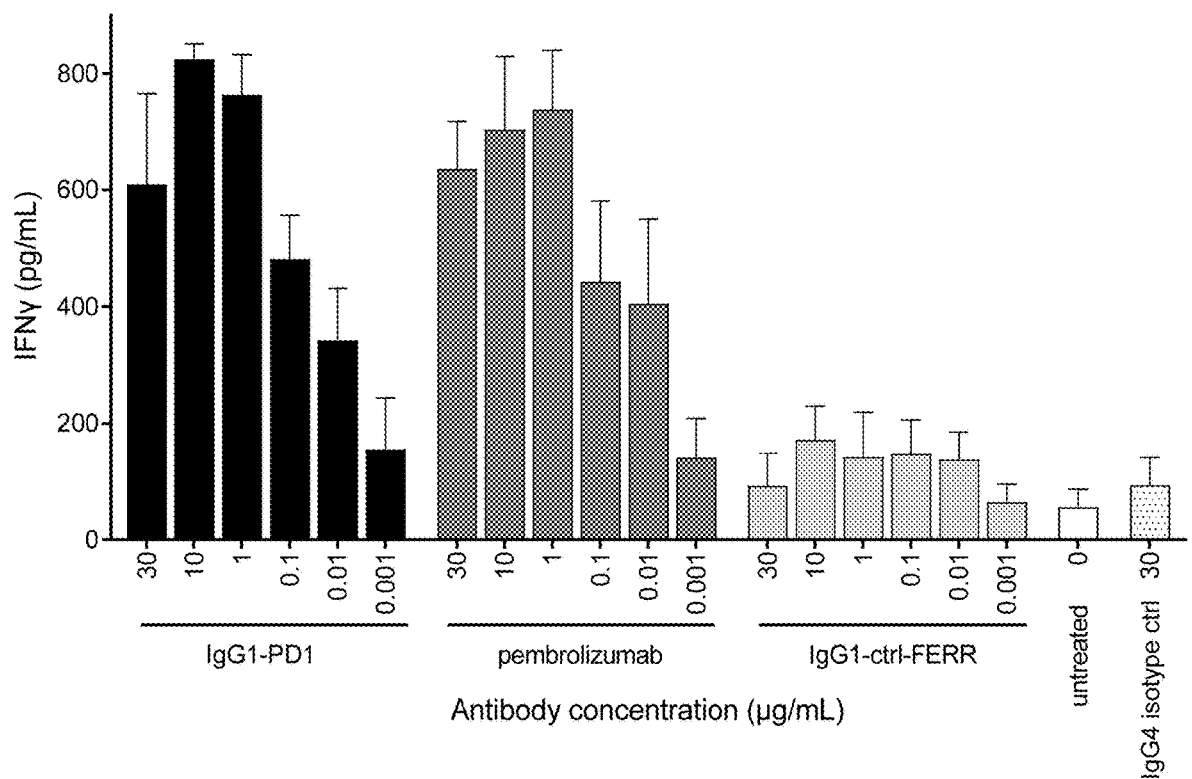
FIG. 5 shows IgG1-PD1-induced IFNγ secretion in an allogeneic MLR assay. Three unique donor pairs of allogeneic human mDCs and CD8+ T cells were cocultured in the presence of IgG1-PD1 or pembrolizumab for 5 d. IgG1-ctrl-FERR and an IgG4 isotype control were included as negative controls. IFNγ secretion was analyzed in the supernatant using an IFNγ-specific immunoassay. Data shown are mean±standard error of the mean (SEM) concentration for three unique allogeneic donor pairs. Abbreviations: FERR=L234F/L235E/G236R-K409R; IFN=interferon; IgG=immunoglobulin G; mDC=mature dendritic cell; MLR=mixed lymphocyte reaction; SEM=standard error of the mean.
Figure 6:
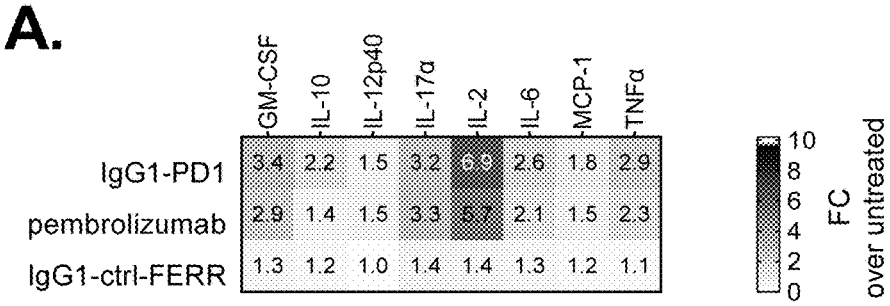
FIG. 6 shows IgG1-PD1-induced cytokine secretion in an allogeneic MLR assay. Three unique donor pairs of allogeneic human mDCs and CD8$^+$ T cells were cocultured in the presence of 1 µg/mL IgG1-PD1 or pembrolizumab for 5 d. IgG1-ctrl-FERR was included as a negative control. Cytokine secretion was analyzed in the supernatant using Luminex. (A) Cytokine levels are represented as the average fold change over the cytokine levels measured in untreated cocultures. (B) Shown are the levels of cytokine production of three unique allogeneic donor pairs, with horizontal lines indicating the mean, upper, and lower limits. Abbreviations: FC=fold change; FERR=L234F/L235E/G236R-K409R; GM-CSF=granulocyte macrophage colony-stimulating factor; IgG=immunoglobulin G; IL=interleukin; MCP-1=monocyte chemoattractant protein 1; mDC=mature dendritic cell; MLR=mixed lymphocyte reaction; TNF=tumor necrosis factor.
Figure 6:
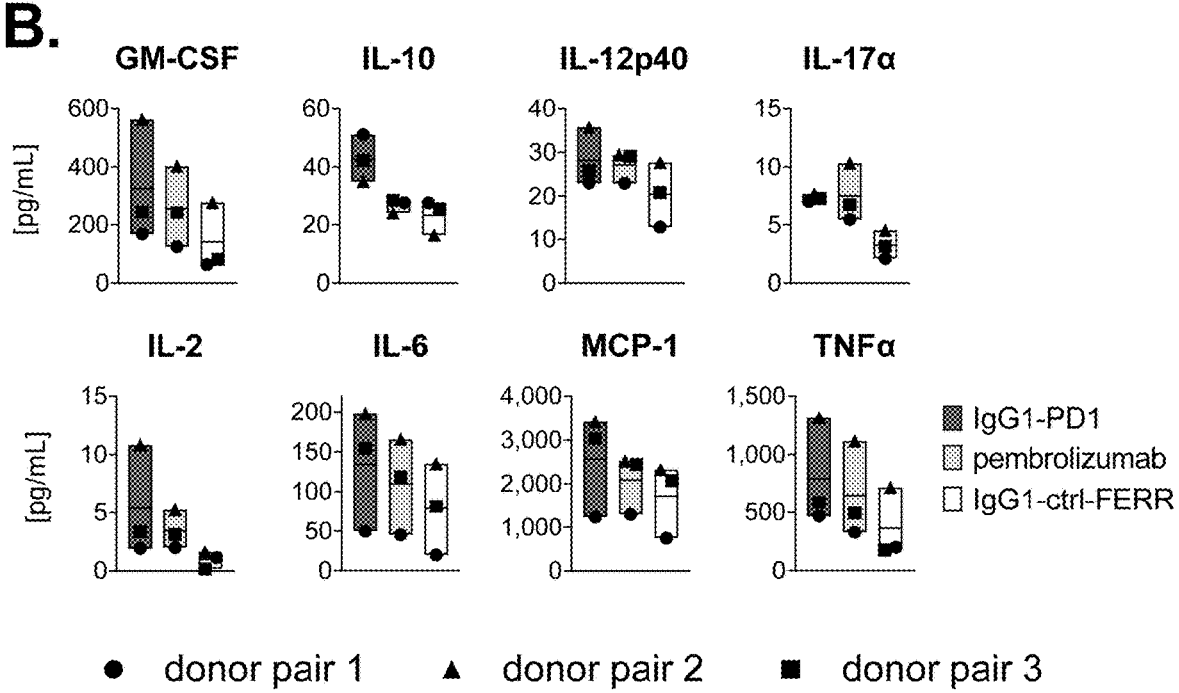

IgG1-PD1 consistently enhanced secretion of IFNγ (FIG. 5) in a dose-dependent manner. IgG1-PD1 also enhanced secretion of MCP-1, GM-CSF, IL-2, IL-6, IL-12p40, IL-17α, IL-10, and TNFα (FIG. 6). Pembrolizumab had a comparable effect on cytokine secretion.

Example 7: Evaluation of C1q Binding to IgG1-PD1

Binding of complement protein C1q to IgG1-PD1 harboring the FER Fc-silencing mutations in the constant heavy chain region was assessed using activated human CD8$^+$ T cells. As a positive control, IgG1-CD52-E430G was included, which has $V_H$ and $V_L$ domains based on the CD52 antibody CAMPATH-1H and which has an Fc-enhanced backbone that is known to efficiently bind C1q when bound to the cell surface. As non-binding negative control antibodies, IgG1-ctrl-FERR and IgG1-ctrl were included.

Human CD8$^+$ T cells were purified (enriched) from buffy coats obtained from healthy volunteers (Sanquin) by negative selection using the RosetteSep™ Human CD8$^+$ T Cell Enrichment Cocktail (Stemcell Technologies, cat. no. 15023C.2) or by positive selection via magnetic activated cell sorting (MACS), using CD8 MicroBeads (Miltenyi Biotec, cat. no. 130-045-201) and LS columns (Miltenyi Biotec, cat. no. 130-042-401), all according to the manufacturer's instructions. Purified T cells were resuspended in T-cell medium (Roswell Park Memorial Institute [RPMI]-1640 medium with 25 mM HEPES and L-glutamine [Lonza, cat. no. BE12-115F], supplemented with 10% heat-inactivated donor bovine serum with iron [DBSI; Gibco, cat. no. 20731-030] and penicillin/streptomycin [pen/strep; Lonza, cat. no. DE17-603E]).

Anti-CD3/CD28 beads (Dynabeads™ Human T-Activator CD3/CD28; ThermoFisher Scientific, cat. no. 11132D) were washed with PBS and resuspended in T-cell medium. The beads were added to the enriched human CD8$^+$ T cells at a 1:1 ratio and incubated at 37° C., 5% $CO_2$ for 48 h. Next, the beads were removed using a magnet, and the cells were washed twice in PBS and counted again.

PD-1 expression on the activated CD8$^+$ T cells was confirmed by flow cytometry, using IgG1-PD1 (30 µg/mL) and R-phycoerythrin (PE)-conjugated goat-anti-human IgG F(ab')$_2$ (diluted 1:200 in GMB FACS buffer; Jackson ImmunoResearch, cat. no. 109-116-098), or a commercial PE-conjugated PD-1 antibody (BioLegend, cat. no. 329906; diluted 1:50).

Activated CD8$^+$ T cells were seeded in a round-bottom 96-well plate (30,000 or 50,000 cells/well), pelleted, and resuspended in 30 µL assay medium (RPMI-1640 with 25 mM HEPES and L-glutamine, supplemented with 0.1% [w/v] bovine serum albumin fraction V [BSA; Roche, cat. no. 10735086001] and penicillin/streptomycin). Subsequently, 50 µL of IgG1-PD1, IgG1-ctrl-FERR, IgG1-CD52-E430G, or IgG1-ctrl (final concentrations of $1.7 \times 10^{-4}$-30 µg/mL in 3-fold dilution steps in assay medium) was added to each of the wells and incubated at 37° C. for 15 min to allow the antibodies to bind to the cells.

Human serum (20 µL/well; Sanquin, lot 20L15-02), as a source of C1q, was added to a final concentration of 20%. Cells were incubated on ice for 45 min, followed by two washes with cold GMB FACS buffer and incubation with 50 µL fluorescein isothiocyanate (FITC)-conjugated rabbit anti-human C1q (final concentration of 20 µg/mL [DAKO, cat no. F0254]; diluted 1:75 in GMB FACS buffer) in the presence or absence of allophycocyanin-conjugated mouse-anti-CD8 (BD Biosciences, cat. no. 555369; diluted 1:50 in GMB FACS buffer) in the dark at 4° C. for 30 min. Cells were washed twice with cold GMB FACS buffer, resuspended in 20 µL of GMB FACS buffer supplemented with 2 mM ethylenediaminetetraacetic acid (EDTA; Sigma-Aldrich, cat. no. 03690) and 4',6-diamidino-2-phenylindole (DAPI) viability dye (1:5,000; BD Pharmingen, cat. no. 564907). C1q binding to viable cells (as identified by DAPI exclusion) was analyzed by flow cytometry on an IntelliCyt® iQue Screener PLUS (Sartorius) or iQue3 (Sartorius). Binding curves were analyzed using non-linear regression analysis (sigmoidal dose-response with variable slope) using GraphPad Prism software.

Figure 7:
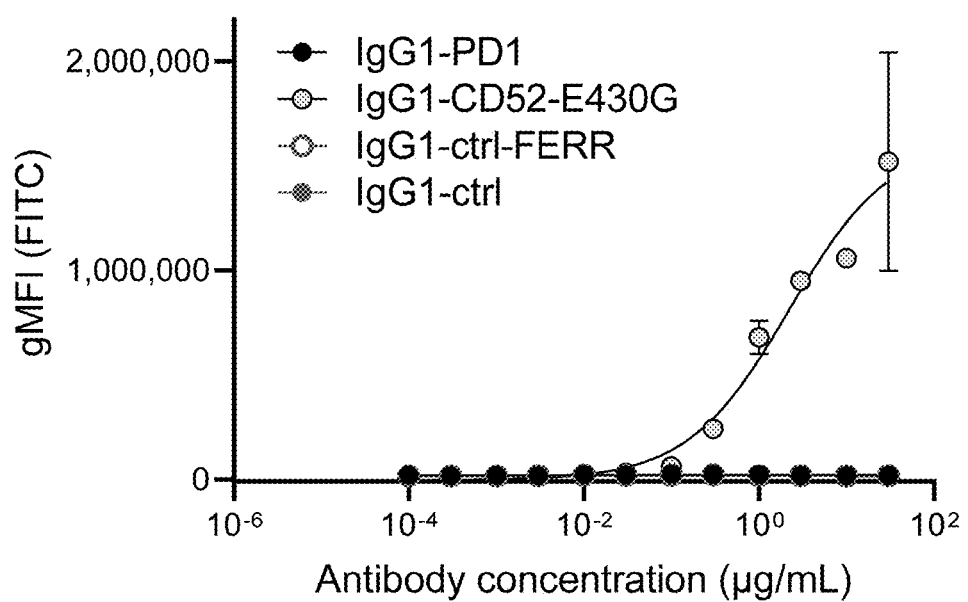
FIG. 7 shows C1q binding to membrane-bound IgG1-PD1. Binding of C1q to IgG1-PD1 was analyzed using stimulated human CD8$^+$ T cells. After incubation with IgG1-PD1, IgG1-ctrl-FERR, IgG1-ctrl, or positive control antibody IgG1-CD52-E430G (without inertness mutations and with a hexamerization-enhancing mutation), cells were incubated with human serum as a source of C1q. Binding of C1q was detected with a FITC-conjugated rabbit anti-C1q antibody. Data shown are the geometric mean fluorescence intensities (gMFI)±standard deviation (SD) from duplicate wells from one representative donor out of seven donors across three comparable experiments. Abbreviations: FITC=fluorescein isothiocyanate; gMFI=geometric mean fluorescence intensity; PE=R-phycoerythrocyanin.

Whereas dose-dependent C1q binding was observed to membrane-bound IgG1-CD52-E430G, no C1q binding was observed to membrane-bound IgG1-PD1 or to the non-binding control antibodies (FIG. 7).

These results indicate that the functionally inert backbone of IgG1-PD1 does not bind C1q.

Example 8: Binding of IgG1-PD1 to Fcγ Receptors as Determined by SPR

The binding of IgG1-PD1 to immobilized FcγRs (FcγRIa, FcγRIIa, FcγRIIb and FcγRIIIa) was assessed in vitro by SPR. Both polymorphic variants were included for FcγRIIa (H131 and R131) and FcγRIIIa (V158 and F158). As a positive control for FcγR binding, IgG1-ctrl with a wild-type Fc region was included.

In a first experiment, binding of IgG1-PD1, or IgG1-ctrl to immobilized human recombinant FcγR variants (FcγRIa, FcγRIIa, FcγRIIb, and FcγRIIIa) was analyzed using a Biacore 8K SPR system. In a second set of experiments, using the same method, binding of IgG1-PD1, nivolumab (Bristol-Meyers Squibb, lot no. ABP6534), pembrolizumab (Merck Sharp & Dohme, lot no. U013442), dostarlimab (GlaxoSmithKline, lot. no. 1822049), cemiplimab (Regeneron, lot no. 1F006A), IgG1-ctrl, or IgG4-ctrl was analyzed.

Biacore Series S Sensor Chips CM5 (Cytiva, cat. no. 29104988) were covalently coated with anti-Histidine (His) antibody using amine-coupling and His capture kits (Cytiva, cat. no. BR100050 and cat. no. 29234602) according to the manufacturer's instructions. FcγRIa, FcγRIIa (H131 and R131), FcγRIIb and FcγRIIIa (V158 and F158) (SinoBiological, cat. no. 10256-H08S-B, 10374-H08H1, 10374-H27H, 10259-H27H, 10389-H27H1, and 10389-H27H, respectively) diluted in HBS-EP+ (Cytiva, cat. no. BR100669) were captured onto the surface of the anti-His coated sensor chip with a flow rate of 10 μL/min and a contact time of 60 seconds to result in captured levels of approximately 350-600 resonance units (RU).

After three start-up cycles of HBS-EP+ buffer, test antibodies (IgG1-PD1, nivolumab, pembrolizumab, dostarlimab, cemiplimab, IgG1-ctrl, or IgG4-ctrl) were injected to generate binding curves, using antibody ranges as indicated in Table 14. Each sample that was analyzed on a surface with captured FcγRs (active surface) was also analyzed on a parallel flow cell without captured FcγRs (reference surface), which was used for background correction. The third start-up cycle containing HBS-EP+ as a (mock) analyte was subtracted from other sensorgrams to yield double-referenced data.

Figure 8:
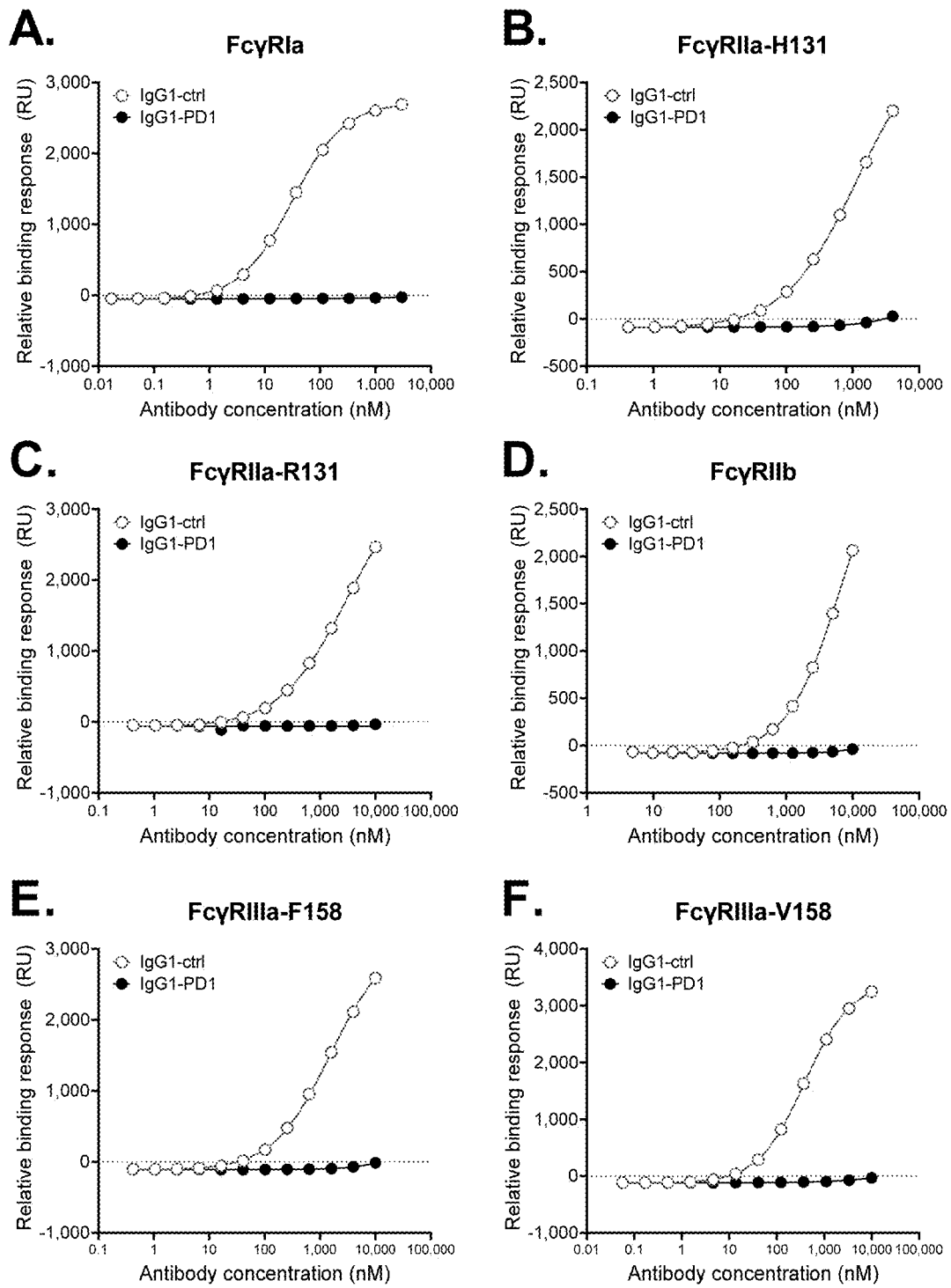
FIG. 8 shows FcγR binding of IgG1-PD1. The binding of IgG1-PD1 to immobilized human recombinant FcγR constructs was analyzed by SPR in a qualified assay (n=1). FcγRIa (A), FcγRIIa-H131 (B), FcγRIIa-R131 (C), FcγRIIb (D), FcγRIIIa-F158 (E), and FcγRIIIa-V158 (F) binding of IgG1-PD1. The antibody IgG1-ctrl (without the FER inertness mutations) was included as a positive control for binding. Abbreviations: ctrl=control; FcγR=Fc gamma receptor; IgG=immunoglobulin G; PD-1=programmed cell death protein 1; RU=resonance units.
Figure 9:
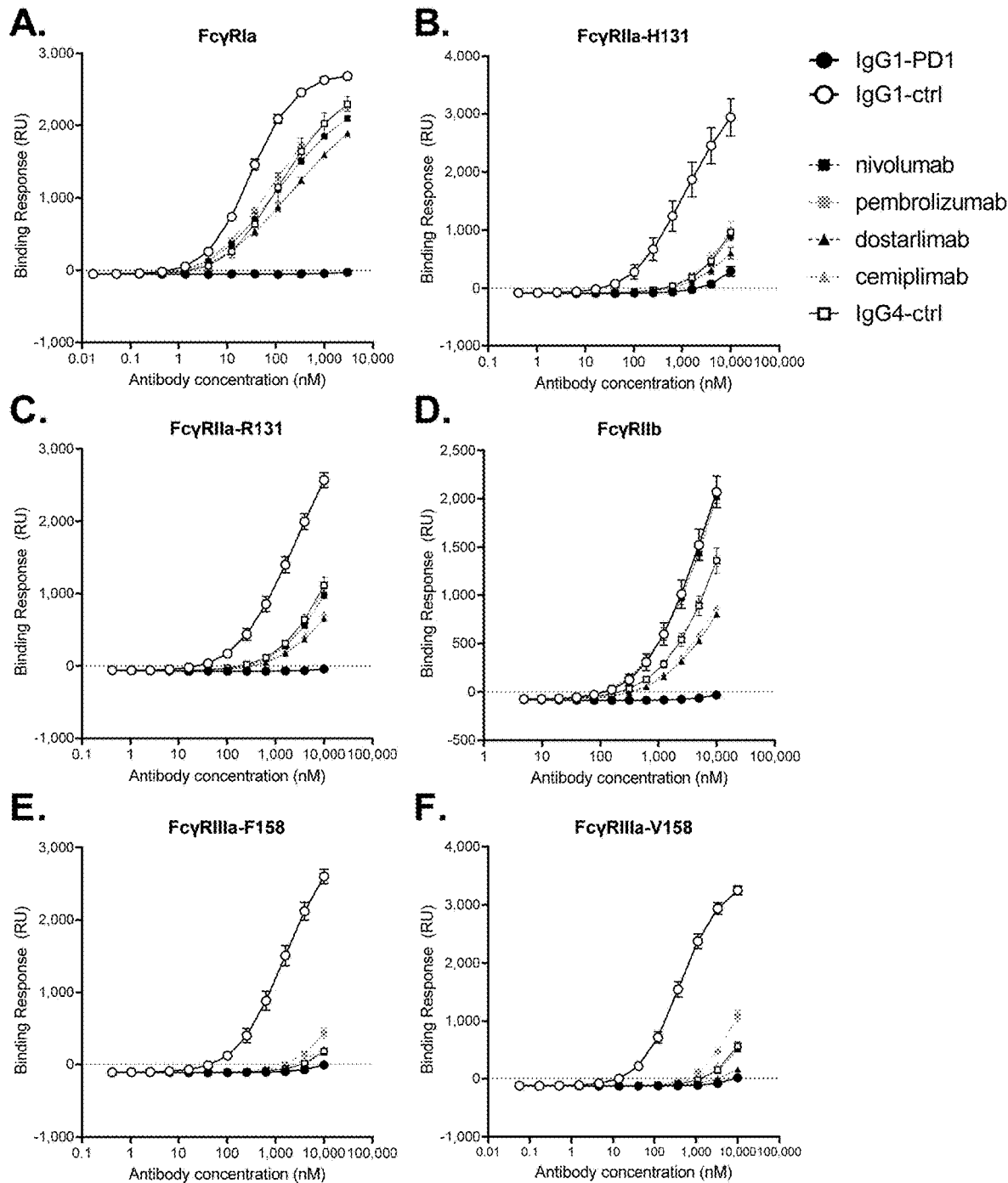
FIG. 9 shows FcγR binding of IgG1-PD1 and several other anti-PD-1 antibodies. The binding of IgG1-PD1, nivolumab, pembrolizumab, dostarlimab, and cemiplimab to immobilized human recombinant FcγR constructs was analyzed by SPR (n=3). FcγRIa (A), FcγRIIa-H131 (B), FcγRIIa-R131 (C), FcγRIIb (D), FcγRIIIa-F158 (E), and FcγRIIIa-V158 (F) binding of the test antibodies. The IgG1-ctrl and IgG4-ctrl antibodies were included as positive controls for FcγR binding of IgG1 and IgG4 molecules with wild-type Fc regions. Shown is the binding response ±SD of three separate experiments. Abbreviations: ctrl=control; FcγR=Fc gamma receptor; IgG=immunoglobulin G; PD-1=programmed cell death protein 1; RU=resonance units.

At the end of each cycle, the surface was regenerated using 10 mM Glycine-HCl pH 1.5 (Cytiva, cat. no. BR100354). Sensorgrams were generated using Biacore Insight Evaluation software (Cytiva) and a four-parameter logistic fit was applied on end-point measurements (binding plateau versus post-capture baseline). Data of the first experiment (n=1; qualified SPR assay) is shown in FIG. 8; data of the second set of experiments (n=3) is shown in FIG. 9.

TABLE 14

Test conditions for binding to individual FcγRs

| FcγR | Anti-PD-1 antibody concentration range tested | | |
|---|---|---|---|
| | Start concentration (nM) | Fold dilution | Lowest concentration (nM) |
| FcγRIa | 3,000 | 1:3 | 0.02 |
| FcγRIIa-H131 | 10,000 | 1:2.5 | 0.42 |
| FcγRIIa-R131 | 10,000 | 1:2.5 | 0.42 |
| FcγRIIb | 10,000 | 1:2 | 4.9 |
| FcγRIIIa-V158 | 10,000 | 1:3 | 0.06 |
| FcγRIIIa-F158 | 10,000 | 1:2.5 | 0.42 |

Results from the first experiment showed binding of IgG1-ctrl to all FcγRs, while no binding was observed for IgG1-PD1 to FcγRIa, FcγRIIa (H131 and R131), FcγRIIb, and FcγRIIIa (V158 and F158) (FIG. 8).

Results from the second set of experiments confirmed lack of FcγR binding for IgG1-PD1 (FIG. 9). IgG4-ctrl and the other anti-PD-1 antibodies tested (nivolumab, pembrolizumab, dostarlimab, and cemiplimab; all of the IgG4 subclass) demonstrated clear binding to FcγRIa, FcγRIIa-H131, FcγRIIa-R131, and FcγRIIb, and minimal to very minimal binding to FcγRIIIa-F158 and FcγRIIIa-V158.

These data confirm lack of FcγR binding for the Fc domain of IgG1-PD1 and demonstrate FcγR binding to nivolumab, pembrolizumab, dostarlimab, and cemiplimab. Taken together, these data suggest that the Fc domain of IgG1-PD1 is unable to induce FcγR-mediated effector functions (ADCC, ADCP).

Example 9: Binding of IgG1-PD1 to Cell Surface Expressed FcγRIa as Determined by Flow Cytometry Binding of IgG1-PD1, nivolumab, pembrolizumab, dostarlimab, and cemiplimab to human cell surface expressed FcγRIa was analyzed using flow cytometry.

FcγRIa was expressed on transiently transfected CHO-S cells, and cell surface expression was confirmed by flow cytometry using FITC-conjugated anti-FcγRI antibody (BioLegend, cat. no. 305006; 1:25). Binding of anti-PD-1 antibodies to transfected CHO-S cells was assessed as described in Example 2. Briefly, antibody dilutions (final concentrations: $1.69 \times 10^{-4}$-10 μg/mL, 3-fold dilutions) of IgG1-PD1, nivolumab (Bristol-Meyers Squibb, lot no. ABP6534), pembrolizumab (Merck Sharp & Dohme, lot no. U013442), dostarlimab (GlaxoSmithKline, lot. no. 1822049), cemiplimab (Regeneron, lot no. 1F006A), IgG1-ctrl, and IgG1-ctrl-FERR were prepared in GMB FACS buffer. Cells were centrifuged, supernatant was removed, and cells (30,000 cells in 50 μL) were incubated with 50 μL of the antibody dilutions for 30 min at 4° C. Cells were washed twice with GMB FACS buffer and incubated with 50 μL secondary antibody (PE-conjugated goat-anti-human IgG F(ab')$_2$; 1:500) for 30 min at 4° C., protected from light. Cells were washed twice with GMB FACS buffer and resuspended in GMB FACS buffer supplemented with 2 mM EDTA and DAPI viability marker (1:5,000).

Antibody binding to viable cells was analyzed by flow cytometry on an Intellicyt iQue PLUS Screener (Intellicyt Corporation) using FlowJo software by gating on PE-positive, DAPI-negative cells. Binding curves were analyzed using non-linear regression analysis (four-parameter dose-response curve fits) in GraphPad Prism.

Figure 10:
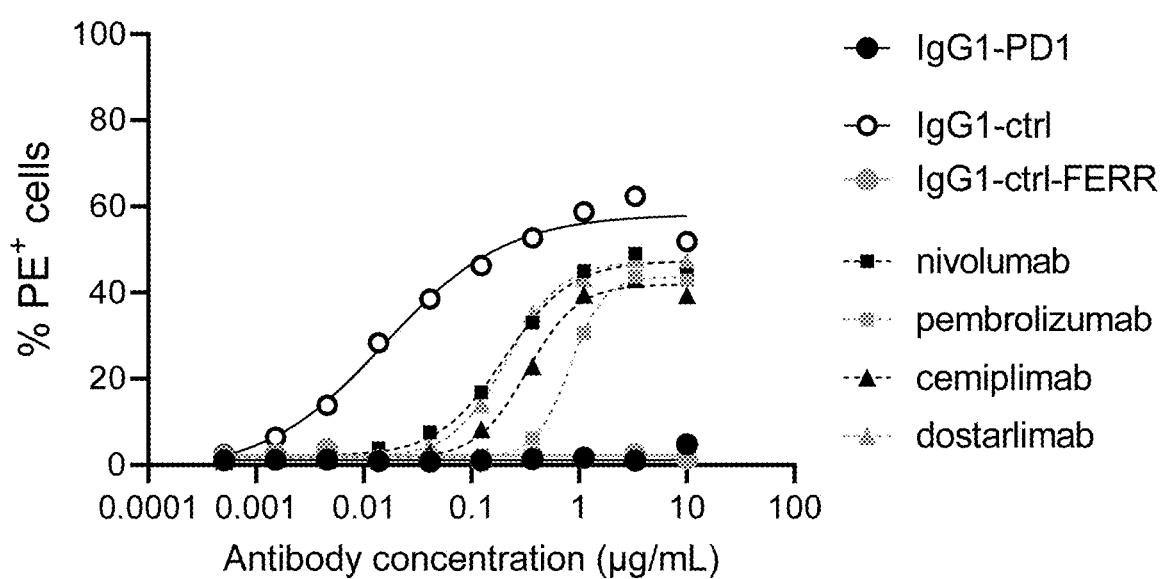
FIG. 10 shows FcγRIa binding of IgG1-PD1 and several other anti-PD-1 antibodies. The binding of IgG1-PD1, nivolumab, pembrolizumab, dostarlimab, and cemiplimab to CHO-S cells transiently expressing human FcγRIa was analyzed by flow cytometry. IgG1-ctrl and IgG1-ctrl-FERR were included as a positive and negative control, respectively. Abbreviations: ctrl=control; FcγR=Fc gamma receptor; FERR=L234F/L235E/G236R-K409R; huIgG=human immunoglobulin G; PD-1=programmed cell death protein 1; PE=R-phycoerythrin.

In the flow cytometry binding assays, the positive control antibody IgG1-ctrl (with a wild-type Fc region) showed binding to cells transiently expressing FcγRIa, while no binding was observed for the negative control antibody IgG1-ctrl-FERR (with an Fc region containing the FER inertness mutations and an additional, in the context of this study functionally irrelevant, K409R mutation) (FIG. 10). No binding was observed for IgG1-PD1, while concentration-dependent binding was observed for pembrolizumab, nivolumab, cemiplimab, and dostarlimab.

These data confirm lack of FcγRIa binding for the Fc domain of IgG1-PD1 and demonstrate FcγRIa binding to nivolumab, pembrolizumab, dostarlimab, and cemiplimab. Taken together, these data suggest that the Fc domain of IgG1-PD1 is unable to induce FcγRIa-mediated effector functions.

Example 10: Binding to Neonatal Fc Receptor by IgG1-PD1

The neonatal Fc receptor (FcRn) is responsible for the long plasma half-life of IgG by protecting IgG from degradation. IgG binds to FcRn in an acidic (pH 6.0) endosomal environment but dissociates from FcRn at neutral pH (pH 7.4). This pH-dependent binding of antibodies to FcRn causes recycling of the antibody together with FcRn, preventing intracellular antibody degradation, and therefore is an indicator for the in vivo pharmacokinetics of that antibody. The binding of IgG1-PD1 to immobilized FcRn was assessed in vitro at pH 6.0 and pH 7.4 by means of surface plasmon resonance (SPR).

Binding of IgG1-PD1 to immobilized human FcRn was analyzed using a Biacore 8K SPR system. Biacore Series S Sensor Chips CM5 (Cytiva, cat. no. 29104988) were covalently coated with anti-histidine (His) antibody using amine coupling and His capture kits (Cytiva, cat. no. BR100050 and cat. no. 29234602) according to the manufacturer's instructions. FcRn (SinoBiological, cat. no. CT071-H27H-B) diluted to a 5 nM coating concentration in PBS-P+ buffer pH 7.4 (Cytiva, cat. no. 28995084) or in PBS-P+ buffer with the pH adjusted to 6.0 (by addition of hydrochloric acid [Sigma-Aldrich, cat. no. 07102]) was captured onto the surface of the anti-His coated sensor chip with a flow rate of 10 µL/min and a contact time of 60 seconds. This resulted in captured levels of approximately 50 RU. After three start-up cycles of pH 6.0 or pH 7.4 PBS-P+ buffer, test antibodies (6.25-100 nM two-fold dilution series of IgG1-PD1, pembrolizumab (MSD, lot. no. T019263), or nivolumab (Bristol-Myers Squibb, lot. no. ABP6534) in pH 6.0 or pH 7.4 PBS-P+ buffer) were injected to generate binding curves. Each sample that was analyzed on a surface with captured FcRn (active surface) was also analyzed on a parallel flow cell without captured FcRn (reference surface), which was used for background correction. The third start-up cycle containing HBS-EP+ as a (mock) analyte was subtracted from other sensorgrams to yield double-referenced data. At the end of each cycle, the surface was regenerated using 10 mM Glycine HCl pH 1.5 (Cytiva, cat. no. BR100354). The data were analyzed using the predefined "Multi-cycle kinetics using capture" evaluation method in the Biacore Insight Evaluation software (Cytiva). Data is based on three separate experiments with technical duplicates.

At pH 6.0, IgG1-PD1 bound FcRn with an average affinity ($K_D$) of 50 nM (Table 15), which is comparable to an IgG1-ctrl antibody with a wild-type Fc region (a broad range of affinities is reported for wild-type IgG1 molecules in literature; in previous in-house experiments with the same assay set-up, an average $K_D$ of 34 nM was measured for IgG1-ctrl across 12 data points). The affinity of pembrolizumab and nivolumab was approximately two-fold lower ($K_D$ of 116 nM and 133 nM, respectively). No FcRn binding was observed at pH 7.4 (not shown). Taken together, these results demonstrate that the FER inertness mutations in the IgG1-PD1 Fc region do not affect FcRn binding and suggest that IgG1-PD1 will retain typical IgG pharmacokinetic properties in vivo.

TABLE 15

Affinity for FcRn as determined by SPR
Binding of IgG1-PD1, pembrolizumab, and nivolumab to sensor chips coated with human FcRn was analyzed by SPR.
The average affinity and SD are based on three independent measurements with technical duplicates.

| Antibody | $K_D$ (M) | | $k_a$ (1/M × s) | | $k_d$ (1/s) | |
|---|---|---|---|---|---|---|
| | Average | SD | Average | SD | Average | SD |
| IgG1-PD1 | 4.99 × $10^{-8}$ | 6.85 × $10^{-9}$ | 8.65 × $10^5$ | 6.79 × $10^4$ | 4.29 × $10^{-2}$ | 4.88 × $10^{-3}$ |
| Nivolumab | 1.33 × $10^{-7}$ | 2.01 × $10^{-8}$ | 5.18 × $10^5$ | 4.70 × $10^4$ | 6.89 × $10^{-2}$ | 1.19 × $10^{-2}$ |
| Pembrolizumab | 1.16 × $10^{-7}$ | 1.69 × $10^{-8}$ | 5.46 × $10^5$ | 4.42 × $10^4$ | 6.36 × $10^{-2}$ | 1.15 × $10^{-2}$ |

Abbreviations:
$K_D$ = equilibrium dissociation constant;
$k_a$ = association rate constant;
$k_d$ = dissociation rate constant or off-rate;
SD = standard deviation.

Example 11: Pharmacokinetic Analysis of IgG1-PD1 in Absence of Target Binding

The pharmacokinetic properties of IgG1-PD1 were analyzed in mice. PD-1 is expressed mainly on activated B and T cells, and as such, its expression is expected to be limited in non-tumor bearing SCID mice, which lack mature B and T cells. Furthermore, IgG1-PD1 shows substantially reduced cross-reactivity to cells transiently overexpressing mouse PD-1 (Example 2). Therefore, the pharmacokinetic (PK) properties of IgG1-PD1 in non-tumor bearing SCID mice are expected to reflect the PK properties of IgG1-PD1 in absence of target binding.

The mice in this study were housed in the Central Laboratory Animal Facility (Utrecht, the Netherlands). All mice were kept in individually ventilated cages with food and water provided ad libitum. All experiments were in compliance with the Dutch animal protection law (WoD) translated from the directives (2010/63/EU) and were approved by the Dutch Central Commission for animal experiments and by the local Ethical committee). SCID mice (C.B-17/IcrHan® Hsd-Prkdc$^{scid}$, Envigo) were injected intravenously with 1 or 10 mg/kg IgG1-PD1, using 3 mice per group. Blood samples (40 µL) were collected from the saphenous vein or the cheek veins at 10 min, 4 h, 1 day, 2 days, 8 days, 14 days, and 21 days after antibody administration. Blood was collected into vials containing $K_2$-ethylenediaminetetraacetic acid and stored at −65° C. until determination of antibody concentrations.

By a total human IgG (hIgG) electrochemiluminescence immunoassay (ECLIA), specific hIgG concentrations were determined. Meso Scale Discovery (MSD) standard plates (96-well MULTI-ARRAY plate, cat. no. L15XA-3) were coated with mouse anti-hIgG capture antibody (IgG2amm-1015-6A05) diluted in PBS (Lonza, cat. no. BE17-156Q) for 16-24 h at 2-8° C. After washing the plate with PBS-Tween (PBS-T; PBS supplemented with 0.05% (w/v) Tween-20 [Sigma, cat. no. P1379]) to remove non-bound antibody, the unoccupied surfaces were blocked for 60±5 min at RT (PBS-T supplemented with 3% (w/v) Blocker-A [MSD, cat. no. R93AA-1]) followed by washing with PBS-T. Mouse plasma samples were initially diluted 50-fold (2% mouse plasma) in assay buffer (PBS-T supplemented with 1% (w/v) Blocker-A). To create a reference curve, IgG1-PD1 (same batch as the material used for injection) was diluted (measuring range: 0.156-20.0 µg/mL; anchor points: 0.0781 and 40.0 µg/mL) in Calibrator Diluent (2% mouse plasma [$K_2$EDTA, pooled plasma, BIOIVT, cat. no. MSE00PLK2PNN] in assay buffer). To accommodate for the expected wide range of antibody concentrations present in the samples, samples were additionally diluted 1:10 or 1:50 in Sample Diluent (2% mouse plasma in assay buffer). The coated and blocked plates were incubated with 50 μL diluted mouse samples, the reference curve, and appropriate quality control samples (pooled mouse plasma spiked with IgG1-PD1, covering the range of the reference curve) at RT for 90±5 min. After washing with PBS-T, the plates were incubated with SULFO-TAG-conjugated mouse anti-hIgG detection antibody IgG2amm-1015-4A01 at RT for 90±5 min. After washing with PBS-T, immobilized antibodies were visualized by adding Read Buffer (MSD GOLD Read Buffer, cat. no. R92TG-2) and measuring light emission at ~620 nm using an MSD Sector S600 plate reader. Processing of analytical data was performed using SoftMax Pro GxP Software v7.1. Extrapolation below the run lower limit of quantitation (LLOQ) or above the upper limit of quantitation (ULOQ) was not allowed.

Figure 11:
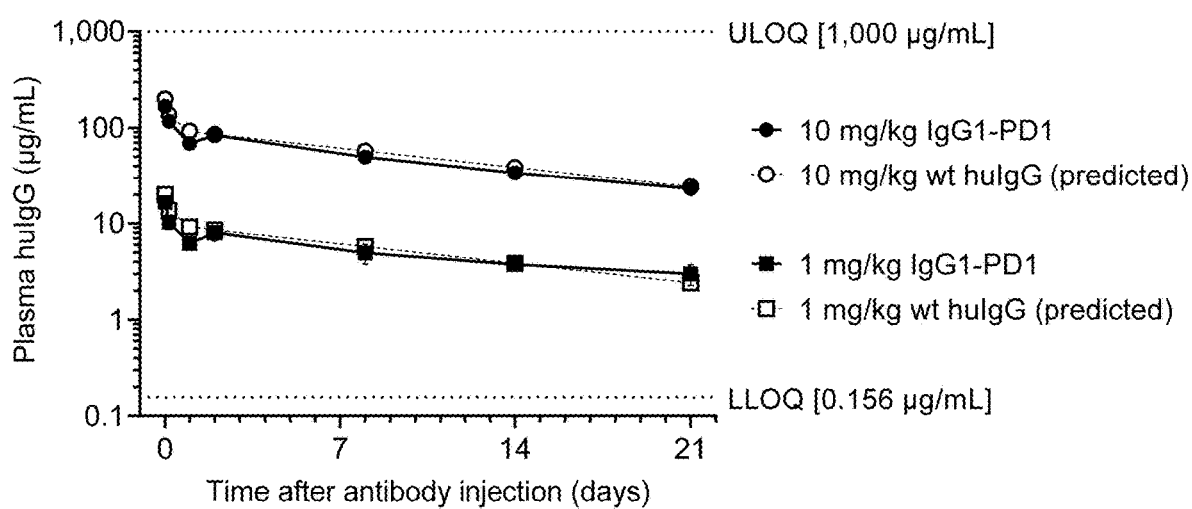
FIG. 11 shows total human IgG in mouse plasma samples. Mice were injected intravenously with 1 or 10 mg/kg IgG1-PD1 at t=0 and serial plasma samples were taken at 10 min, 4 h, 1 d, 2 d, 8 d, 14 d, and 21 d after injection. Total huIgG in plasma samples was determined by ECLIA for each mouse. Data are represented as mean huIgG concentration ±SD of three individual mice. Dashed lines indicate the plasma concentrations of wild-type (wt) huIgG predicted by a two-compartment model based on IgG clearance in humans (Bleeker et al., 2001, Blood. 98(10):3136-42). Dotted lines indicate the LLOQ and ULOQ. Abbreviations: huIgG=human IgG; IgG=immunoglobulin G; LLOQ=lower limit of quantitation; PD-1=programmed cell death protein 1; SD=standard deviation; ULOQ=upper limit of quantitation.

The plasma clearance profile of IgG1-PD1 in absence of target binding was comparable to the clearance profile of a wild-type human IgG1 antibody in SCID mice predicted by a two-compartment model based on IgG1 clearance in humans (Bleeker et al., 2001, Blood. 98(10):3136-42) (FIG. 11). No clinical observations were noted, and no body weight loss was observed.

In conclusion, these data indicate that the PK properties of IgG1-PD1 are comparable to those of normal human IgG antibodies in absence of target binding.

Example 12: Anti-Tumor Activity of IgG1-PD1 in Human PD-1 Knock-In Mice

IgG1-PD1 shows only limited binding to cells transiently overexpressing mouse PD-1 (Example 2). Therefore, to assess anti-tumor activity of IgG1-PD1 in vivo, C57BL/6 mice engineered to express the human PD-1 extracellular domain (ECD) in the mouse PD-1 gene locus (hPD-1 knock-in [KI] mice) were used.

All animal experiments were performed at Crown Bioscience Inc. and approved by their Institutional Animal Care and Use Committee (IACUC) prior to execution. Animals were housed and handled in accordance with good animal practice as defined by the regulations of the Association for Assessment and Accreditation of Laboratory Animal Care (AAALAC). Female homozygous human PD-1 knock-in mice on a C57BL/6 background (hPD-1 KI mice; Beijing Biocytogen Co., Ltd; C57BL/6-Pdcd1$^{tm1(PDCD1)}$/Bcgen, stock no. 110003), 7-9 weeks old, were injected subcutaneously (SC) with syngeneic MC38 colon cancer cells ($1\times10^6$ cells) in the right lower flank. Tumor growth was evaluated using a caliper (three times per week after randomization), and tumor volumes ($mm^3$) were calculated from caliper measurements as: tumor volume=$0.5\times(\text{length}\times\text{width}^2)$, where the length is the longest tumor dimension, and the width is the longest tumor dimension perpendicular to the length. Mice were randomized (9 mice per group) based on tumor volume and body weight when tumors had reached an average volume of approximately 60 $mm^3$ (denoted as Day 0). At the start of treatment, mice were injected intravenously (IV; dosing volume 10 mL/kg in PBS) with 0.5, 2, or 10 mg/kg IgG1-PD1 or pembrolizumab (obtained from Merck by Crown Bioscience Inc., lot no. T042260), or with 10 mg/kg isotype control antibody IgG1-ctrl-FERR. Subsequent doses were administered intraperitoneally (IP). A dosing regimen of two doses weekly for three weeks (2QW× 3) was used. Animals were monitored daily for morbidity and mortality and monitored routinely for other clinical observations. The experiment ended for individual mice when the tumor volume exceeded 1,500 $mm^3$ or when the animals reached other humane endpoints.

To compare progression-free survival between the groups, curve fits were applied to the individual tumor growth graphs to establish the day of progression beyond a tumor volume of 500 $mm^3$ for each mouse. These day values were plotted in a Kaplan-Meier survival curve and used to perform a Mantel-Cox analysis between individual curves using SPSS software. The difference in tumor volumes between the groups was compared using a nonparametric Mann-Whitney analysis (in GraphPad Prism) on the last day that all groups were still intact (ie, until the first tumor-related death in the study, ie, Day 11). P-values are presented accompanied by median values (per group) including the 95% confidence interval of the difference in median (Hodges Lehmann).

The mice showed no signs of illness, but two mice were found dead (one in the 2 mg/kg IgG1-PD1 group and one in the 2 mg/kg pembrolizumab treatment group). The cause of these deaths was undetermined.

Figure 12:
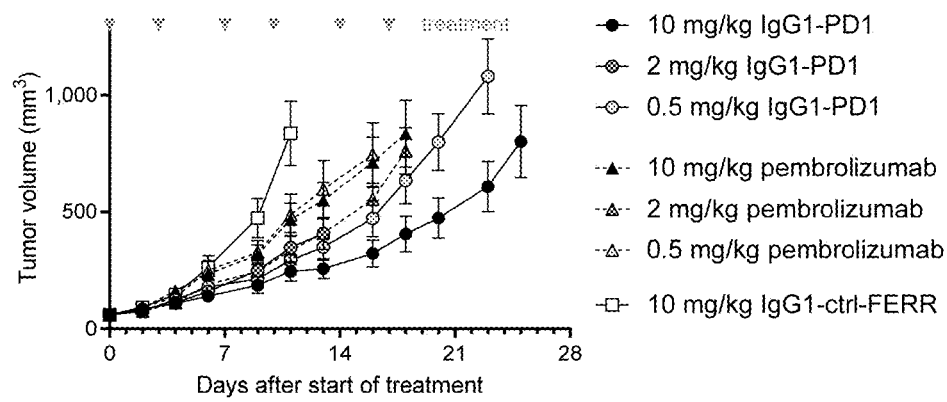
FIG. 12 shows anti-tumor activity of IgG1-PD1 in human PD-1 knock-in mice. The MC38 colon cancer syngeneic tumor model was established by SC implantation in hPD-1 KI mice. Mice were administered 0.5, 2, or 10 mg/kg IgG1-PD1 or pembrolizumab or 10 mg/kg IgG1-ctrl-FERR 2QW×3 (9 mice per group). (A) Average tumor volume ±SEM in each group, until the last time point the group was complete. (B) Tumor volumes of the different groups on the last day all groups were complete (Day 11). Data shown are the tumor volumes in individual mice in each treatment group, as well as mean tumor volume ±SEM per treatment group. Mann-Whitney analysis was used to compare tumor volumes of the treatment groups to the IgG1-ctrl-FERR-treated group, with *p<0.05, p<0.01, and *p<0.001. C. Progression-free survival, defined as the percentage of mice with tumor volume smaller than 500 mm$^3$, is shown as a Kaplan-Meier curve. Analysis excluded one mouse from the 2 mg/kg IgG1-PD1 group that was found dead due to undetermined cause on day 16, before the tumor volume had exceeded 500 mm$^3$. Abbreviations: 2QW×3=twice per week for three weeks; ctrl=control; FERR=L234F/L235E/G236R/K409R mutations; IgG=immunoglobulin G; KI=knock-in; PD-1=programmed cell death protein 1; SC=subcutaneous; SEM=standard error of the mean.
Figure 12:
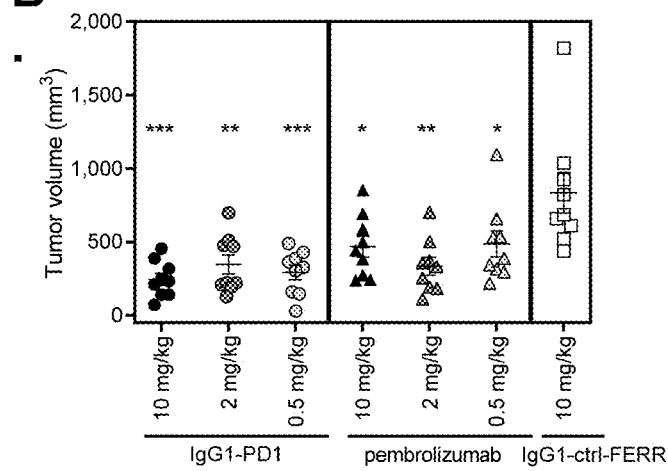
Figure 12:
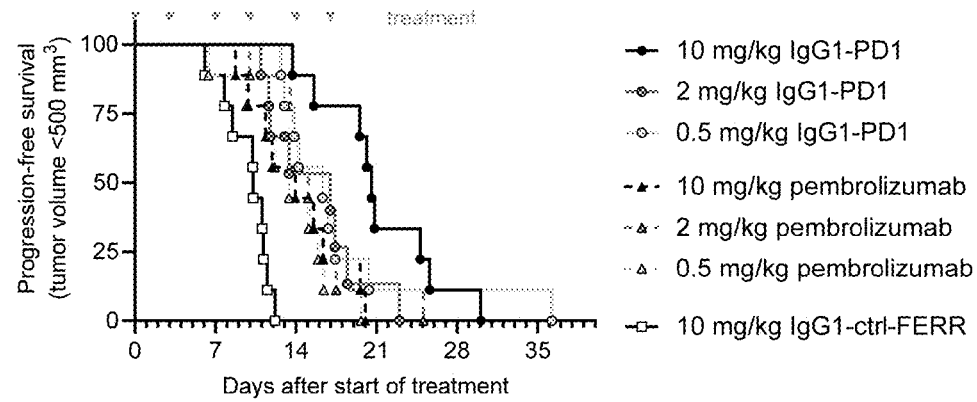

Treatment with IgG1-PD1 and pembrolizumab inhibited tumor growth at all doses tested (FIG. 12A). On Day 11, the last day that all treatment groups were complete, tumors in mice treated with IgG1-PD1 or pembrolizumab were significantly smaller at all doses tested than tumors in mice treated with 10 mg/kg IgG1-ctrl-FERR (FIG. 12B). In addition, at 10 mg/kg, tumor volumes in mice treated with IgG1-PD1 were significantly smaller than in mice treated with an equivalent dose of pembrolizumab (Mann-Whitney test, p=0.0188).

Treatment with IgG1-PD1 or pembrolizumab significantly increased progression-free survival (PFS) at all doses tested compared to mice treated with 10 mg/kg IgG1-ctrl-FERR (FIG. 12C). At 10 mg/kg, progression-free survival in mice treated with IgG1-PD1 was significantly extended as compared to mice treated with pembrolizumab (median PFS 10 mg/kg IgG1-PD1: 20.56 days, median PFS 10 mg/kg pembrolizumab: 13.94 days; P-value=0.0021).

In conclusion, IgG1-PD1 exhibited potent anti-tumor activity in MC38 tumor-bearing hPD-1 KI mice.

Example 13: PD Activity of IgG1-PD1 in Human PD-1 Knock-In Mice

IgG1-PD1 showed potent anti-tumor activity in MC38 tumor-bearing hPD-1 KI mice (Example 12). To explore the pharmacodynamic effects of IgG1-PD1 treatment, MC38 tumor-bearing hPD-1 KI mice were treated with IgG1-PD1, and blood, spleen, and tumor samples were collected at predetermined timepoints. The effect of IgG1-PD1 treatment on immune cells was determined using flow cytometry and immunohistochemistry (IHC).

The MC38 tumor-bearing hPD-1 KI mouse model was established as described in Example 12. Mice were randomized (12 mice per group) based on tumor volume when tumors had reached an average volume of approximately 60 $mm^3$ (denoted as Day 0). At the start of treatment, mice were injected IV (dosing volume 10 mL/kg in PBS) with 0.5 or 10 mg/kg IgG1-PD1, with 10 mg/kg pembrolizumab (obtained from Merck by Crown Bioscience Inc., lot no. U036695), or with 10 mg/kg isotype control antibody IgG1-ctrl-FERR on Day 0, 3, and 7. Animals were monitored daily for morbidity and mortality and monitored routinely for other clinical observations. The mice showed no signs of illness. On Day 2, 4, and 8, animals were euthanized, and blood was collected through cardiac puncture (4 mice per treatment group at each time point) for the immunophenotyping of peripheral blood cells. In addition, the spleens and tumors were harvested. The tumors were formalin-fixed and paraffin-embedded for IHC analysis.

The spleens were enzymatically dissociated using the gentleMACS™ Dissociator (130-096-427, Miltenyi) according to the manufacturer's instructions. The resulting cell suspension was filtered through a 70 m cell strainer (Falcon, cat. no. 352350), washed with 5 mL of FACS wash buffer (10% FBS [Gibco, cat. no. 10099-141], 40 mM EDTA [Boston BioProducts, cat. no. BM-711-K], in PBS). Red blood cells were lysed using RBC Lysing Buffer (Bio-gems, cat. no. 64010-00-100). Cells were washed twice with FACS wash buffer and resuspended in PBS for cell counting.

The blood samples and dissociated spleen samples were incubated with Mouse BD Fc Block™ (BD Biosciences, cat. no. 553141) in the dark at 4° C. for 10 min, after which cells were stained with the antibody panel described in Table 16 diluted in Fc blocking buffer at 4° C. for 30 min. Subsequently, the blood samples were incubated with RBC Lysing buffer for an additional 10 min incubation at RT. Next, cells from both the blood and dissociated spleen samples were washed with wash buffer three times. To each sample, 100 µL of 123count eBeads (eBioscience, cat. no. 01-1234-42) was added, after which the samples were analyzed by flow cytometry. Flow cytometry data were analyzed using Kaluza Analysis Software.

combined with HQ signal amplification kit, Roche, cat. no. 06472320001) to avoid binding to potential remaining mouse IgG. Cellular quantitation within viable tumor regions was performed on digital images with tailored image analysis algorithms using HALO software (Indica Labs). Cellular quantitation readouts were generated by calculating the percentage of marker-positive cells of all nucleated cells within viable (non-necrotic) tumor areas.

Figure 13:
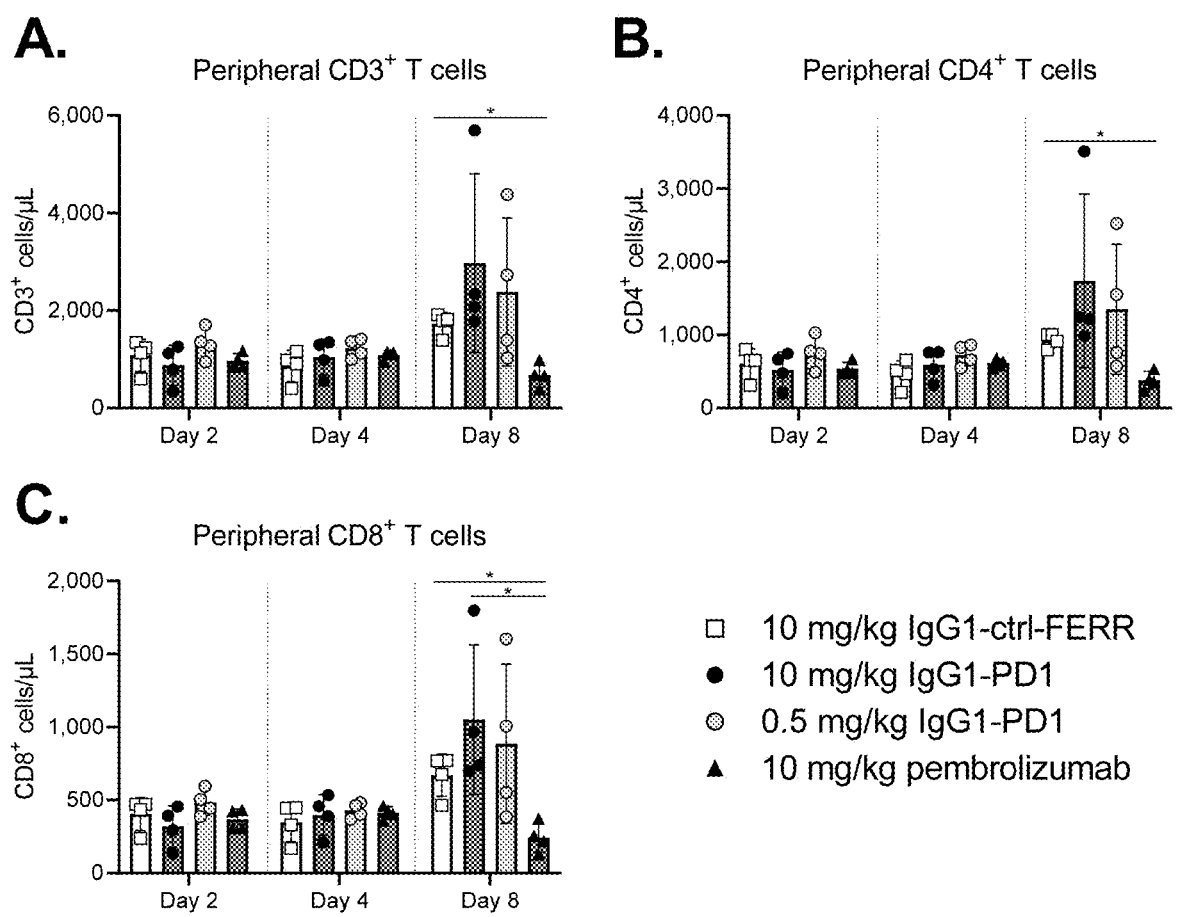
FIG. 13 shows peripheral T-cell count dynamics in human PD-1 knock-in mice treated with IgG1-PD1. The MC38 colon cancer syngeneic tumor model was established by SC implantation in hPD-1 KI mice. Mice were administered 0.5 or 10 mg/kg IgG1-PD1, 10 mg/kg pembrolizumab, or 10 mg/kg IgG1-ctrl-FERR on Day 0, 3, and 7 (12 mice per group). Peripheral blood samples were collected after euthanasia from four mice per group on Day 2, 4, and 8 and analyzed by flow cytometry. Shown is the mean±SD of the number of $CD3^+$ (A), $CD4^+$ (B), and $CD8^+$ (C) T cells per L blood within the viable $CD45^+$ leukocyte subpopulation. Mann-Whitney analysis was used to compare the treatment groups to the IgG1-ctrl-FERR-treated group, and the 10 mg/kg IgG1-PD1 group with the 10 mg/kg pembrolizumab group, with *p<0.05. Abbreviations: ctrl=control; FERR=L234F/L235E/G236R/K409R mutations; IgG=immunoglobulin G; KI=knock-in; PD-1=programmed cell death protein 1; SC=subcutaneous; SD=standard deviation.
Figure 14:
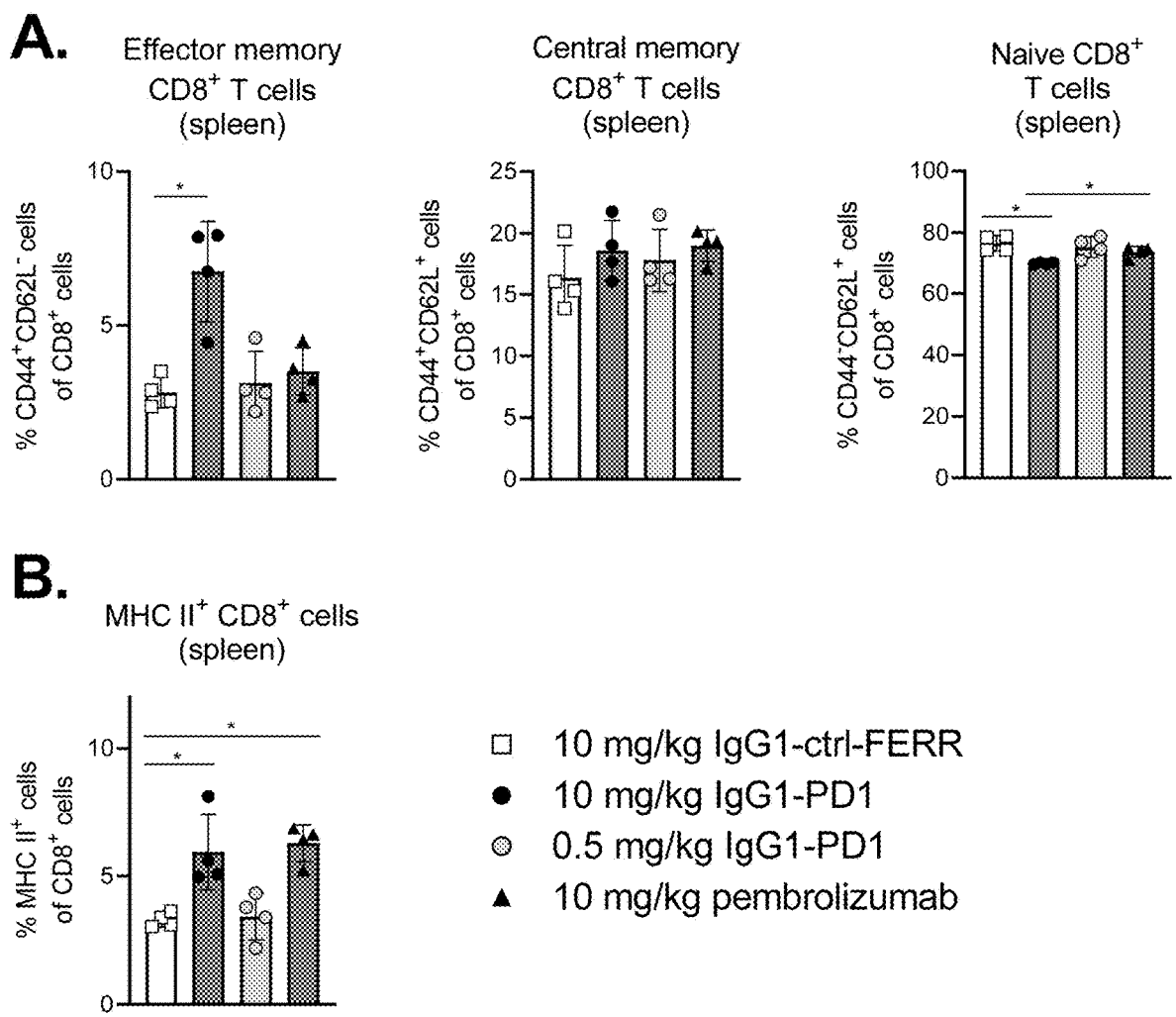
FIG. 14 shows PD markers on splenic T-cell subsets in human PD-1 knock-in mice treated with IgG1-PD1. The MC38 colon cancer syngeneic tumor model was established by SC implantation in hPD-1 KI mice. Mice were administered 0.5 or 10 mg/kg IgG1-PD1, 10 mg/kg pembrolizumab, or 10 mg/kg IgG1-ctrl-FERR on Day 0, 3, and 7 (12 mice per group). Spleens were harvested on Day 2, 4, and 8 (n=4 mice per group and timepoint) and analyzed by flow cytometry. Shown is the mean±SD of the percentage of effector memory ($CD44^+CD62L^-$), central memory ($CD44^+CD62L^+$), and naïve ($CD44^-CD62L^+$) $CD8^+$ T cells (A), and the percentage of MHC class $II^+$ cells within the total $CD8^+$ T-cell population (B) in the spleen on Day 8. Mann-Whitney analysis was used to compare the treatment groups to the IgG1-ctrl-FERR-treated group, and the 10 mg/kg IgG1-PD1 group with the 10 mg/kg pembrolizumab group, with *p<0.05. Abbreviations: ctrl=control; FERR=L234F/L235E/G236R/K409R mutations; IgG=immunoglobulin G; KI=knock-in; PD-1=programmed cell death protein 1; SC=subcutaneous; SD=standard deviation.

Compared to the non-binding control antibody IgG1-ctrl-FERR, treatment with 10 mg/kg IgG1-PD1 resulted in a clear trend of an increased number of T cells ($CD3^+$, $CD4^+$, and $CD8^+$) in peripheral blood on Day 8, while treatment with 10 mg/kg pembrolizumab led to a statistically significant decrease in the number of peripheral T cells (FIG. 13). In parallel, the percentage of effector memory ($CD44^+$ $CD62L^-$) $CD8^+$ T cells was significantly increased on Day 8 in the spleens of mice treated with 10 mg/kg IgG1-PD1, but not in the spleens of mice treated with 10 mg/kg pembrolizumab (FIG. 14A), when compared to control treatment. A concomitant significant decrease in the percentage of naïve ($CD44^-CD62L^+$) $CD8^+$ T cells was observed in the spleens of mice treated with 10 mg/kg IgG1-PD1 when compared to control mice and mice treated with 10 mg/kg pembrolizumab. Treatment with 10 mg/kg IgG1-PD1 significantly increased the percentage of MHC class $II^+$ $CD8^+$ T cells in the spleen on Day 8, suggestive of increased T-cell activation (FIG. 14B). A comparable increase in the per-

TABLE 16

Immunophenotyping antibody panel

| Marker | Fluorophore | Clone | Vendor | Cat. no. | Isotype | Dilution |
| --- | --- | --- | --- | --- | --- | --- |
| CD45 | PerCP-Cy5.5 | 30-F11 | BioLegend | 103132 | Rat IgG2b, κ | 1:50 |
| CD3 | BUV395 | 17A2 | BD Biosciences | 740268 | Rat IgG2b, κ | 1:50 |
| CD4 | BV510 | GK1.5 | BioLegend | 100449 | Rat IgG2b, κ | 1:40 |
| CD8 | PE-eF610 | 53-6.7 | eBioscience | 61-0081-82 | Rat IgG2a, κ | 1:50 |
| CD44 | AF700 | IM7 | BioLegend | 103026 | Rat IgG2b, κ | 1:50 |
| CD62L | BV785 | MEL-14 | BioLegend | 104440 | Rat IgG2a, κ | 1:50 |
| CD19 [a] | FITC | 6D5 | BioLegend | 115506 | Rat IgG2a, κ | 1:50 |
| CD11b [a] | FITC | M1/70 | BioLegend | 101206 | Rat IgG2b, κ | 1:50 |
| I-A/I-E (MHC II) | BV711 | M5/114.15.2 | BioLegend | 107643 | Rat IgG2b, κ | 1:50 |
| Fixable Viability Dye | eF780 | N.A. | eBioscience | 65-0865-14 | N.A. | 1:100 |

[a] CD19 and CD11b were combined in a single channel to exclude cells expressing CD19 and/or CD11b.

Abbreviations:
BUV = Brilliant Ultra Violet;
BV = Brilliant Violet;
CD = cluster of differentiation;
Cy = cyanine;
eF = eFluor;
FITC = fluorescein isothiocyanate;
IgG = immunoglobulin G;
MHC = major histocompatibility complex;
N.A. = not applicable;
PE = phycoerythrin;
PerCP = peridinin-chlorophyll-protein.

Expression of CD3, CD4, CD8, and granzyme B (GZMB) in xenograft tumor tissues was assessed in IHC using rabbit anti-CD3ε (Ventana, clone 2GV6, cat. no. 790-4341; final concentration 0.4 µg/mL), rabbit anti-CD4 (Abcam, clone EPR19514, cat. no. ab183685; final concentration 5 µg/mL), rabbit anti-CD8 (Cell Signaling, clone D4W2Z, cat. no. 98941; diluted 1:200), and rabbit anti-GZMB antibody (Abeam, clone EPR22645-206, cat. no. ab255598; final concentration 5 µg/mL) followed by an anti-rabbit specific detection protocol (OmniMap DAB anti-Rb detection kit, Roche, cat. no. 05269679001, for the CD8 IHC assay centage of MHC class $II^+$ $CD8^+$ T cells was observed in the spleens of mice treated with 10 mg/kg pembrolizumab.

Figure 15:
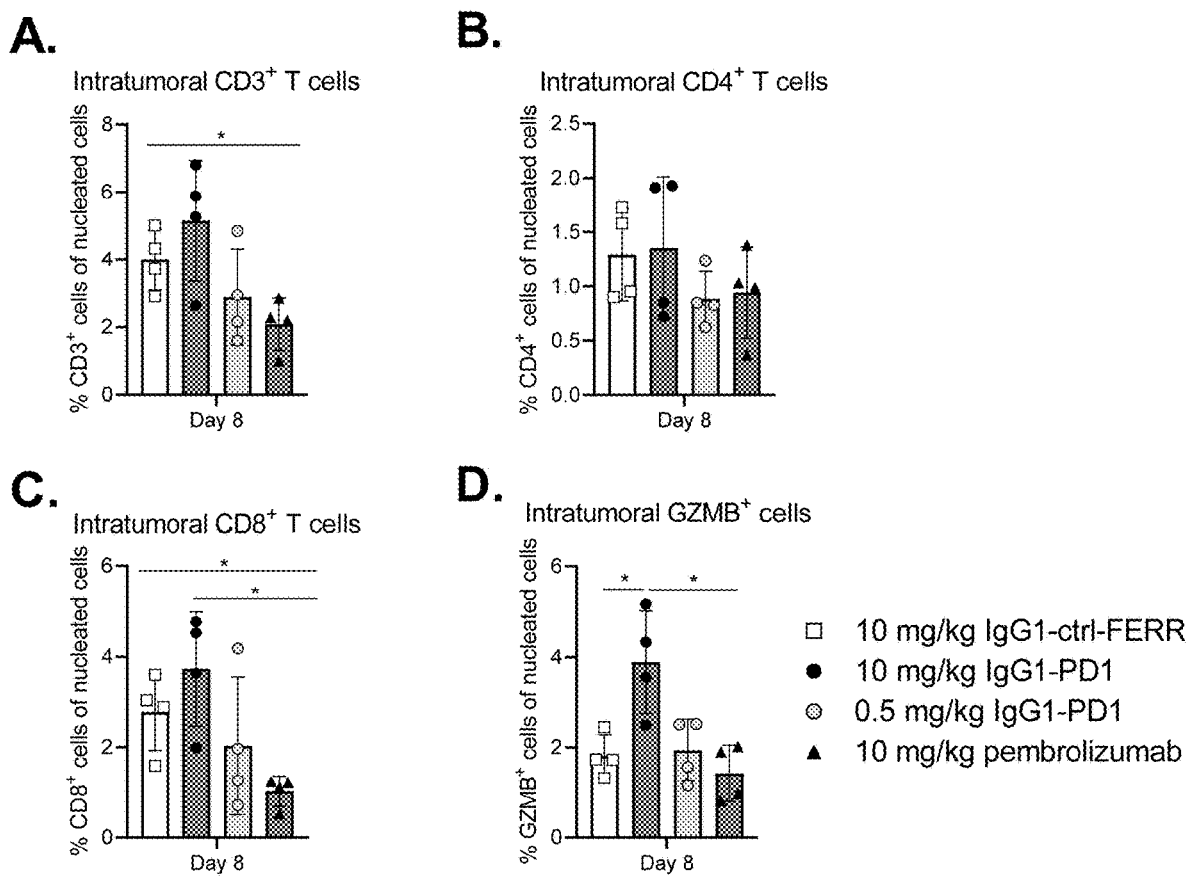
FIG. 15 shows changes in intratumoral cells in human PD-1 knock-in mice treated with IgG1-PD1. The MC38 colon cancer syngeneic tumor model was established by SC implantation in hPD-1 KI mice. Mice were administered 0.5 or 10 mg/kg IgG1-PD1, 10 mg/kg pembrolizumab, or 10 mg/kg IgG1-ctrl-FERR on Day 0, 3, and 7 (12 mice per group). Xenograft tumors were excised on Day 8 (n=4 mice per group) and analyzed by IHC. Shown is the mean±SD of the percentage of $CD3^+$ T cells (A), $CD4^+$ T cells (B), $CD8^+$ T cells (C), and $GZMB^+$ cells (D) of all nucleated cells on Day 8. Mann-Whitney analysis was used to compare the treatment groups to the IgG1-ctrl-FERR-treated group, and the 10 mg/kg IgG1-PD1 group with the 10 mg/kg pembrolizumab group, with *p<0.05. Abbreviations: ctrl=control; FERR=L234F/L235E/G236R/K409R mutations; GZMB=granzyme B; IgG=immunoglobulin G; KI=knock-in; PD-1=programmed cell death protein 1; SC=subcutaneous; SD=standard deviation.

On Day 8, the number of intratumoral $CD3^+$ and $CD8^+$ T cells was significantly lower in mice treated with 10 mg/kg pembrolizumab than in the control mice (FIG. 15A-C). Furthermore, on Day 8, the percentage of intratumoral cells expressing the cytotoxic effector molecule GZMB was significantly higher in mice treated with 10 mg/kg IgG1-PD1 than in mice treated with 10 mg/kg pembrolizumab and in control mice (FIG. 15D).

In conclusion, in vivo anti-tumor activity of IgG1-PD1 was associated with an increase in the number of peripheral blood and intratumoral T cells, an increased percentage of effector memory and activated (MHC class II$^+$) CD8$^+$ T cells in the spleen, and an increased percentage of intratumoral GZMB$^+$ cells. In comparison, pembrolizumab-treated mice showed limited pharmacodynamic changes.

Example 14: Macrophage Binding by IgG1-PD1

IgG1-PD1 showed no binding to FcγRs, while nivolumab, pembrolizumab, dostarlimab, and cemiplimab did (Example 8). The capacity of these antibodies to bind FcγR-expressing M2c-like macrophages was assessed in vitro using flow cytometry.

Human peripheral blood mononuclear cells (PBMCs) were purified from buffy coats of three healthy human donors (Sanquin blood supply foundation, the Netherlands) in LeucoSep™ tubes (Greiner, cat. no. 227290) by density gradient centrifugation (20 min at 800×g, with low brake) over Lymphocyte Separation Medium (Promocell, cat. no. C-44010), according to the manufacturer's instructions. Human monocytes were purified from PBMCs by MACS technology using anti-CD14 MicroBeads (Miltenyi; cat. no. 130-050-201), according to the manufacturer's instructions. CD14$^+$ monocytes were resuspended at a density of 1.0×10$^6$ cells/mL in CellGenix® GMP DC medium (CellGenix, cat. no. 20801-0500) supplemented with 50 ng/mL M-CSF (Gibco, cat. no. PHC9501). For the polarization of monocytes towards M2c-like macrophages, purified monocytes were plated in 100 mm$^2$ Nunc™ dishes with UpCell™ Surface (8×10$^6$ cells/dish at a density of 1.0×10$^6$ cells/mL; Thermo Fisher Scientific, cat. no. 174902) in M-CSF-supplemented CellGenix GMP DC medium and cultured (37° C., 5% CO$_2$) for 7 d, followed by 3 d of culture in CellGenix GMP DC medium supplemented with 50 ng/mL M-CSF, 50 ng/mL IL-4 (R&D Systems, cat. no. 204-IL), and 50 ng/mL IL-10 (R&D Systems, cat. no. 1064-IL/CF). Next, macrophages were detached from the culture dish surface by leaving the dish at RT for 40 to 60 min. Detached macrophages were pelleted by centrifugation (5 min at 300×g), counted, and resuspended at a density of 1.5×10$^6$ cells/mL in CellGenix GMP DC medium. The M2c-like phenotype of the monocyte-derived macrophages was confirmed by flow cytometry using a mixture of Brilliant Violet (BV)421-conjugated anti-human CD163 (BioLegend, cat. no. 333612; diluted 1:200) and BV711-conjugated anti-human CD206 (BioLegend, cat. no. 321136; diluted 1:200). FcγR and PD-1 expression on M2c-like macrophages was assessed using FITC-conjugated anti-human CD64 (FcγRIa; BioLegend, cat. no. 305006; diluted 1:25), FITC-conjugated anti-human CD32 (FcγRII; BD Pharmingen, cat. no. 552883; diluted 1:50), PE-conjugated anti-human CD16a (FcγRIIIa; BD Pharmingen, cat. no. 555407; diluted 1:50), PE-conjugated anti-PD-1 antibody (BioLegend, cat. no. 329906, diluted 1:50), a FITC-conjugated IgG1 isotype control (BioLegend, cat. no. 400108; diluted 1:25), and a PE-conjugated IgG1 isotype control (BD Pharmingen, cat. no. 555749; diluted 1:50). The M2c-like macrophages were incubated with IgG1-PD1, pembrolizumab (MSD, lot no. U013442), nivolumab (Bristol-Myers Squibb, lot no. ABP6534), IgG4 isotype control (BioLegend, cat. no. 403702), IgG1-ctrl, and IgG1-ctrl-FERR for 24 h, and washed twice with FACS buffer. Cells were incubated with PE-conjugated goat anti-human IgG F(ab')$_2$ (Jackson ImmunoResearch, cat. no. 109-116-097; diluted 1:200) diluted in FACS buffer at 4° C. for 30 min. After two washes with FACS buffer, cells were resuspended in FACS buffer supplemented with the viability dye 4',6-diamidino-2-phenylindole (DAPI; BD Pharmingen, cat. no. 564907; diluted 1:5,000) and subsequently measured on a BD LSRFortessa™ Cell Analyzer and analyzed in FlowJo.

Figure 16:
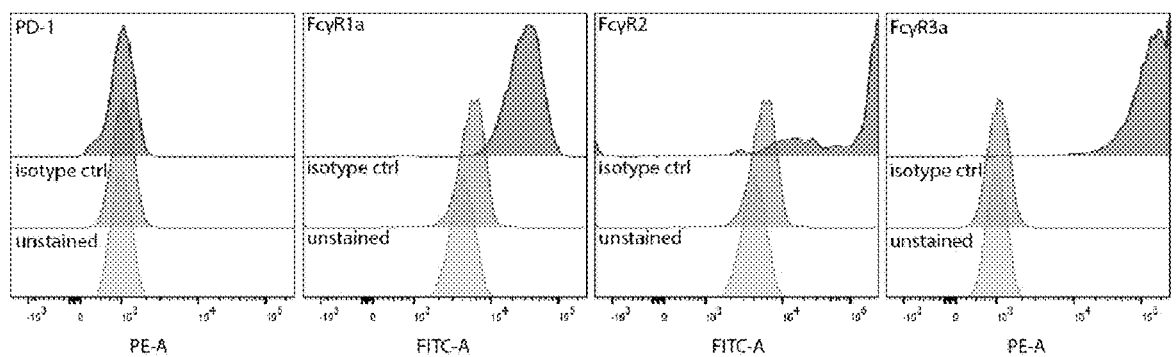
FIG. 16 shows binding of IgG1-PD1 and other anti-PD-1 antibodies to human monocyte-derived FcγR+ M2c-like macrophages. (A) Expression of FcγRIa, FcγRII, FcγRIIIa, and PD-1, relative to the relevant isotype controls and unstained M2c-like macrophages, visualized in overlay histograms of normalized data, of one representative donor out of three donors tested. (B) The binding of IgG1-PD1, pembrolizumab, nivolumab, and control antibodies to human monocyte-derived FcγR+ M2c-like macrophages after 24 h of incubation was analyzed by flow cytometry. Binding is shown relative to that of the background control (binding with secondary antibody only, indicated by the dotted black line). Dots represent three individual donors measured in two independent experiments, and bar graphs and error bars represent the mean±SD of the three donors, respectively. Abbreviations: ctrl=control; FERR=L234F/L235E/G236R/K409R mutations; PD-1=programmed cell death protein 1; SD=standard deviation.
Figure 16:
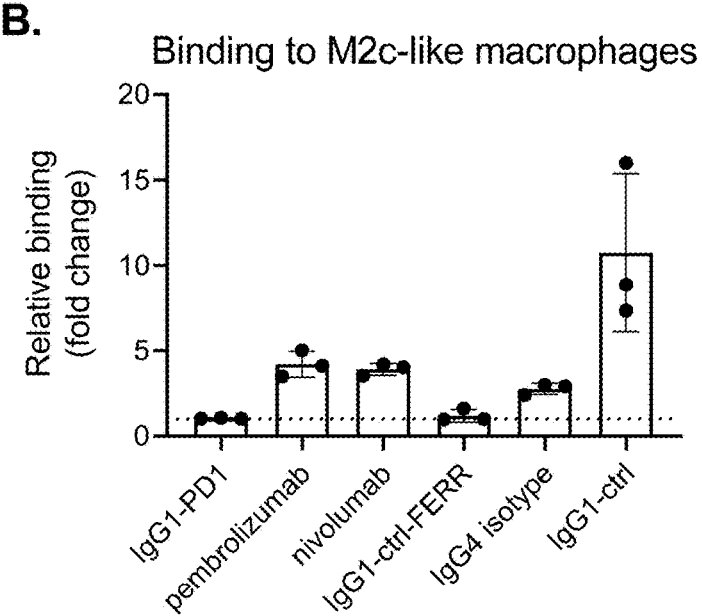

Binding of IgG1-PD1, pembrolizumab, and nivolumab to FcγRs expressed on the cell membrane was evaluated using human monocyte-derived M2c-like macrophages (from three healthy donors). Expression of FcγRIa, FcγRII, and FcγRIIIa and absence of PD-1 expression were first confirmed by flow cytometry (FIG. 16A). IgG1-ctrl, which has a wild-type IgG1 Fc domain, Fc-inert IgG1-ctrl-FERR, and an IgG4 isotype control were included as controls. Whereas IgG1-ctrl showed efficient binding to the M2c-like macrophages after 24 h of incubation, no binding was observed for IgG1-PD1 or IgG1-ctrl-FERR for any of the donors tested (FIG. 16B). Conversely, pembrolizumab, nivolumab, and the IgG4 isotype control antibody all showed binding above that of the background control. Together, these data demonstrate that IgG1-PD1 does not bind to FcγR-expressing M2c-like macrophages, while pembrolizumab and nivolumab do.

Example 15: FcγR Signaling Induced by IgG1-PD1

IgG1-PD1 showed no binding to FcγRs or to M2c-like macrophages, while anti-PD-1 antibodies with an IgG4 backbone did (Examples 8 and 14). The capacity of these antibodies to induce FcγR signaling was assessed in vitro using cell-based Fc effector activity reporter assays.

FcγRI, FcγRIIa-H131, FcγRIIa-R131, and FcγRIIb signaling induced by IgG1-PD1, nivolumab, pembrolizumab, dostarlimab, and cemiplimab was evaluated using bioluminescent cell-based reporter assays (Promega, cat. no. GA1341, G988A, CS178B11, and G988ACS1781E01, respectively), essentially as described by the manufacturer. Briefly, CHO cells transfected with PD-1 (generated in-house; Example 1) were preincubated with serially diluted IgG1-PD1, pembrolizumab (MSD, lot no. W003098), nivolumab (Bristol-Myers Squibb, lot no. 8006768), dostarlimab (GlaxoSmithKline, lot. no. 1822049), cemiplimab (Regeneron, lot no. 1F006A), IgG1-ctrl-FERR, or IgG4 isotype (BioLegend, cat. no. 403702) (final in-assay concentrations in FcγRI assay: 30—1.23×10$^{-7}$ µg/mL in 25-fold dilutions; final assay concentrations in other FcγR assays: 30—0.00192 µg/mL in 5-fold dilutions) for 15 min at 37° C., 5% CO$_2$. IgG1-CD52-E430G, with the hexamerization-enhancing E430G mutation, was included as a positive control. Genetically engineered FcγRI, FcγRIIa-H (FcγRIIa-H131), FcγRIIa-R (FcγRIIa-R131), and FcγRIIb effector cells were added to the cultures at a 1:1 ratio, after which the samples were incubated for 5 h at 37° C., 5% CO$_2$. Next, the samples were incubated at RT with reconstituted Bio-Glo™ for 10 min at RT, after which luminescence (in RLU) was measured using an EnVision Multilabel Plate Reader (PerkinElmer).

Figure 17:
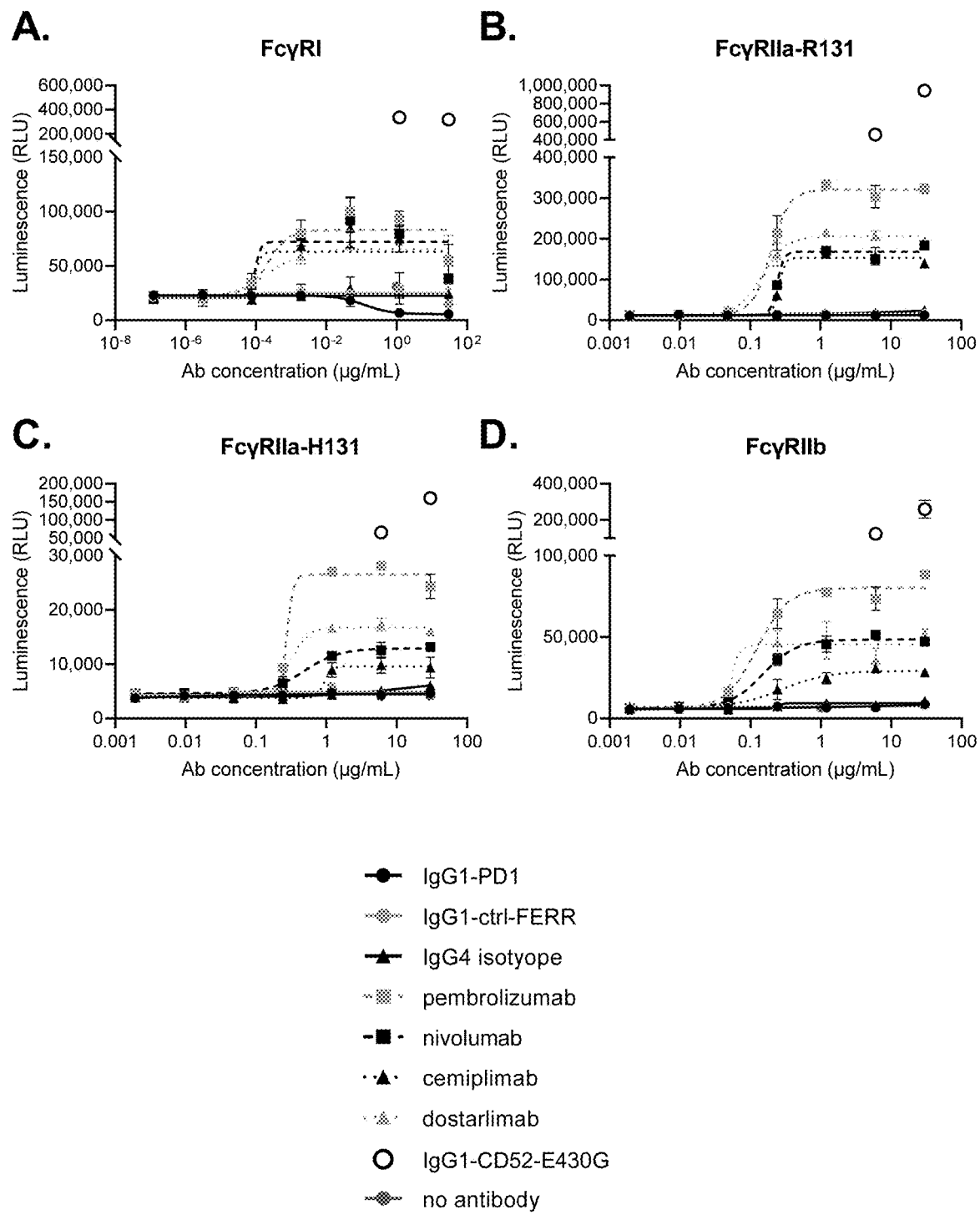
FIG. 17 shows FcγR signaling induced by membrane-bound IgG1-PD1 and other anti-PD-1 antibodies. FcγR signaling induced by membrane-bound IgG1-PD1 and several other anti-PD-1 antibodies was tested using cell-based bioluminescent FcγRI (A), FcγRIIa-R131 (B), FcγRIIa-H131 (C), and FcγRIIb (D) reporter assays. IgG1-CD52-E430G with the hexamerization-enhancing E430G mutation was included as a positive control. Data shown are mean relative light units ±SD of duplicate wells in one representative experiment out of three experiments. Abbreviations: Ab=antibody; FERR=L234F/L235E/G236R/K409R mutations; PD-1=programmed cell death protein 1; RLU=relative light units; SD=standard deviation.

Membrane-bound IgG1-CD52-E430G, with the E430G hexamerization-enhancing mutation, induced strong FcγRI, FcγRIIa-R131, FcγRIIa-H131, and FcγRIIb signaling. Membrane-bound pembrolizumab, nivolumab, cemiplimab, and dostarlimab (all of the IgG4 subclass) also induced FcγRI, FcγRIIa-R131, FcγRIIa-H131, and FcγRIIb signaling, but to a lesser extent, while membrane-bound IgG1-PD1 and the non-binding control antibodies (IgG1-ctrl-FERR, IgG4 isotype) did not (FIG. 17).

Taken together, these data demonstrate that membrane-bound nivolumab, pembrolizumab, dostarlimab, and cemiplimab induce FcγRI, FcγRIIa-R131, FcγRIIa-H131, and FcγRIIb signaling. In contrast, membrane-bound IgG1-PD1 is unable to induce FcγR-mediated signaling, confirming the functional inertness of the Fc domain of IgG1-PD1.

The invention claimed is:

1. An antibody or antigen-binding fragment thereof having the ability to bind to PD-1, wherein the antibody or the antigen-binding fragment thereof comprises a heavy chain having a heavy chain constant region (CH) and a heavy chain variable region (VH) and a light chain having a light chain constant region (CL) and a light chain variable region (VL), wherein the heavy chain constant region is a human IgG1 constant region that comprises phenylalanine at the position corresponding to position 234 in a human IgG1 heavy chain according to EU numbering, glutamate at the position corresponding to position 235 in a human IgG1 heavy chain according to EU numbering, and arginine at the position corresponding to position 236 in a human IgG1 heavy chain according to EU numbering, and wherein (i) the heavy chain variable region (VH) comprises a HCDR1, HCDR2, and HCDR3 sequence, wherein the HCDR1, HCDR2 and HCDR3 sequences according to Kabat numbering comprise or have the sequence as set forth in SEQ ID NO: 12, SEQ ID NO: 11, and SEQ ID NO: 8, respectively, and the light chain variable region (VL) comprises a LCDR1, LCDR2, and LCDR3 sequence, wherein the LCDR1, LCDR2 and LCDR3 sequences according to Kabat numbering comprise or have the sequence as set forth in SEQ ID NO: 17, SEQ ID NO: 15, and SEQ ID NO: 14, respectively; or (ii) the heavy chain variable region (VH) comprises a HCDR1, HCDR2, and HCDR3 sequence, wherein the HCDR1, HCDR2 and HCDR3 sequences according to IMGT numbering comprise or have the sequence as set forth in SEQ ID NO: 13, SEQ ID NO: 10, and SEQ ID NO: 9, respectively, and the light chain variable region (VL) comprises a LCDR1, LCDR2, and LCDR3 sequence, wherein the LCDR1, LCDR2 and LCDR3 sequences according to IMGT numbering comprise or have the sequence as set forth in SEQ ID NO: 16, QAS, and SEQ ID NO: 14, respectively.

2. The antibody or the antigen-binding fragment thereof of claim 1, wherein the heavy chain constant region comprises a sequence having at least 70%, at least 75%, at least 80%, at least 85%, at least 90%, at least 95%, at least 97%, at least 99%, or 100% identity to the amino acid sequence of the heavy chain constant region sequence as set forth in SEQ ID NO: 2.

3. The antibody or the antigen-binding fragment thereof of claim 1, wherein the heavy chain constant region comprises the sequence as set forth in SEQ ID NO: 2 or 55.

4. The antibody or the antigen-binding fragment thereof of claim 1, wherein the HCDR1, HCDR2 and HCDR3 sequences according to Kabat numbering comprise or have the sequence as set forth in SEQ ID NO: 12, SEQ ID NO: 11, and SEQ ID NO: 8, respectively, and the LCDR1, LCDR2 and LCDR3 sequences according to Kabat numbering comprise or have the sequence as set forth in SEQ ID NO: 17, SEQ ID NO: 15, and SEQ ID NO: 14, respectively.

5. The antibody or the antigen-binding fragment thereof of claim 1, wherein the HCDR1, HCDR2 and HCDR3 sequences according to IMGT numbering comprise or have the sequence as set forth in SEQ ID NO: 13, SEQ ID NO: 10, and SEQ ID NO: 9, respectively, and the LCDR1, LCDR2 and LCDR3 sequences according to IMGT numbering comprise or have the sequence as set forth in SEQ ID NO: 16, QAS, and SEQ ID NO: 14, respectively.

6. The antibody or the antigen-binding fragment thereof of claim 1, wherein the heavy chain variable region (VH) comprises a sequence having at least 70%, at least 75%, at least 80%, at least 85%, at least 90%, at least 95%, at least 97%, at least 99%, or 100% identity to the amino acid sequence of the VH sequence as set forth in SEQ ID NO: 20, and the light chain variable region (VL) comprises a sequence having at least 70%, at least 75%, at least 80%, at least 85%, at least 90%, at least 95%, at least 97%, at least 99%, or 100% identity to the amino acid sequence of the VH sequence as set forth in SEQ ID NO: 21.

7. The antibody or the antigen-binding fragment thereof of claim 1, wherein
the heavy chain comprises the heavy chain variable region (VH) comprising the sequence as set forth in SEQ ID NO: 20, and the heavy chain constant region comprising the sequence as set forth in SEQ ID NO: 2 or SEQ ID NO: 55, and
the light chain comprises the light chain variable region (VL) comprising the sequence as set forth in SEQ ID NO: 21, and the light chain constant region comprising the sequence as set forth in SEQ ID NO: 6.

8. The antibody or the antigen-binding fragment thereof of claim 1, wherein the heavy chain comprises the sequence as set forth in SEQ ID NO: 56, and the light chain comprises the sequence as set forth in SEQ ID NO: 57.

9. The antibody or the antigen-binding fragment thereof of claim 1, which is a monoclonal, chimeric or humanized antibody.

10. The antibody or the antigen-binding fragment thereof of claim 1, wherein the PD-1 has or comprises the amino acid sequence as set forth in SEQ ID NO: 22 or SEQ ID NO: 23, or the amino acid sequence of PD-1 has at least 70%, at least 75%, at least 80%, at least 85%, at least 90%, at least 95%, at least 97%, at least 99%, or 100% identity to the amino acid sequence as set forth in SEQ ID NO: 22 or SEQ ID NO: 23, or is an immunogenic fragment thereof.

11. The antibody or the antigen-binding fragment thereof of claim 1, which binds to a native epitope of PD-1 present on the surface of living cells.

12. A nucleic acid comprising a nucleic acid sequence encoding an antibody or an antigen-binding fragment thereof, the antibody or the antigen-binding fragment thereof having the ability to bind to PD-1, wherein the antibody or the antigen-binding fragment thereof comprises a heavy chain having a heavy chain constant region (CH) and a heavy chain variable region (VH) and a light chain having a light chain variable region (VL),
wherein the heavy chain constant region is a human IgG1 constant region that comprises phenylalanine at the position corresponding to position 234 in a human IgG1 heavy chain according to EU numbering, glutamate at the position corresponding to position 235 in a human IgG1 heavy chain according to EU numbering, and arginine at the position corresponding to position 236 in a human IgG1 heavy chain according to EU numbering, and
wherein (i) the heavy chain variable region (VH) comprises a HCDR1, HCDR2, and HCDR3 sequence, wherein the HCDR1, HCDR2 and HCDR3 sequences according to Kabat numbering comprise or have the sequence as set forth in SEQ ID NO: 12, SEQ ID NO: 11, and SEQ ID NO: 8, respectively, and
the light chain variable region (VL) comprises a LCDR1, LCDR2, and LCDR3 sequence, wherein the LCDR1, LCDR2 and LCDR3 sequences according to Kabat numbering comprise or have the sequence as set forth in SEQ ID NO: 17, SEQ ID NO: 15, and SEQ ID NO: 14, respectively; or
(ii) the heavy chain variable region (VH) comprises a HCDR1, HCDR2, and HCDR3 sequence, wherein the HCDR1, HCDR2 and HCDR3 sequences according to IMGT numbering comprise or have the sequence as set forth in SEQ ID NO: 13, SEQ ID NO: 10, and SEQ ID NO: 9, respectively, and
the light chain variable region (VL) comprises a LCDR1, LCDR2, and LCDR3 sequence, wherein the LCDR1, LCDR2 and LCDR3 sequences according to IMGT numbering comprise or have the sequence as set forth in SEQ ID NO: 16, QAS, and SEQ ID NO: 14, respectively.

13. The nucleic acid of claim 12, wherein the nucleic acid is RNA.

14. The nucleic acid of claim 12, wherein the encoded heavy chain constant region comprises a sequence having at least 70%, at least 75%, at least 80%, at least 85%, at least 90%, at least 95%, at least 97%, at least 99%, or 100% identity to the amino acid sequence of the heavy chain constant region sequence as set forth in SEQ ID NO: 2.

15. The nucleic acid of claim 12, wherein the encoded heavy chain constant region comprises the sequence as set forth in SEQ ID NO: 2 or 55.

16. The nucleic acid of claim 12, wherein the encoded HCDR1, HCDR2 and HCDR3 sequences according to Kabat numbering comprise or have the sequence as set forth in SEQ ID NO: 12, SEQ ID NO: 11, and SEQ ID NO: 8, respectively, and the encoded LCDR1, LCDR2 and LCDR3 sequences according to Kabat numbering comprise or have the sequence as set forth in SEQ ID NO: 17, SEQ ID NO: 15, and SEQ ID NO: 14, respectively.

17. The nucleic acid of claim 12, wherein the encoded HCDR1, HCDR2 and HCDR3 sequences according to IMGT numbering comprise or have the sequence as set forth in SEQ ID NO: 13, SEQ ID NO: 10, and SEQ ID NO: 9, respectively, and the encoded LCDR1, LCDR2 and LCDR3 sequences according to IMGT numbering comprise or have the sequence as set forth in SEQ ID NO: 16, QAS, and SEQ ID NO: 14, respectively.

18. The nucleic acid of claim 12, wherein the encoded heavy chain variable region (VH) comprises a sequence having at least 70%, at least 75%, at least 80%, at least 85%, at least 90%, at least 95%, at least 97%, at least 99%, or 100% identity to the amino acid sequence of the VH sequence as set forth in SEQ ID NO: 20, and the encoded light chain variable region (VL) comprises a sequence having at least 70%, at least 75%, at least 80%, at least 85%, at least 90%, at least 95%, at least 97%, at least 99%, or 100% identity to the amino acid sequence of the VH sequence as set forth in SEQ ID NO: 21.

19. The nucleic acid of claim 12, wherein
the encoded heavy chain comprises the heavy chain variable region (VH) comprising the sequence as set forth in SEQ ID NO: 20, and the heavy chain constant region comprising the sequence as set forth in SEQ ID NO: 2 or SEQ ID NO: 55, and
the encoded light chain comprises the light chain variable region (VL) comprising the sequence as set forth in SEQ ID NO: 21, and the light chain constant region comprising the sequence as set forth in SEQ ID NO: 6.

20. The nucleic acid of claim 12, wherein the encoded heavy chain comprises the sequence as set forth in SEQ ID NO: 56, and the encoded light chain comprises the sequence as set forth in SEQ ID NO: 57.

21. A pharmaceutical composition comprising an active agent and a pharmaceutically acceptable carrier, wherein the active agent is an antibody having the ability to bind to PD-1, wherein the antibody comprises a heavy chain having a heavy chain constant region (CH) and a heavy chain variable region (VH) and a light chain having a light chain variable region (VL),
wherein the heavy chain constant region is a human IgG1 constant region that comprises phenylalanine at the position corresponding to position 234 in a human IgG1 heavy chain according to EU numbering, glutamate at the position corresponding to position 235 in a human IgG1 heavy chain according to EU numbering, and arginine at the position corresponding to position 236 in a human IgG1 heavy chain according to EU numbering,
and
wherein (i) the heavy chain variable region (VH) comprises a HCDR1, HCDR2, and HCDR3 sequence, wherein the HCDR1, HCDR2 and HCDR3 sequences according to Kabat numbering comprise or have the sequence as set forth in SEQ ID NO: 12, SEQ ID NO: 11, and SEQ ID NO: 8, respectively, and
the light chain variable region (VL) comprises a LCDR1, LCDR2, and LCDR3 sequence, wherein the LCDR1, LCDR2 and LCDR3 sequences according to Kabat numbering comprise or have the sequence as set forth in SEQ ID NO: 17, SEQ ID NO: 15, and SEQ ID NO: 14, respectively; or
(ii) the heavy chain variable region (VH) comprises a HCDR1, HCDR2, and HCDR3 sequence, wherein the HCDR1, HCDR2 and HCDR3 sequences according to IMGT numbering comprise or have the sequence as set forth in SEQ ID NO: 13, SEQ ID NO: 10, and SEQ ID NO: 9, respectively, and
the light chain variable region (VL) comprises a LCDR1, LCDR2, and LCDR3 sequence, wherein the LCDR1, LCDR2 and LCDR3 sequences according to IMGT numbering comprise or have the sequence as set forth in SEQ ID NO: 16, QAS, and SEQ ID NO: 14, respectively.

22. The pharmaceutical composition of claim 21, wherein the HCDR1, HCDR2 and HCDR3 sequences according to Kabat numbering comprise or have the sequence as set forth in SEQ ID NO: 12, SEQ ID NO: 11, and SEQ ID NO: 8, respectively, and the LCDR1, LCDR2 and LCDR3 sequences according to Kabat numbering comprise or have the sequence as set forth in SEQ ID NO: 17, SEQ ID NO: 15, and SEQ ID NO: 14, respectively.

23. The pharmaceutical composition of claim 21, wherein the HCDR1, HCDR2 and HCDR3 sequences according to IMGT numbering comprise or have the sequence as set forth in SEQ ID NO: 13, SEQ ID NO: 10, and SEQ ID NO: 9, respectively, and the LCDR1, LCDR2 and LCDR3 sequences according to IMGT numbering comprise or have the sequence as set forth in SEQ ID NO: 16, QAS, and SEQ ID NO: 14, respectively.

24. The pharmaceutical composition of claim 21, wherein the heavy chain of the antibody comprises the sequence as set forth in SEQ ID NO: 56, and the light chain of the antibody comprises the sequence as set forth in SEQ ID NO: 57.

25. A pharmaceutical composition comprising an active agent and a pharmaceutically acceptable carrier, wherein the active agent is a nucleic acid comprising a nucleic acid sequence encoding an antibody or an antigen-binding fragment thereof, the antibody or the antigen-binding fragment thereof having the ability to bind to PD-1, wherein the antibody or the antigen-binding fragment thereof comprises a heavy chain having a heavy chain constant region (CH) and a heavy chain variable region (VH) and a light chain having a light chain variable region (VL),
wherein the heavy chain constant region is a human IgG1 constant region that comprises phenylalanine at the position corresponding to position 234 in a human IgG1 heavy chain according to EU numbering, glutamate at the position corresponding to position 235 in a human IgG1 heavy chain according to EU numbering, and arginine at the position corresponding to position 236 in a human IgG1 heavy chain according to EU numbering, and
wherein (i) the heavy chain variable region (VH) comprises a HCDR1, HCDR2, and HCDR3 sequence, wherein the HCDR1, HCDR2 and HCDR3 sequences according to Kabat numbering comprise or have the sequence as set forth in SEQ ID NO: 12, SEQ ID NO: 11, and SEQ ID NO: 8, respectively, and
the light chain variable region (VL) comprises a LCDR1, LCDR2, and LCDR3 sequence, wherein the LCDR1, LCDR2 and LCDR3 sequences according to Kabat numbering comprise or have the sequence as set forth in SEQ ID NO: 17, SEQ ID NO: 15, and SEQ ID NO: 14, respectively; or
iii) the heavy chain variable region (VH) comprises a HCDR1, HCDR2, and HCDR3 sequence, wherein the HCDR1, HCDR2 and HCDR3 sequences according to IMGT numbering comprise or have the sequence as set forth in SEQ ID NO: 13, SEQ ID NO: 10, and SEQ ID NO: 9, respectively, and
the light chain variable region (VL) comprises a LCDR1, LCDR2, and LCDR3 sequence, wherein the LCDR1, LCDR2 and LCDR3 sequences according to IMGT numbering comprise or have the sequence as set forth in SEQ ID NO: 16, QAS, and SEQ ID NO: 14, respectively.

26. The pharmaceutical composition of claim 25, wherein the nucleic acid is RNA.

27. The pharmaceutical composition of claim 25, wherein the encoded heavy chain comprises the sequence as set forth in SEQ ID NO: 56, and the encoded light chain comprises the sequence as set forth in SEQ ID NO: 57.

28. A vector or host cell comprising the nucleic acid of claim 12.

29. A method for treating cancer in a subject comprising administering to the subject the pharmaceutical composition of claim 21.

30. A method for treating cancer in a subject comprising administering to the subject the pharmaceutical composition of claim 25.

* * * * *

UNITED STATES PATENT AND TRADEMARK OFFICE
CERTIFICATE OF CORRECTION

PATENT NO. : 11,932,693 B2
APPLICATION NO. : 18/315686
DATED : March 19, 2024
INVENTOR(S) : Ugur Sahin et al.

It is certified that error appears in the above-identified patent and that said Letters Patent is hereby corrected as shown below:

In the Claims

Column 150, Line 35, "iii) the heavy" should be changed to --(ii) the heavy--.

Signed and Sealed this
Twenty-eighth Day of May, 2024

Katherine Kelly Vidal
*Director of the United States Patent and Trademark Office*